(12) United States Patent
Zucker et al.

(10) Patent No.: US 10,751,470 B2
(45) Date of Patent: Aug. 25, 2020

(54) SEMI DISPOSABLE AUTO INJECTOR

(71) Applicant: E3D A.C.A.L., Merom Hagalil (IL)

(72) Inventors: Menachem Zucker, Haifa (IL); Lior Raday, MP Hof Ashkelon (IL); David Daily, Herzliya (IL)

(73) Assignee: E3D A.C.A.L LTD, Merom Hagalil (IL)

( * ) Notice: Subject to any disclaimer, the term of this patent is extended or adjusted under 35 U.S.C. 154(b) by 192 days.

(21) Appl. No.: 15/117,592

(22) PCT Filed: Feb. 10, 2015

(86) PCT No.: PCT/IL2015/050155
§ 371 (c)(1),
(2) Date: Aug. 9, 2016

(87) PCT Pub. No.: WO2015/118550
PCT Pub. Date: Aug. 13, 2015

(65) Prior Publication Data
US 2016/0354556 A1 Dec. 8, 2016

Related U.S. Application Data

(60) Provisional application No. 61/937,681, filed on Feb. 10, 2014.

(51) Int. Cl.
*A61M 5/20* (2006.01)
*A61M 5/32* (2006.01)
(Continued)

(52) U.S. Cl.
CPC ............ *A61M 5/2033* (2013.01); *A61M 5/24* (2013.01); *A61M 5/3202* (2013.01);
(Continued)

(58) Field of Classification Search
CPC .... A61M 2005/2013; A61M 2005/206; A61M 2005/208; A61M 2005/3217;
(Continued)

(56) References Cited

U.S. PATENT DOCUMENTS 7,175,055 B2 * 2/2007 Hansen ............. A61M 5/14546
222/325
9,999,734 B2 6/2018 Cowe
(Continued)

FOREIGN PATENT DOCUMENTS

| WO | 2010/018411 A1 | 2/2010 |
| WO | 2012/038721 A2 | 3/2012 |
| WO | 2013034984 A2 | 3/2013 |

*Primary Examiner* — Lauren P Farrar
*Assistant Examiner* — James D Ponton
(74) *Attorney, Agent, or Firm* — Sughrue Mion, PLLC

(57) ABSTRACT

An automatic injection device including a reusable driving assembly having a forward injection end and an engagement element and a disposable cassette assembly including an injectable liquid to be injected at an injection site, wherein the disposable cassette assembly is removably insertable into the reusable driving assembly at the forward injection end and is removably retained within the reusable driving assembly by snap fit engagement therewith, the snap fit engagement being effected at least partially by the engagement element, which is displaced rearwardly by insertion of the disposable cassette assembly in the reusable driving assembly.

18 Claims, 102 Drawing Sheets

(51) Int. Cl.
  *A61M 5/24*   (2006.01)
  *A61M 5/46*   (2006.01)
  *A61M 5/31*   (2006.01)
  *A61M 5/315*  (2006.01)

(52) U.S. Cl.
  CPC .......... *A61M 5/326* (2013.01); *A61M 5/3213* (2013.01); *A61M 5/46* (2013.01); *A61M 5/31511* (2013.01); *A61M 5/3204* (2013.01); *A61M 2005/206* (2013.01); *A61M 2005/208* (2013.01); *A61M 2005/2026* (2013.01); *A61M 2005/244* (2013.01); *A61M 2005/2411* (2013.01); *A61M 2005/2485* (2013.01); *A61M 2005/3125* (2013.01); *A61M 2005/3142* (2013.01); *A61M 2205/583* (2013.01)

(58) Field of Classification Search
  CPC .. A61M 2005/3246; A61M 2005/3247; A61M 2005/2403; A61M 2005/2407; A61M 2005/2411; A61M 2005/2414; A61M 5/2033; A61M 5/321; A61M 5/3213; A61M 5/3219; A61M 5/3243; A61M 5/3245; A61M 5/3257; A61M 5/326; A61M 5/24; A61M 5/3202; A61M 2005/2026; A61M 2005/244; A61M 2005/2485; A61M 2005/3142; A61B 5/46; A61B 5/31511; A61B 5/3204
  See application file for complete search history.

(56) References Cited

U.S. PATENT DOCUMENTS

| | | |
|---|---|---|
| 2007/0129686 A1 | 6/2007 | Daily et al. |
| 2009/0312707 A1* | 12/2009 | Bishop .................. A61M 5/24 604/135 |
| 2012/0191047 A1 | 7/2012 | Raday et al. |
| 2012/0265136 A1* | 10/2012 | Lawlis .................. A61K 38/24 604/110 |
| 2013/0218128 A1* | 8/2013 | Cowe .................. A61M 5/2033 604/506 |
| 2014/0012229 A1 | 1/2014 | Bokelman et al. |
| 2018/0133106 A1* | 5/2018 | Mounce .................. A61M 5/20 |

\* cited by examiner

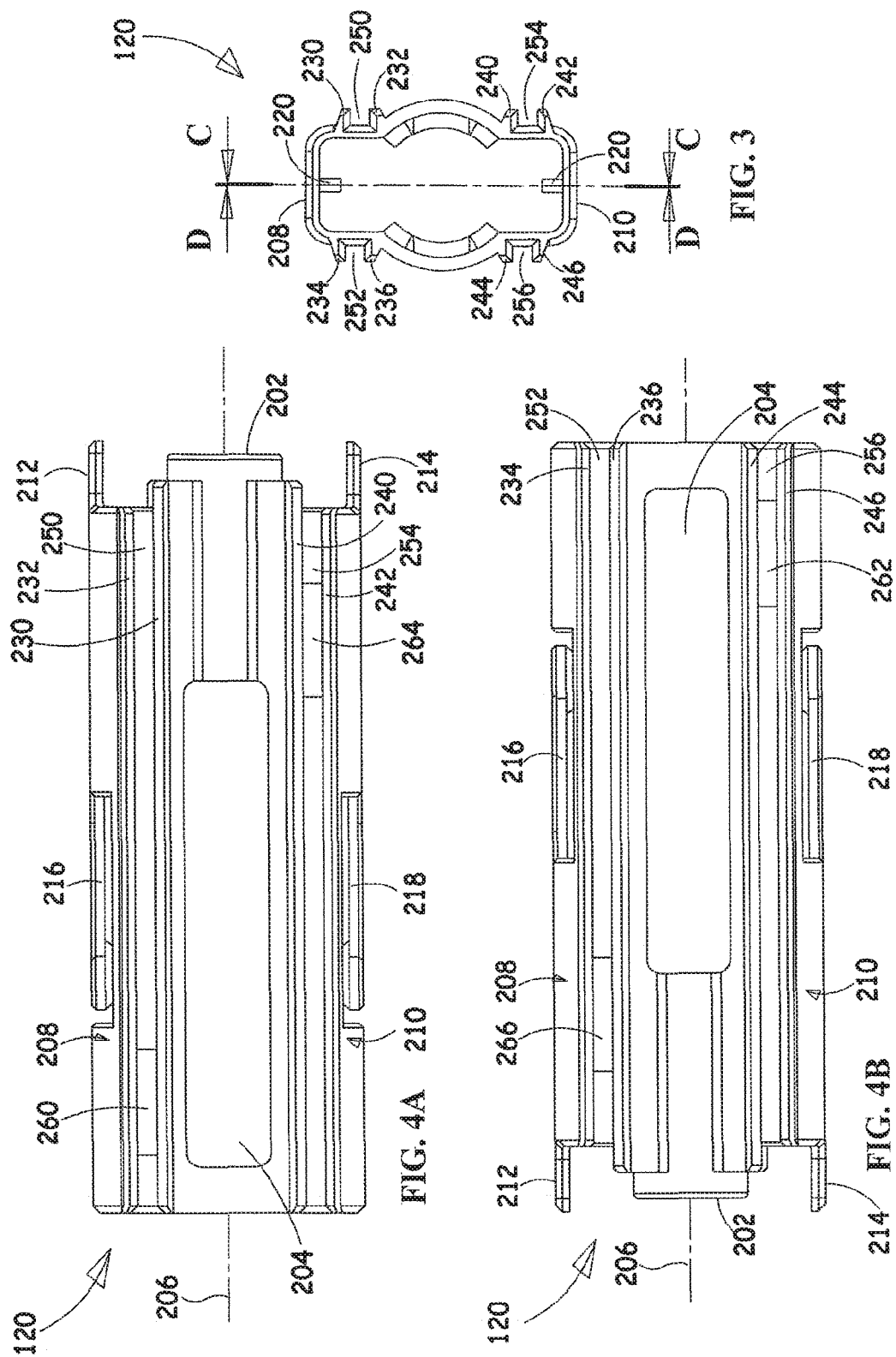

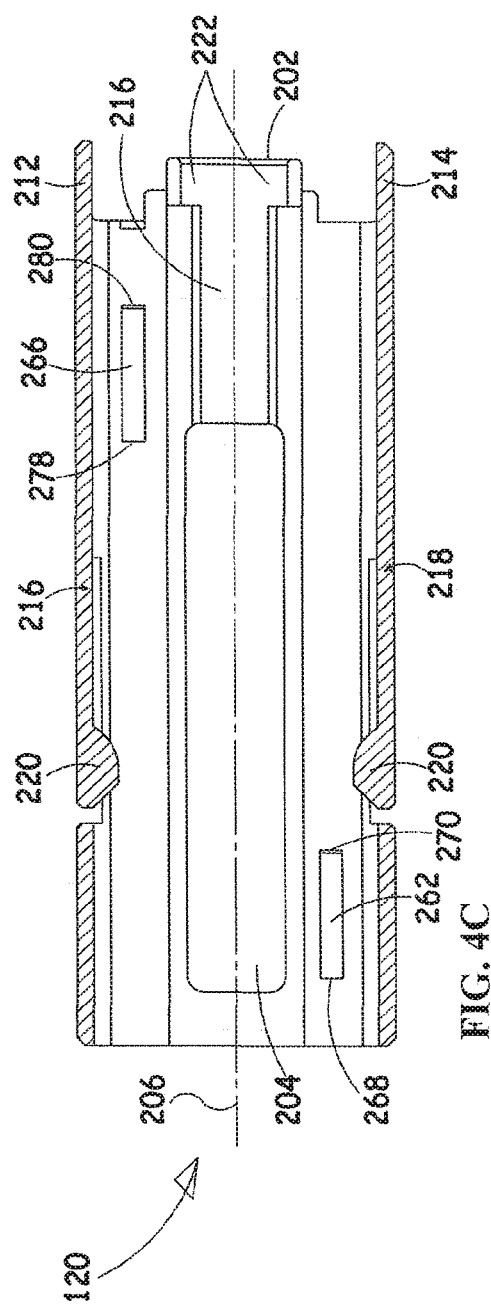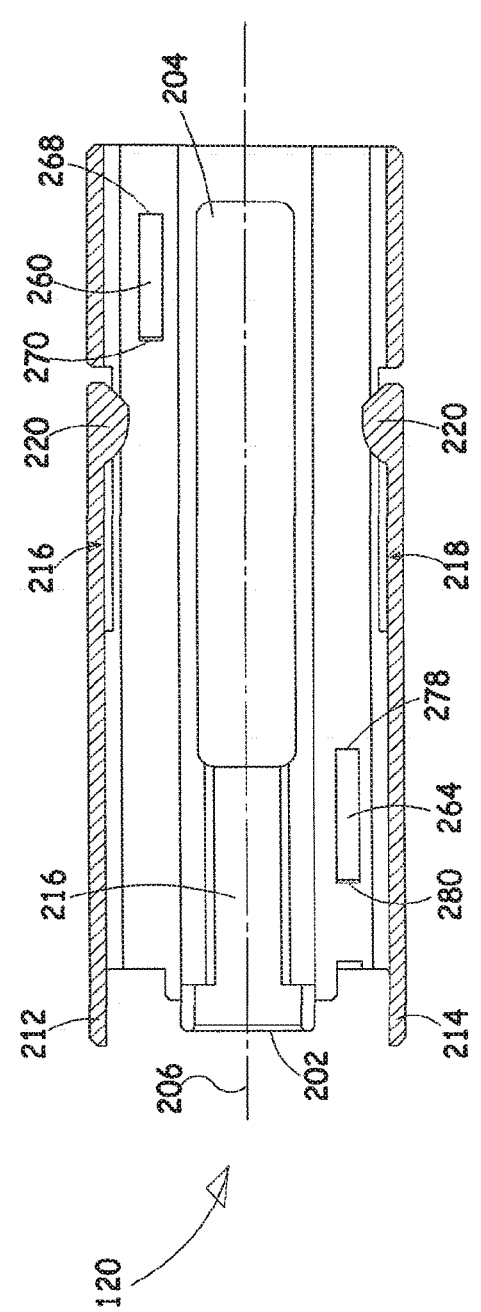

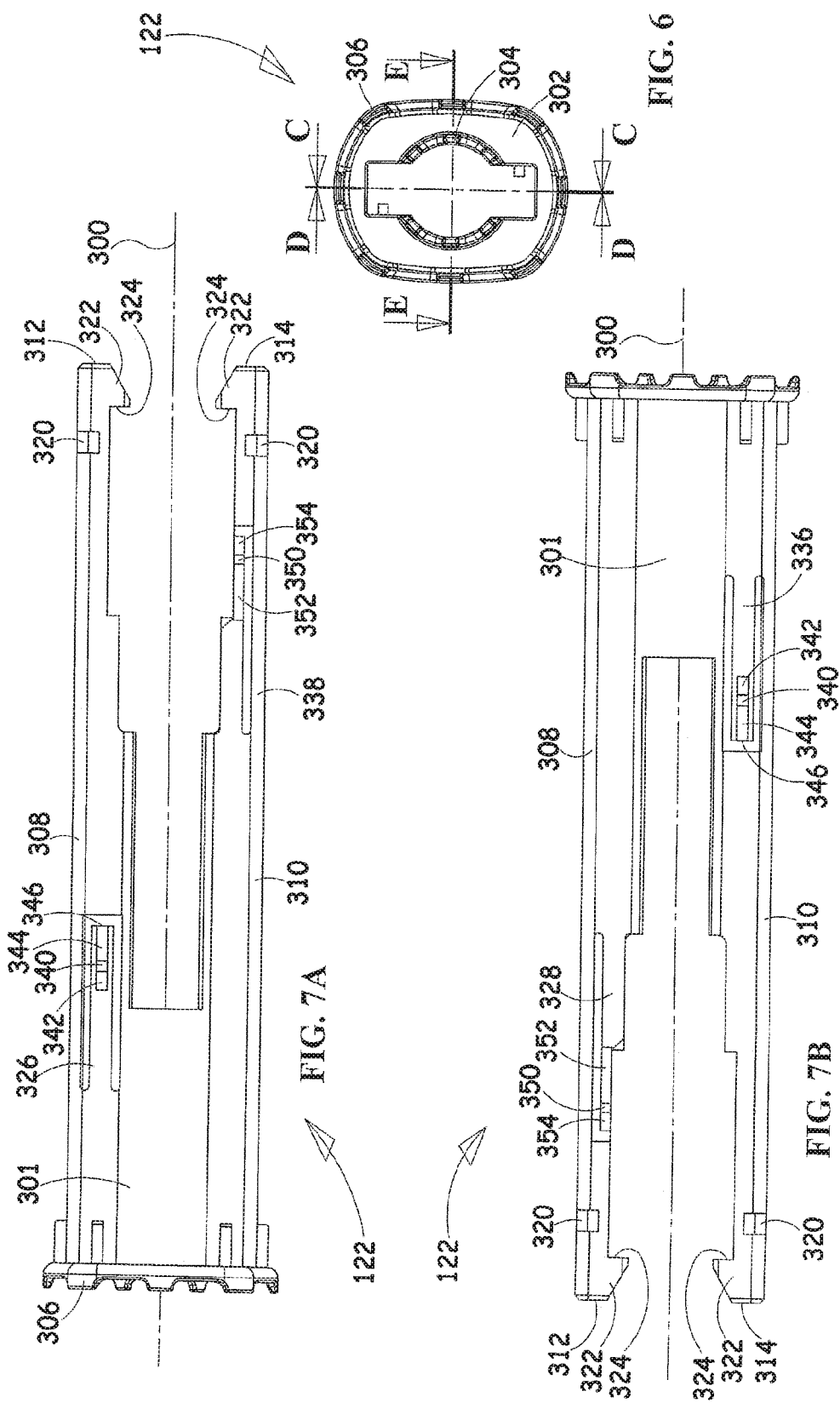

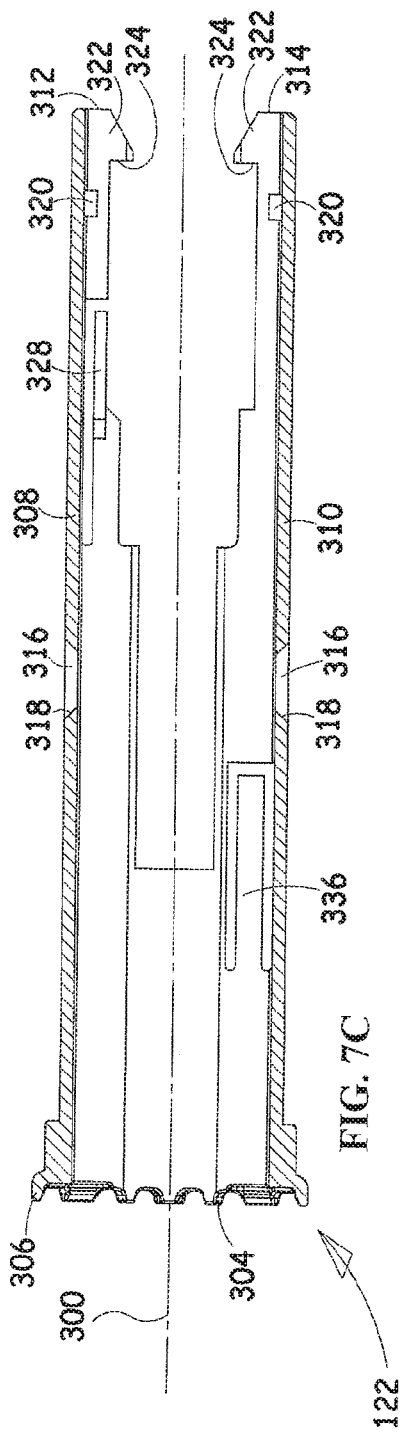
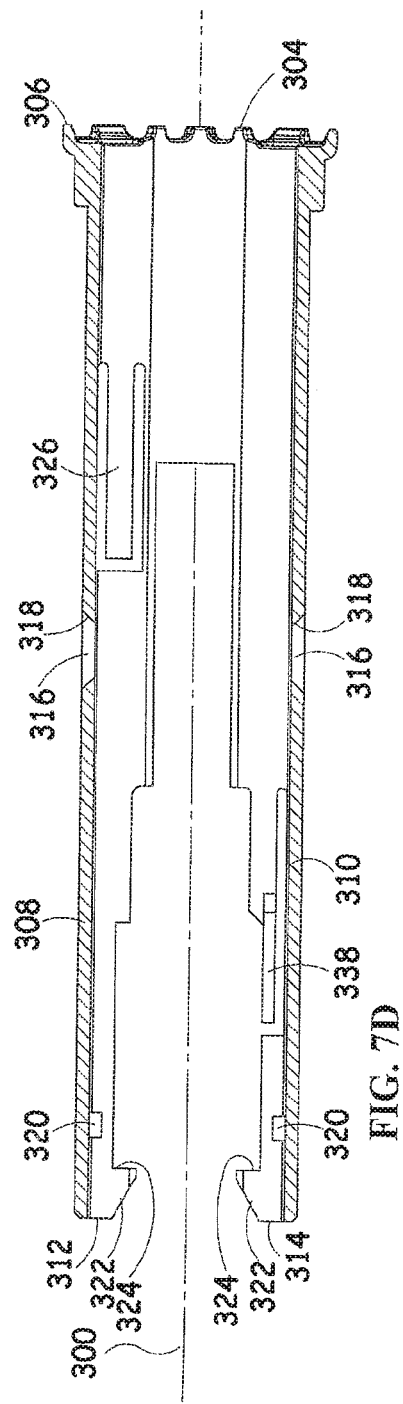

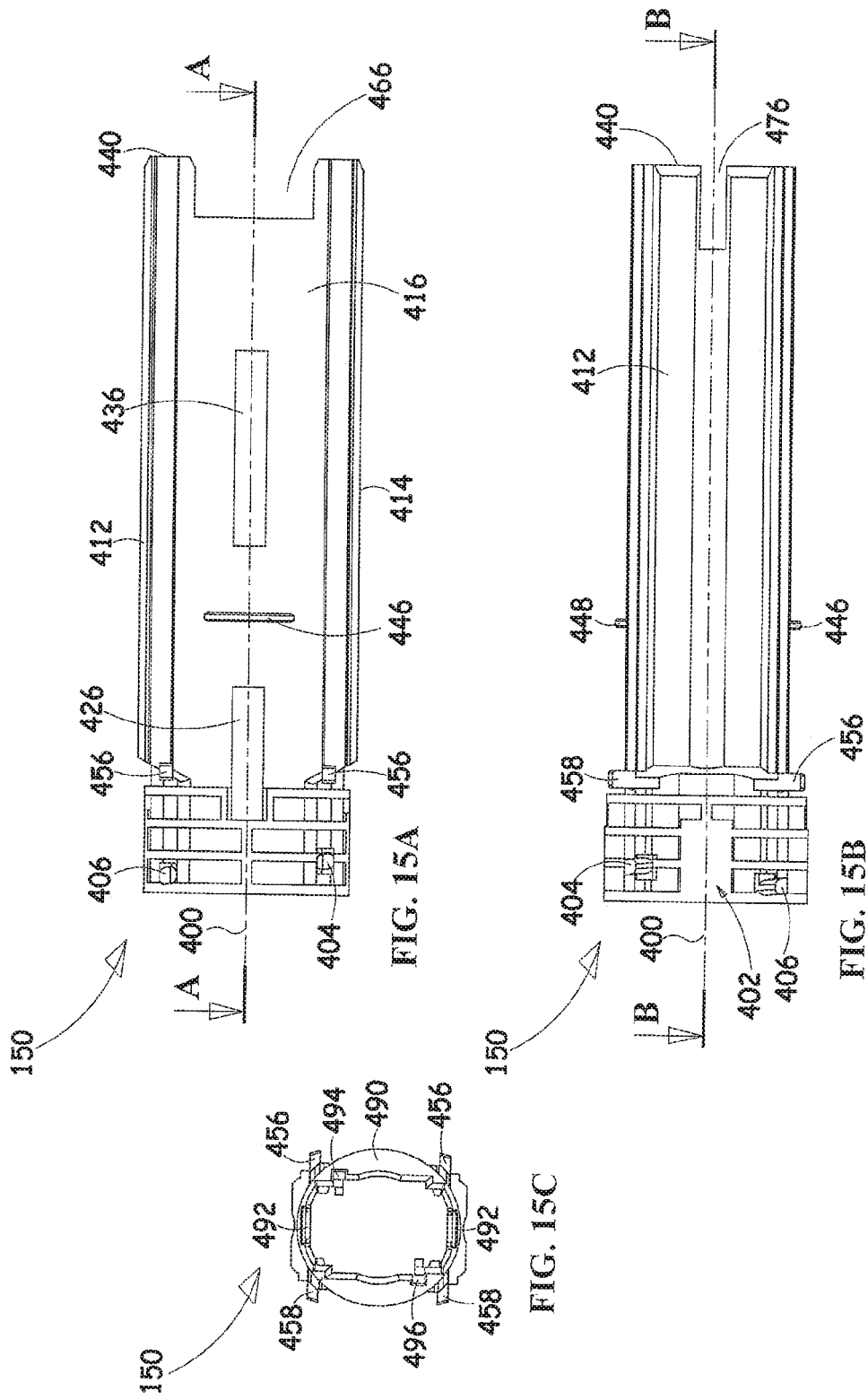

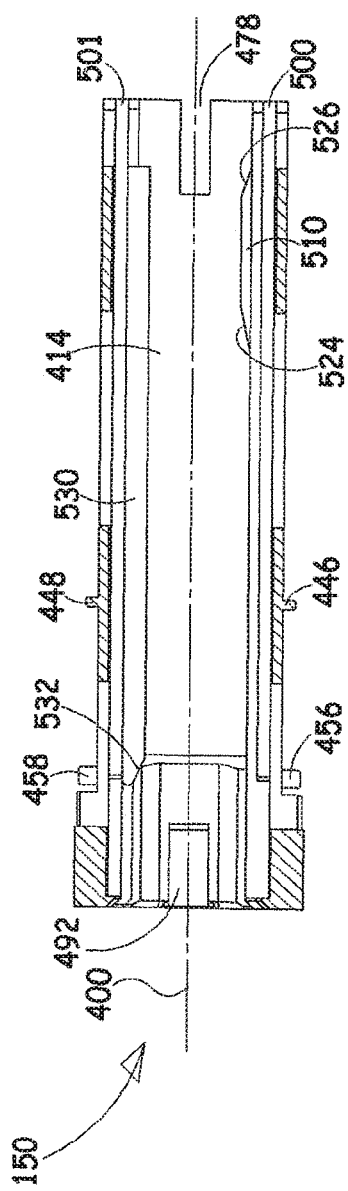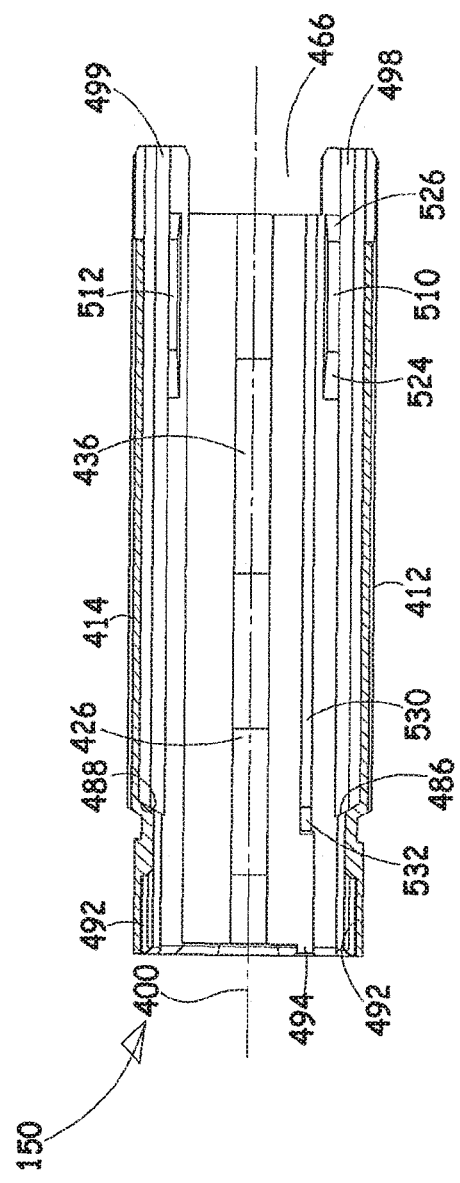
FIG. 16A
FIG. 16B

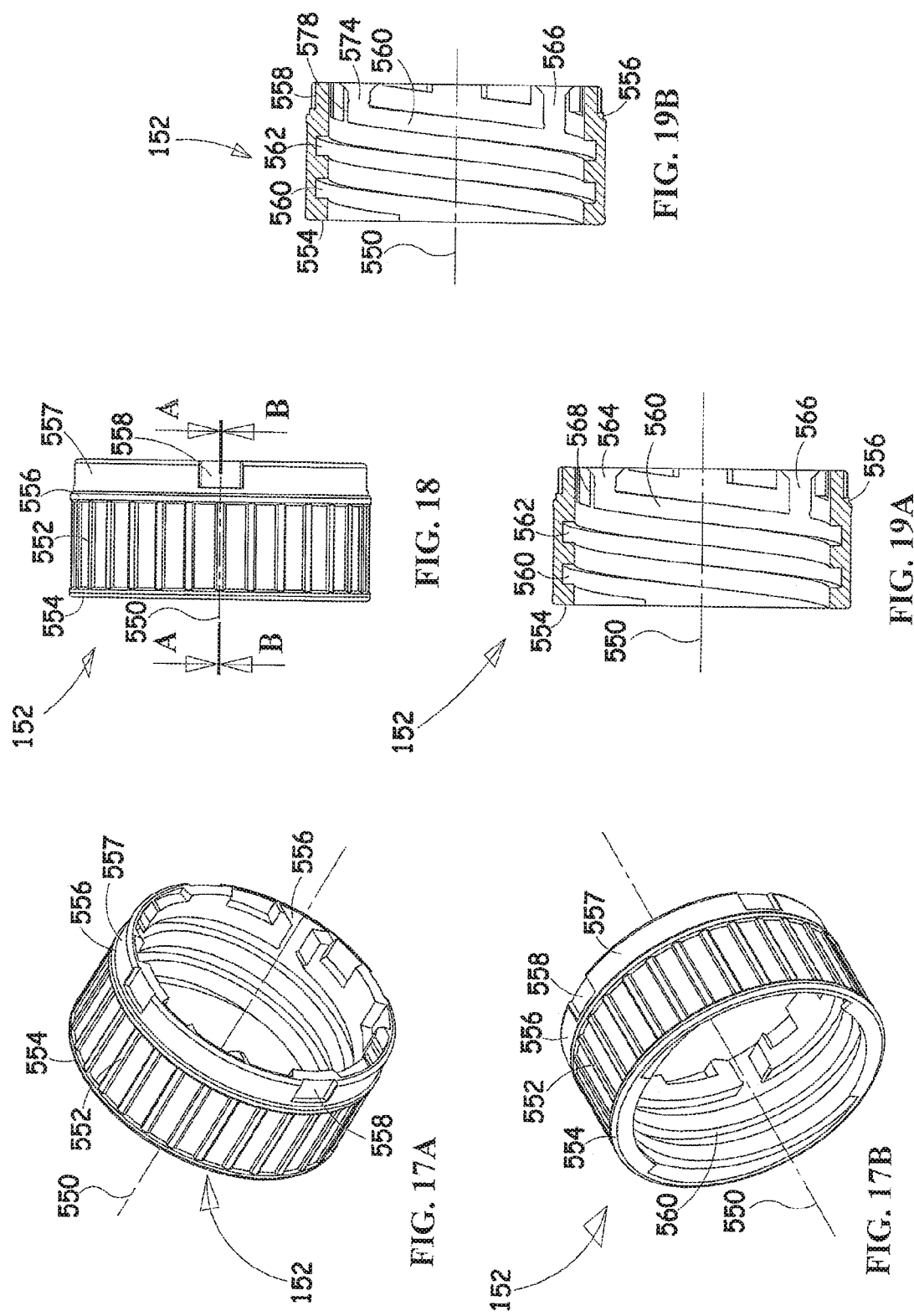

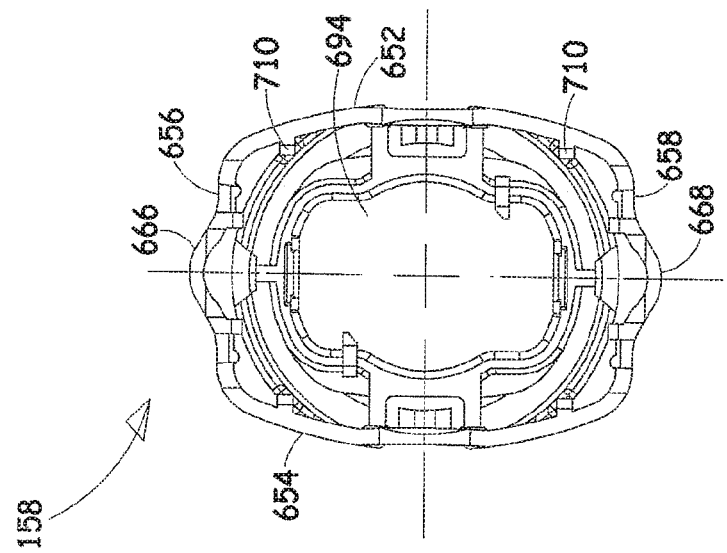
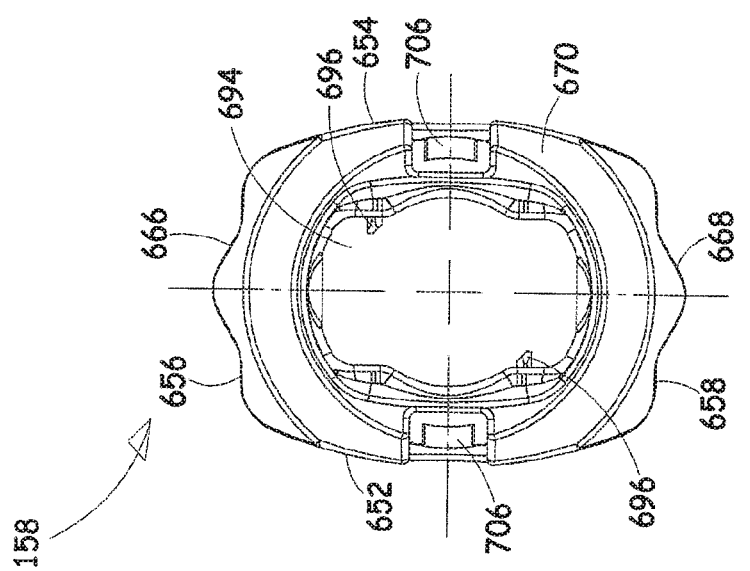

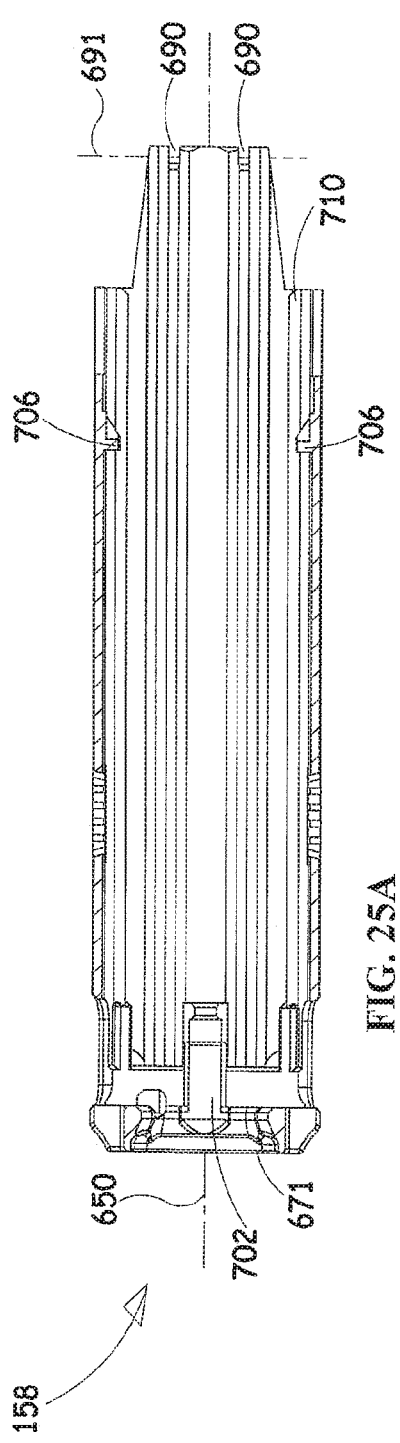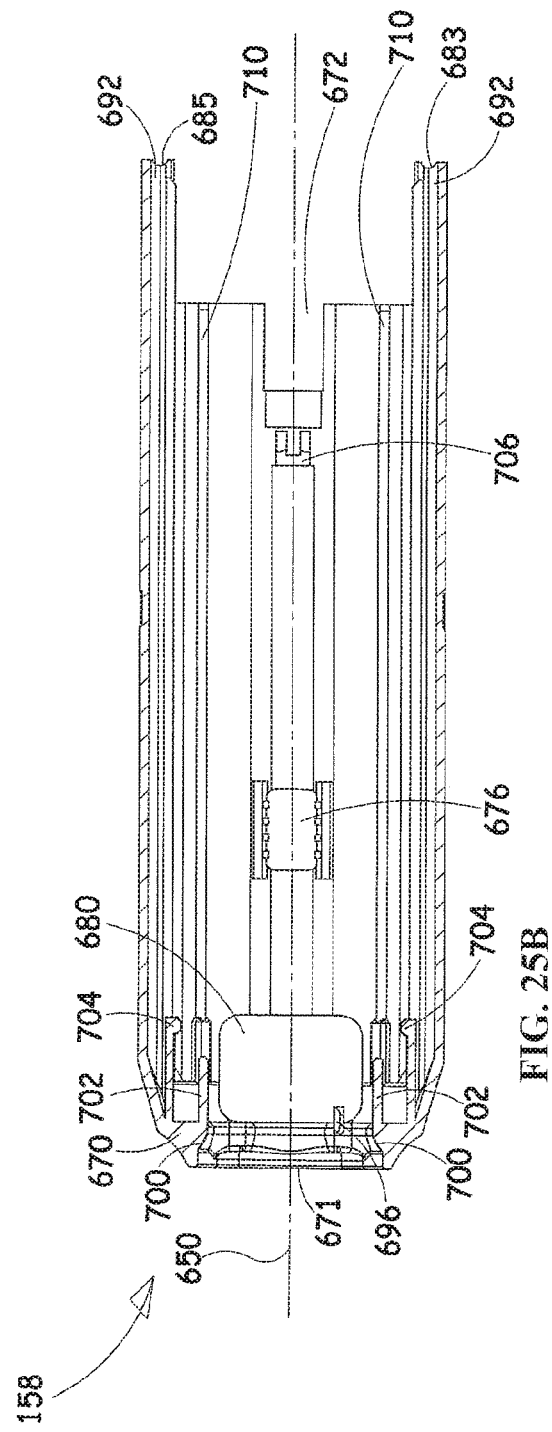
FIG. 25A
FIG. 25B

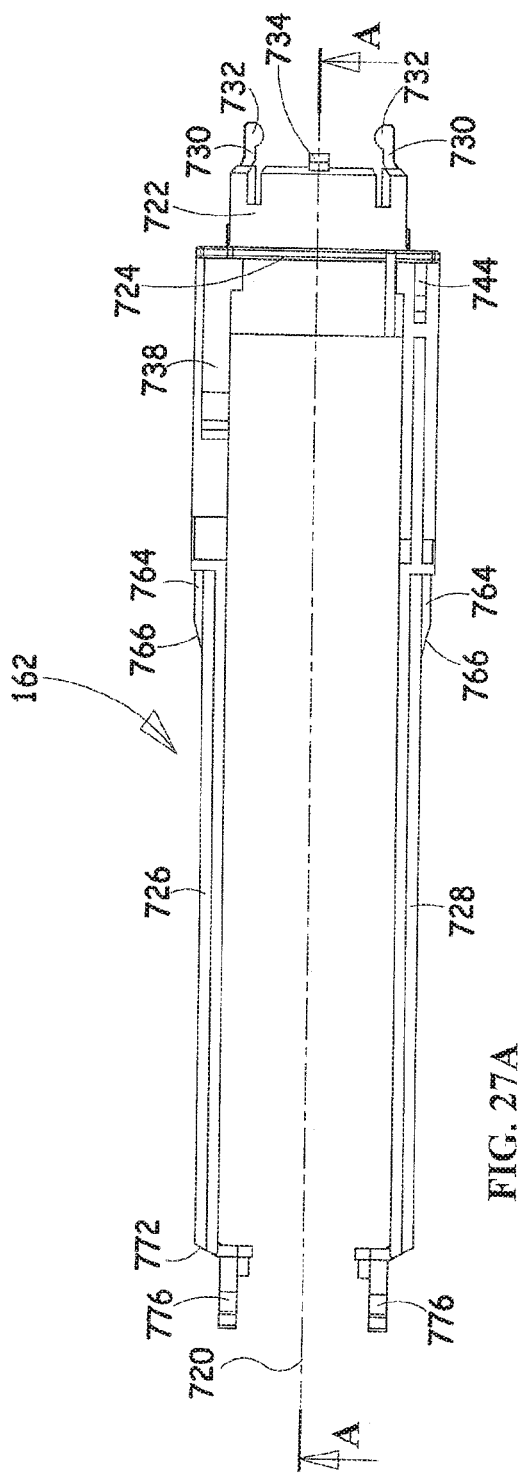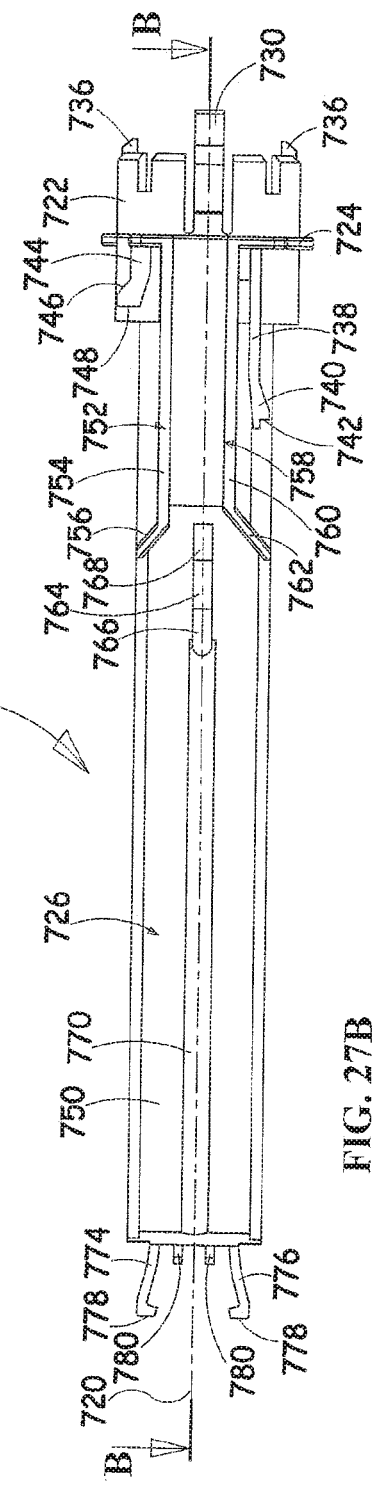
FIG. 27A
FIG. 27B

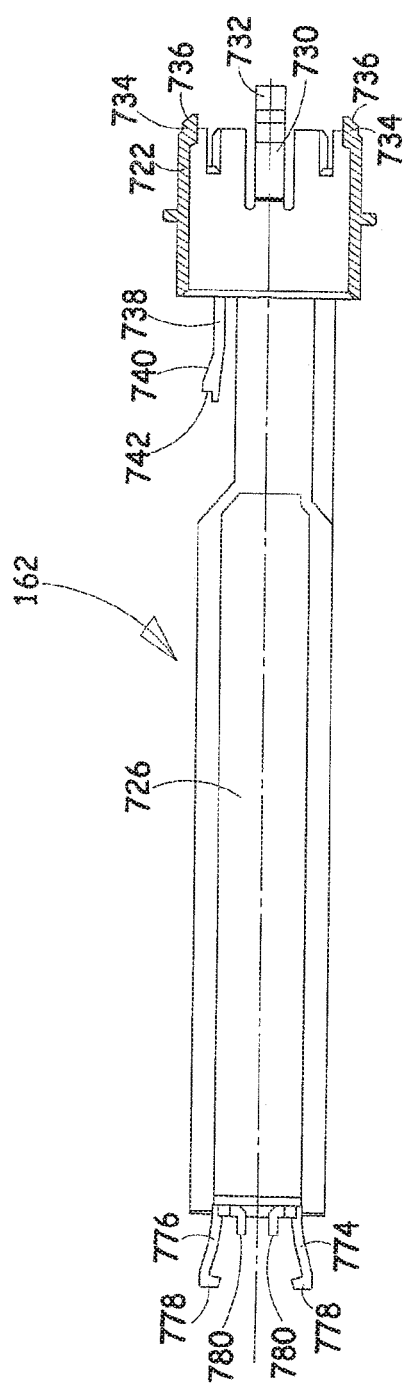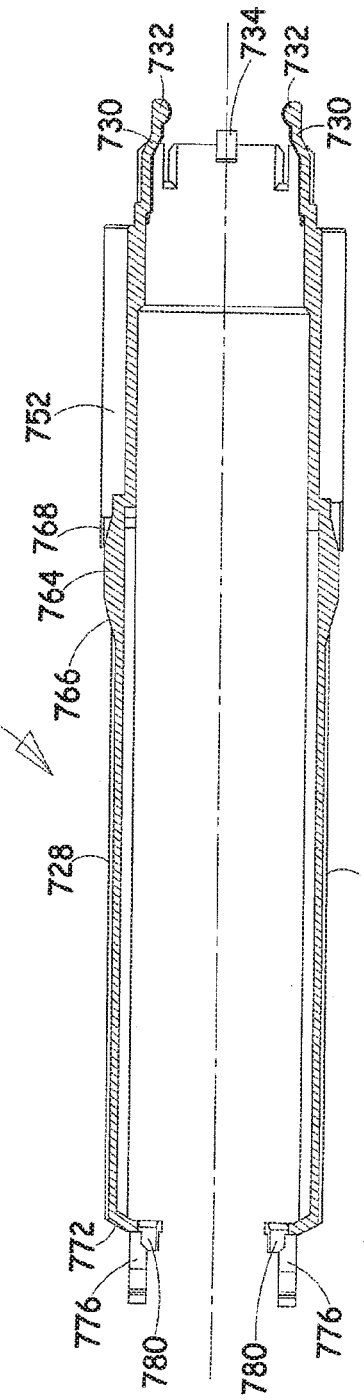
FIG. 28A
FIG. 28B

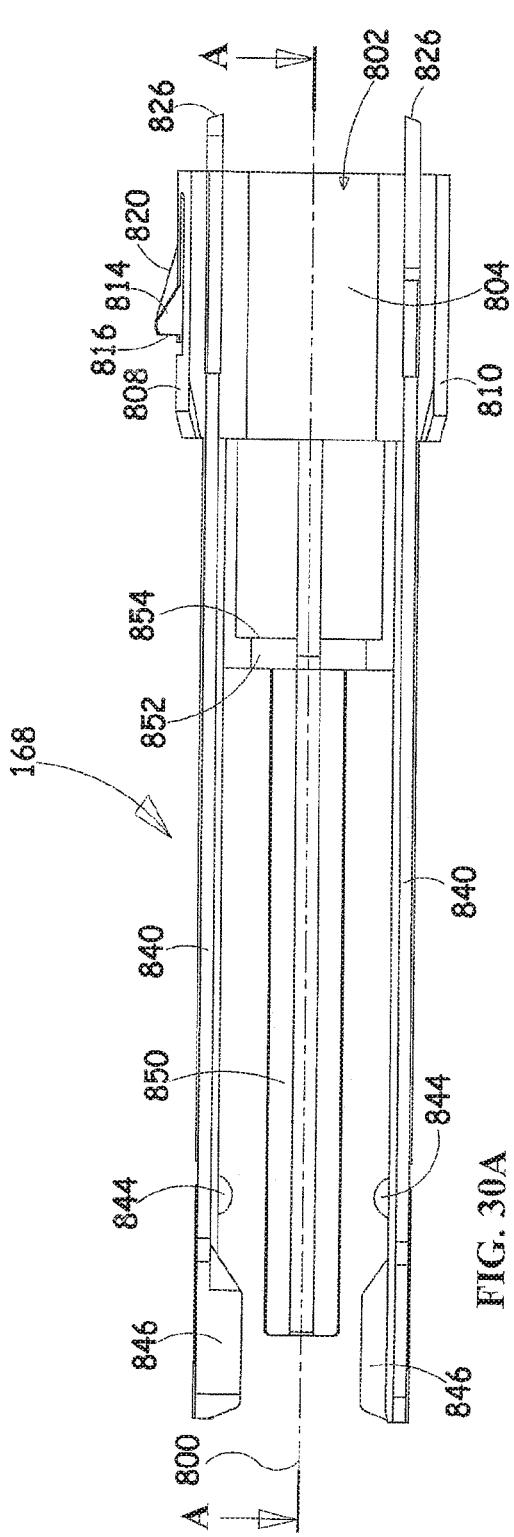
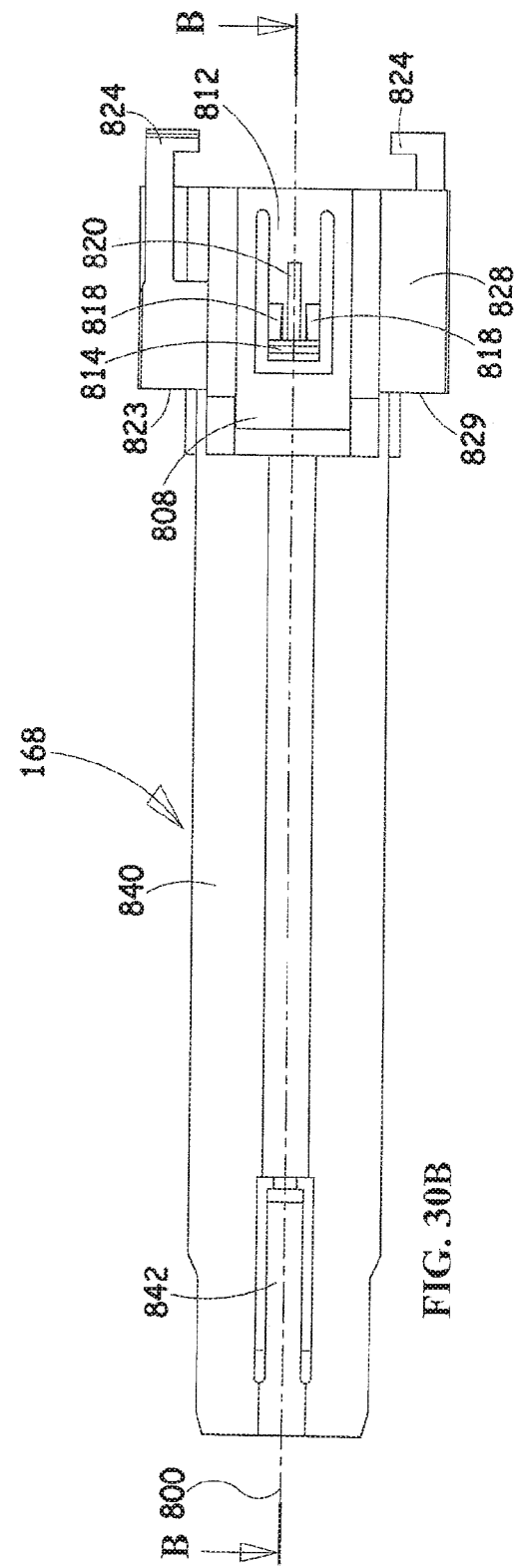
FIG. 30A
FIG. 30B

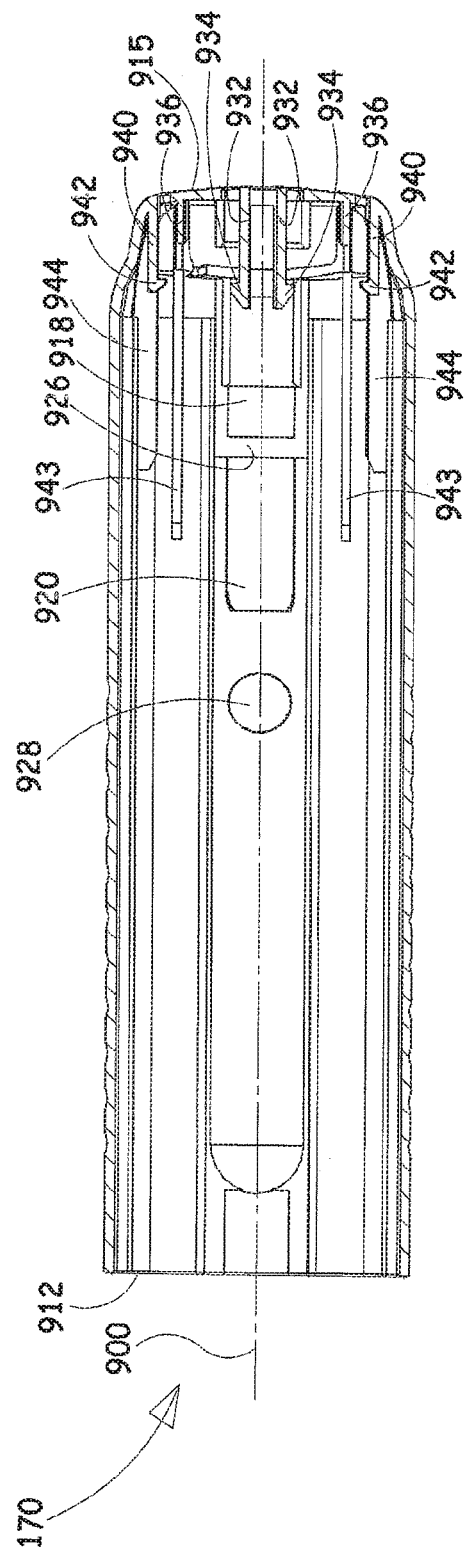
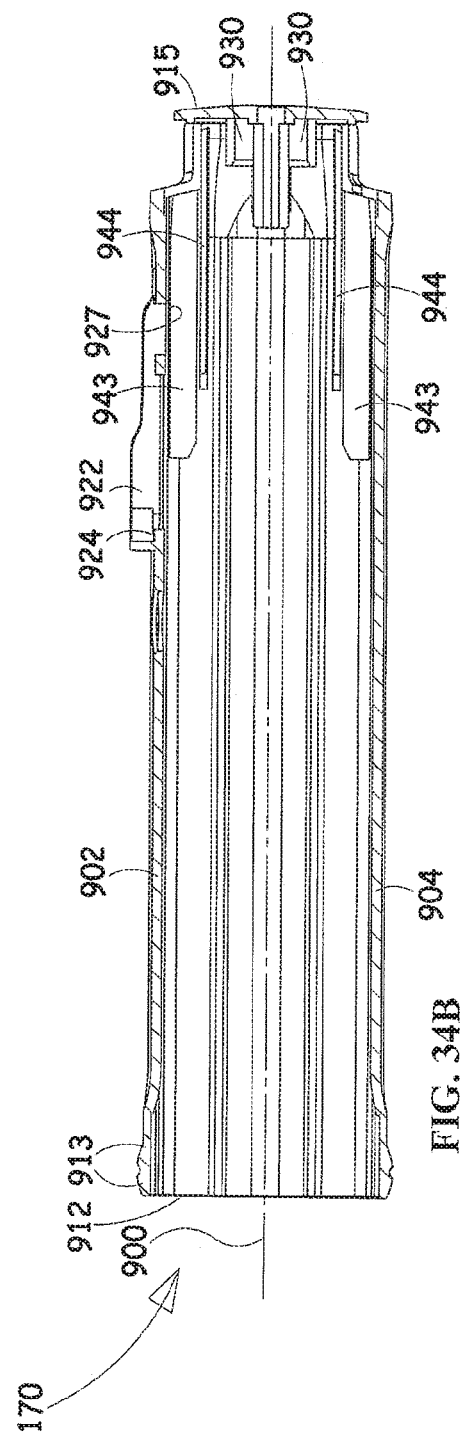
FIG. 34A
FIG. 34B

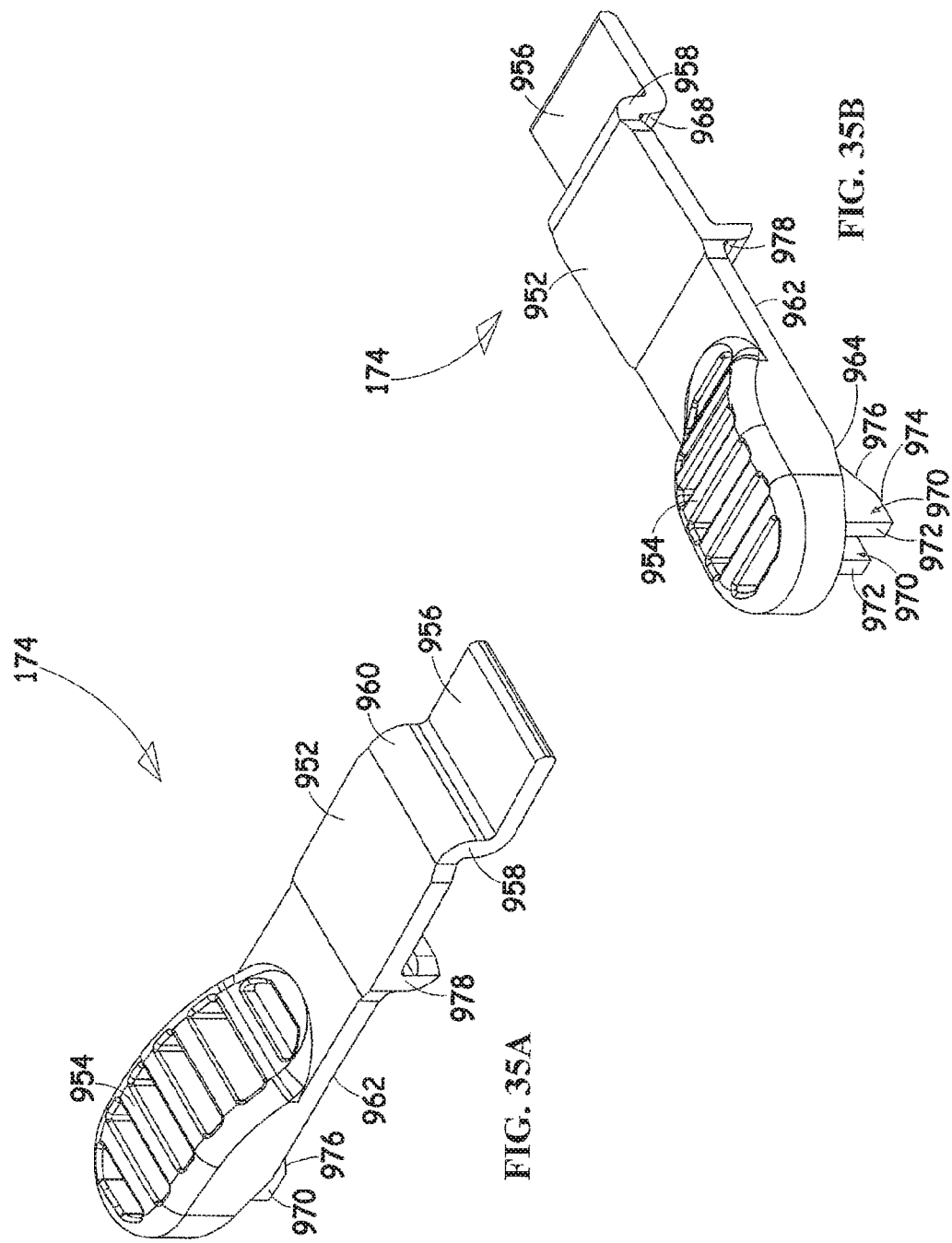

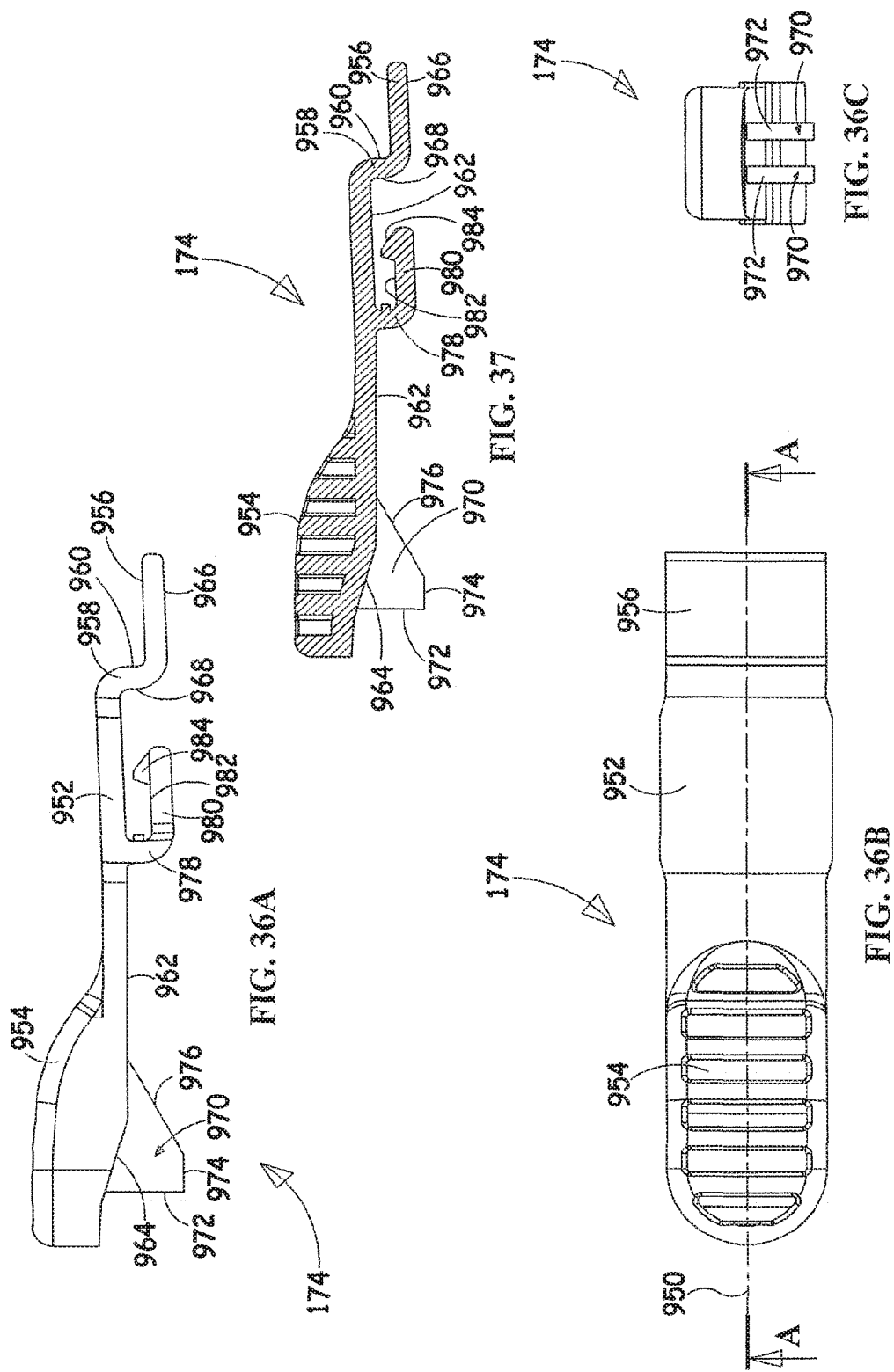

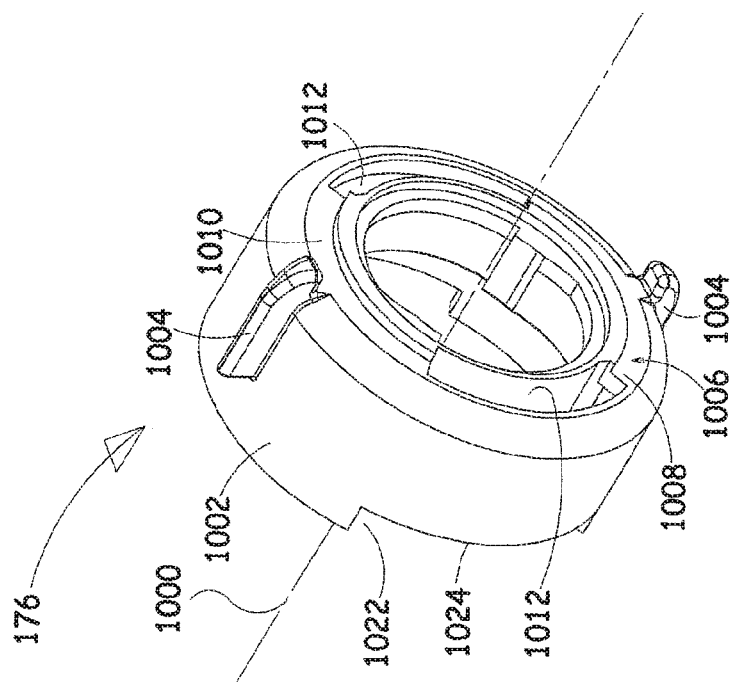
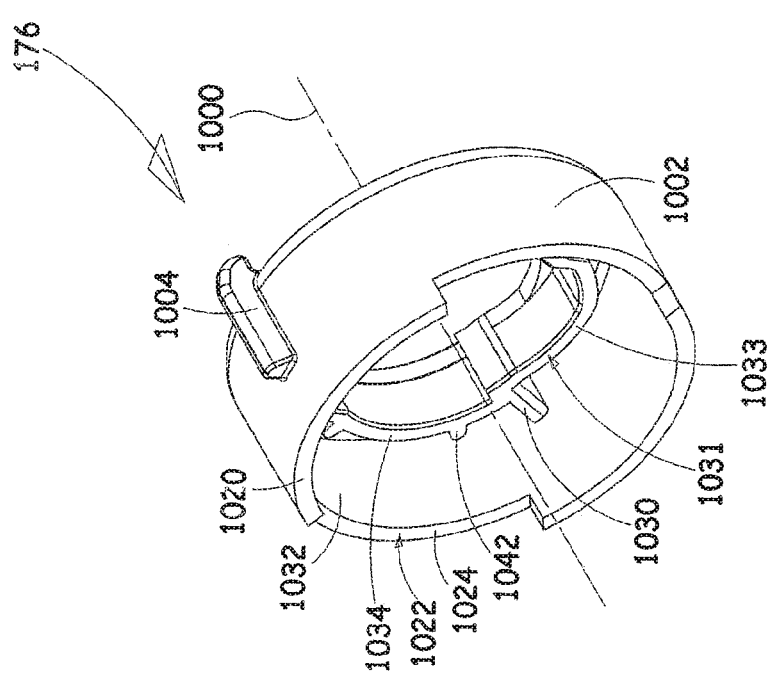
FIG. 38A
FIG. 38B

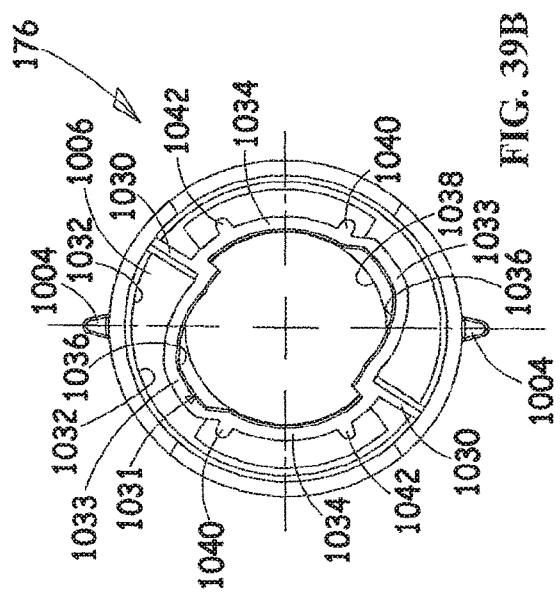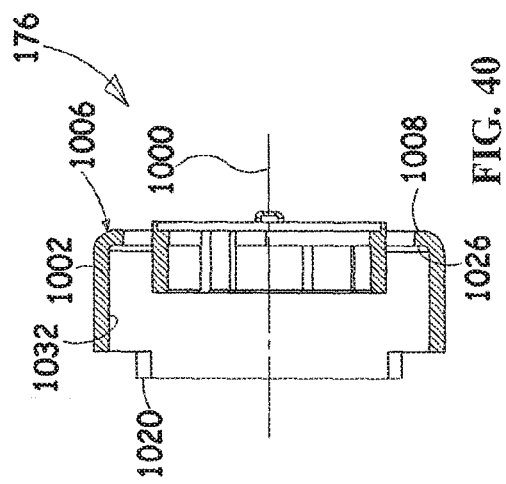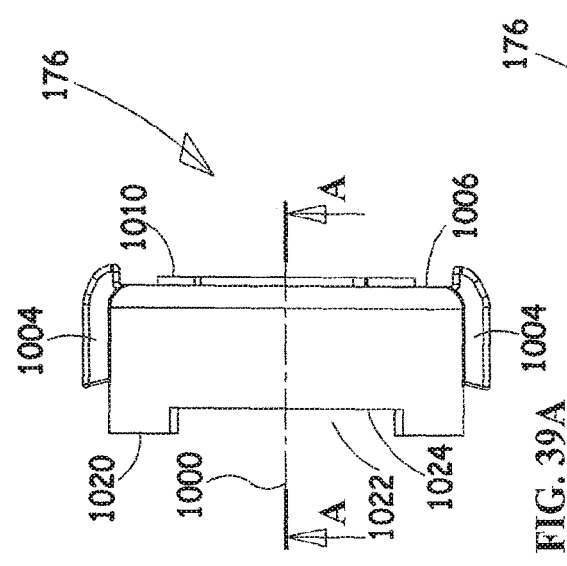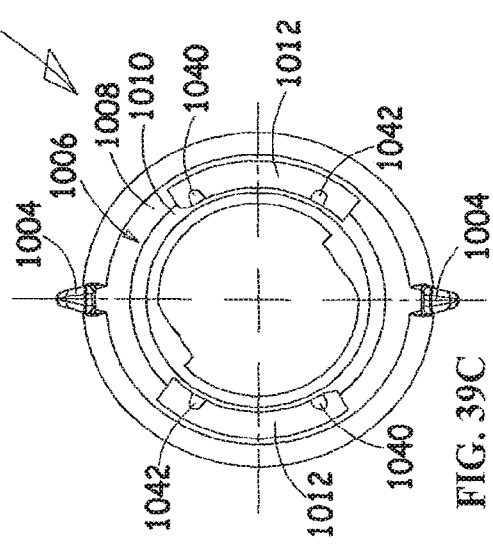

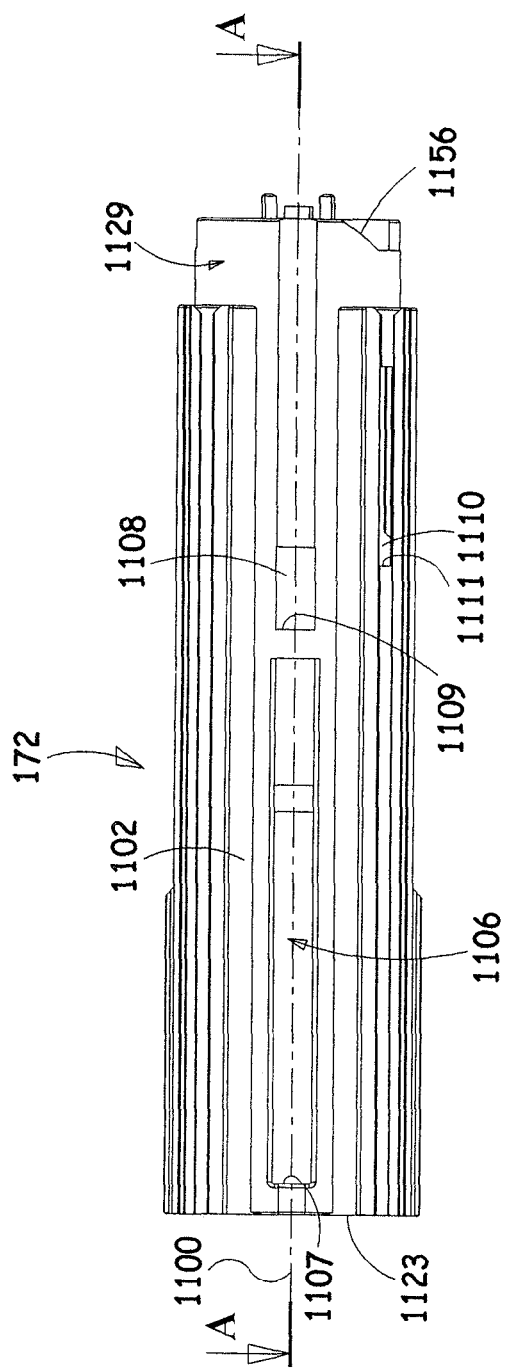
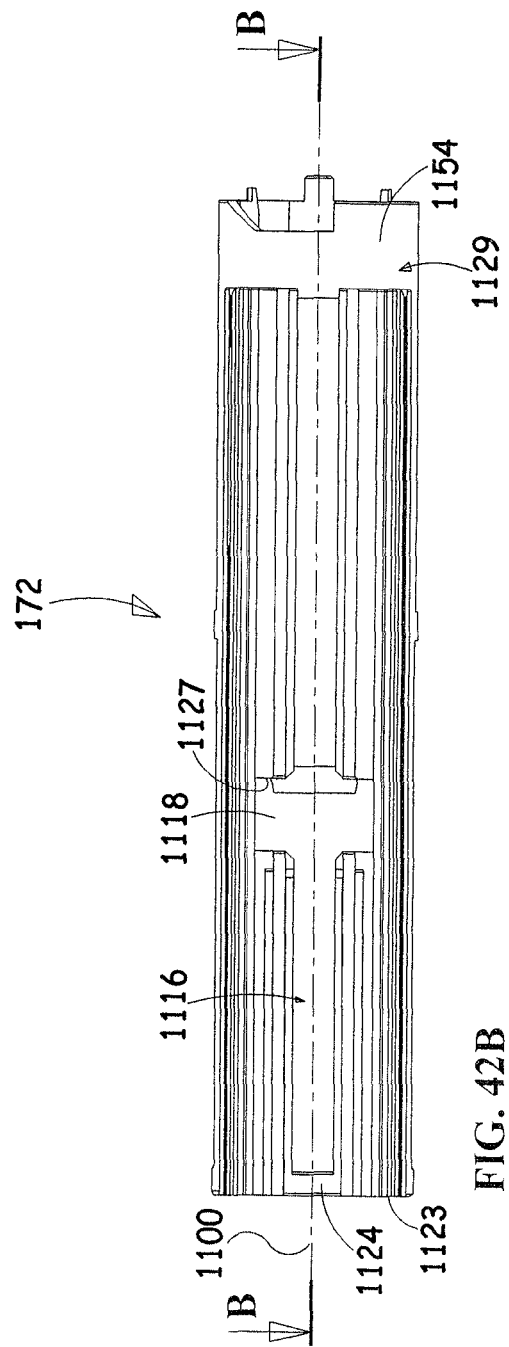
FIG. 42A
FIG. 42B

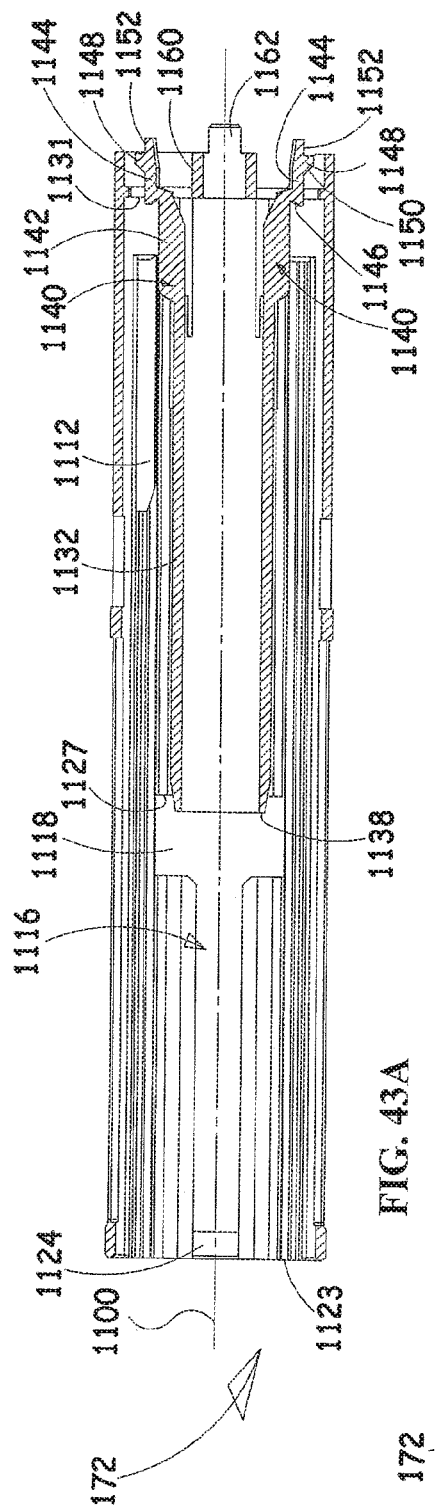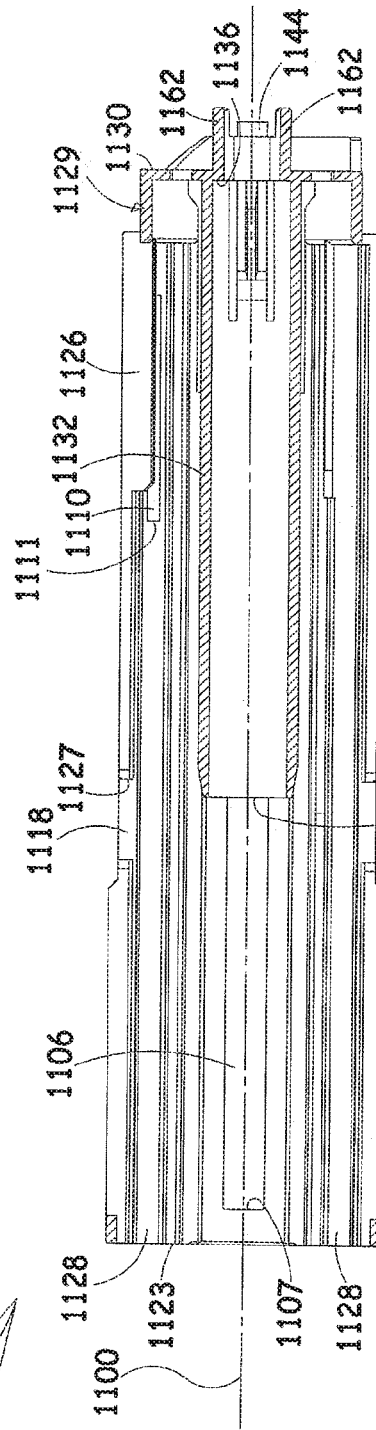
FIG. 43A
FIG. 43B

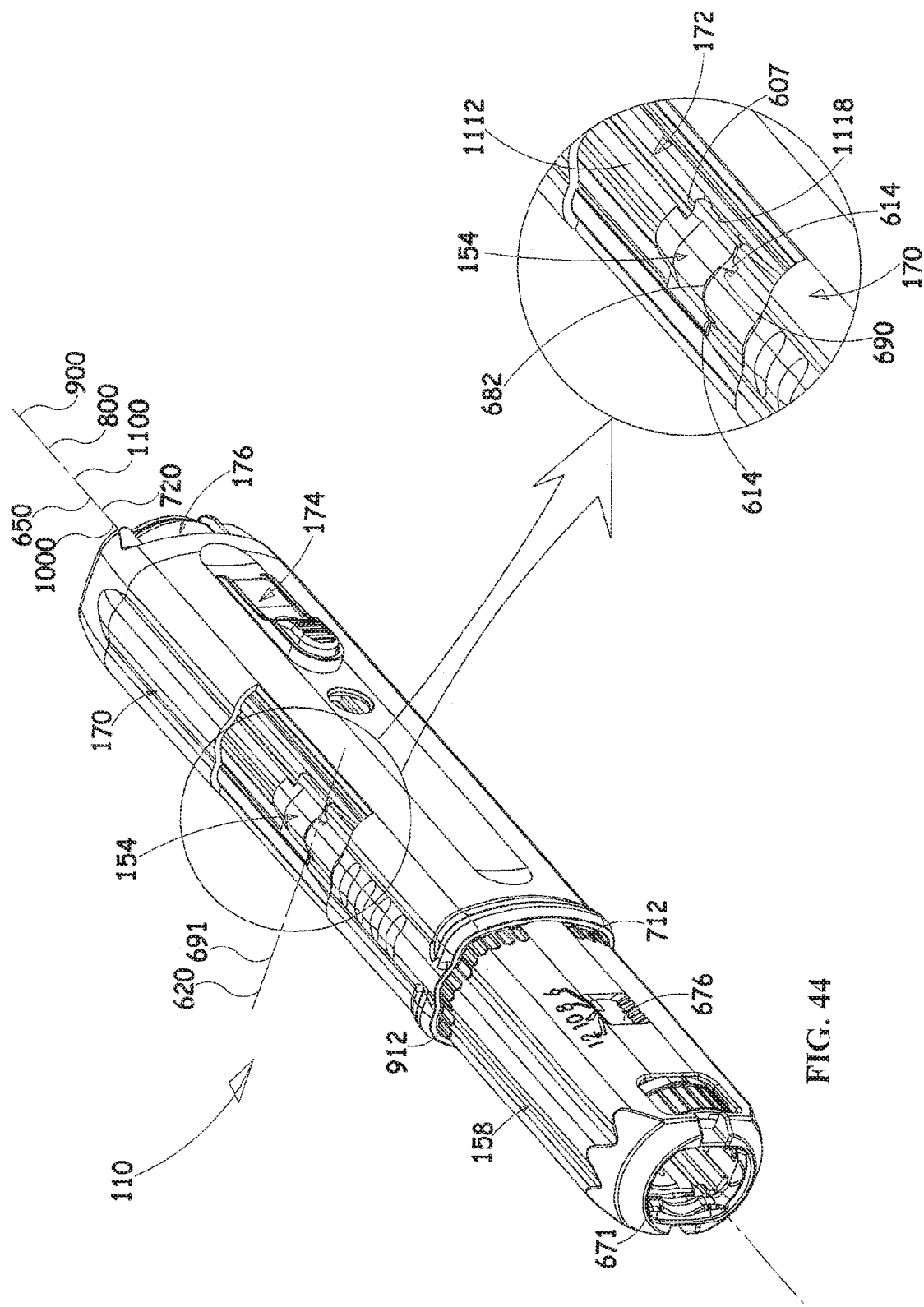

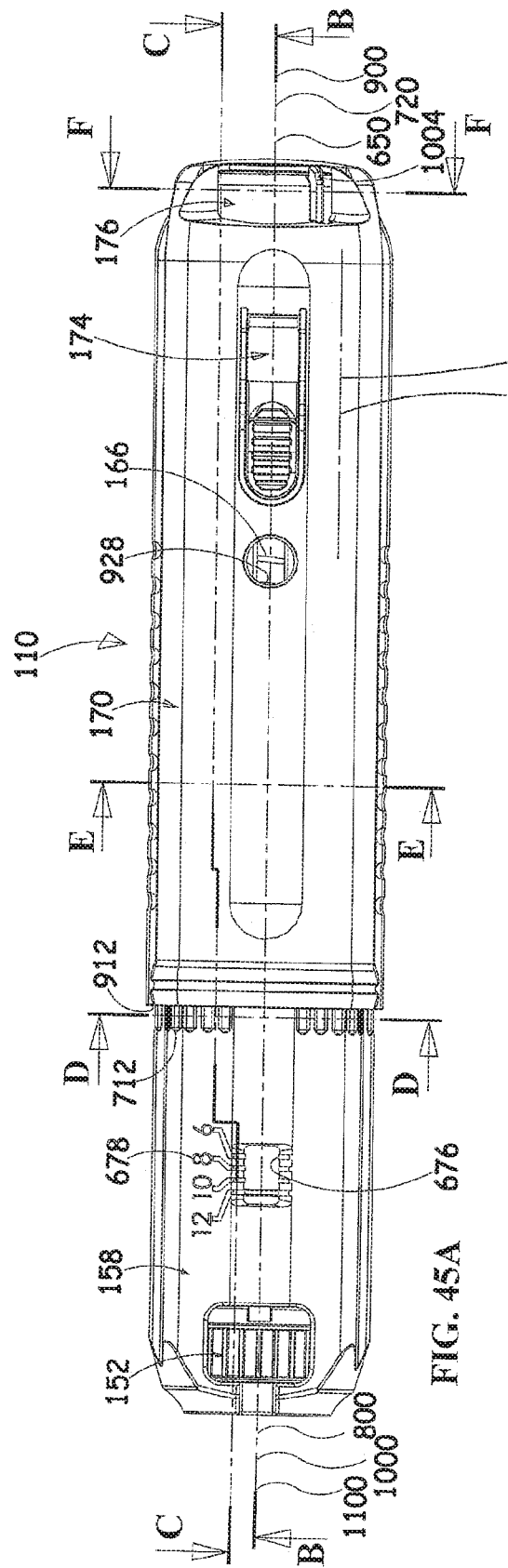
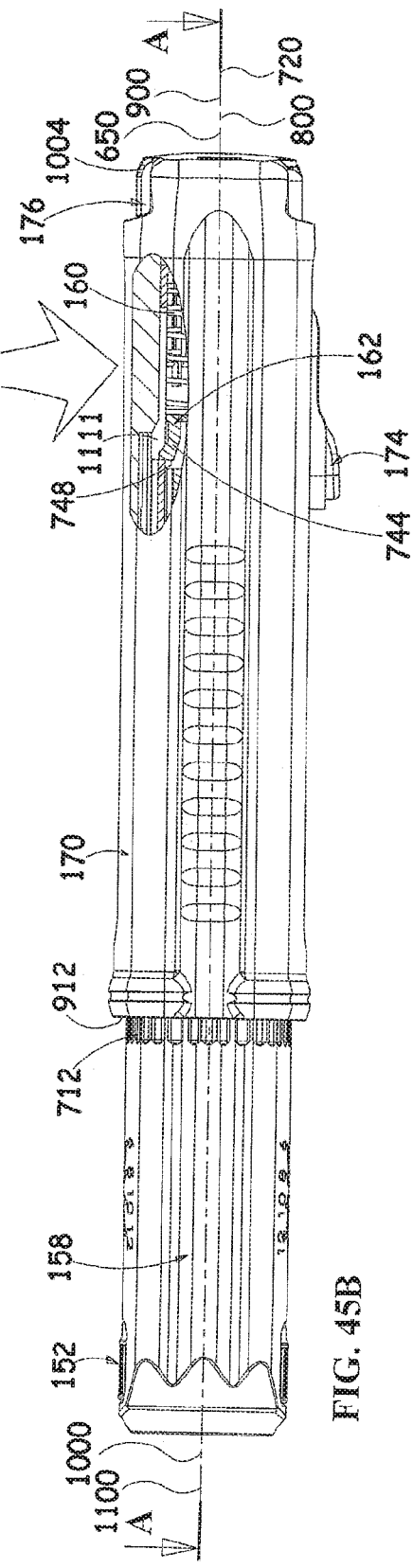
FIG. 45A
FIG. 45B

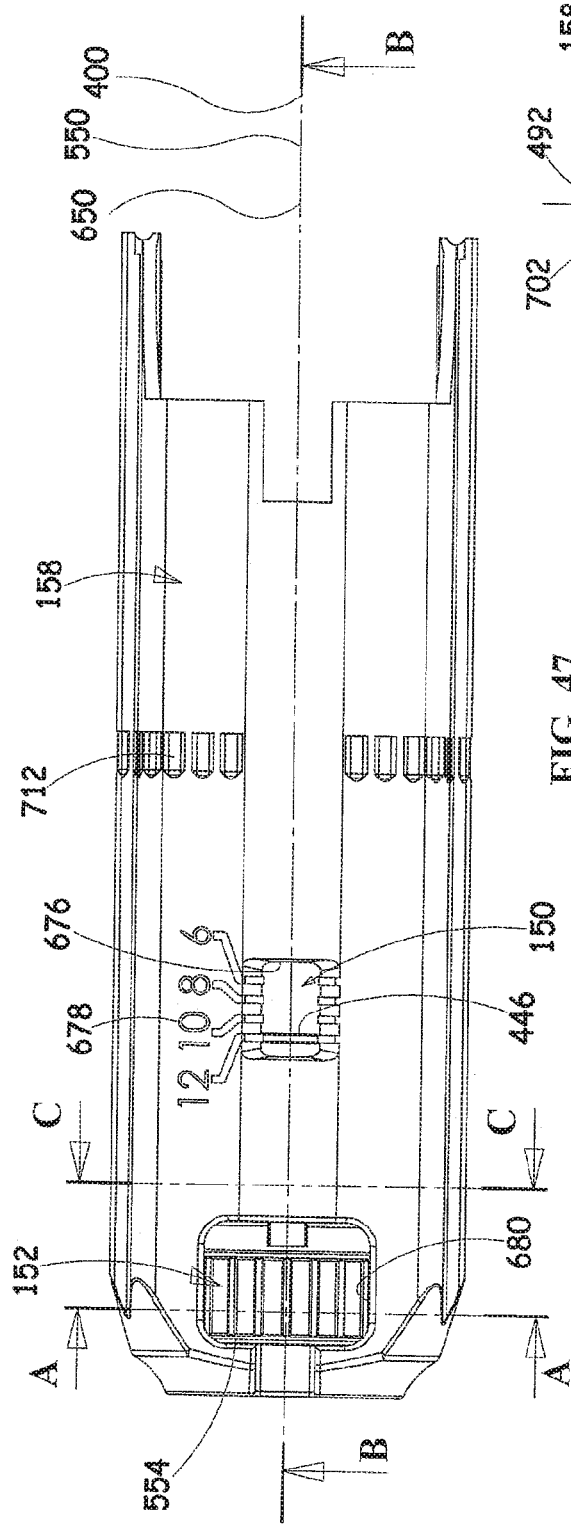
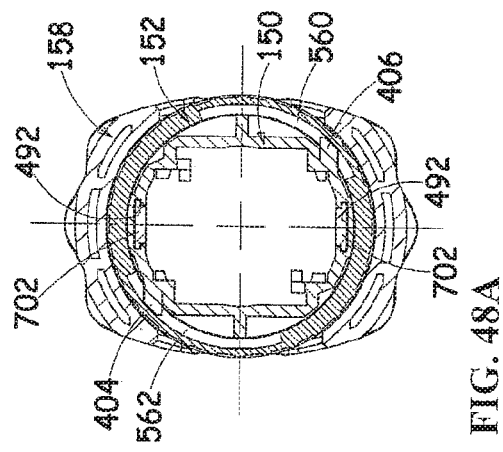
FIG. 47
FIG. 48A

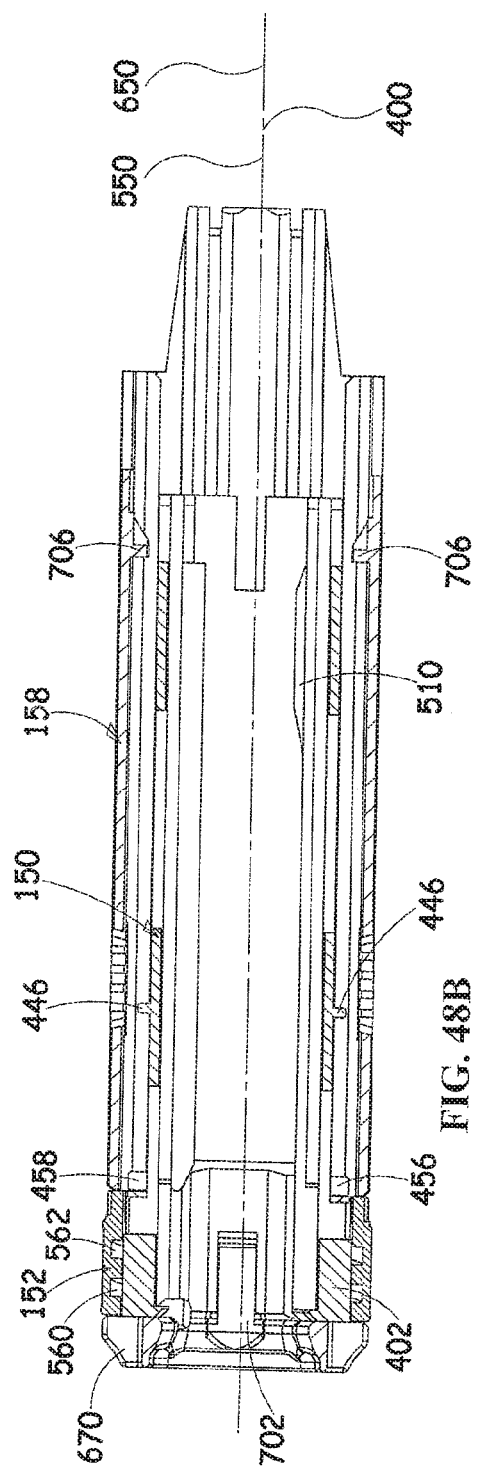

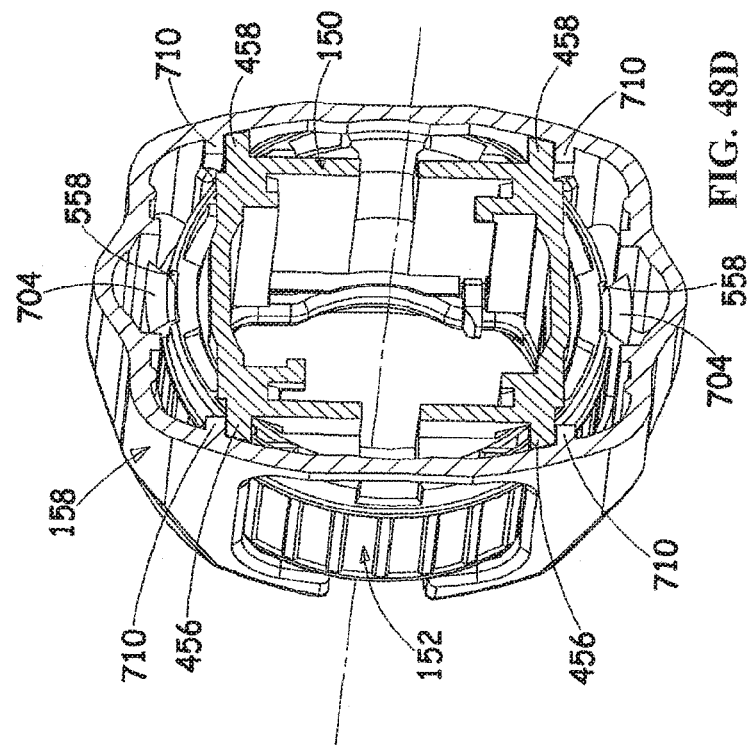
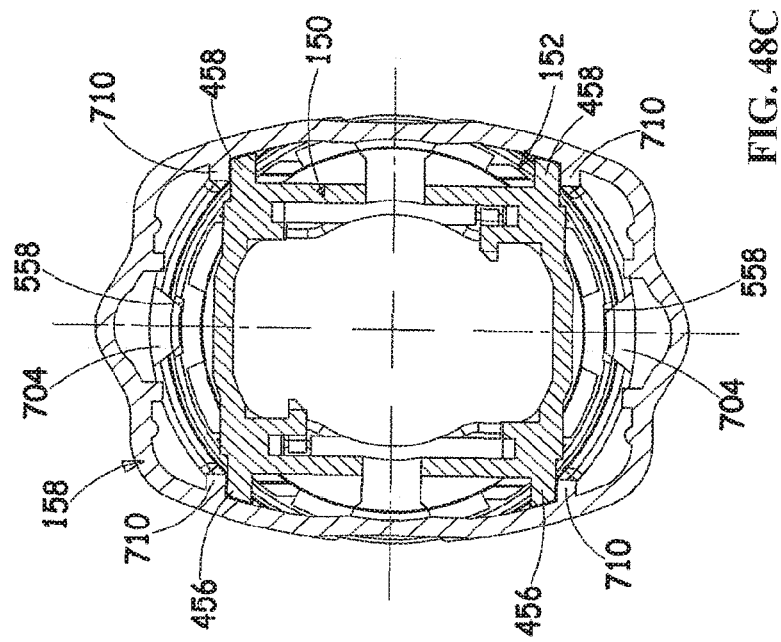
FIG. 48D
FIG. 48C

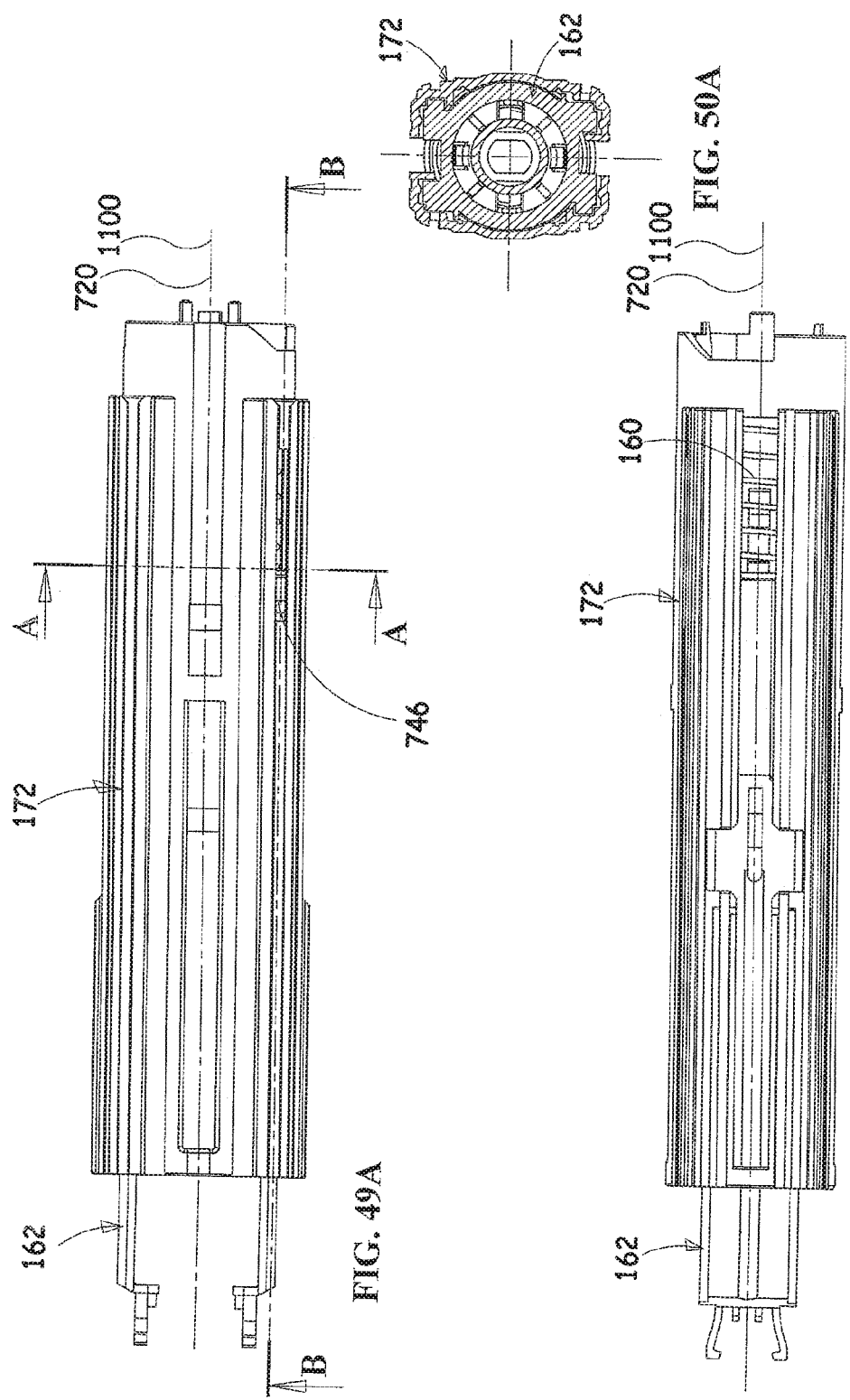

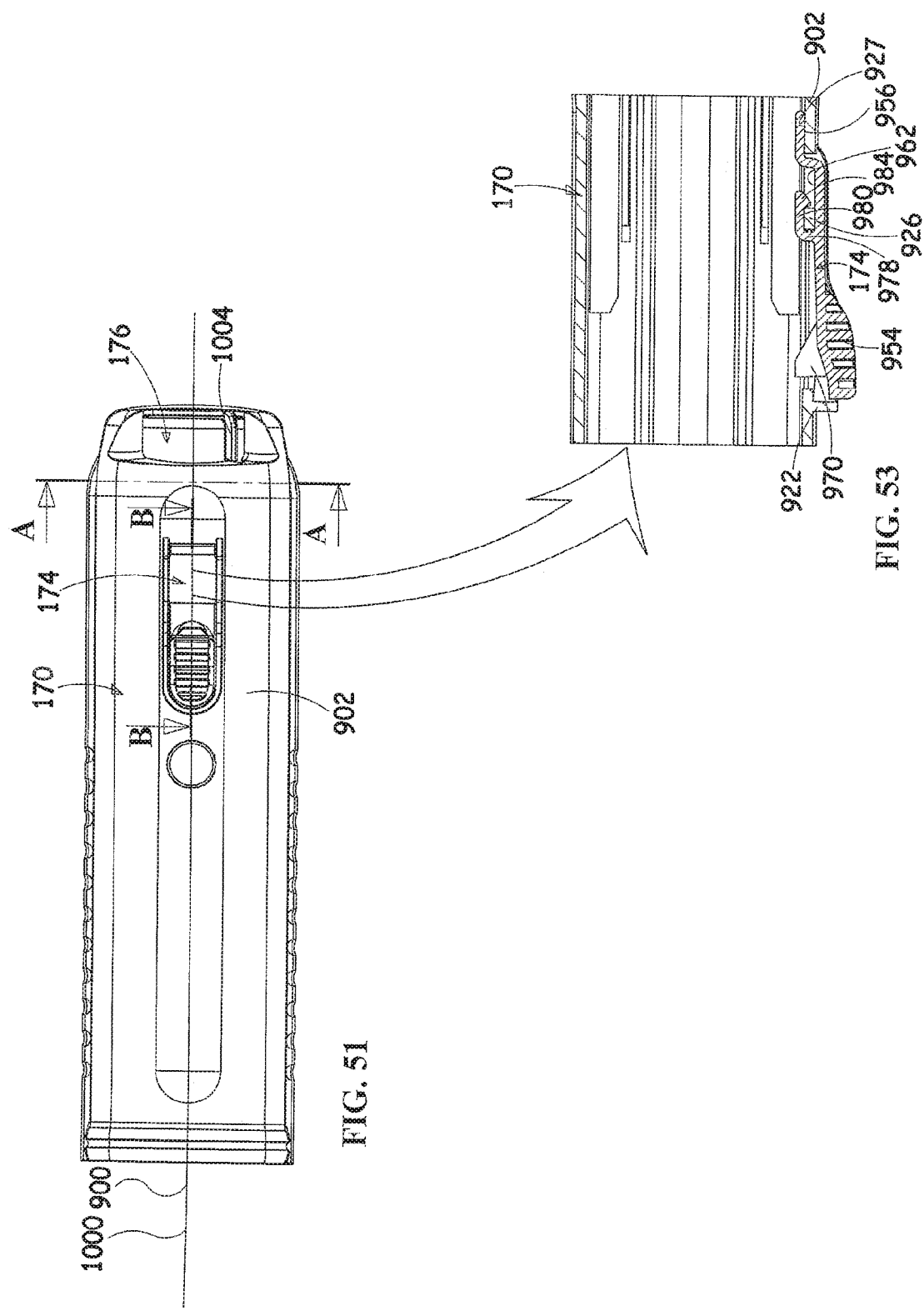

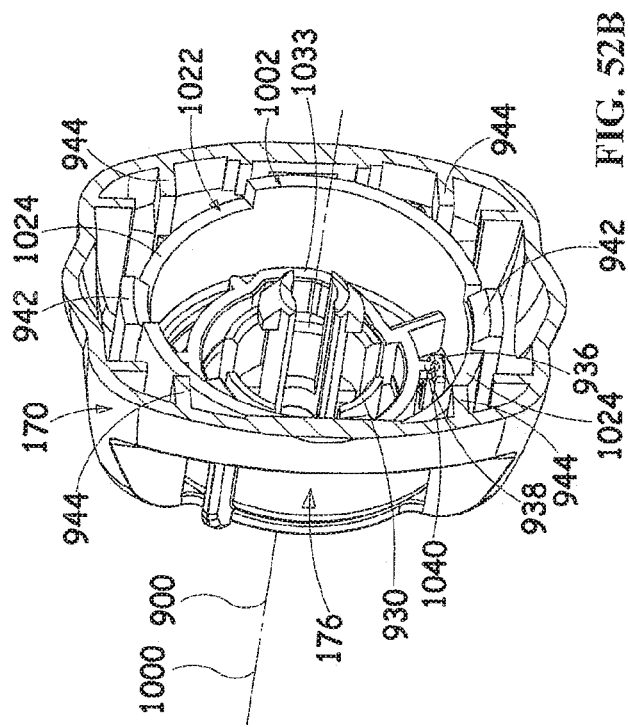
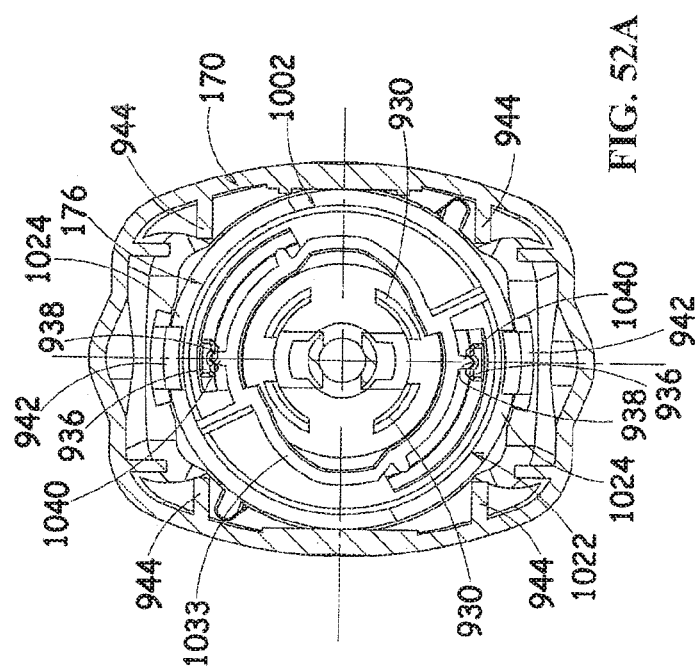
FIG. 52A
FIG. 52B

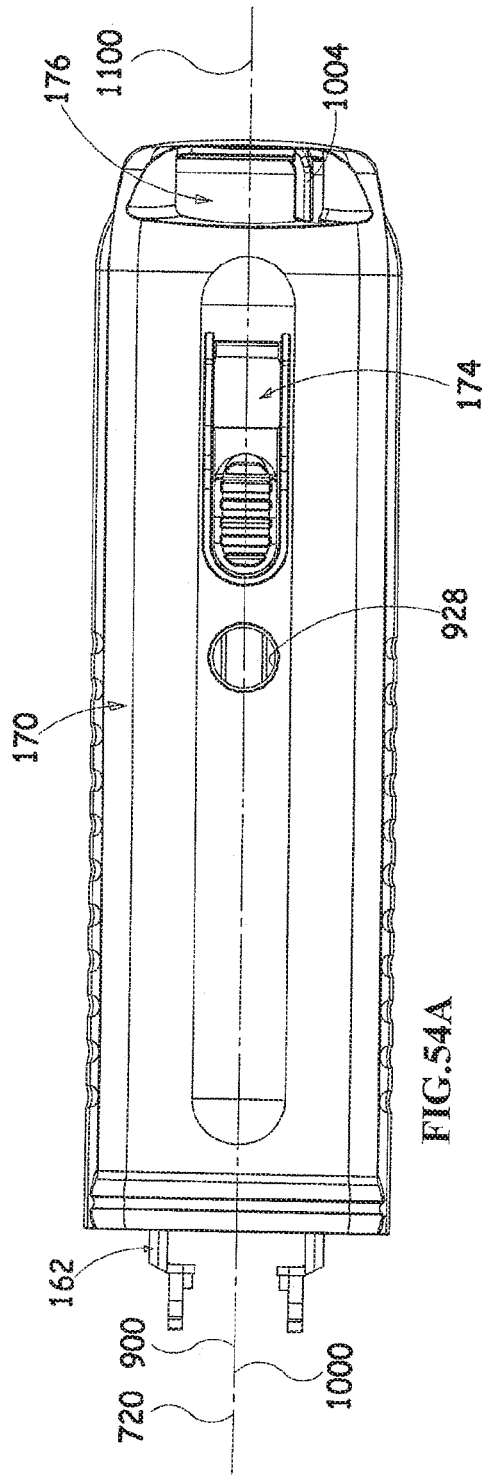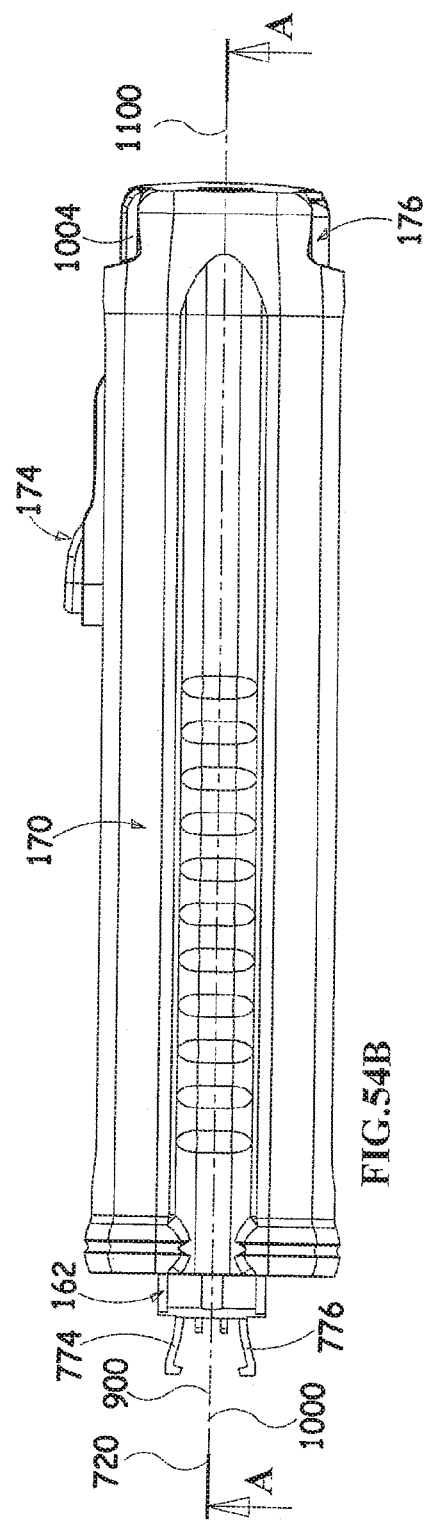
FIG.54A
FIG.54B

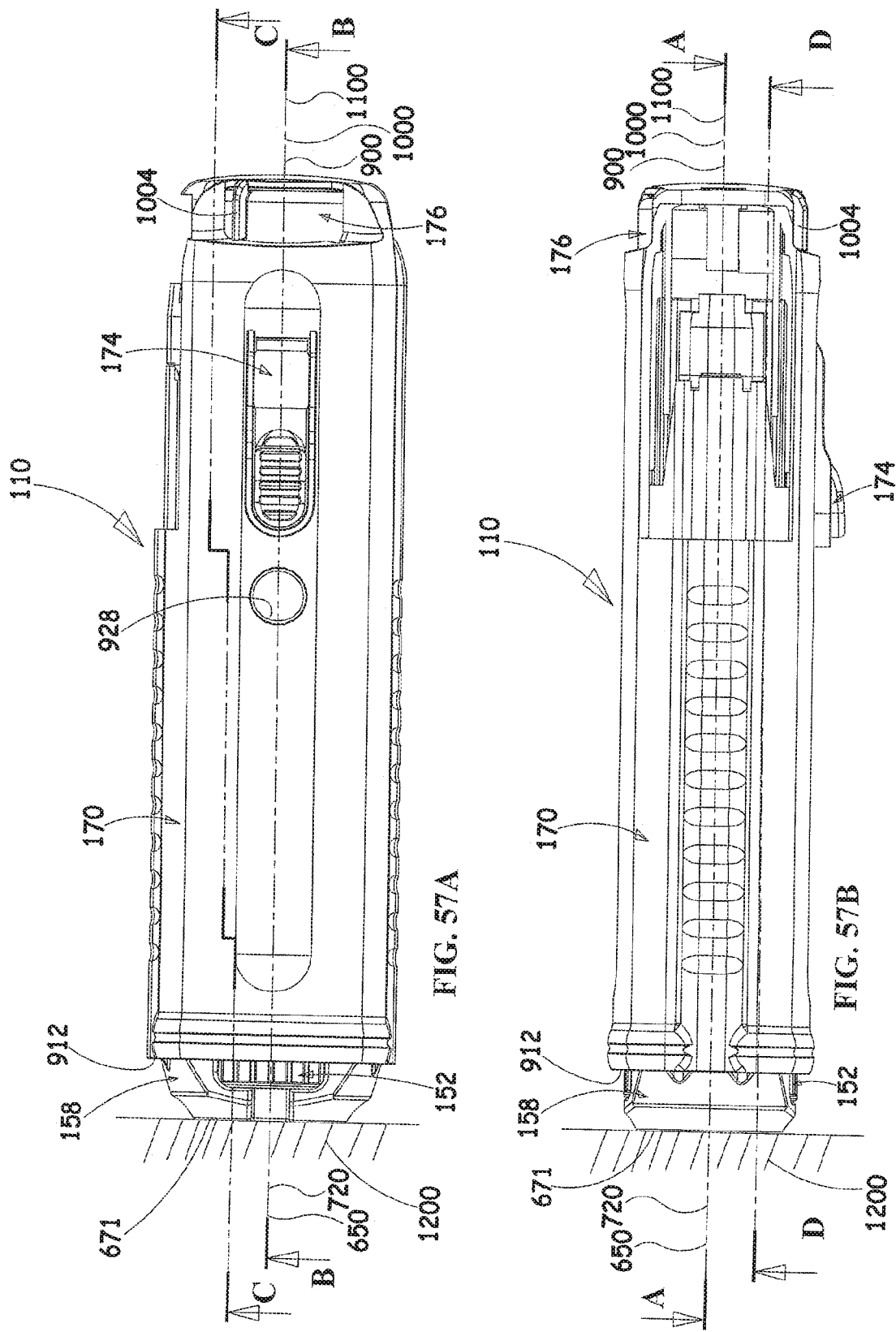

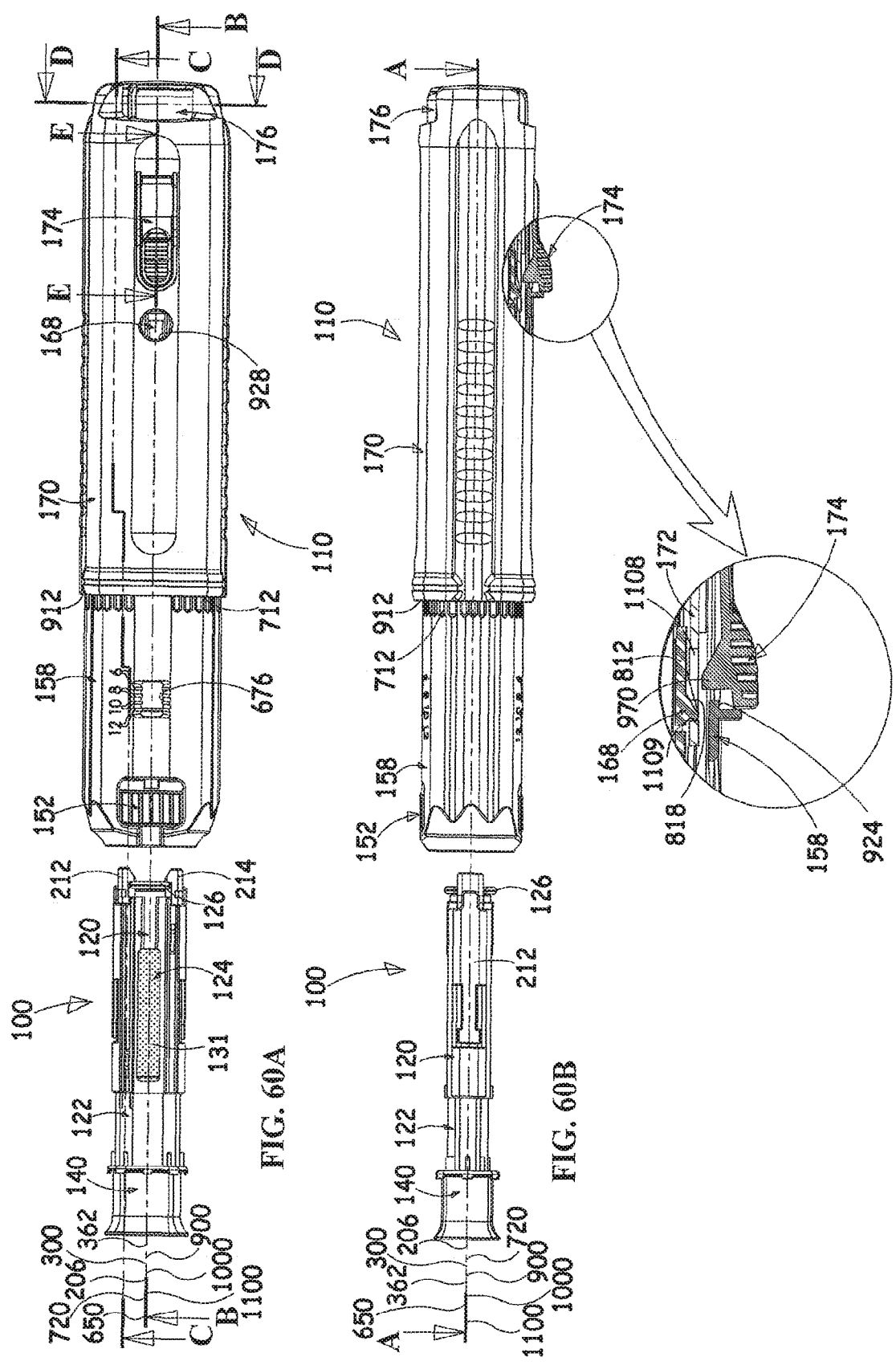

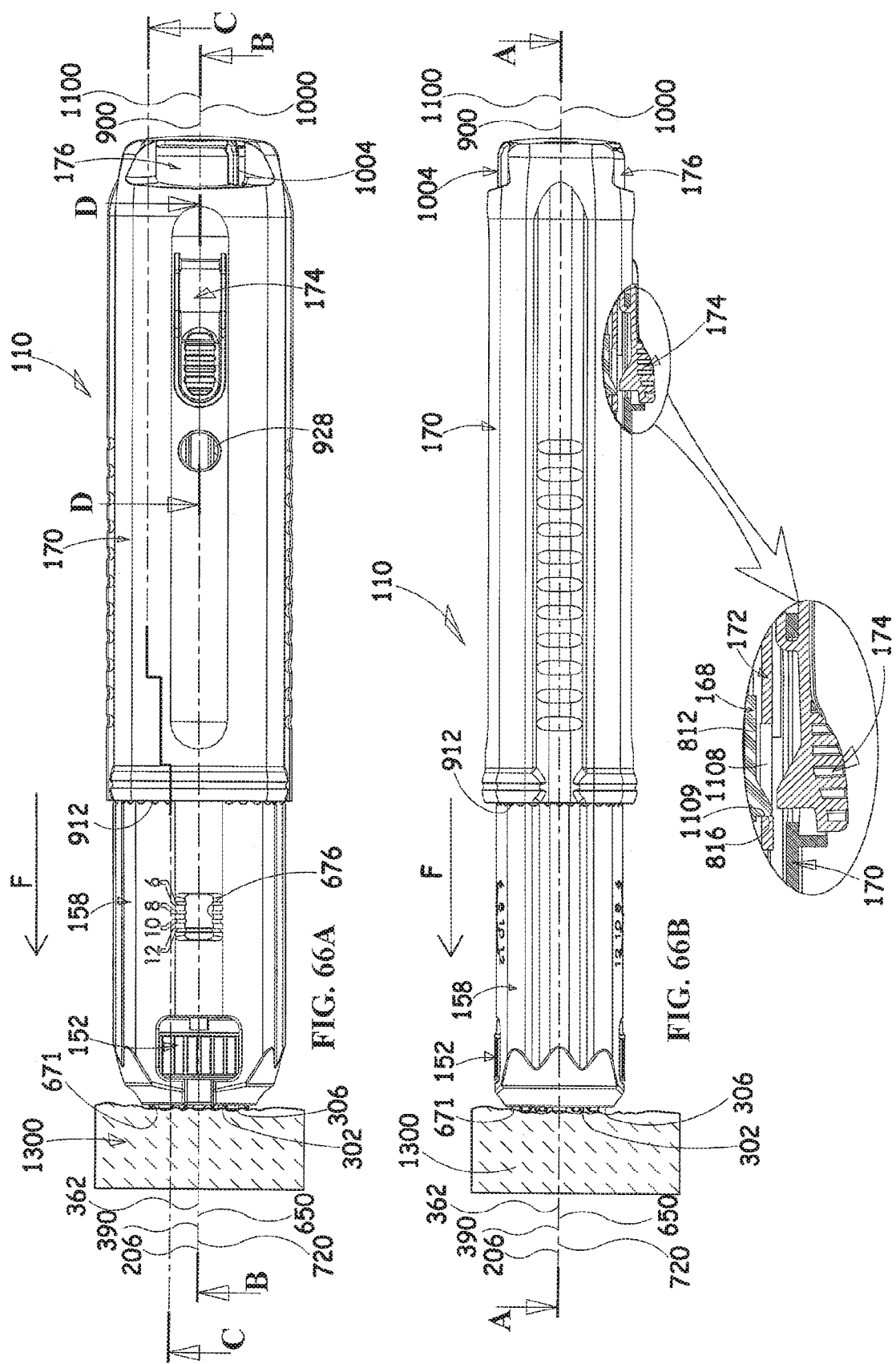

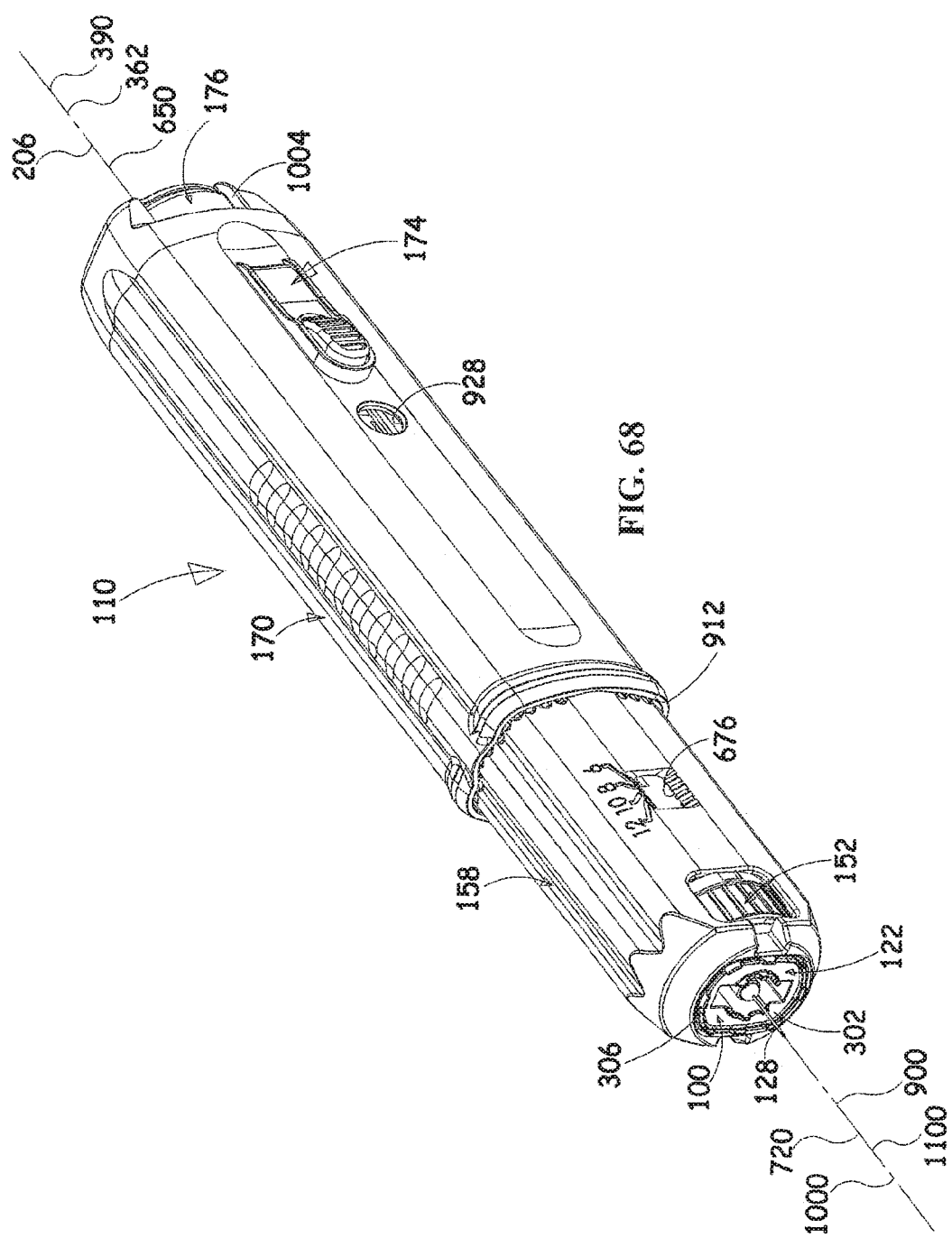

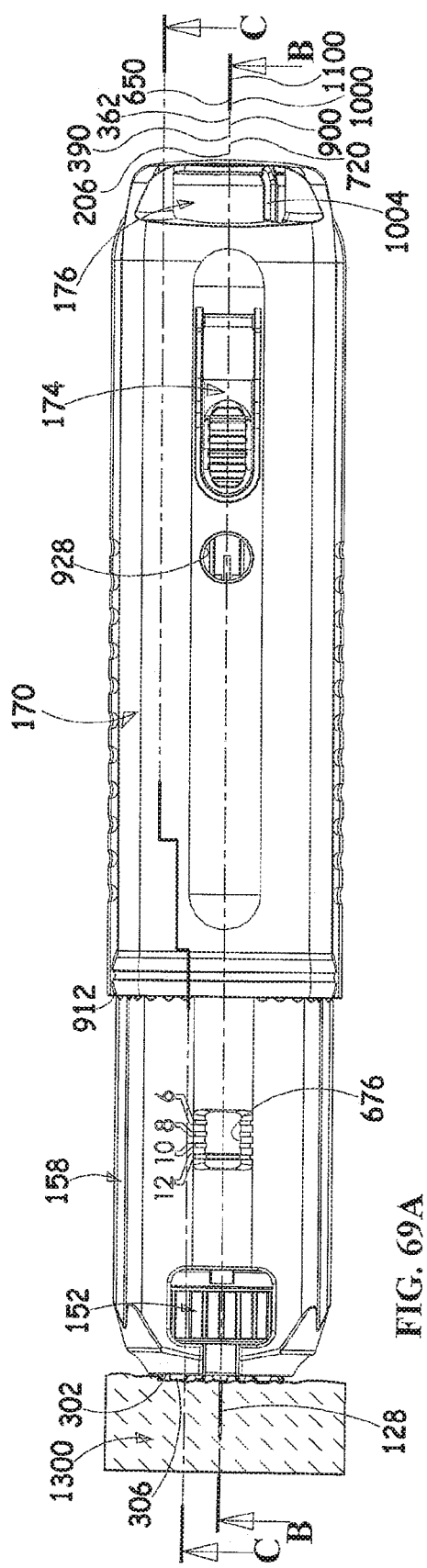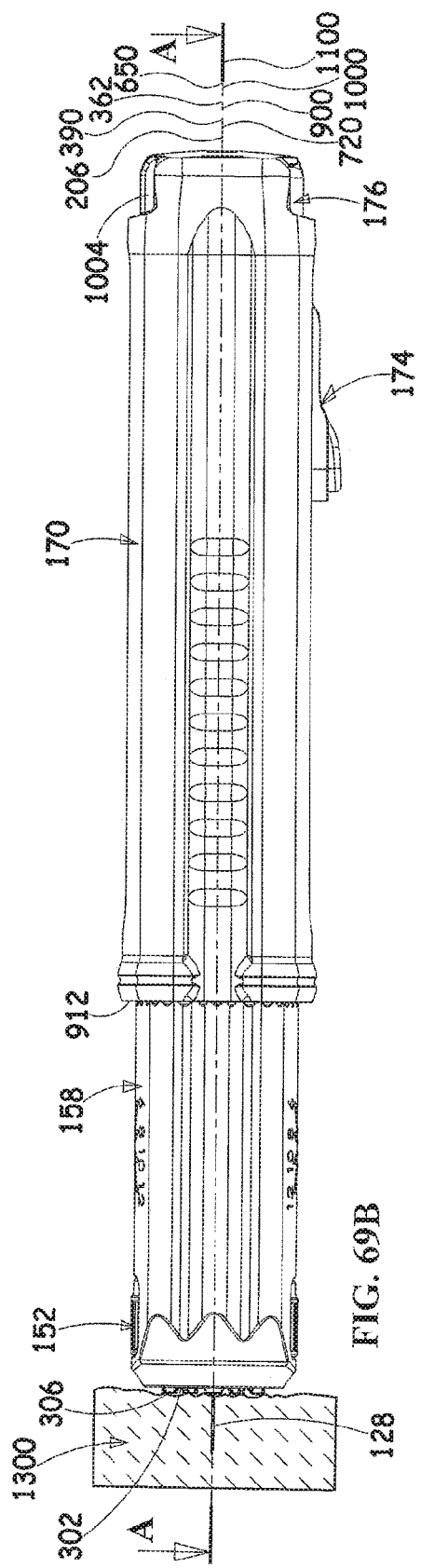
FIG. 69A
FIG. 69B

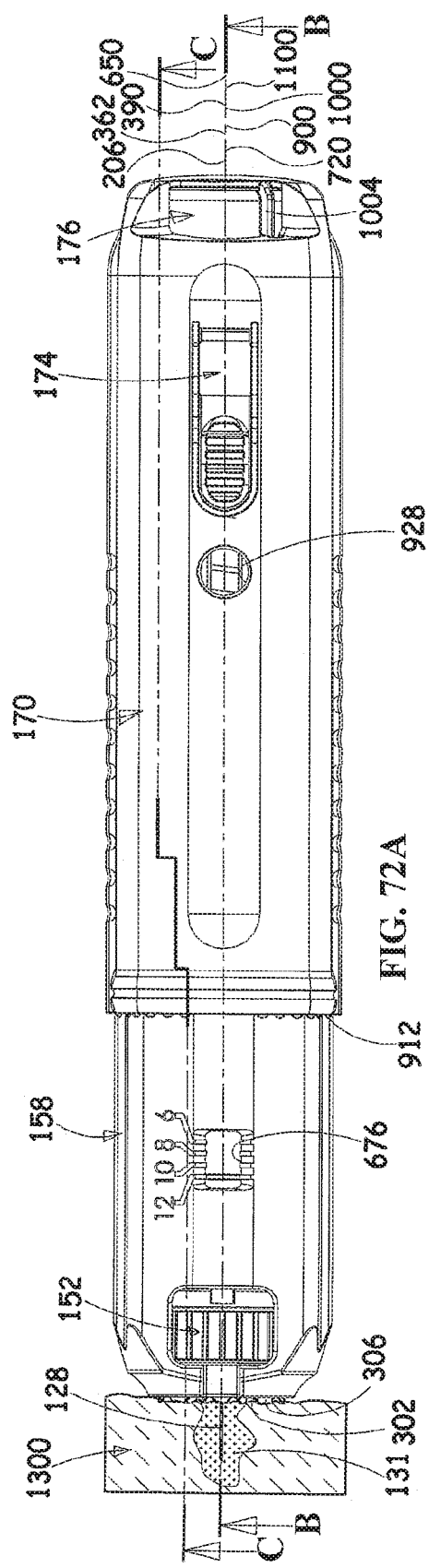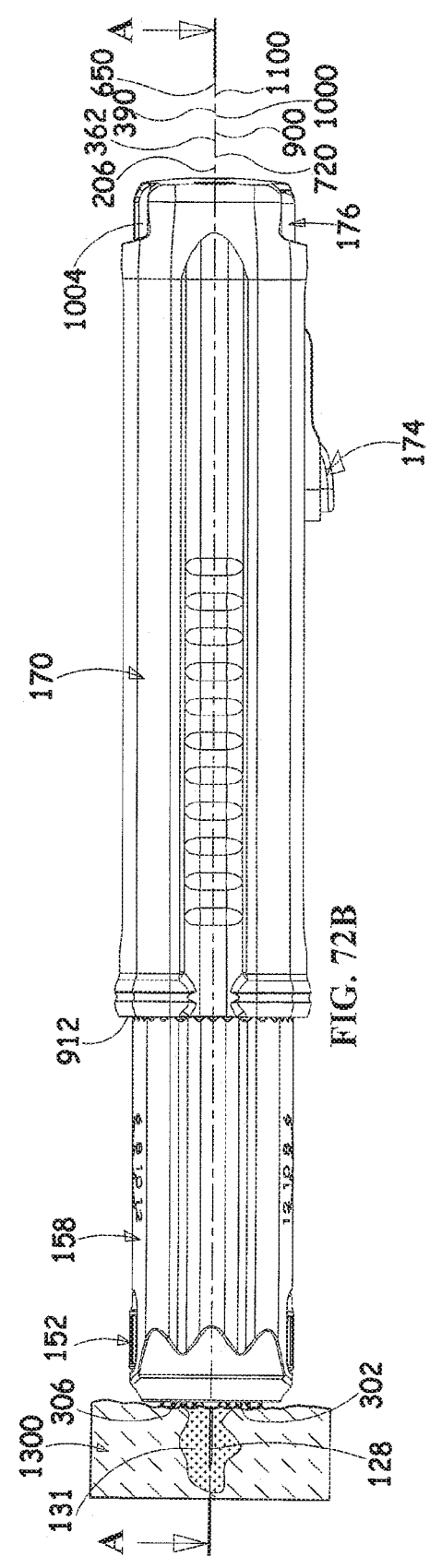
FIG. 72A
FIG. 72B

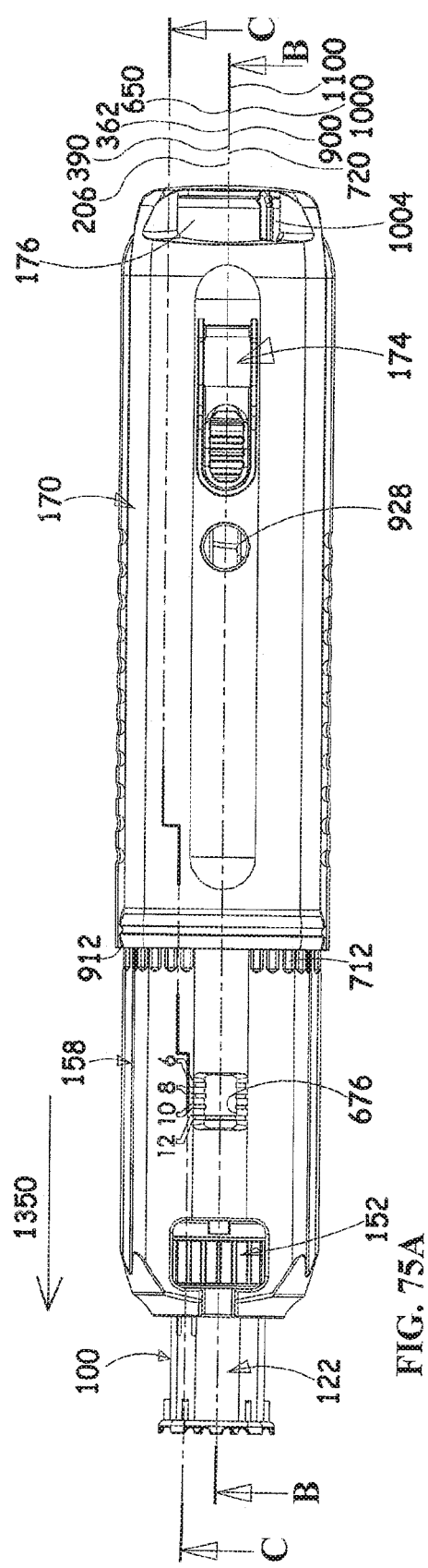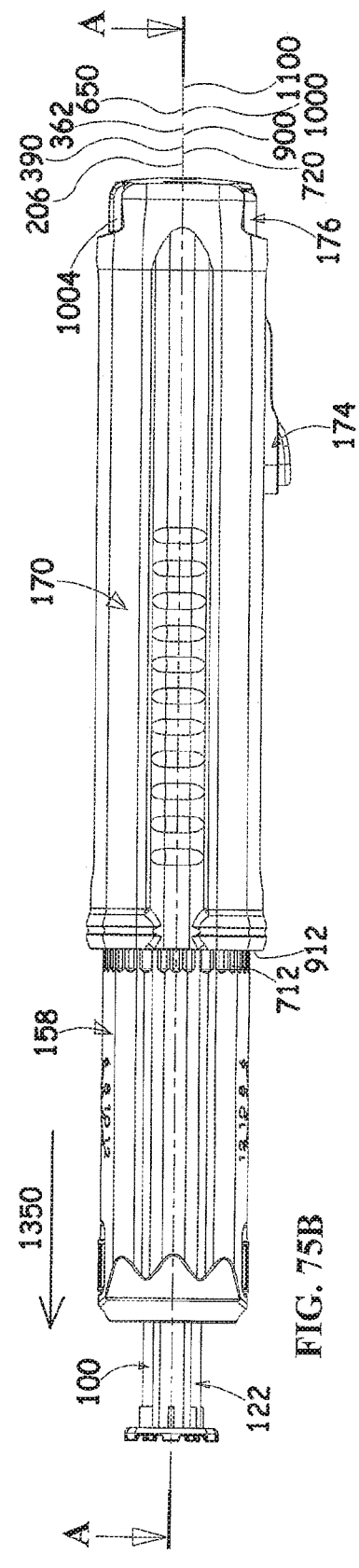

SEMI DISPOSABLE AUTO INJECTOR

REFERENCE TO RELATED APPLICATIONS

This application is a National Stage of International Application No. PCT/IL2015/050155 filed Feb. 10, 2015, claiming priority based on U.S. Provisional Patent Application No. 61/937,681, filed Feb. 10, 2014, the contents of all of which are incorporated herein by reference in their entirety.

FIELD OF THE INVENTION

The present invention generally relates to an auto injector, and more specifically to a semi disposable and safe auto-injector adapted for parenteral administration of substances (e.g., a medication) to a living organism (human or animal).

BACKGROUND OF THE INVENTION

As many as ten percent of patients may experience needle phobia, a condition recognized by the American Psychiatric Association, and may be hesitant to inject themselves (J. Hamilton, "Needle Phobia: a Neglected Diagnosis." Journal of Family Practice, 1995; 41:169-175).

Moreover, in the U.S., a recent law requires health care employers to implement "safer medical devices" to minimize needle sticks that could result in serious infections (such as HIV and Hepatitis) from viruses or bacteria in the blood. Interest in safety-needle protective devices is now increasing in all areas of healthcare. A particular drug may be used in various care settings.

SUMMARY OF THE INVENTION

The present invention seeks to provide a semi disposable auto injector.

There is thus provided in accordance with a preferred embodiment of the present invention an automatic injection device including a reusable driving assembly having a forward injection end and an engagement element and a disposable cassette assembly including an injectable liquid to be injected at an injection site, the disposable cassette assembly is removably insertable into the reusable driving assembly at the forward injection end and is removably retained within the reusable driving assembly by snap fit engagement therewith, the snap fit engagement being effected at least partially by the engagement element, which is displaced rearwardly by insertion of the disposable cassette assembly in the reusable driving assembly.

Preferably, the disposable cassette assembly includes a needle guard element having arms formed with notches, the engagement element is a needle guard deploying element, having fingers formed with inwardly directed protrusions, and the insertion of the disposable cassette assembly into the reusable driving assembly produces rearward displacement of the needle guard deploying element, thereby enabling engagement of the inwardly directed protrusions of the needle guard deploying element with the notches of the arms of the needle guard element.

Preferably, the reusable driving assembly also includes a needle guard deploying spring, the arms have rearward facing edges, the needle guard deploying element has a forward-facing surface and the rearward displacement of the needle guard deploying element causes engagement of the rearward facing edges of the arms of the needle guard element of the disposable cassette assembly with the forward facing surface of the needle guard deploying element, against the urging of the needle guard deploying spring.

Further preferably, the reusable driving assembly has at least cocked and uncocked operative orientations, the reusable driving assembly includes a safety catch element having engaged and disengaged operative orientations and the snap fit engagement occurs only when the reusable driving assembly is in the cocked operative orientation and when the safety catch element is in the engaged operative orientation.

In accordance with a preferred embodiment of the present invention the disposable cassette assembly includes a cassette housing element, a syringe including a needle, and a needle guard element. The cassette housing element, the syringe and the needle guard element being arranged such that prior to insertion of the disposable cassette assembly into the reusable driving assembly, the syringe is locked against axial displacement in a first direction relative to the cassette housing element by engagement with the cassette housing element and is locked against axial displacement in a second direction, opposite to the first direction, relative to the cassette housing element by engagement with the needle guard element.

Preferably, the syringe is a prefilled syringe.

In accordance with a preferred embodiment of the present invention the reusable driving assembly has a needle insertion operative orientation. The cassette housing element, the prefilled syringe and the needle guard element are arranged such that subsequent to insertion of the disposable cassette assembly into the reusable driving assembly but prior to the reusable driving assembly being in the needle insertion operative orientation, the prefilled syringe is locked by the cassette housing element and the needle guard element against axial displacement in either direction relative to the cassette housing element, but the syringe is not locked against axial displacement relative to the needle guard element at at least some other times.

Preferably, when the reusable driving assembly is in the needle insertion operative orientation, the syringe moves axially forwardly together with the cassette housing element relative to the needle guard element, thereby exposing the needle at the forward injection end of the reusable driving assembly.

Further preferably, the cassette housing element and the needle guard element are arranged such that prior to both the disposable cassette assembly having been inserted into the reusable driving assembly and the reusable driving assembly being in the needle insertion operative orientation, the relative axial displacement between the cassette housing element and the needle guard element is prevented.

In accordance with a preferred embodiment of the present invention the cassette housing element is arranged such that upon the reusable driving assembly being in a needle insertion operative orientation, resulting axial displacement of the syringe produces outward displacement of a portion of the cassette housing element into engagement with a forward base element of the reusable driving assembly, thereby limiting the penetration depth of the needle.

Preferably, the reusable driving assembly includes a forward injection end and multiple mutually axially displaceable elements, the needle is suitable for injecting an injectable liquid at an injection site, the disposable cassette assembly is removably insertable into the reusable driving assembly at the forward injection end and following insertion of the disposable cassette assembly into the reusable driving assembly, the automatic injection device may be caused to assume an injection site engagement operative orientation by pressing the forward injection end of the reusable driving assembly against the injection site, thereby producing mutual axial displacement of at least some of the multiple mutually axially displaceable elements but not producing relative axial displacement between the needle guard element and the cassette housing element of the disposable cassette assembly.

Further preferably, following insertion of the disposable cassette assembly into the reusable driving assembly, the automatic injection device may be caused to assume an injection site engagement operative orientation, following assumption of the pre-needle insertion operative orientation, the automatic injection device may be caused to assume a needle insertion operative orientation by pressing the trigger button element, thereby causing forward axial displacement of the cassette housing element and resulting penetration of the injection site by the needle to a penetration depth defined by engagement of the cassette housing element with the forward base element of the reusable driving assembly.

In accordance with a preferred embodiment of the present invention following injection the disposable cassette assembly extends partially outside of the reusable driving assembly at the forward injection end and is releasably retained in the reusable driving assembly and the disposable cassette assembly may thereafter be fully disengaged from the reusable driving assembly by axially pulling the disposable cassette assembly out of the reusable driving assembly.

Preferably, only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

Further preferably, the reusable driving assembly includes a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation.

In accordance with a preferred embodiment of the present invention the forward cover element and the rearward cover element move towards each other in assuming the cocked operative orientation and when in the cocked operative orientation are locked against mutual axial displacement.

Preferably, the disposable cassette assembly includes a cassette housing element, a prefilled syringe including a needle for injecting an injectable liquid at an injection site and a needle guard element, and following injection and removal of the needle from the injection site, assumption of the cocked operative orientation is possible thereafter only following forward displacement of the needle guard element relative to the needle.

Still preferably, the reusable driving assembly includes a forward injection end, a safety catch element and a trigger button element, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, the disposable cassette assembly is inserted and retained in the reusable driving assembly, and the safety catch element is in a disengaged operative orientation.

Yet preferably, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation; and thereafter the disposable cassette assembly is fully inserted and retained in the reusable driving assembly, and thereafter the safety catch element is in a disengaged operative orientation.

There is also provided in accordance with another preferred embodiment of the present invention, a disposable cassette assembly for use with a reusable driving assembly in an automatic injection device, the disposable cassette assembly including a cassette housing element, a syringe including a needle and a needle guard element. The cassette housing element, the syringe and the needle guard element being arranged such that prior to insertion of the disposable cassette assembly into the reusable driving assembly, the syringe is locked against axial displacement in a first direction relative to the cassette housing element by engagement with the cassette housing element and is locked against axial displacement in a second direction, opposite to the first direction, relative to the cassette housing element by engagement with the needle guard element.

Preferably, the syringe is a prefilled syringe.

Further preferably, the reusable driving assembly has a needle insertion operative orientation. The cassette housing element, the prefilled syringe and the needle guard element are arranged such that subsequent to insertion of the disposable cassette assembly into the reusable driving assembly but prior to the reusable driving assembly being in the needle insertion operative orientation, the prefilled syringe is locked by the cassette housing element and the needle guard element against axial displacement in either direction relative to the cassette housing element, but the syringe is not locked against axial displacement relative to the needle guard element at at least some other times.

In accordance with a preferred embodiment of the present invention the cassette housing element and the needle guard element are arranged such that prior to both the disposable cassette assembly having been inserted into the reusable driving assembly and the reusable driving assembly being in the needle insertion operative orientation, the relative axial displacement between the cassette housing element and the needle guard element is prevented.

Preferably, the disposable cassette has a pre-use operative orientation, which is suitable for storage thereof and in the pre-use operative orientation, the needle guard element is locked to the cassette housing element by snap fit engagement of protrusions of the needle guard element in slots formed in the cassette housing element.

There is further provided in accordance with yet another preferred embodiment of the present invention a reusable driving assembly having a needle insertion operative orientation and a disposable cassette assembly including a cassette housing element, a prefilled syringe including a needle and a needle guard element. The cassette housing element and the needle guard element being arranged such that prior to both the disposable cassette assembly having been inserted into the reusable driving assembly and the reusable driving assembly being in the needle insertion operative orientation, the relative axial displacement between the cassette housing element and the needle guard element is prevented.

Preferably, the arrangement of the cassette housing element and the needle guard element is such that the relative axial displacement between the cassette housing element and the needle guard element is prevented by first and second engagements, the first engagement being released upon insertion of the disposable cassette assembly into the reusable driving assembly and the second engagement being released when the reusable driving assembly is in the needle insertion operative orientation.

Still preferably, the first engagement is provided by mutual engagement of at least one first protrusion of the needle guard element with at least one first slot of the cassette housing element and the second engagement is provided by mutual engagement of at least one second protrusion of the needle guard element with at least one second slot of the cassette housing element.

Yet preferably, the disposable cassette has a pre-use operative orientation, which is suitable for storage. In the pre-use operative orientation, the needle guard element is locked to the cassette housing element by snap fit engagement of at least one protrusion of the needle guard element in at least one slot formed in the cassette housing element.

In accordance with a preferred embodiment of the present invention the cassette housing element is arranged such that upon the reusable driving assembly being in the needle insertion operative orientation, resulting axial displacement of the syringe produces outward displacement of a portion of the cassette housing element into engagement with a forward base element of the reusable driving assembly, thereby limiting the penetration depth of the needle.

Preferably, the axial position of the forward base element of the reusable driving assembly is adjustable.

Further preferably, the reusable driving assembly includes a forward injection end and multiple mutually axially displaceable elements, the needle is suitable for injecting an injectable liquid at an injection site, the disposable cassette assembly is removably insertable into the reusable driving assembly at the forward injection end and following insertion of the disposable cassette assembly into the reusable driving assembly, the automatic injection device may be caused to assume an injection site engagement operative orientation by pressing the forward injection end of the reusable driving assembly against the injection site, thereby producing mutual axial displacement of at least some of the multiple mutually axially displaceable elements but not producing relative axial displacement between the needle guard element and the cassette housing element of the disposable cassette assembly.

Still preferably, following insertion of the disposable cassette assembly into the reusable driving assembly, the automatic injection device may be caused to assume an injection site engagement operative orientation. Following assumption of the pre-needle insertion operative orientation, the automatic injection device may be caused to assume a needle insertion operative orientation by pressing the trigger button element, thereby causing forward axial displacement of the cassette housing element and resulting penetration of the injection site by the needle to a penetration depth defined by engagement of the cassette housing element with the forward base element of the reusable driving assembly.

In accordance with a preferred embodiment of the present invention following injection the disposable cassette assembly extends partially outside of the reusable driving assembly at the forward injection end and is releasably retained in the reusable driving assembly and the disposable cassette assembly may thereafter be fully disengaged from the reusable driving assembly by axially pulling the disposable cassette assembly out of the reusable driving assembly.

Preferably, wherein only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

Further preferably, the reusable driving assembly includes a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation.

Still preferably, the forward cover element and the rearward cover element move towards each other in assuming the cocked operative orientation and when in the cocked operative orientation are locked against mutual axial displacement.

Yet preferably, the disposable cassette assembly includes a cassette housing element, a prefilled syringe including a needle for injecting an injectable liquid at an injection site and a needle guard element, and following injection and removal of the needle from the injection site, assumption of the cocked operative orientation is possible thereafter only following forward displacement of the needle guard element relative to the needle.

In accordance with a preferred embodiment of the present invention the reusable driving assembly includes a forward injection end, a safety catch element and a trigger button element. The automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, the disposable cassette assembly is inserted and retained in the reusable driving assembly, and the safety catch element is in a disengaged operative orientation.

Preferably, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, and thereafter the disposable cassette assembly is fully inserted and retained in the reusable driving assembly, and thereafter the safety catch element is in a disengaged operative orientation.

There is even further provided in accordance with still another preferred embodiment of the present invention an automatic injection device including a reusable driving assembly having a needle insertion operative orientation and having a forward base element and a disposable cassette assembly including a cassette housing element, a syringe including a needle and a needle guard element. The cassette housing element being arranged such that upon the reusable driving assembly being in the needle insertion operative orientation, resulting axial displacement of the syringe produces outward displacement of a portion of the cassette housing element into engagement with the forward base element of the reusable driving assembly, thereby limiting the penetration depth of the needle.

Preferably, the axial position of the forward base element of the reusable driving assembly is adjustable.

Further preferably, the reusable driving assembly includes a forward injection end and multiple mutually axially displaceable elements, the needle is suitable for injecting an injectable liquid at an injection site, the disposable cassette assembly is removably insertable into the reusable driving assembly at the forward injection end and following insertion of the disposable cassette assembly into the reusable driving assembly, the automatic injection device may be caused to assume an injection site engagement operative orientation by pressing the forward injection end of the reusable driving assembly against the injection site, thereby producing mutual axial displacement of at least some of the multiple mutually axially displaceable elements but not producing relative axial displacement between the needle guard element and the cassette housing element of the disposable cassette assembly.

Still preferably, following insertion of the disposable cassette assembly into the reusable driving assembly, the automatic injection device may be caused to assume an injection site engagement operative orientation. Following assumption of the pre-needle insertion operative orientation, the automatic injection device may be caused to assume a needle insertion operative orientation by pressing the trigger button element, thereby causing forward axial displacement of the cassette housing element and resulting penetration of the injection site by the needle to a penetration depth defined by engagement of the cassette housing element with the forward base element of the reusable driving assembly.

In accordance with a preferred embodiment of the present invention following injection the disposable cassette assembly extends partially outside of the reusable driving assembly at the forward injection end and is releasably retained in the reusable driving assembly and the disposable cassette assembly may thereafter be fully disengaged from the reusable driving assembly by axially pulling the disposable cassette assembly out of the reusable driving assembly.

Preferably, only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

Further preferably, the reusable driving assembly includes a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation.

In accordance with a preferred embodiment of the present invention the forward cover element and the rearward cover element move towards each other in assuming the cocked operative orientation and when in the cocked operative orientation are locked against mutual axial displacement.

Preferably, the disposable cassette assembly includes a cassette housing element, a prefilled syringe including a needle for injecting an injectable liquid at an injection site and a needle guard element and following injection and removal of the needle from the injection site, assumption of the cocked operative orientation is possible thereafter only following forward displacement of the needle guard element relative to the needle.

Further preferably, the reusable driving assembly includes a forward injection end, a safety catch element and a trigger button element, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, the disposable cassette assembly is inserted and retained in the reusable driving assembly, and the safety catch element is in a disengaged operative orientation.

Still preferably, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation and thereafter the disposable cassette assembly is fully inserted and retained in the reusable driving assembly, and thereafter the safety catch element is in a disengaged operative orientation.

There is even further provided in accordance with still another preferred embodiment of the present invention an automatic injection device including a reusable driving assembly having a forward injection end and multiple mutually axially displaceable elements and a disposable cassette assembly including a cassette housing element, a prefilled syringe including a needle for injecting an injectable liquid at an injection site and a needle guard element. The disposable cassette assembly is removably insertable into the reusable driving assembly at the forward injection end, following insertion of the disposable cassette assembly into the reusable driving assembly, the automatic injection device may be caused to assume an injection site engagement operative orientation by pressing the forward injection end of the reusable driving assembly against the injection site, thereby producing mutual axial displacement of at least some of the multiple mutually axially displaceable elements but not producing relative axial displacement between the needle guard element and the cassette housing element of the disposable cassette assembly.

Preferably, following insertion of the disposable cassette assembly into the reusable driving assembly, the automatic injection device may be caused to assume an injection site engagement operative orientation. Following assumption of the pre-needle insertion operative orientation, the automatic injection device may be caused to assume a needle insertion operative orientation by pressing the trigger button element, thereby causing forward axial displacement of the cassette housing element and resulting penetration of the injection site by the needle to a penetration depth defined by engagement of the cassette housing element with the forward base element of the reusable driving assembly.

Further preferably, following injection the disposable cassette assembly extends partially outside of the reusable driving assembly at the forward injection end and is releasably retained in the reusable driving assembly and the disposable cassette assembly may thereafter be fully disengaged from the reusable driving assembly by axially pulling the disposable cassette assembly out of the reusable driving assembly.

Still preferably, only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

In accordance with a preferred embodiment of the present invention the reusable driving assembly includes a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation.

Preferably, the forward cover element and the rearward cover element move towards each other in assuming the cocked operative orientation and when in the cocked operative orientation are locked against mutual axial displacement.

Further preferably, the disposable cassette assembly includes a cassette housing element, a prefilled syringe including a needle for injecting an injectable liquid at an injection site and a needle guard element, and following injection and removal of the needle from the injection site, assumption of the cocked operative orientation is possible thereafter only following forward displacement of the needle guard element relative to the needle.

In accordance with a preferred embodiment of the present invention the reusable driving assembly includes a forward injection end, a safety catch element and a trigger button element. The automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, the disposable cassette assembly is inserted and retained in the reusable driving assembly, and the safety catch element is in a disengaged operative orientation.

Preferably, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation and thereafter the disposable cassette assembly is fully inserted and retained in the reusable driving assembly, and thereafter the safety catch element is in a disengaged operative orientation.

There is also provided in accordance with yet another preferred embodiment of the present invention an automatic injection device including a reusable driving assembly having a forward injection end, a forward base element, and a trigger button element and a disposable cassette assembly including a cassette housing element, a syringe including a needle for injecting an injectable liquid at an injection site and a needle guard element. The disposable cassette assembly is removably insertable into the reusable driving assembly at the forward injection end. Following insertion of the disposable cassette assembly into the reusable driving assembly, the automatic injection device may be caused to assume an injection site engagement operative orientation and following assumption of the pre-needle insertion operative orientation, the automatic injection device may be caused to assume a needle insertion operative orientation by pressing the trigger button element, thereby causing forward axial displacement of the cassette housing element and resulting penetration of the injection site by the needle to a penetration depth defined by engagement of the cassette housing element with the forward base element of the reusable driving assembly.

Preferably, following injection the disposable cassette assembly extends partially outside of the reusable driving assembly at the forward injection end and is releasably retained in the reusable driving assembly and the disposable cassette assembly may thereafter be fully disengaged from the reusable driving assembly by axially pulling the disposable cassette assembly out of the reusable driving assembly.

Further preferably, only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

In accordance with a preferred embodiment of the present invention the reusable driving assembly includes a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation.

Preferably, the forward cover element and the rearward cover element move towards each other in assuming the cocked operative orientation and when in the cocked operative orientation are locked against mutual axial displacement.

Further preferably, the disposable cassette assembly includes a cassette housing element, a prefilled syringe including a needle for injecting an injectable liquid at an injection site and a needle guard element, and following injection and removal of the needle from the injection site, assumption of the cocked operative orientation is possible thereafter only following forward displacement of the needle guard element relative to the needle.

Still preferably, the reusable driving assembly includes a forward injection end, a safety catch element and a trigger button element and the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, the disposable cassette assembly is inserted and retained in the reusable driving assembly, and the safety catch element is in a disengaged operative orientation.

Yet further preferably, the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation and thereafter the disposable cassette assembly is fully inserted and retained in the reusable driving assembly, and thereafter the safety catch element is in a disengaged operative orientation.

There is still further provided in accordance with a further preferred embodiment of the present invention an automatic injection device including a reusable driving assembly having a forward injection end, and a disposable cassette assembly. The disposable cassette assembly is removably insertable into the reusable driving assembly at the forward injection end, following injection, the disposable cassette assembly extends partially outside of the reusable driving assembly at the forward injection end and is releasably retained in the reusable driving assembly and the disposable cassette assembly may thereafter be fully disengaged from the reusable driving assembly by axially pulling the disposable cassette assembly out of the reusable driving assembly.

Preferably, only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

Further preferably, the reusable driving assembly includes a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation.

There is yet further provided in accordance with a still further preferred embodiment of the present invention an automatic injection device including a reusable driving assembly having a forward injection end and a trigger button element and a disposable cassette assembly. The disposable cassette assembly is removably insertable and retainable into the reusable driving assembly at the forward injection end and only following insertion and retention of the disposable cassette assembly in the reusable driving assembly, the automatic injection device may be caused to assume a needle insertion operative orientation by pressing the trigger button element, thereby causing forward axial displacement of the cassette housing element and resulting penetration of the injection site by the needle.

There is still further provided in accordance with a yet further preferred embodiment of the present invention an automatic injection device including a reusable driving assembly including a plunger element, a forward cover element and a rearward cover element, a spring and at least one cocked orientation retaining element operative in a cocked operative orientation of the reusable driving assembly for cocking the plunger element against the urging of the spring and retaining the plunger element in the cocked operative orientation and a disposable cassette assembly which is removably insertable in the reusable driving assembly and includes a needle.

There is yet further provided in accordance with a still further preferred embodiment of the present invention an automatic injection device including a reusable driving assembly including a plunger element, a rearward cover element, a forward cover element, a spring which applies an axial force to said rearward cover element and the forward cover element and at least one cocked orientation retaining element operative in a cocked operative orientation of the reusable driving assembly for cocking the plunger element against the urging of the spring and retaining the plunger element in the cocked operative orientation and a safety-catch element having engaged and disengaged operative orientations and a disposable cassette assembly which is removably insertable in the reusable driving assembly only when the reusable driving assembly is in the cocked operative orientation and the safety catch element is in said engaged operative orientation.

There is still further provided in accordance with a yet further preferred embodiment of the present invention an automatic injection device including a reusable driving assembly having a forward injection end, a safety catch element and a trigger button element and a disposable cassette assembly. The disposable cassette assembly is removably insertable and retainable into the reusable driving assembly at the forward injection end and the automatic injection device may be caused to assume a needle insertion operative orientation by pressing the trigger button element, thereby causing forward axial displacement of the cassette housing element and resulting penetration of the injection site by the needle, only when all of the following conditions are met: the reusable driving assembly is in a cocked operative orientation, the disposable cassette assembly is inserted and retained in the reusable driving assembly, and the safety catch element is in a disengaged operative orientation.

BRIEF DESCRIPTION OF THE DRAWINGS

The present invention will be understood and appreciated more fully from the following detailed description, taken in conjunction with the drawings in which:

FIG. 3 is a front view simplified planar illustration of the cassette housing element of FIG. 2;

FIGS. 4A & 4B are two different side view simplified planar illustrations of the cassette housing element of FIG. 2;

FIGS. 4C & 4D are sectional illustrations of the cassette housing element taken along respective section lines C-C and D-D in FIG. 3;

FIG. 6 is a front view simplified planar illustration of the needle guard element of FIG. 5;

FIGS. 7A & 7B are two different side view simplified planar illustrations of the needle guard element of FIG. 5;

FIGS. 7C-7E are sectional illustrations of the needle guard element taken along respective section lines C-C; D-D and E-E in FIG. 6;

FIGS. 15A, 15B and 15C are respective side, top and front views of the forward base of FIGS. 14A & 14B;

FIGS. 16A & 16B are sectional illustrations of the forward base of FIGS. 14A & 14B taken along respective section lines A-A and B-B in FIGS. 15A and 15B;

FIGS. 17A & 17B are simplified pictorial illustrations of needle penetration depth selector of the automatic injection device of FIG. 1:

FIG. 18 is simplified side view of the needle penetration depth selector of FIGS. 17A & 17B;

FIGS. 19A & 19B are sectional illustrations of the needle penetration depth selector taken along respective section lines A-A in FIG. 18 and B-B in FIG. 17A;

FIGS. 24A, 24B, 24C and 24D are respective simplified side, top, front and back views of forward cover element of FIGS. 23A & 23B;

FIGS. 25A & 25B are simplified sectional illustrations of the forward cover element taken along respective section lines A-A and B-B in FIGS. 24A and 24B;

FIGS. 27A, 27B, 27C and 27D are simplified respective side, top, front and back views of the needle guard deploying element of FIGS. 26A & 26B;

FIGS. 28A & 28B are simplified sectional illustrations of the needle guard deploying element taken along respective section lines A-A and B-B in FIGS. 27A & 27B;

FIGS. 30A, 30B, 30C and 30D are simplified respective top, side, front and back views of the plunger element of FIGS. 29A & 29B;

FIGS. 34A & 34B are simplified sectional illustrations of the rear cover element taken along respective section lines A-A and B-B in FIGS. 33A & 33B;

FIGS. 35A & 35B are simplified pictorial illustrations of a trigger button element of the automatic injection device of FIG. 1:

FIGS. 36A, 36B and 36C are simplified respective side, top and front views of the trigger button element of FIGS. 35A & 35B;

FIG. 37 is a simplified sectional illustration of the trigger button taken along section line A-A in FIG. 36B;

FIGS. 38A & 38B are simplified pictorial illustrations of a safety-catch element of the automatic injection device of FIG. 1;

FIGS. 39A, 39B and 39C, which are simplified respective side, front and back views of the safety-catch element of FIGS. 38A & 38B:

FIG. 40 is a simplified sectional illustration of the safety-catch element taken along section line A-A in FIG. 39A;

FIGS. 42A, 42B, 42C and 42D are simplified respective side, top, front and back views of the rear base element of FIGS. 41A & 41B;

FIGS. 43A & 43B are simplified sectional illustrations of the rear base element taken along respective section lines A-A and B-B in FIGS. 42A & 42B;

FIG. 44 is a simplified assembled view illustration of the reusable driving assembly of the automatic injection device of FIG. 1 in a storage operative orientation;

FIGS. 45A & 45B are simplified respective side and top views of the assembled view illustration of the reusable driving assembly of FIG. 44;

FIG. 47 is a simplified side view illustration in the sense of FIGS. 44-46C of an assembly including the forward cover element of FIGS. 23A-25B, the needle penetration depth selector of FIGS. 17A-19B and the forward base element of FIGS. 14A-16B;

FIGS. 48A, 48B and 48C are simplified cross-sectional illustrations taken along respective lines A-A, B-B and C-C in FIG. 47 and FIG. 48D is a pictorial cross-sectional illustration taken along lines C-C in FIG. 47;

FIGS. 49A & 49B are simplified respective side and top views, in the sense of FIGS. 44-46D, of an assembly of needle guard deploying spring, needle guard deploying element of FIGS. 26A-28B and rear base element of FIGS. 41A-43B:

FIGS. 50A & 50B are simplified respective sectional illustrations taken along lines A-A and B-B in FIG. 49A;

FIG. 51 is a simplified side view, in the sense of FIGS. 44-46D, of an assembly of rear cover element of FIGS. 32A-34B, trigger button element of FIGS. 35A-37 and safety catch element of FIGS. 38A-40;

FIGS. 52A & 52B are simplified respective planar and pictorial cross-sectional view both taken along lines A-A in FIG. 51;

FIG. 53 is a simplified cross-sectional view taken along lines B-B in FIG. 51;

FIGS. 54A & 54B are simplified respective side and bottom view illustrations of an assembly which includes the assembly of FIGS. 49A-50B mounted within the assembly of FIGS. 51-53;

FIGS. 57A & 57B are simplified respective side and top views of the reusable driving assembly of FIG. 56;

FIGS. 60A & 60B are simplified respective side and top views of the reusable driving assembly of FIG. 59 and of disposable cassette assembly arranged coaxially therewith ready for insertion thereinto;

FIGS. 66A & 66B are simplified respective side and top views of the reusable driving assembly of FIG. 65;

FIG. 68 is a simplified assembled view illustration of the reusable driving assembly of the automatic injection device of FIG. 1 in a needle insertion operative orientation;

FIGS. 69A & 69B are simplified respective side and top views of the reusable driving assembly of FIG. 68;

FIGS. 72A & 72B are simplified respective side and top views of the reusable driving assembly of FIG. 71;

FIGS. 75A & 75B are simplified respective side and top views of the reusable driving assembly of FIG. 74.

DETAILED DESCRIPTION OF PREFERRED EMBODIMENT

Figure 1:
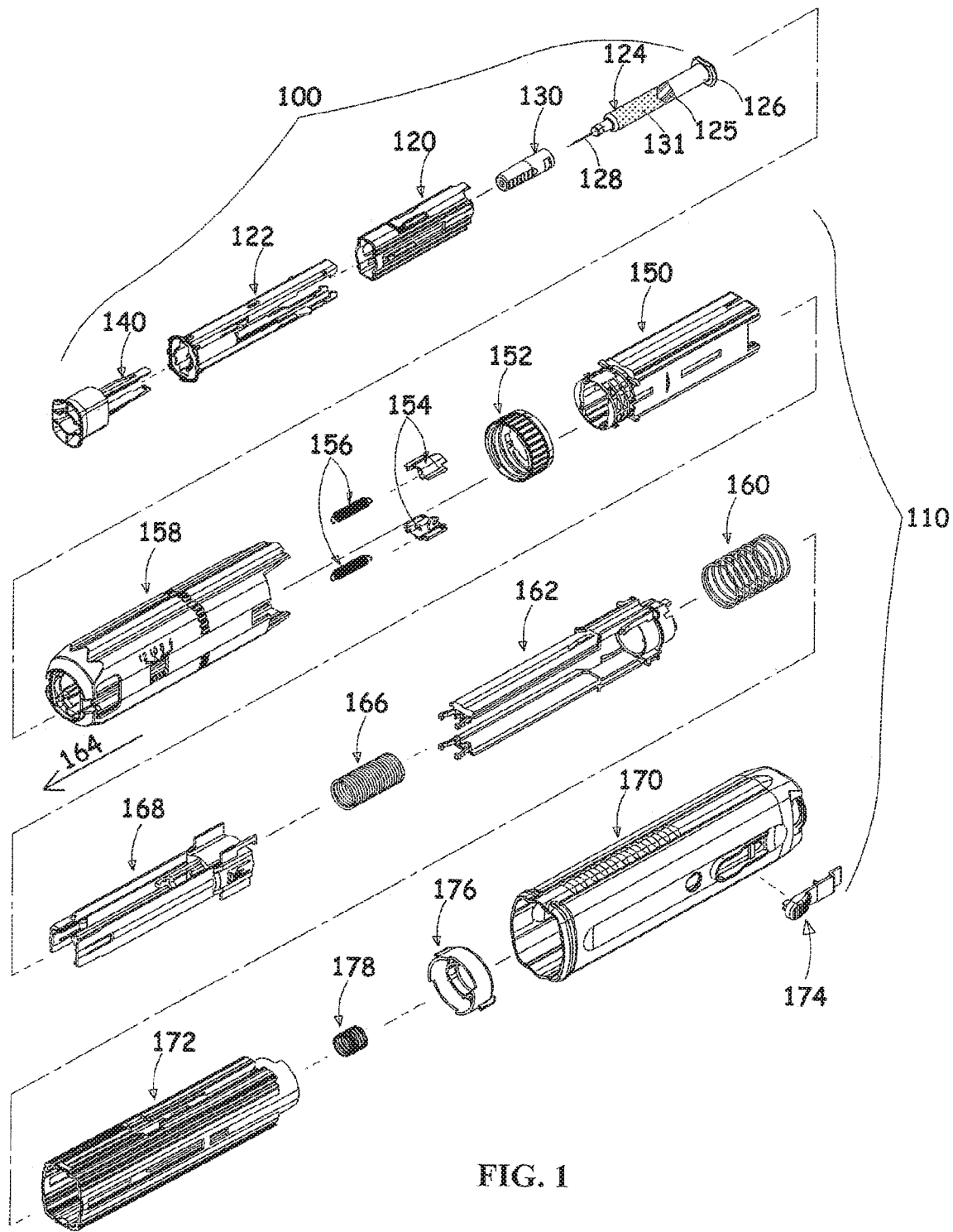
FIG. 1 is a simplified exploded view illustration of an automatic injection device constructed and operative in accordance with an embodiment of the present invention.
Figure 2:
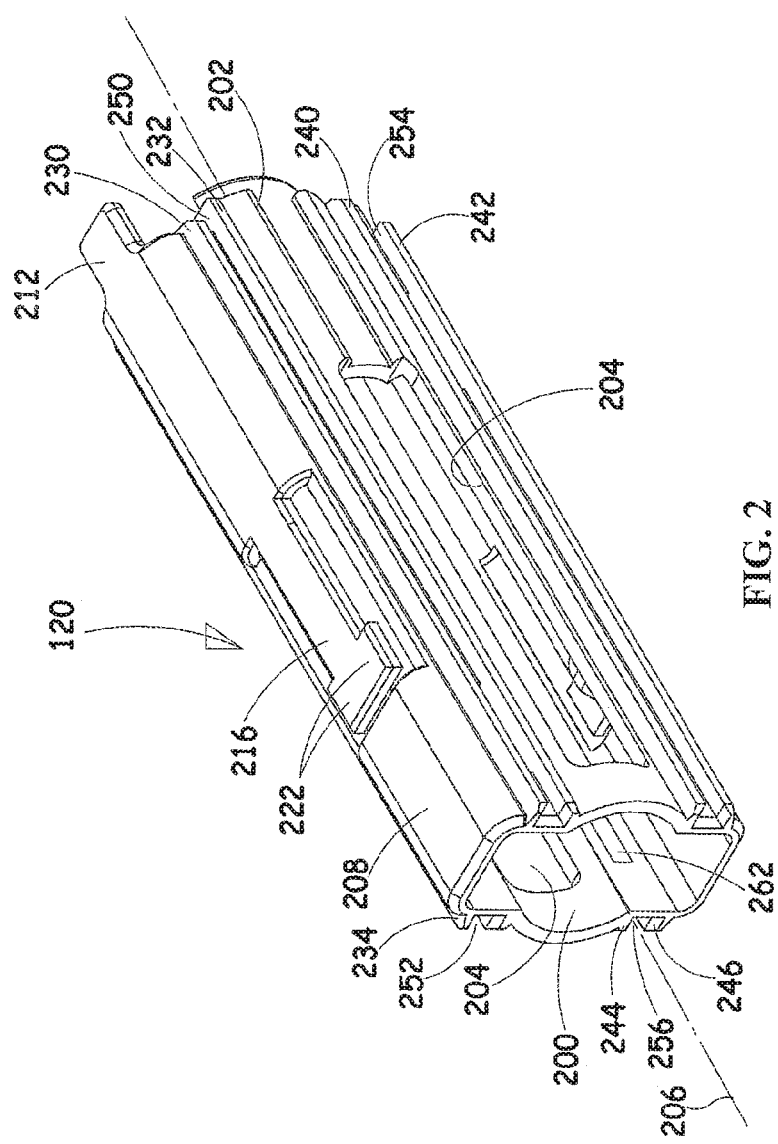
FIG. 2 is a simplified pictorial illustration of a cassette housing element which forms part of the automatic injection device of FIG. 1.
Figure 5:
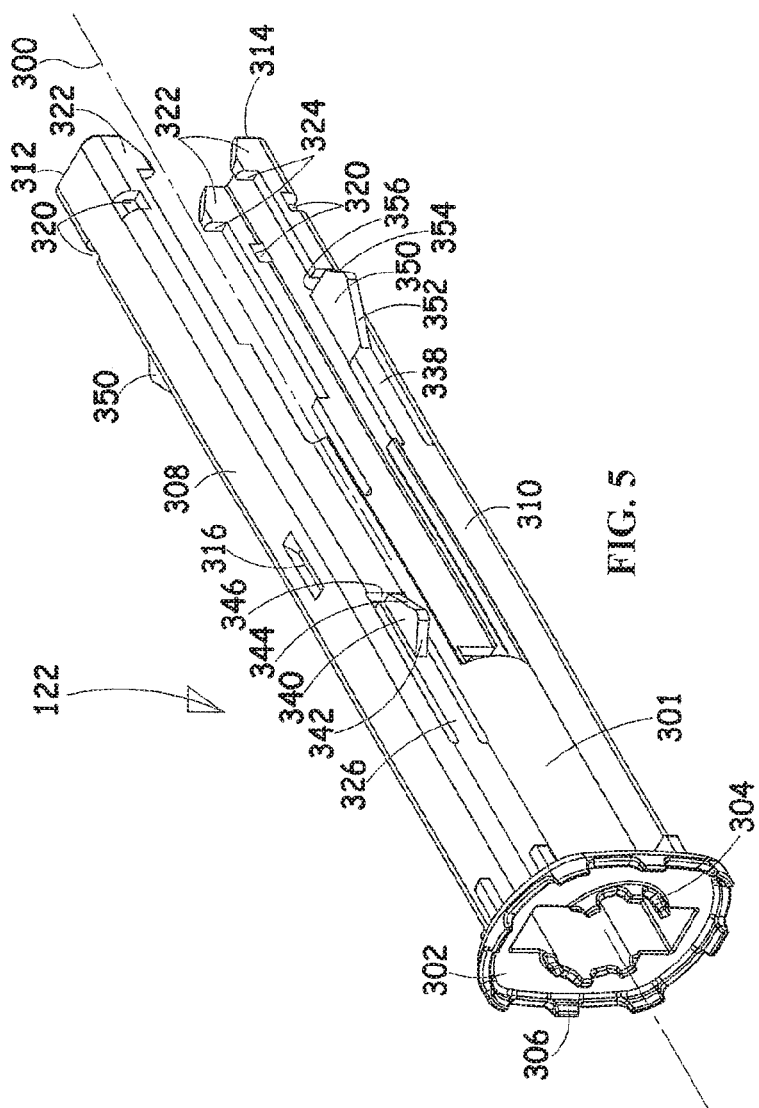
FIG. 5 is a simplified pictorial illustration of a needle guard element which forms part of the automatic injection device of FIG. 1.
Figure 7E:
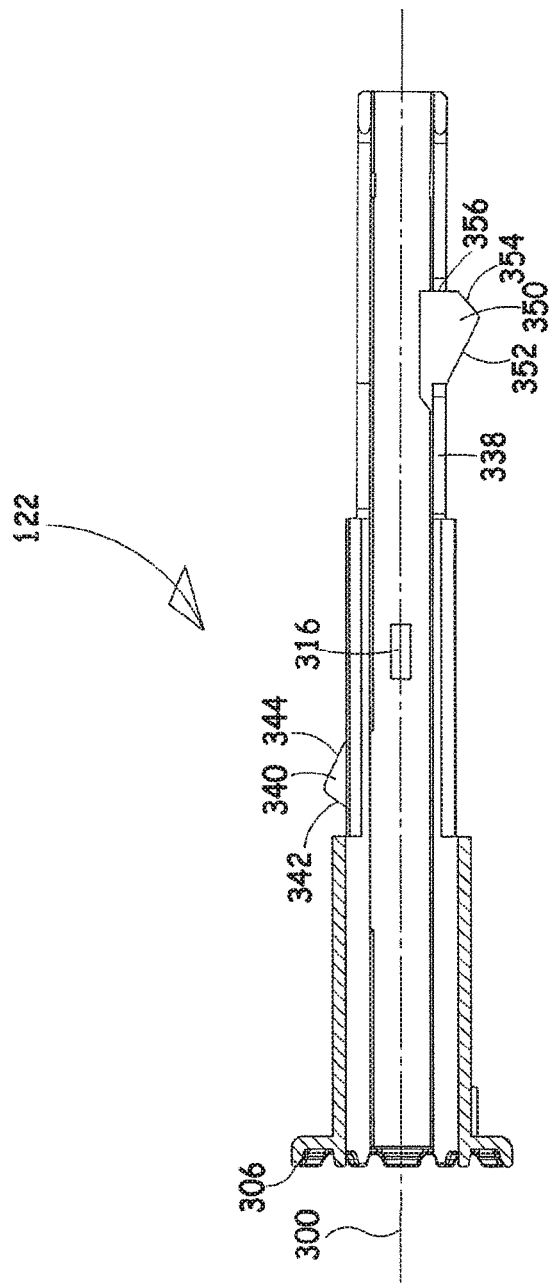
Figure 9:
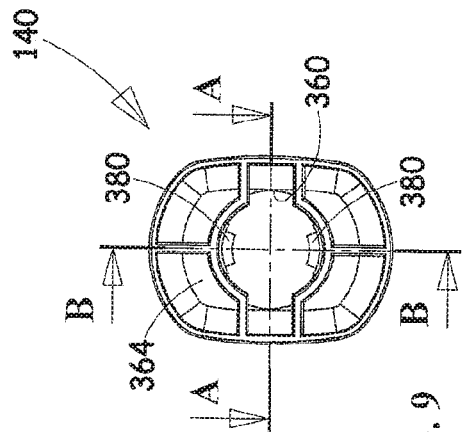
FIG. 9 is a front view simplified planar illustration of the needle shield remover element of FIG. 8.
Figure 10B:
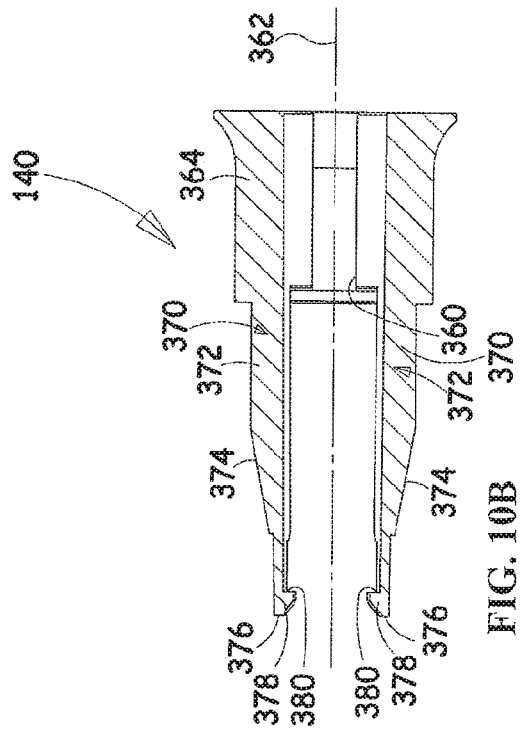
FIGS. 10A & 10B are sectional illustrations of the needle shield remover element taken along respective section lines A-A and B-B in FIG. 9.
Figure 8:
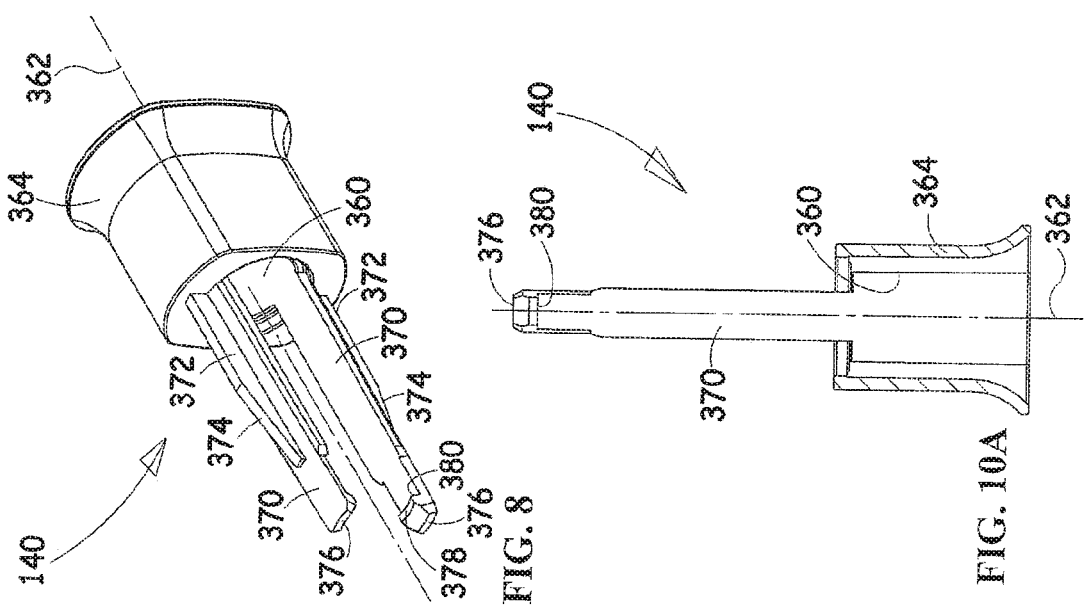
FIG. 8 is a simplified pictorial illustration of a needle shield remover element which forms part of the automatic injection device of FIG. 1.
Figure 10A:
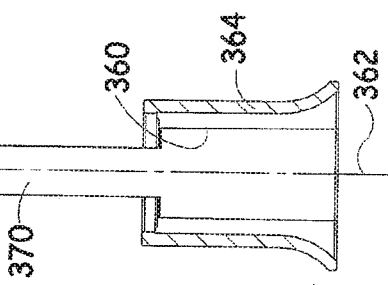

Reference is now made to FIG. 1, which illustrates elements of an automatic injection device constructed and operative in accordance with a preferred embodiment of the present invention.

As seen in FIG. 1, the automatic injection device preferably comprises a disposable cassette assembly 100, which is described hereinbelow in greater detail with reference to FIGS. 11-13C, and a reusable driving assembly 110, which is described hereinbelow in greater detail with reference to FIGS. 44-46C. The disposable cassette assembly 100 comprises a cassette housing element 120 in which is seated a needle guard element 122 and a syringe 124 including a piston 125, a flange 126 and a hypodermic needle 128, which is preferably covered by a needle shield 130. The syringe 124 is preferably pre-filled with liquid 131. Syringe 124 may be any suitable conventional syringe, such as a commercially available syringe sold under the catalog designation BD-Hypak™.

A needle shield remover 140 preferably forms part of the disposable cassette assembly 100. Alternatively it could be provided as a reusable part which is mounted onto the disposable cassette assembly 100 by the end user.

The reusable driving assembly 110 preferably comprises a forward base element 150, onto a front end of is preferably screwed a needle penetration depth selector 152, a pair of orientation retaining elements 154 and a pair of cocking springs 156, each which is mounted at a back end thereof onto one of the cocked orientation retaining elements 154. A forward cover element 158 generally encloses the forward base element 150 and the needle penetration depth selector 152.

A needle guard deploying spring 160 urges an engagement element, here a needle guard deploying element 162, in a forward direction indicated generally by an arrow 164 and a main spring 166 urges a plunger element 168 in the forward direction indicated generally by arrow 164.

A rear cover element 170 generally encloses a rear base element 172, which in turn, generally encloses elements 160, 162, 166 and 168. A trigger button element 174 cooperates with rear cover element 170. Rear cover element 170 also generally encloses a safety-catch element 176 and an injection site engagement sensing spring 178.

Rear base element 172 provides a rear spring seats for the main spring 166 and for injection site engagement sensing spring 178 and provides front spring seats for cocking springs 156.

Reference is now made to FIGS. 2, 3, 4A, 4B. 4C & 4D which illustrate cassette housing element 120. As seen in FIGS. 2-4B, the cassette housing element 120 preferably is an integrally formed element, preferably injection molded of plastic and preferably has a generally cylindrical configuration including a generally tubular portion 200, which defines backward-facing generally symmetric edges 202 and generally symmetric side-facing windows 204. Side-facing windows 204 may be obviated, if cassette housing element 120 is formed of a transparent material.

Cassette housing element 120 is preferably side-to-side symmetric about a longitudinal axis 206 and defines a generally round internal surface which slidingly guides syringe 124 (FIG. 1).

Cassette housing element 120 is preferably formed with a pair of generally symmetric top and bottom longitudinal extensions 208 and 210, each having a generally rectangular cross-section. Top and bottom longitudinal extensions 208 and 210 preferably terminate in respective rearward facing flat protrusions 212 and 214.

Finger portions 216 and 218 extend forwardly from respective top and bottom longitudinal extensions 208 and 210 and parallel to longitudinal axis 206, each of finger portions preferably terminating in an inward facing protrusion 220 and a pair of generally symmetric side-to-side facing protrusions 222.

Top longitudinal extension 208 is preferably formed with a pair of mutually spaced longitudinal ribs 230 and 232 on a first side thereof and a pair of mutually spaced longitudinal ribs 234 and 236 on a second side thereof.

Bottom longitudinal extension 210 is preferably formed with a pair of mutually spaced longitudinal ribs 240 and 242 on a first side thereof and a pair of mutually spaced longitudinal ribs 244 and 246 on a second side thereof.

A track 250 is defined by mutually spaced longitudinal ribs 230 and 232 and a track 252 is defined by mutually spaced longitudinal ribs 234 and 236.

A track 254 is defined by mutually spaced longitudinal ribs 240 and 242 and a track 256 is defined by mutually spaced longitudinal ribs 244 and 246.

Forward slots 260 and 262 and rearward slots 264 and 266 are defined along respective tracks 250, 252, 254 and 256. Forward slots 260 and 262 each include a forward facing edge 268 and a rearward facing edge 270. Rearward slots 264 and 266 each include a forward facing edge 278 and a rearward facing edge 280.

Reference is now made to FIGS. 5, 6, 7A, 7B, 7C, 7D & 7E which illustrate needle guard element 122 (FIG. 1). As seen in FIGS. 5-7E, the needle guard element 122 preferably is an integrally formed element, preferably injection molded of plastic and preferably has a generally cylindrical configuration arranged about a longitudinal axis 300, including a generally tubular portion 301 and having a forward facing injection site engaging surface 302, preferably including a pair of mutually concentric ribbed circumferential forward facing injection site rings 304 and 306.

Needle guard element 122 includes a pair of top and bottom mounting arms 308 and 310 extending rearwardly from tubular portion 301 and having respective rearward facing edges 312 and 314. Each of mounting arms 308 and 310 is formed with a slot 316 having a rearward-facing tapered surface 318. Each of mounting arms 308 and 310 is additionally formed with a pair of side-to-side symmetric notches 320.

Slightly forwardly of each of respective rearward facing edges 312 and 314, there are provided a pair of symmetric protrusions 322, each having a forward-facing surface 324.

Mounting arm 308 is formed with respective forward and rearward resilient finger portions 326 and 328. Mounting arm 310 is formed with respective forward and rearward resilient finger portions 336 and 338. Finger portion 326 and 336 each include an outwardly-facing protrusion 340, a forward-facing tapered surface 342, a rearward-facing tapered surface 344 and a rearward facing edge 346. Finger portions 328 and 338 each include an outwardly-facing protrusion 350, a forward-facing tapered surface 352, a rearward-facing tapered surface 354 and a rearward facing edge 356.

Reference is now made to FIGS. 8, 9, 10A & 10B, which illustrate needle shield remover 140. As seen in FIGS. 8-10B, the needle shield remover 140 preferably is an integrally formed element preferably injection molded of plastic and has a generally tubular portion 360, arranged about a longitudinal axis 362 and having an external user finger engagement surface 364. Needle shield remover 140, which when assembled together with needle guard element 122, cassette housing element 120 and syringe 124 defines the disposable cassette assembly 100, such that longitudinal axes 206, 300 and 362 are mutually coaxial.

Needle shield remover 140 includes a pair of symmetrical arms 370 which extend rearwardly of external user finger engagement surface 364 and are each formed with an outwardly-facing rib 372, having backwardly-facing tapered surfaces 374. Each of symmetrical arms 370 is additionally formed adjacent a rearwardly facing end surface 376 thereof with an internally facing protrusion 378, having a forward facing surface 380.

Figure 11:
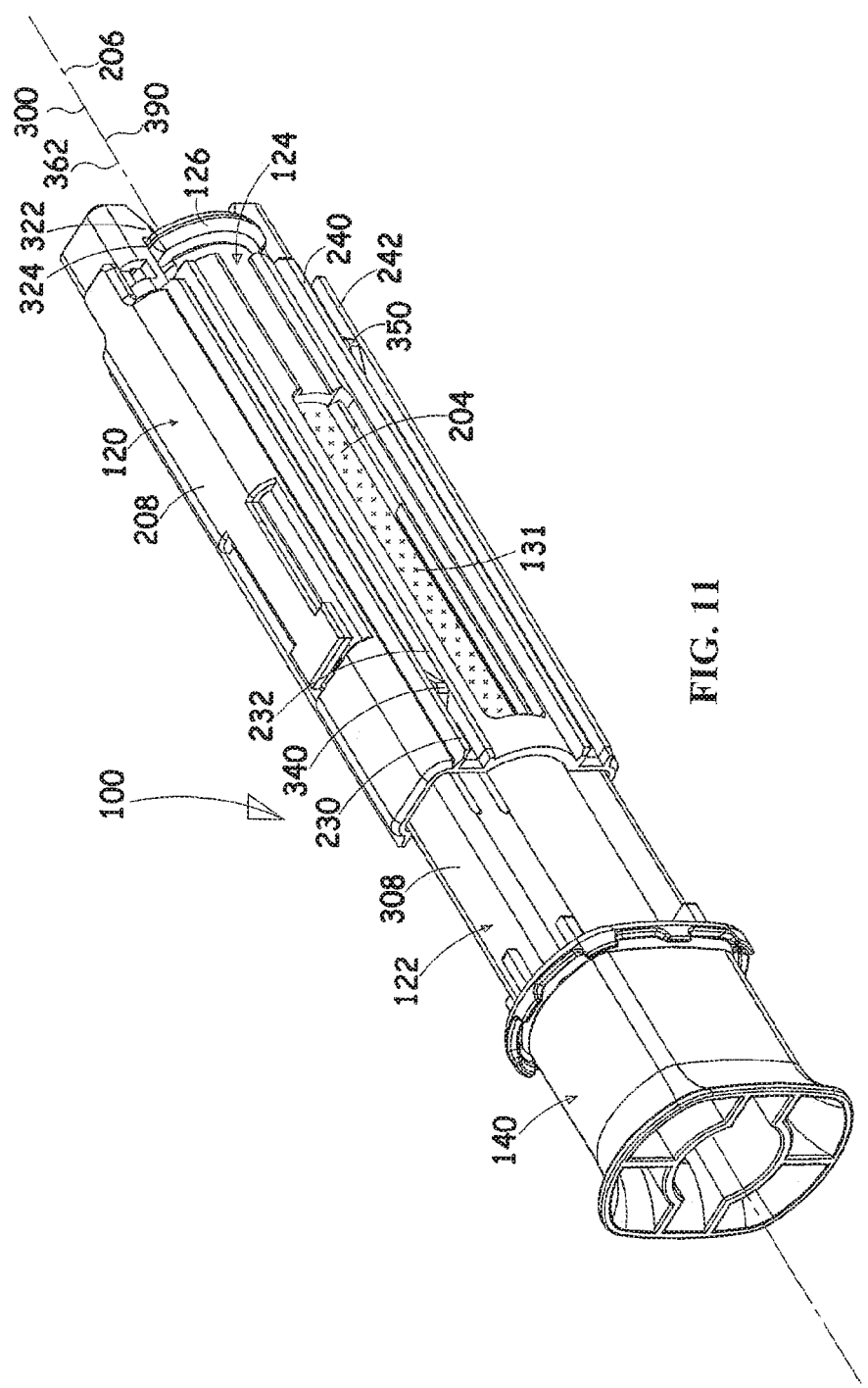
FIG. 11 is a simplified assembled view illustration of the disposable cassette assembly of the automatic injection device of FIG. 1 in a pre-use operative orientation.
Figure 12A:
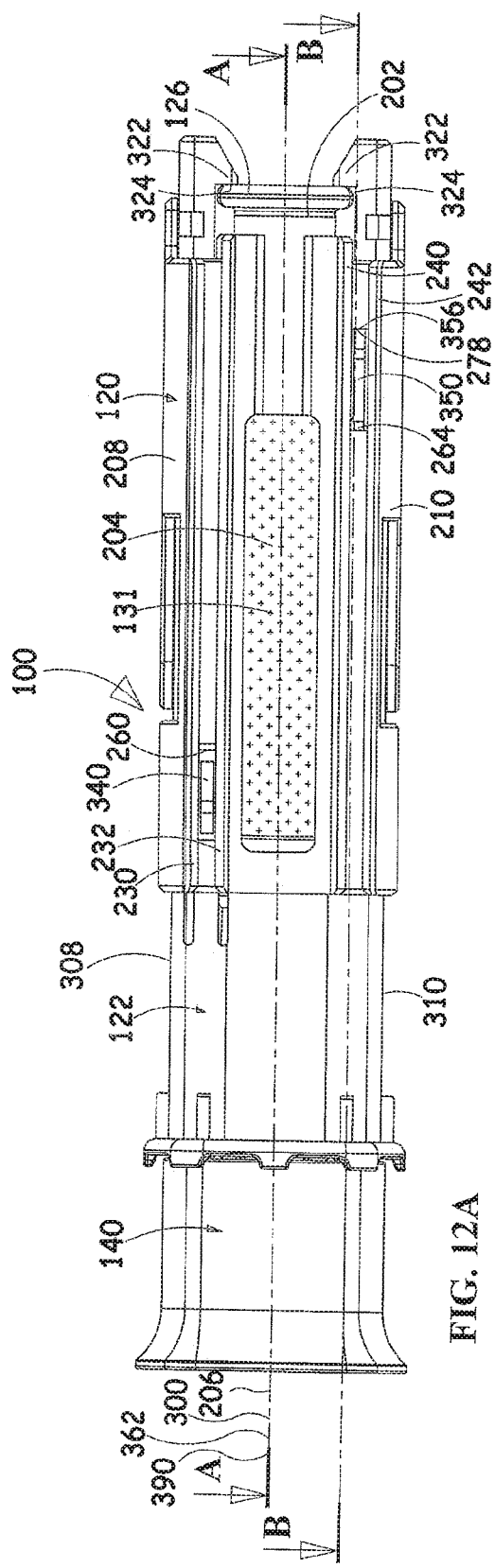
FIGS. 12A & 12B are simplified respective side and top view planar illustrations of the disposable cassette assembly of FIG. 11.
Figure 12B:
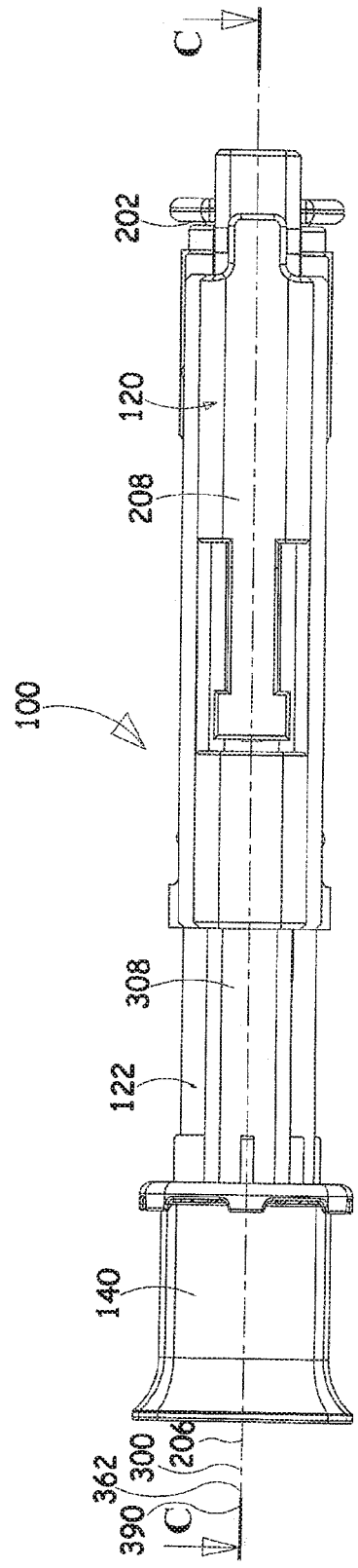
Figure 13A:
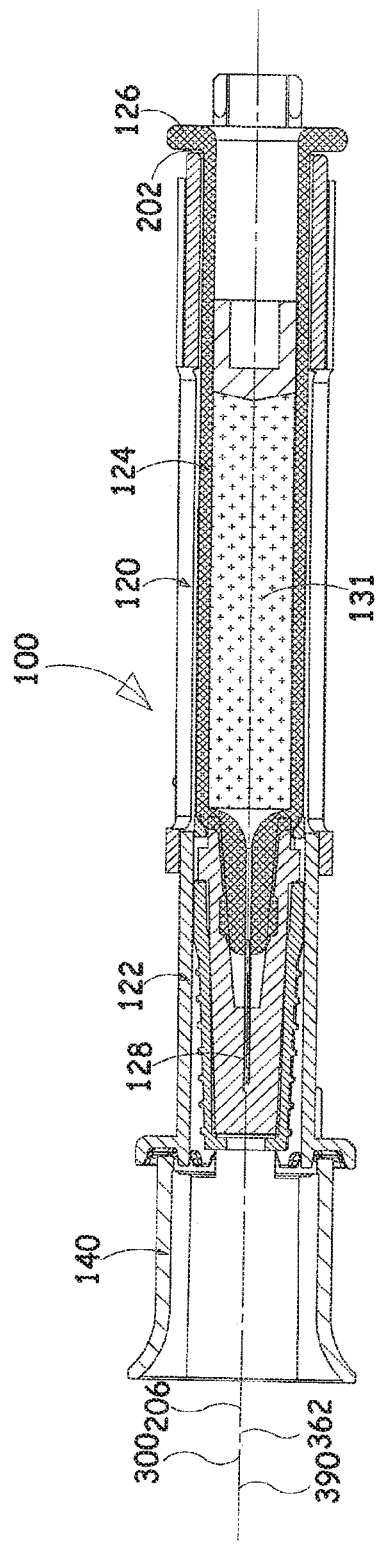
FIGS. 13A, 13B and 13C are sectional illustrations of the disposable cassette assembly taken along respective section lines A-A, B-B and C-C in FIGS. 12A and 12B.
Figure 13B:
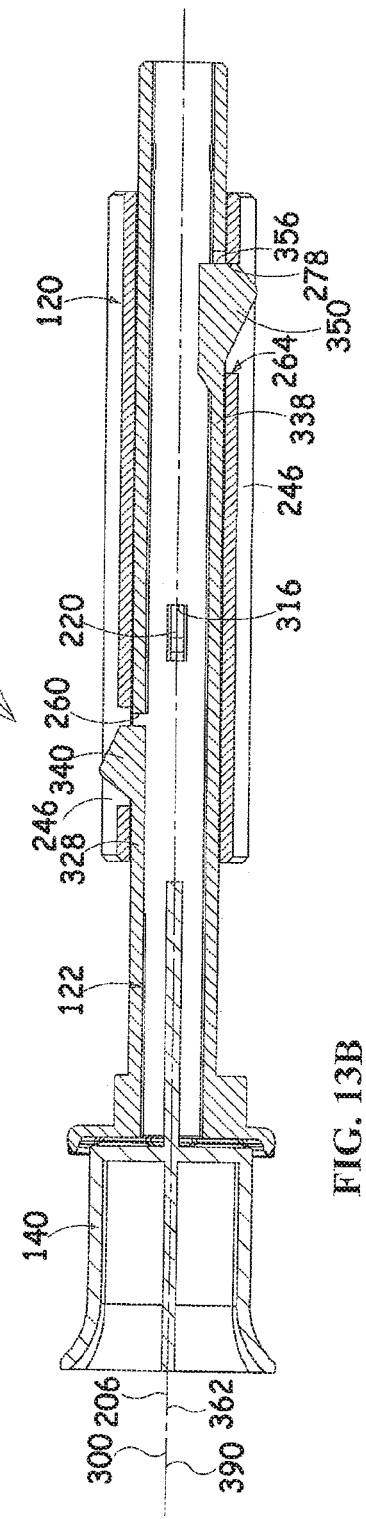
Figure 13C:
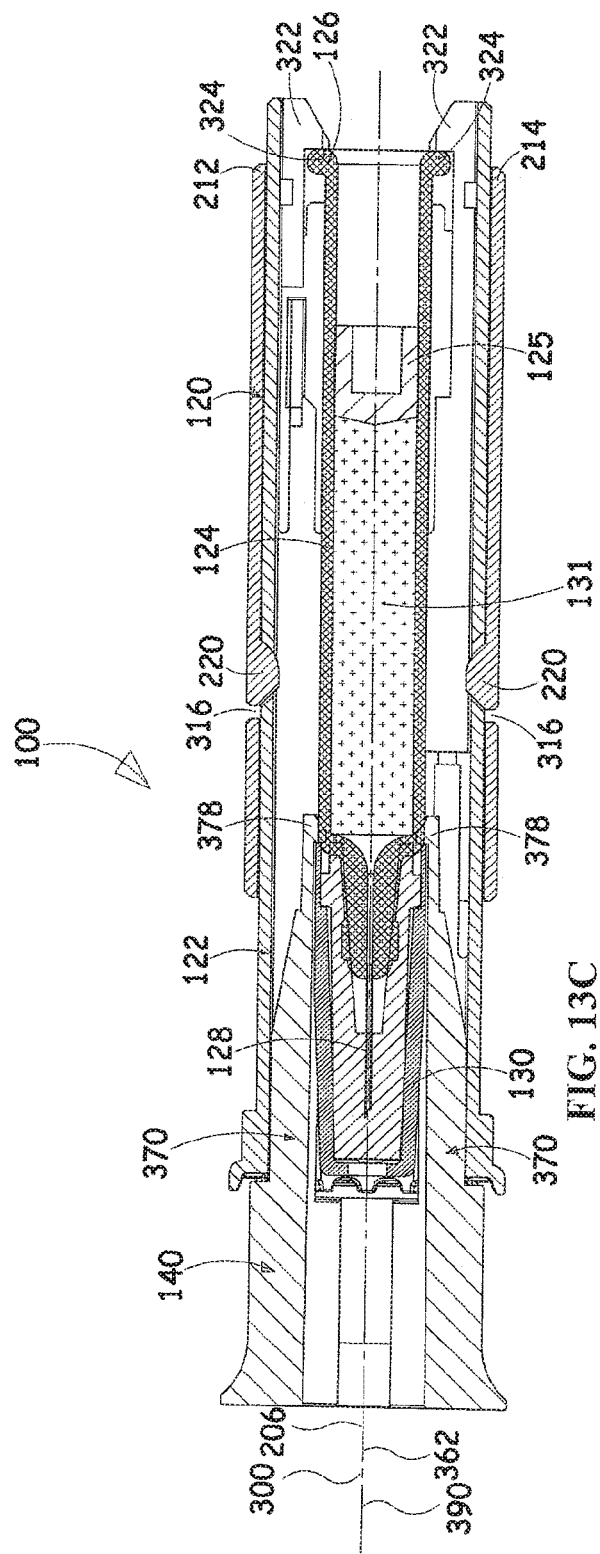

Reference is now made to FIG. 11, which is a simplified assembled view illustration of the disposable cassette assembly 100 of the automatic injection device of FIG. 1 in a pre-use operative orientation arranged along a longitudinal axis 390, to FIGS. 12A and 12B, which are simplified respective side and top view planar illustrations thereof in the sense of FIG. 11 and to FIGS. 13A, 13B and 13C, which are sectional illustrations taken along respective section lines A-A, B-B and C-C in FIGS. 12A and 12B.

As seen in FIGS. 11-13C, in a pre-use operative orientation of the disposable cassette which is suitable for storage, the needle guard element 122 is joined and locked to the cassette housing element 120 by snap fit engagement of outwardly-facing protrusions 340 and protrusions 350 of needle guard element 122 in corresponding forward slots 260 & 262 and rearward slots 264 & 266, respectively formed in the cassette housing element 120.

Rearward facing edge 356 of outwardly-facing protrusion 350 of finger portions 328 and 338 are located against corresponding rearward-facing edges 278 of rearward slots 264 and 266 respectively, thereby limiting forward movement of the syringe 124. Backward movement of the syringe 124 is limited by engagement of the flange 126 with forward-facing surfaces 324 of internally facing symmetric protrusions 322 of mounting arms 308 and 310 of the needle guard element 122. Outward spreading of mounting arms 308 and 310 is limited by generally symmetric top and bottom longitudinal extensions 208 and 210 of the cassette housing element 120 and thus mounting arms 308 and 310 cannot disengage from flange 126.

Syringe 124 is thus retained in a retracted operative orientation by engagement of flange 126 thereof between backward-facing generally symmetric edges 202 formed in cassette housing element 120 and forward-facing surface 324 of needle guard element 122 (FIGS. 2-7C).

Inward facing protrusions 220 of cassette housing element 120 are located in slots 316 of needle guard element 122.

It is noted that outwardly-facing protrusions 340 of needle guard element 122, which are located within respective forward slots 260 & 262, are also each surrounded on two sides thereof between respective pairs of longitudinal ribs 230 & 232 and 244 & 246.

It is also noted that outwardly-facing protrusions 350 of needle guard element 122, which are located within respective rearward slots 264 & 266, are also each surrounded on two sides thereof between respective pairs of longitudinal ribs 234 & 236 and 240 & 242.

The foregoing arrangement of ribs prevents user access to outwardly-facing protrusions 340 and 350 and undesired disengagement thereof from respective forward slots 260 & 262 and rearward slots 264 and 266. As a result, undesired axial movement of the syringe 124 is not possible in this pre-use operative orientation and therefore the hypodermic needle 128 of syringe 124 is safely locked in the disposable cassette assembly 100 and accidental needle stick cannot occur. Furthermore, in the pre-use operative orientation, the hypodermic needle 128 of the syringe 124 is generally hidden from view within the disposable cassette assembly 100, thus reducing user needle phobia.

As also seen in FIGS. 11-13C, in a pre-use operative orientation of the disposable cassette which is suitable for storage, needle shield remover 140 is preferably attached to the disposable cassette assembly 100 with internally facing protrusions 378 of symmetrical arms 370 of needle shield remover 140 being engaged with needle guard element 122 of syringe 124. Arms 370 together with outwardly-facing ribs 372 of needle shield remover 140 support the needle shield remover 140 within the needle guard element 122.

The contents of the syringe 124 can be easily seen through the side-facing windows 204 formed in the cassette housing element 120, thereby allowing visual inspection of the contents of the syringe prior to use.

It is appreciated that the syringe 124 may be supplied with a conventional plunger rod (not shown) to facilitate air-purging, drug titration and drug reconstitution or pumping from a vial/ampoule (not shown). The syringe may be supplied either pre-filled with a ready-to-inject drug, or it may be supplied empty for filling prior to use. It is also acknowledged that the syringe 124 can be inserted into the disposable cassette assembly 100 by a user or a pharmacist.

Figure 14A:
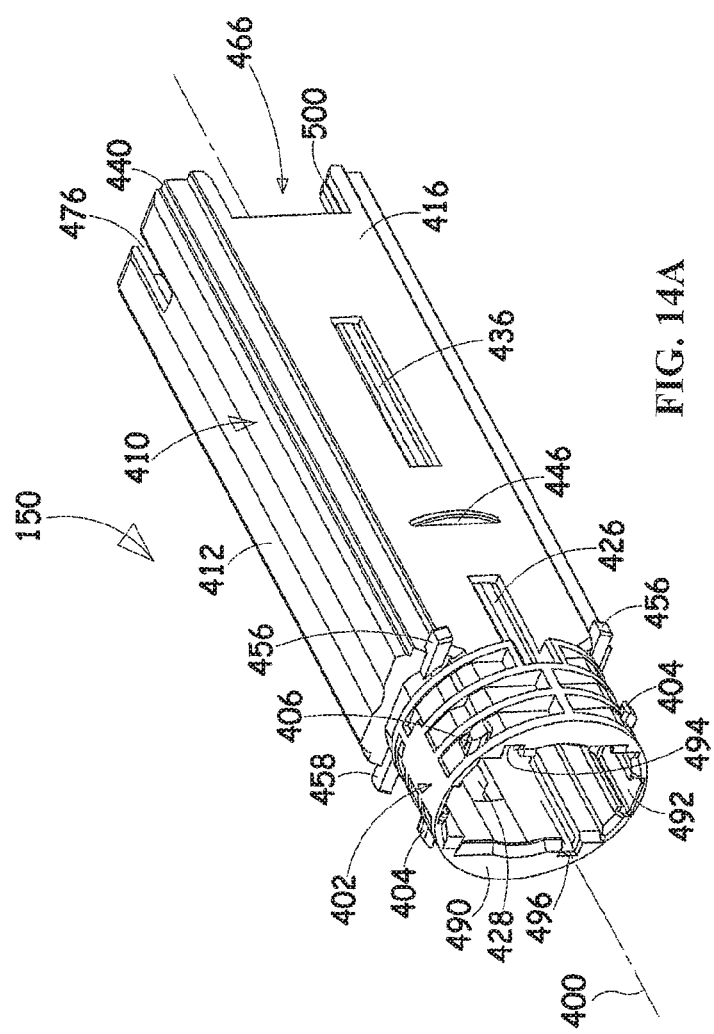
FIGS. 14A & 14B are simplified pictorial illustrations of a forward base element of the automatic injection device of FIG. 1.
Figure 14B:
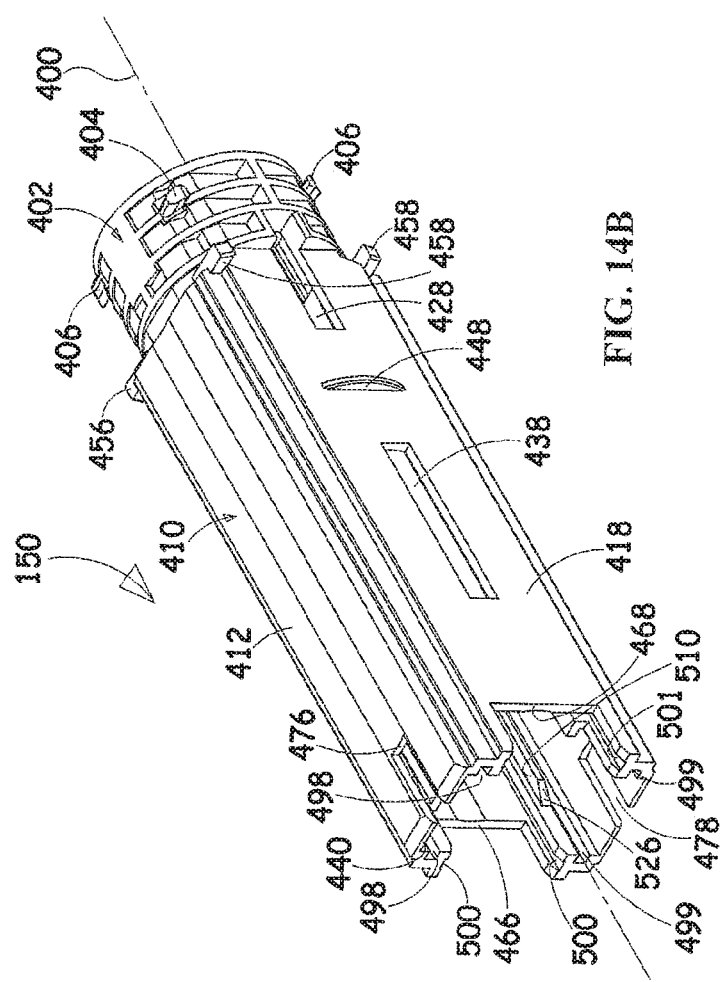

Reference is now made to FIGS. 14A and 14B, which are simplified pictorial illustrations of a forward base element 150, forming part of the reusable driving assembly 110 of the automatic injection device of FIG. 1; to FIGS. 15A, 15B and 15C, which are respective side, top and front views thereof in the sense of FIG. 14A; and to FIGS. 16A and 16B, which are sectional illustrations taken along respective section lines A-A and B-B in FIGS. 15A and 15B.

As seen in FIGS. 14A-16B, the forward base element 150 preferably is an integrally formed element, preferably injection molded of plastic and is arranged along a longitudinal axis 400 and generally has side-to-side symmetry with respect to axis 400.

Forward base element 150 preferably includes a generally forward-facing tubular portion 402, which includes two pairs of outwardly extending protrusions respectively designated by reference numerals 404 and 406, wherein protrusions 404 are located slightly rearwardly of protrusions 406 with respect to longitudinal axis 400.

Forward base element 150 preferably includes a main portion 410 having a general rectangular cross section including top and bottom walls 412 and 414 and side walls 416 and 418. Side walls 416 and 418 are formed with generally symmetric forward slots 426 and 428 respectively and generally symmetric rearward slots 436 and 438 respectively. Forward base element 150 has a rearwardmost edge 440.

Side walls 416 and 418 are also formed with respective partially circular outer facing ribs 446 and 448 and with respective pairs of forward corner protrusions, 456 and 458. Side walls 416 and 418 are also preferably formed with rearward-facing cut outs 466 and 468 respectively. Top and bottom walls 412 and 414 are preferably formed with rearward-facing cut outs 476 and 478 respectively.

Preferably, respective forward facing edges of each of top and bottom walls 412 and 414 are formed as forwardly and inwardly tapered surfaces 486 and 488.

As best seen in FIG. 14A and detail C of FIG. 15C, at a forward-facing tubular portion 402 there is preferably formed an end wall 490 and there are preferably formed a pair of generally rectangular slots 492, each having a generally T-shaped cross section. End wall 490 is preferably formed with a pair of cut outs 494 and 496.

Main portion 410 is preferably formed with a pair of internal elongate recesses 498, which together define a slidable track adjacent top wall 412 and with a pair of internal elongate recesses 499 which together define a slidable track adjacent bottom wall 414.

Main portion 410 is also preferably formed with a pair of internal elongate recesses 500, which together define a slidable track adjacent side wall 416 and with a pair of internal elongate recesses 501 which together define a slidable track adjacent side wall 418. It is appreciated that the tracks defined by recesses 498 and 499 lie in planes which are generally perpendicular to the tracks defined by recesses 500 and 501.

A pair of internally-facing ribs 510 and 512 are provided on side wall 416 and a pair of internally-facing ribs 520 and 522 are provided on side wall 418, internally-facing corresponding ribs 510 and 512. Each of ribs 510, 512, 520 and 522 is preferably provided with a tapered forward-facing edge 524 and a tapered rearward-facing edge 526.

Side walls 416 and 418 are each additionally provided with an internally facing rib 530, having a tapered forwardly-facing edge 532.

Reference is now made to FIGS. 17A and 17B, which are simplified pictorial illustrations of needle penetration depth selector 152, which forms part of the reusable driving assembly 110 of the automatic injection device of FIG. 1, to FIG. 18, which is a simplified side view thereof and to FIGS. 19A and 19B, which are respective sectional illustrations taken along section lines A-A in FIG. 18 and B-B in FIG. 17A.

As seen in FIGS. 17A-19B, needle penetration depth selector 152 is preferably an integrally formed element, preferably injection molded of plastic, and is arranged along a longitudinal axis 550. Needle penetration depth selector 152 preferably is formed as a generally tubular element and is preferably formed with longitudinally oriented splines 552 extending between respective forward and rearward circumferential protrusions 554 and 556. Rearwardly of protrusion 556, an outer surface 557 of needle penetration depth selector 152 is formed with four rearward-facing circumferentially distributed recesses 558.

An internal surface of needle penetration depth selector 152 is preferably formed with a pair of helical internal threadings 560 and 562. Internal threading 560 has a pair of openings 564 and 566 and an internal disengagement preventing wall 568 adjacent opening 564.

Internal threading 562 has a pair of openings 574 and 576 and an internal disengagement preventing wall 578 adjacent opening 574.

Figure 20B:
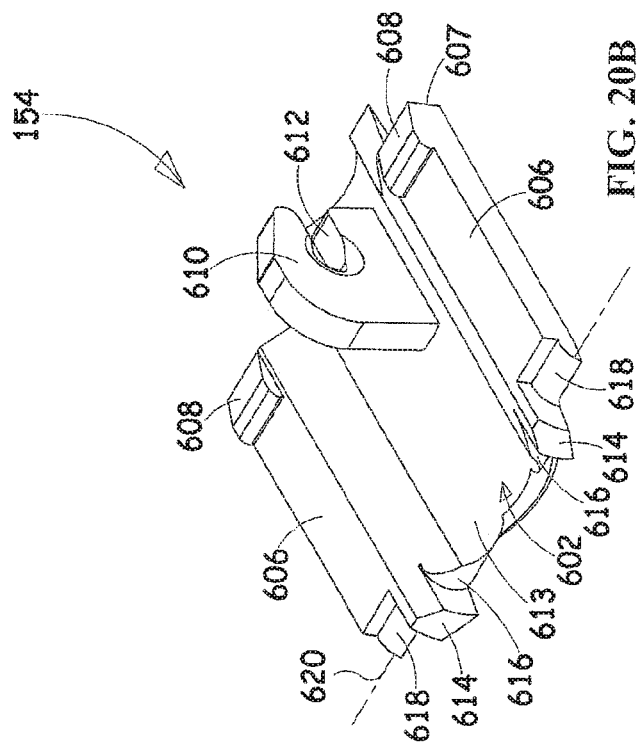
FIGS. 20A & 20B are simplified pictorial illustrations of a cocked orientation retaining element of the automatic injection device of FIG. 1.
Figure 20A:
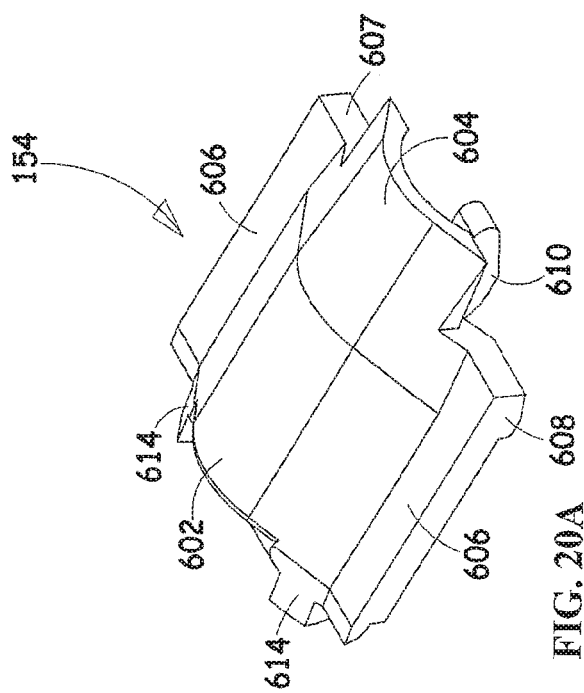
Figure 21C:
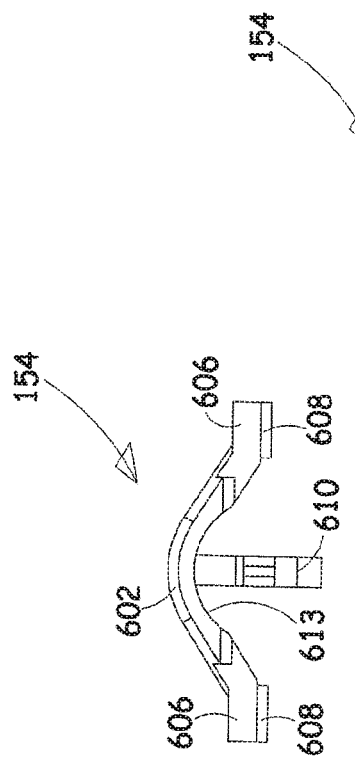
FIGS. 21A, 21B, 21C and 21D, which are simplified respective top, side, back and front views of the cocked orientation retaining element of FIGS. 20A & 20B.
Figure 22:
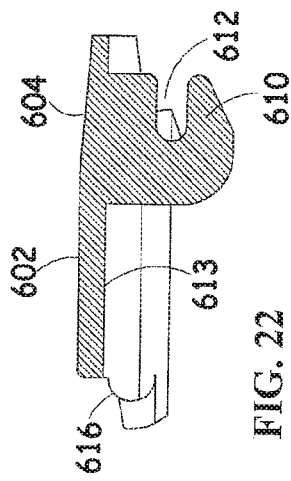
FIG. 22 is a sectional illustration of the cocked orientation retaining element taken along section line A-A in FIG. 21A.
Figure 21A:
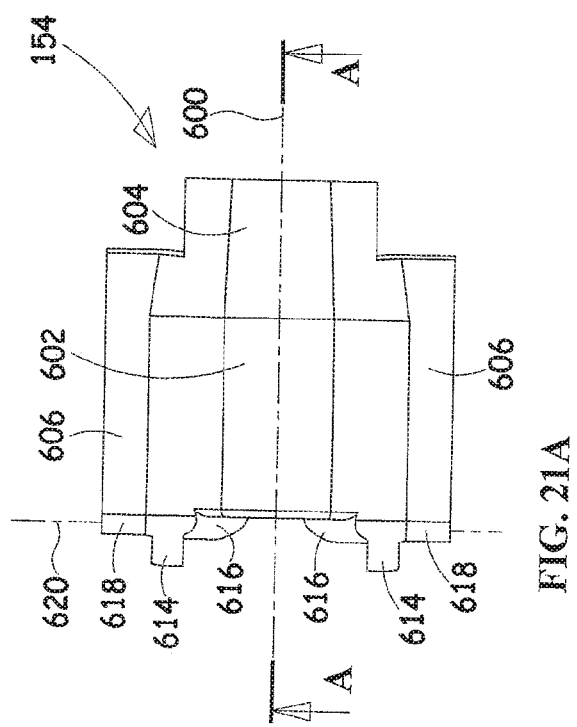
Figure 21D:
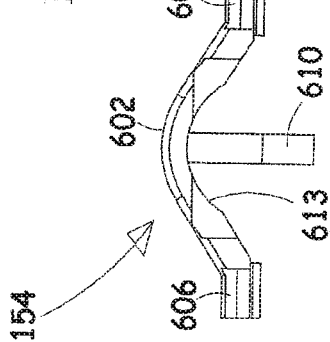
Figure 21B:
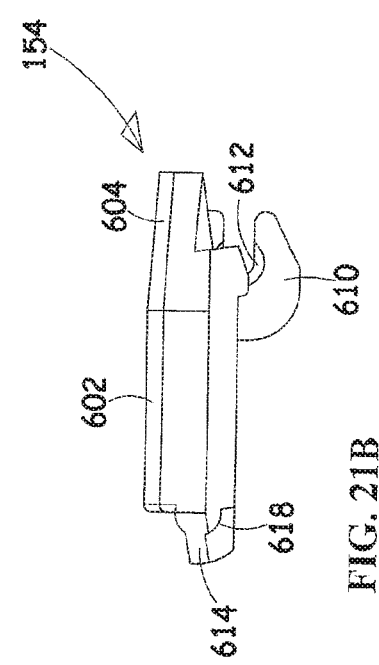

Reference is now made to FIGS. 20A and 20B, which are simplified pictorial illustrations of a cocked orientation retaining element 154, which forms part of the reusable driving assembly 110 of the automatic injection device of FIG. 1, to FIGS. 21A, 21B, 21C and 21D, which are simplified respective top, side, back and front views thereof, and to FIG. 22, which is a sectional illustration taken along section line A-A in FIG. 21A;

As seen in FIGS. 20A-22, the cocked orientation retaining element 154 preferably is an integrally-formed element, preferably injection molded of plastic arranged along a longitudinal axis 600 and includes a generally upward facing convex portion 602, in the sense of FIG. 20A, having a generally truncated frusto-conical rearward facing end portion 604, and a pair of side-to-side symmetric generally flat side extension portions 606.

As seen particularly in FIG. 20B, each of side extension portions 606 includes on an underside thereof, in the sense of FIG. 20A, adjacent a rearward end 607 thereof, a protrusion 608. A hook 610 having a rearward-facing opening 612 extends downwardly in the sense of FIG. 20A from a downward-facing surface 613 of convex portion 602. Hook 610 serves as a spring seat for cocking spring 156.

A pair of forward facing protrusions 614, in the sense of FIG. 20A, are located at a forward end of convex portion 602. Between forward facing protrusions 614 there are provided a pair of forward-facing generally rounded surfaces 616. An additional pair of forward-facing generally rounded surfaces 618 are located adjacent respective protrusions 614 and on opposite sides thereof from surfaces 616. Forward-facing generally rounded surfaces 618 define a rotational axis 620.

Figure 23A:
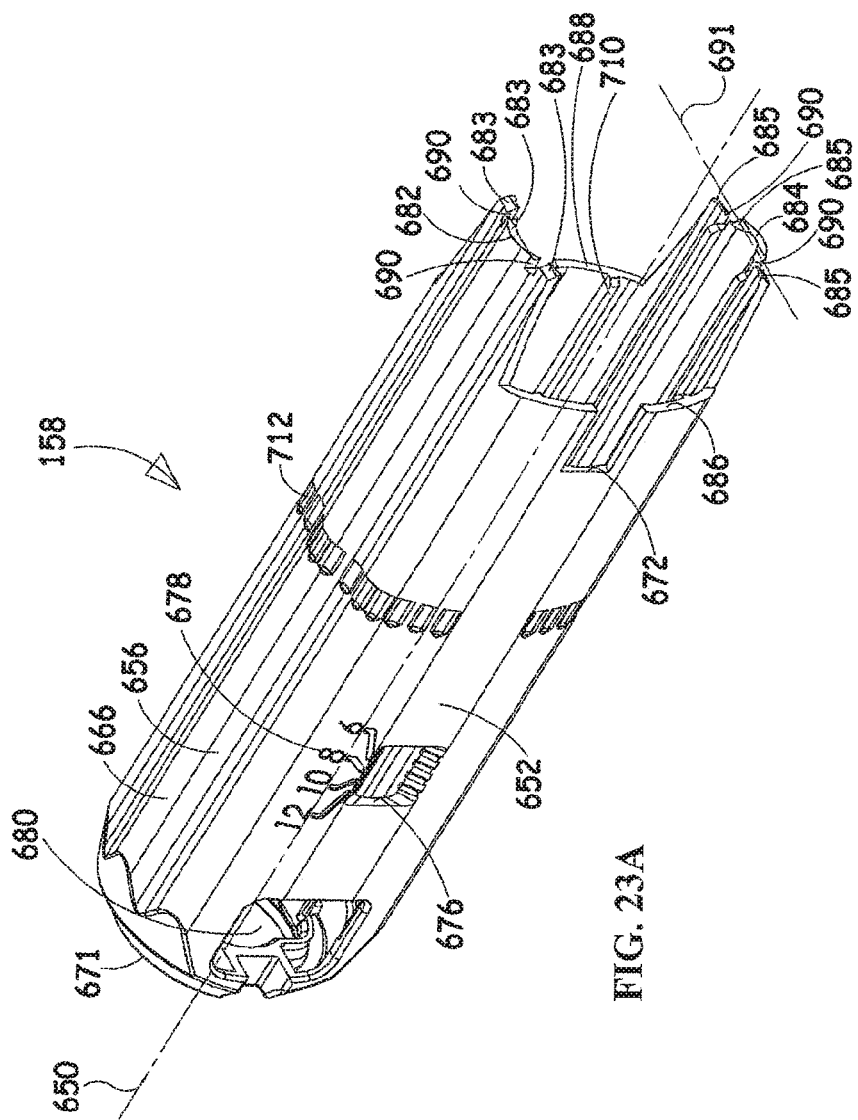
FIGS. 23A & 23B are simplified pictorial illustrations of forward cover element of the automatic injection device of FIG. 1.
Figure 23B:
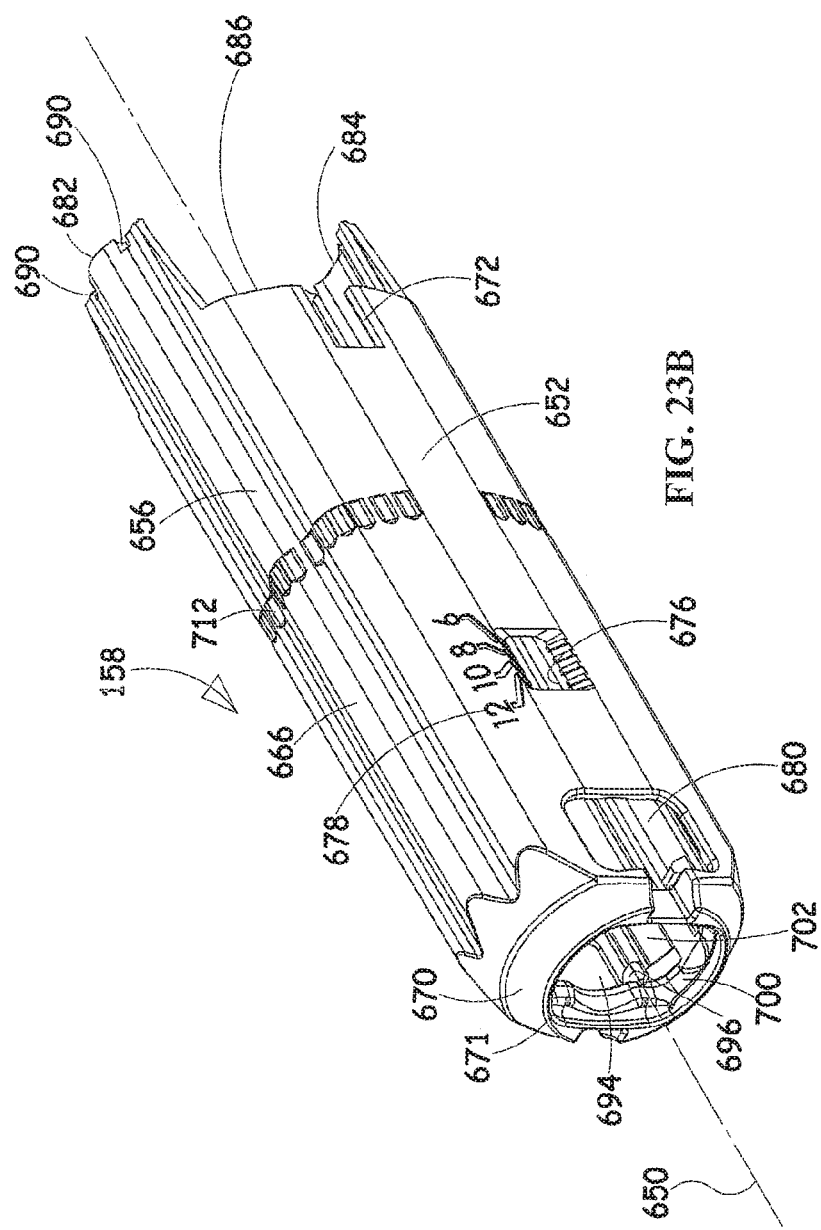
Figure 24A:
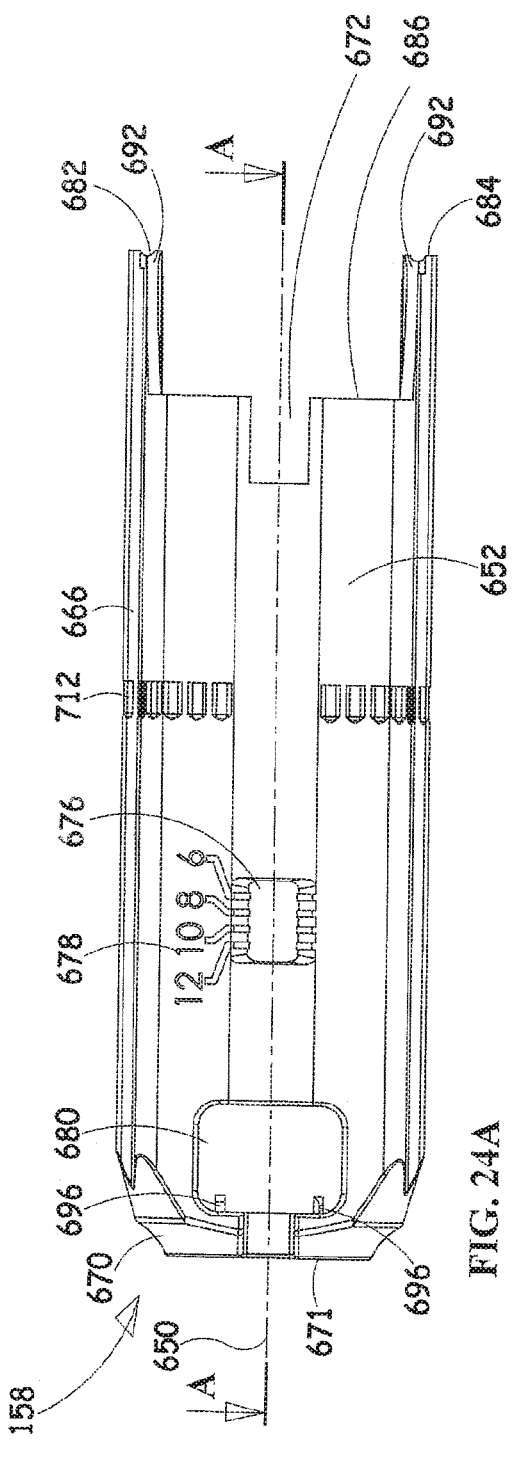
Figure 24B:
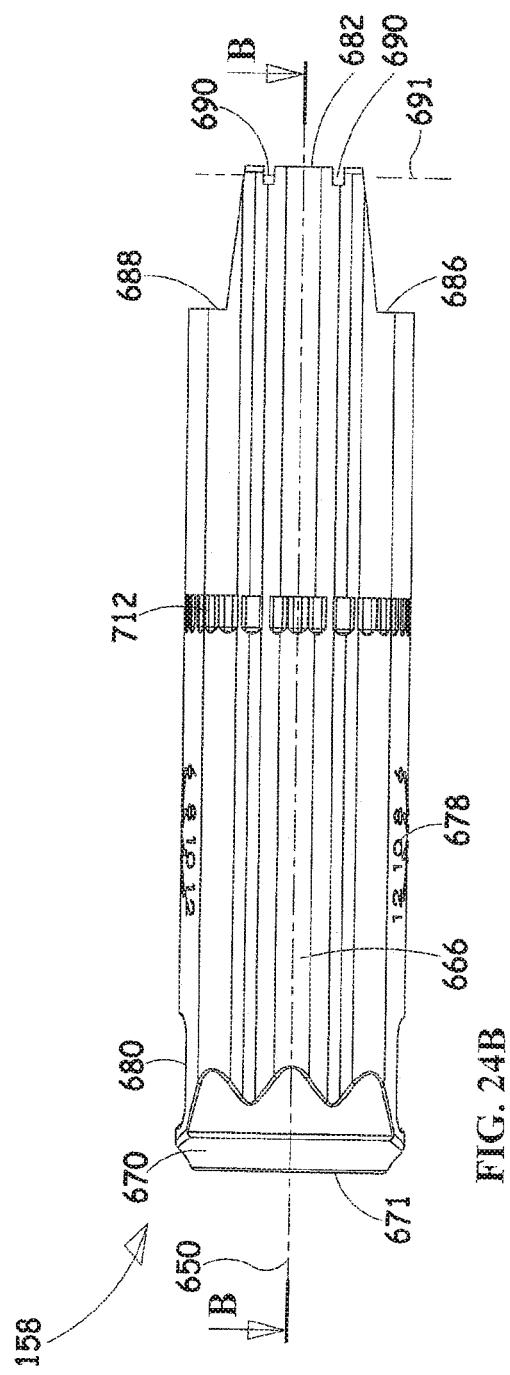

Reference is now made to FIGS. 23A and 23B, which are simplified pictorial illustrations of forward cover element 158, which forms part of the reusable driving assembly 110 of the automatic injection device of FIG. 1, to FIGS. 24A, 24B. 24C and 24D, which are respective simplified side, top, front and back views thereof, and to FIGS. 25A and 25B, which are simplified sectional illustrations taken along respective section lines A-A and B-B in FIGS. 24A and 24B.

As seen in FIGS. 23A-25B, the forward cover element 158 preferably is an integrally formed element, preferably injection molded of plastic, which is arranged along a longitudinal axis 650, and has a generally rectangular cross-section. Forward cover element 158 is preferably formed with a pair of slightly outwardly convex side walls 652 and 654 respectively and top and bottom walls 656 and 658, respectively formed with top and bottom facing longitudinal convex portions 666 and 668.

Top and bottom walls 656 and 658 are somewhat tapered at forward facing ends thereof and terminate together with forward ends of side walls 652 and 654 in a forward-facing generally conical ring portion 670, having a forward-facing edge 671. Side walls 652 and 654 are preferably formed with side-to-side symmetric rearward facing cutouts 672 and 674. Side walls 652 and 654 are each preferably formed with a needle penetration depth setting window 676, above which is provided a needle depth setting scale 678. Side walls 652 and 654 are each preferably formed with a cut-out 680.

Top and bottom walls 656 and 658 preferably terminate rearwardly at respective rearward-facing edges 682 and 684 which are rearward of corresponding rearward-facing edges 686 and 688 of respective side walls 652 and 654. Each of rearward-facing edges 682 and 684 is provided with a pair of mutually spaced notches 690. Rearward-facing edges 682 and 684 form partially circular faces 683 and 685 which form a rotational axis 691.

Interior surfaces of top and bottom walls 656 and 658 are preferably each formed with a pair of grooves 692. An interior circumferential surface of forward-facing generally conical ring portion 670 defines an axial opening 694 and is preferably formed with protrusions 696, and a forwardly and outwardly tapered facing generally circumferential tapered surface 700.

Extending rearward from axial opening 694, internally of respective top and bottom walls 656 and 658, there are preferably provided a pair of tabs 702 and thereunder a pair of flexible snap engagement protrusions 704.

Internal surfaces of side walls 652 and 654 are preferably formed with internally-facing protrusions 706. Internal surfaces of side walls 652 and 654 and top and bottom walls 656 and 658 are formed with multiple longitudinal internally facing ribs 710.

An actuatable operative orientation indicating circumferentially extending line 712 is preferably defined on an outer surface of forward cover element 158.

Figure 26A:
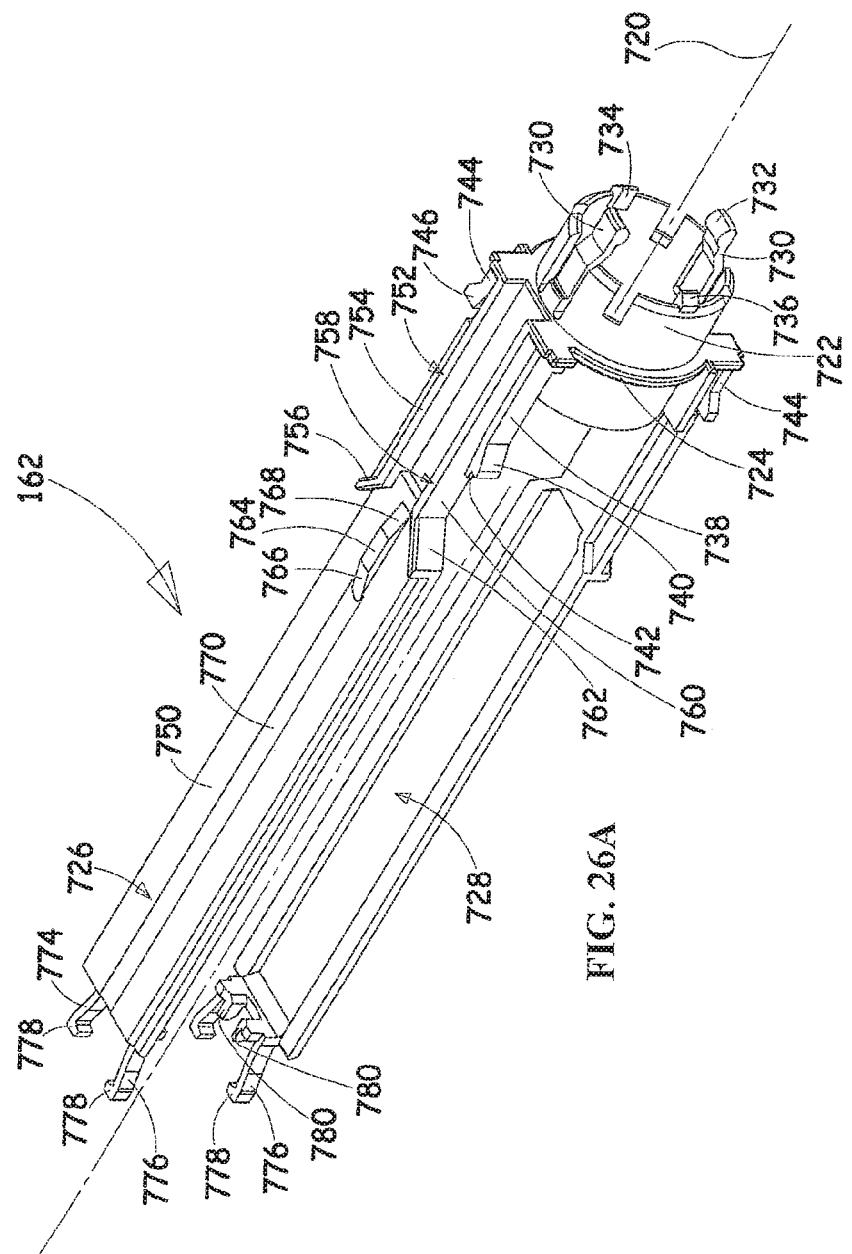
FIGS. 26A & 26B are simplified pictorial illustrations of a needle guard deploying element of the automatic injection device of FIG. 1.
Figure 26B:
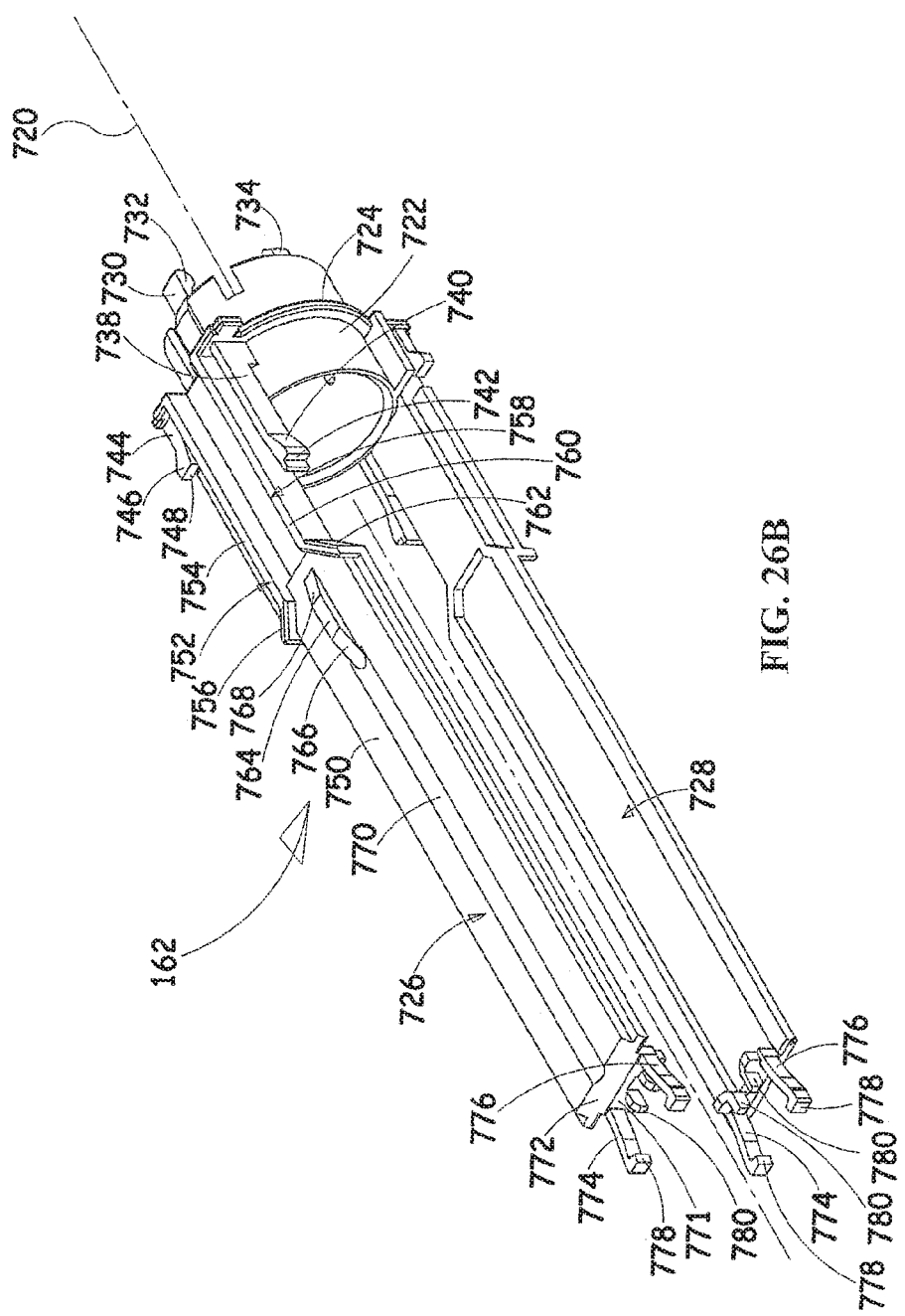
Figure 27D:
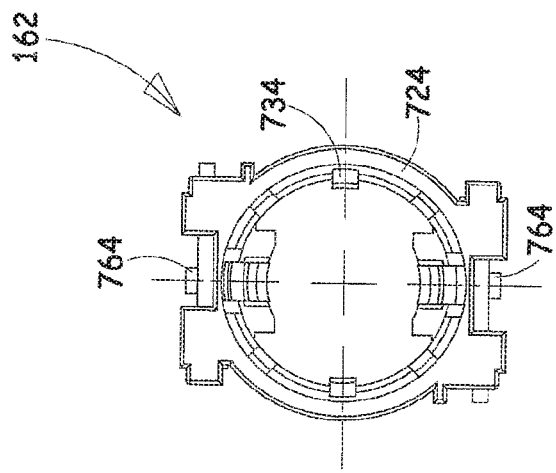
Figure 27C:
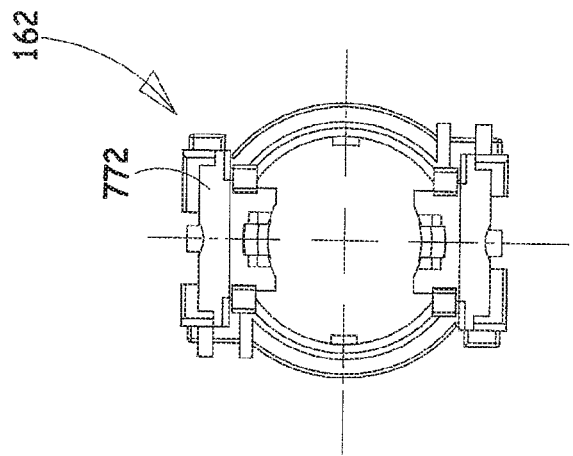

Reference is now made to FIGS. 26A and 26B, which are simplified pictorial illustrations of a needle guard deploying element 162, which forms part of the reusable driving assembly 110 of the automatic injection device of FIG. 1, to FIGS. 27A, 27B, 27C and 27D, which are simplified respective side, top, front and back views thereof, and to FIGS. 28A and 28B, which are simplified sectional illustrations taken along respective section lines A-A and B-B in FIGS. 27A and 27B.

As seen in FIGS. 26A-28B, the needle guard deploying element 162 preferably is an integrally formed element, preferably injection molded of plastic, and is arranged along a longitudinal axis 720. Element 162 includes a generally tubular portion 722 at a rearward end thereof, having an outwardly extending, partially circularly circumferential flange 724. A pair of arms 726 and 728 extend forwardly of flange 724, mutually spaced and parallel to longitudinal axis 720.

Extending rearwardly from flange 724 are a pair of flexible fingers 730, each of which has an inwardly facing, rounded protrusion 732. Extending rearwardly and inwardly from tubular portion 722 are a pair of protrusions 734 preferably having outwardly and rearwardly facing, rearwardly and inwardly tapered surface 736. Extending forwardly from flange 724 and adjacent each of arms 726 and 728 is a finger 738 having a forwardly and outwardly tapered surface 740 facing away from the respective arm. Each of fingers 738 defines a forwardly-facing shoulder 742.

Adjacent each of arms 726 and 728 and alongside a side thereof opposite to the side adjacent to finger 738 is a finger 744. Finger 744 is preferably formed with a forward and outward facing protrusion 746 and a forward-facing surface 748.

Formed on an outer facing surface 750 of each of arms 726 and 728 is a rib 752, a major portion 754 of which extends axially forwardly from the plane of flange 724 and terminates in an angled portion 756. Also formed on an outer facing surface 750 of each of arms 726 and 728 is a rib 758, a major portion 760 of which extends axially forwardly from the plane of flange 724 and terminates in an angled portion 762.

Also formed on an outer facing surface 750 of each of arms 726 and 728 is an elongate protrusion 764, having tapered forward and rearward facing ends 766 and 768 respectively. Forwardly of each protrusion 764 there is provided an axial groove 770.

Each of arms 726 and 728 preferably terminates in forward facing surface 771 having a tapered forward-facing edge 772 from which extend forwardly a pair of generally axial fingers 774 and 776 having mutually facing forward inwardly directed protrusions 778. A pair of forward-facing protrusions 780 also extend forwardly of tapered forward-facing edge 772.

Figure 29A:
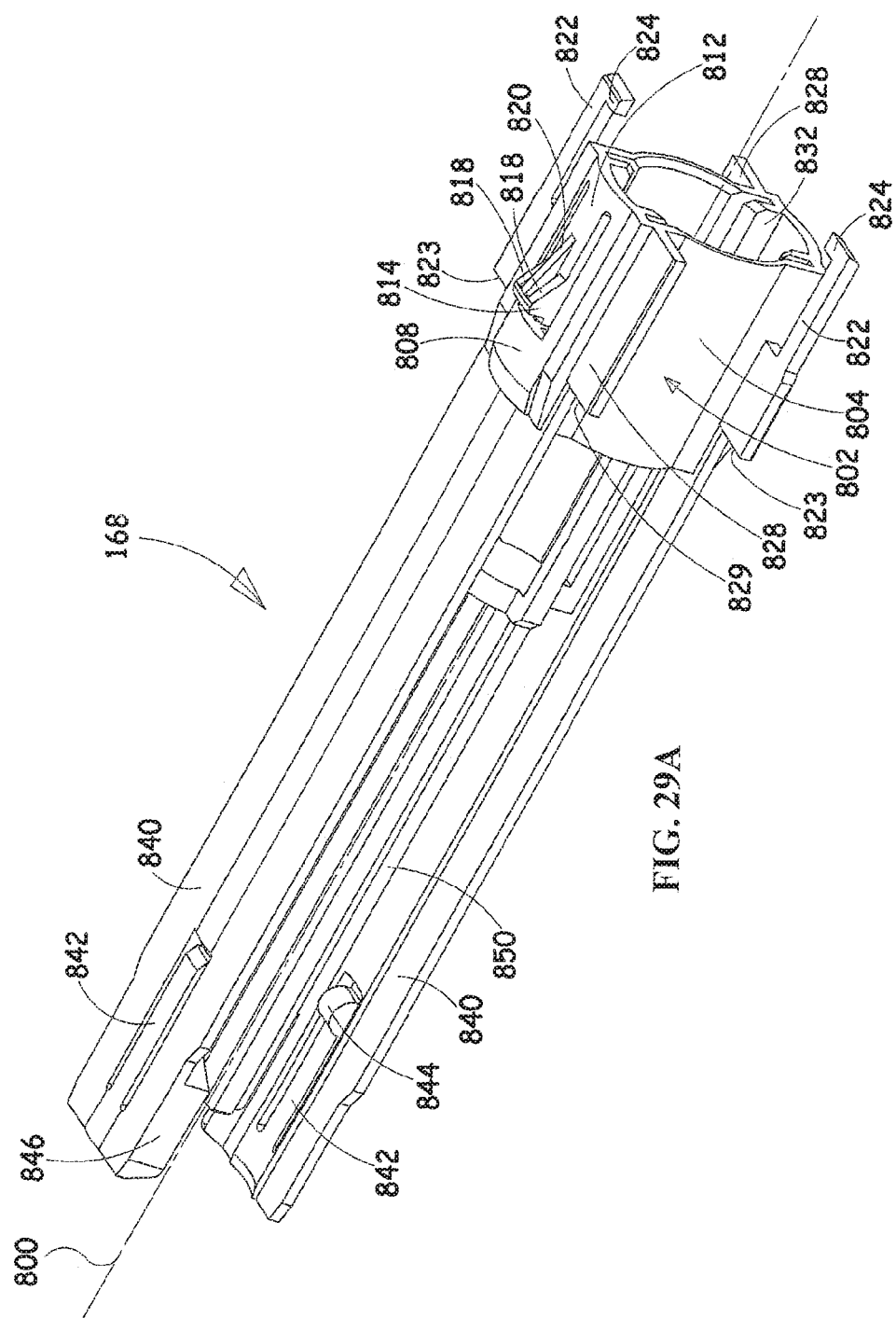
FIGS. 29A & 29B are simplified pictorial illustrations of a plunger element of the automatic injection device of FIG. 1.
Figure 29B:
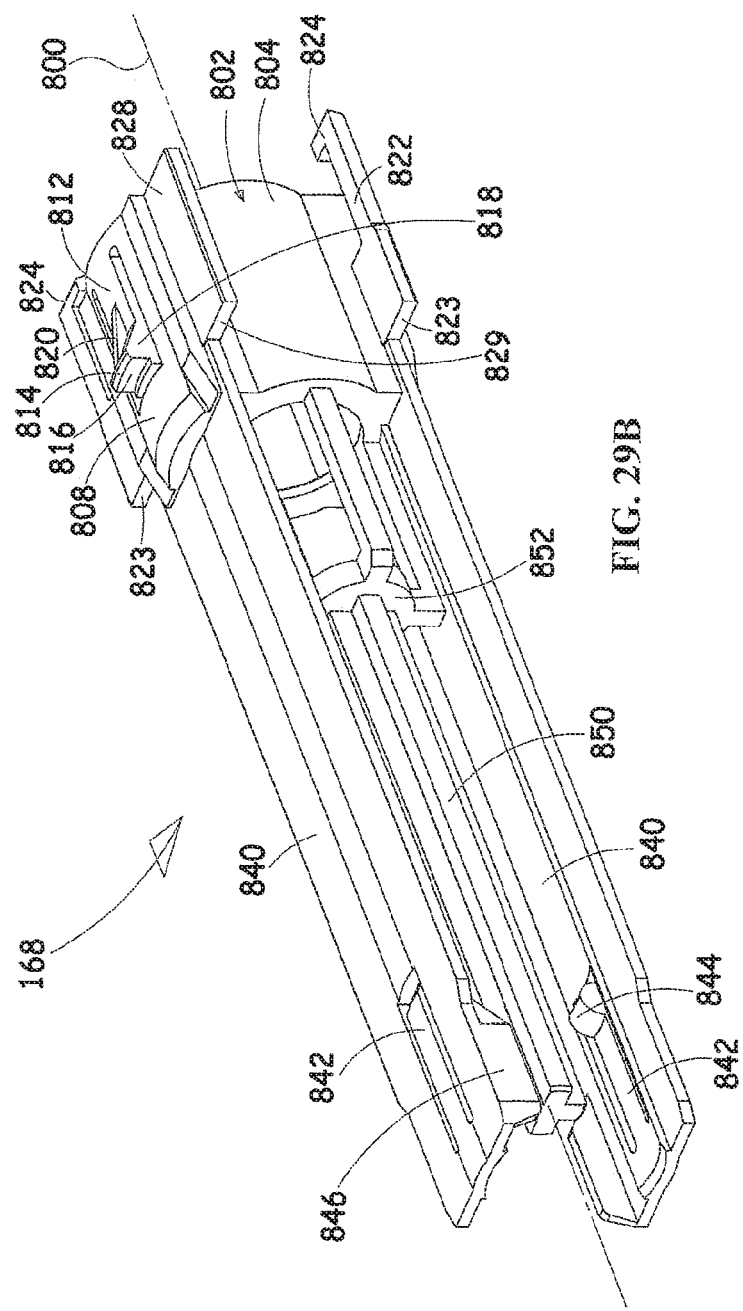
Figure 30D:
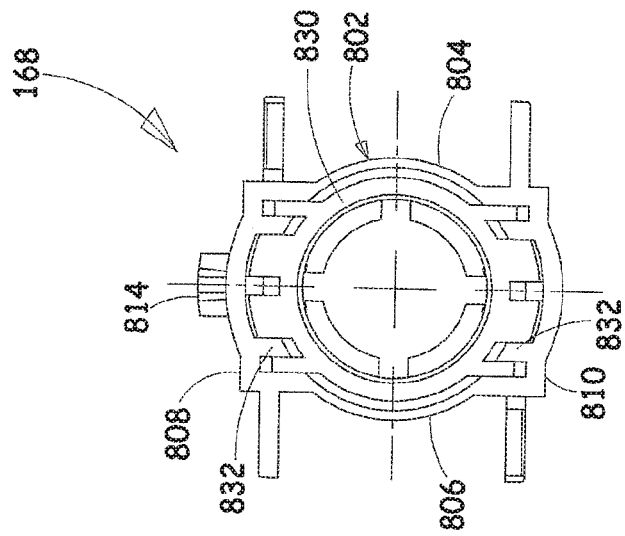
Figure 30C:
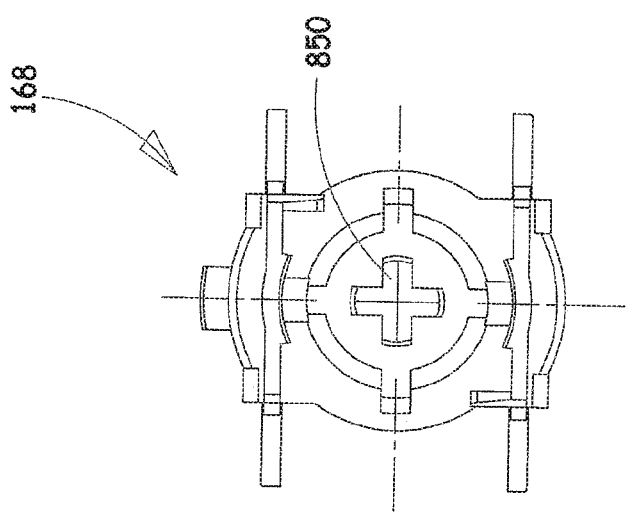
Figures 31A, 31B:
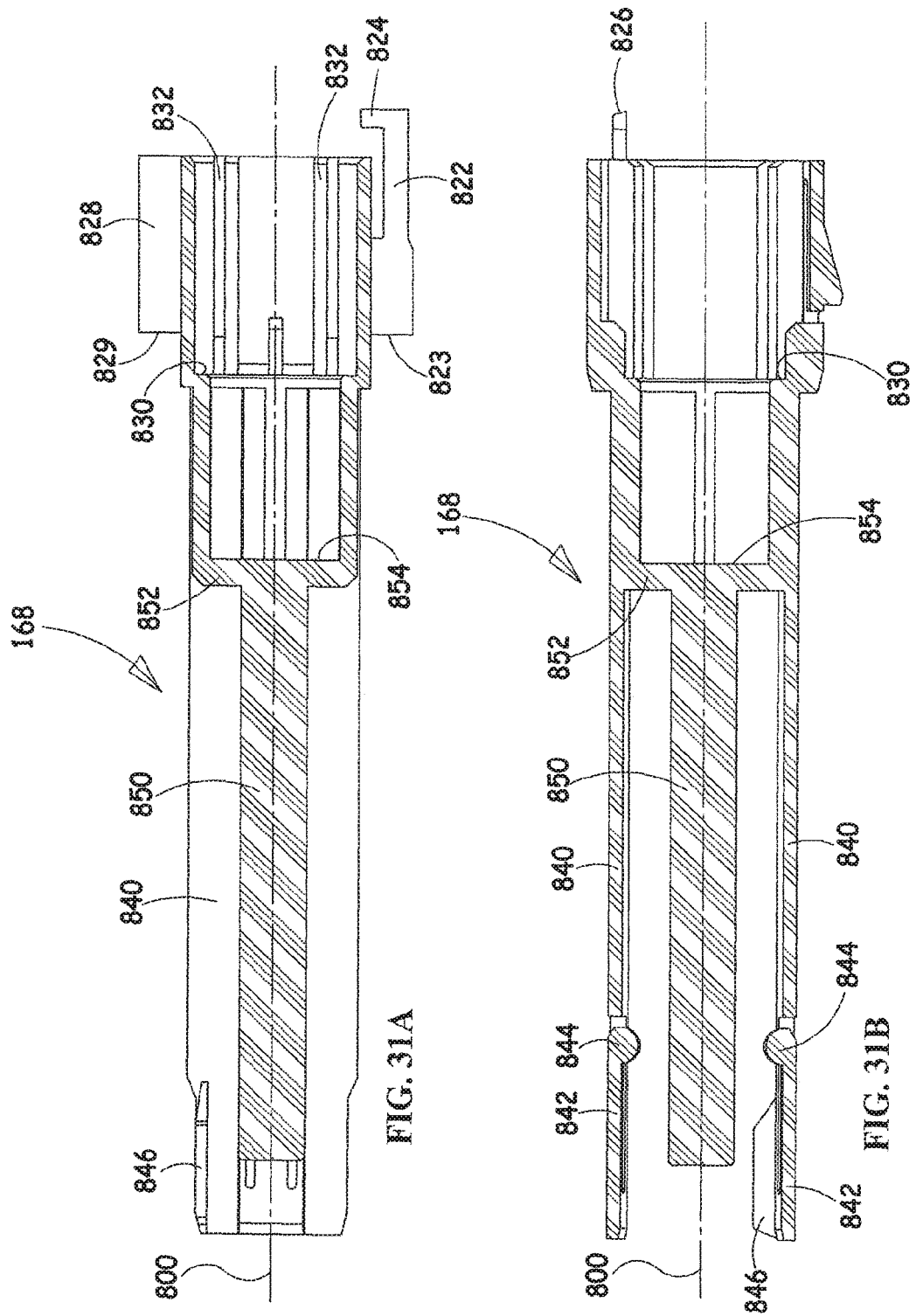
FIGS. 31A & 31B are simplified sectional illustrations of the plunger element taken along respective section lines A-A and B-B in FIGS. 30A & 30B.

Reference is now made to FIGS. 29A and 29B, which are simplified pictorial illustrations of a plunger element 168, which forms part of the reusable driving assembly 110 of the automatic injection device of FIG. 1, to FIGS. 30A, 30B, 30C and 30D, which are simplified respective top, side, front and back views thereof, and to FIGS. 31A and 31B, which are simplified sectional illustrations taken along respective section lines A-A and B-B in FIGS. 30A and 30B.

As seen in FIGS. 29A-31B, the plunger element 168 preferably is an integrally formed element, preferably injection molded of plastic and is arranged along a longitudinal axis 800. Plunger element 168 includes at a rearward end thereof a generally tubular portion 802 which defines side convex surfaces 804 and 806, and respective top and bottom convex surfaces 808 and 810, in the sense of FIGS. 29A and 29B. A flexible snap-engagement finger 812 is preferably provided on convex surface 808 and terminates in an outwardly facing protrusion 814 having a forward-facing surface 816.

Rearwardly of forward-facing surface 816 there are preferably provided a pair of side-by-side inclined outwardly facing ribs 818, and therebetween an inclined outwardly facing rib 820, which is preferably slightly longer than ribs 818.

A pair of flexible fingers 822 each extend axially rearwardly from a forward edge 823 thereof and outwardly of tubular portion 802 at diagonally opposite corners thereof and each terminate at an inwardly facing protrusion 824 having a tapered rearward edge 826.

A pair of ribs 828 extend axially rearwardly from a forward edge 829 thereof and outwardly of tubular portion 802 at diagonally opposite corners thereof, opposite to fingers 822.

Generally tubular portion 802 terminates forwardly at an inwardly-facing flange 830, which defines a forward facing spring seat for main spring 166 (FIG. 1). Extending rearwardly from inwardly-facing flange 830 there are preferably formed four inwardly directed axial ribs 832, which together with the internal surface of generally tubular portion 802, maintain the concentric orientation of main spring 166 within plunger element 168.

Extending forwardly from generally convex surfaces 808 and 810 are mounting arms 840, each of which includes at a forward end thereof a rearwardly extending flexible finger 842, having a rounded inwardly facing protrusion 844.

A pair of axial corner ribs 846 are located at diagonally opposite corners of mounting arms 840.

A plunger rod 850 is mounted on a base 852, which is in turn supported on mounting arms 840 and has a rearward-facing surface 854.

Figure 32A:
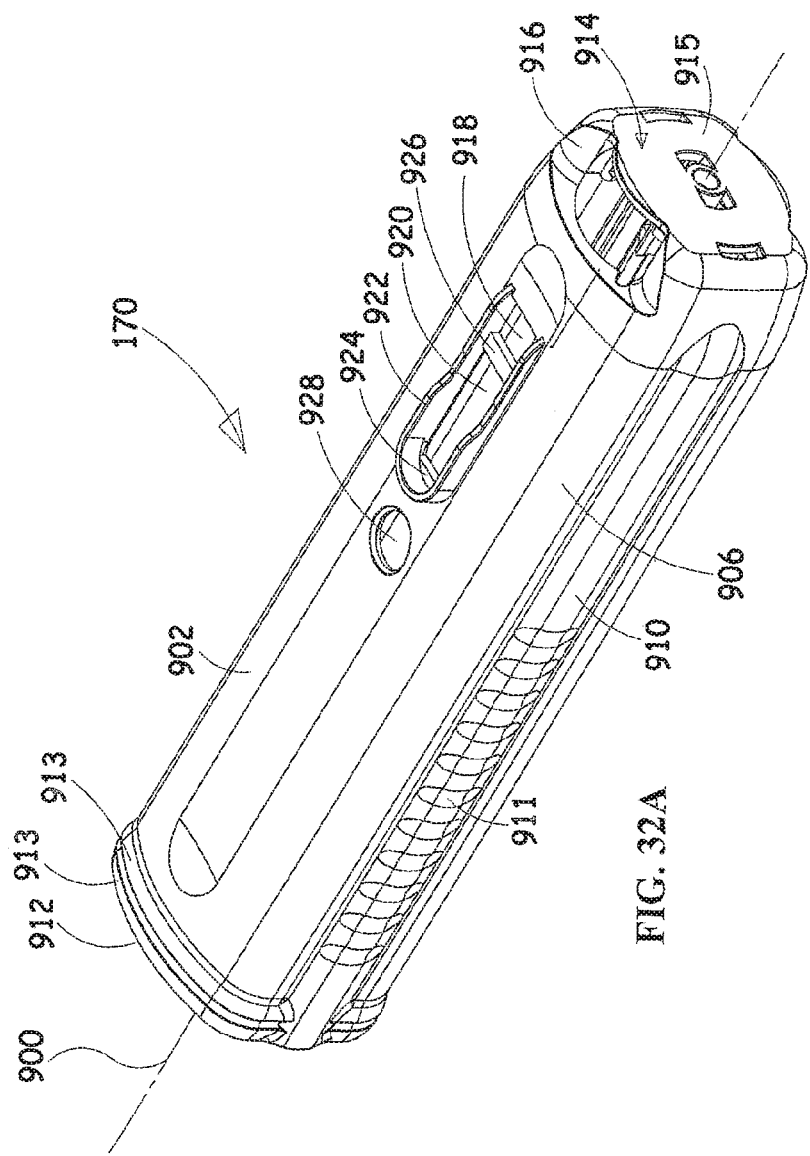
FIGS. 32A & 32B are simplified pictorial illustrations of a rear cover element of the automatic injection device of FIG. 1.
Figure 32B:
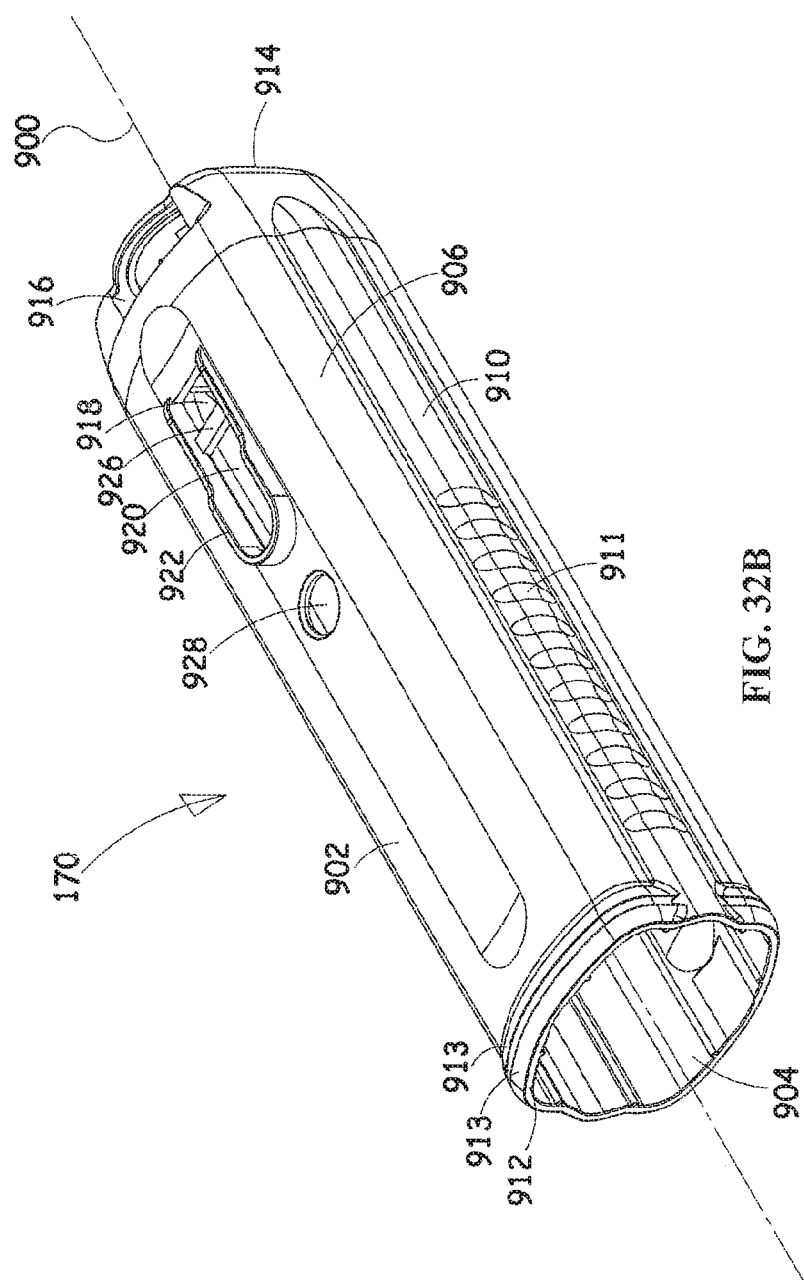
Figure 33A:
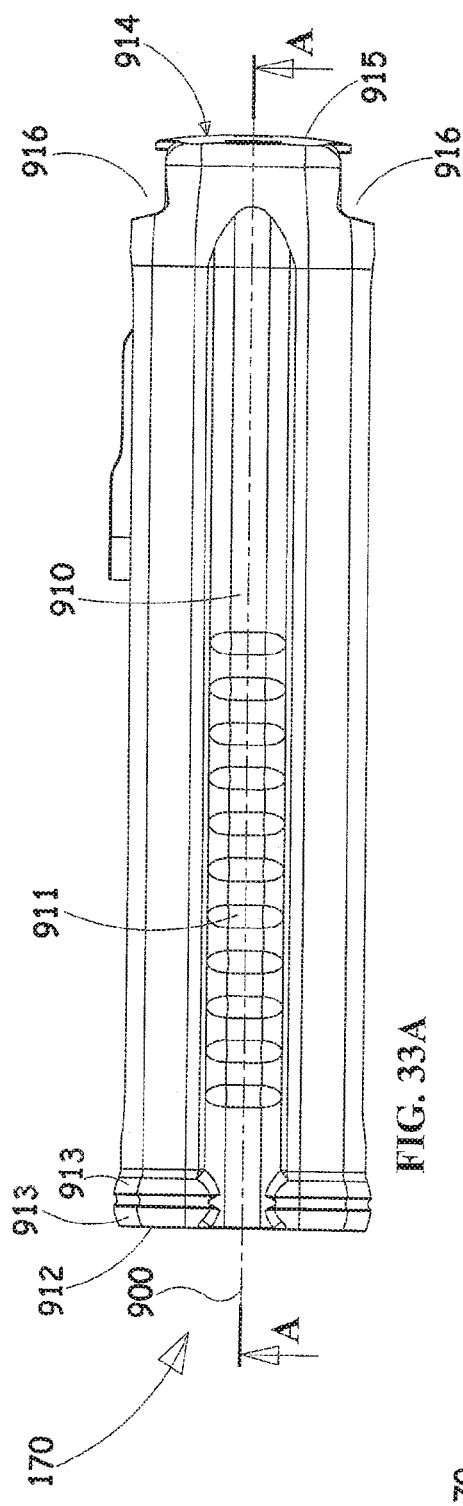
FIGS. 33A, 33B, 33C and 33D are simplified respective side, top, front and back views of the rear cover element of FIGS. 32A & 32B.
Figure 33B:
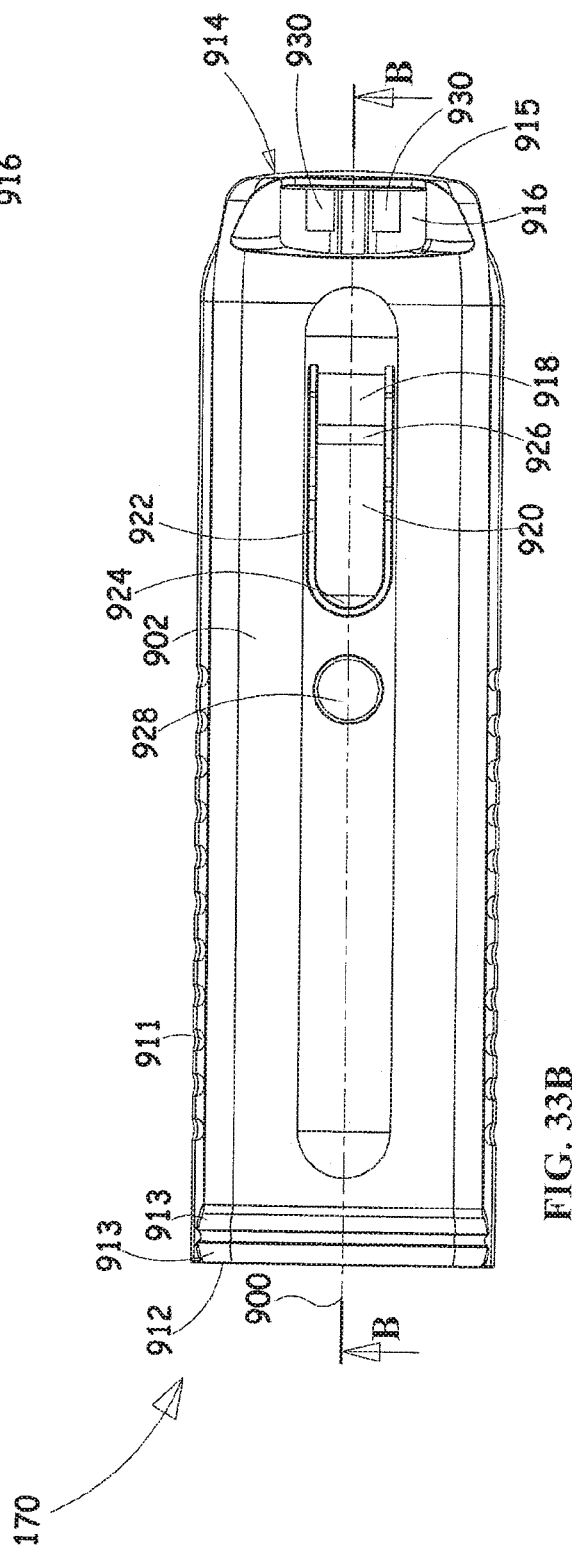
Figure 33D:
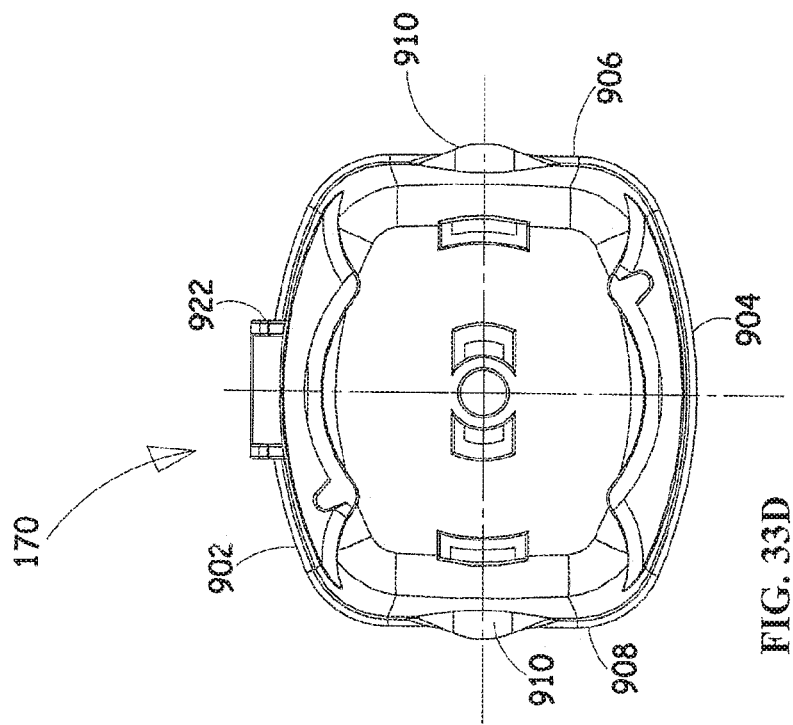
Figure 33C:
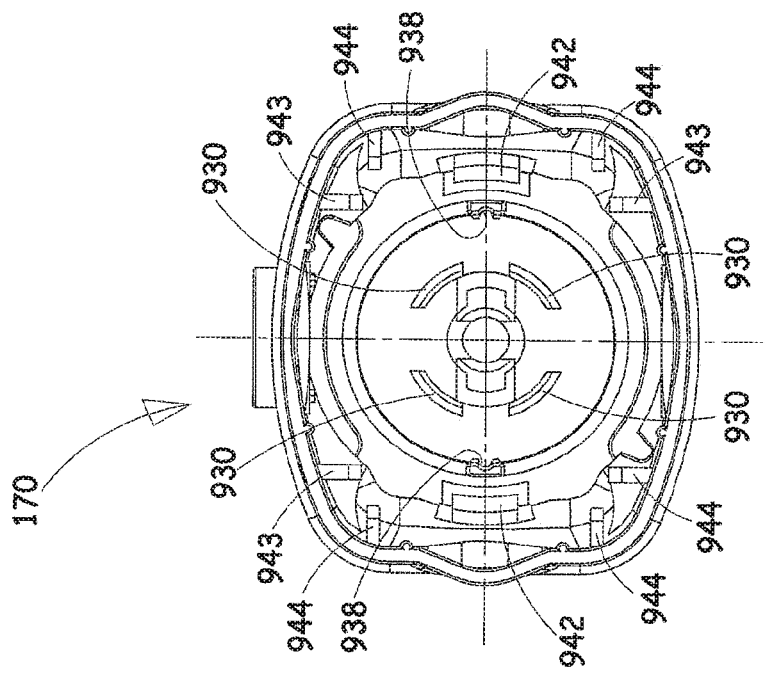

Reference is now made to FIGS. 32A and 32B, which are simplified pictorial illustrations of rear cover element 170 which forms part of the reusable driving assembly 110 of the automatic injection device of FIG. 1, to FIGS. 33A, 33B, 33C and 33D, which are simplified respective side, top, front and back views thereof, and to FIGS. 34A and 34B, which are simplified sectional illustrations taken along respective section lines A-A and B-B in FIGS. 33A and 33B.

As seen in FIGS. 32A-34B, the rear cover element 170 preferably is an integrally formed element, preferably injection molded of plastic and is arranged along a longitudinal axis 900. Rear cover element 190 preferably has a generally rectangular cross-section and includes slightly convex top and bottom walls 902 and 904 in the sense of FIGS. 32A & 32B and side walls 906 and 908.

Side walls 906 and 908 are each preferably formed with a convex longitudinal surface 910, having formed thereon multiple ridges 911, which generally define surfaces which are engaged by a user's fingers. Walls 902, 904, 906 and 908 together terminate at a forward end 912 of rear cover element 170 at which there are provided a pair of mutually adjacent generally circumferential ribs 913.

Walls 902, 904, 906 and 908 together terminate at a rearward end 914 of rear cover element 170 defining a generally planar rearward facing surface 915. Cutouts 916 are provided in walls 902 and 904 adjacent rearward end 914 of rear cover element 170.

Forward of cutout 916, wall 902 is formed with mutually axially aligned respective short and long rectangular apertures 918 and 920, which are together partially surrounded by a rib 922 having a profile which is higher in a forward direction and which tapers to an opening facing rearward end 914. Extending forwardly of aperture 920 to rib 922 is a stop surface 924. A transverse support portion 926 separates apertures 918 and 920. An inner facing surface 927 of wall 902 lies rearward of aperture 918.

Wall 902 is preferably formed with a round window 928, which is located forwardly of rib 922 and which enables a user to see whether the automatic injector device is cocked or not.

Extending internally and forwardly from rearward facing surface 915 are four circularly arranged centering protrusions 930, interiorly of which are located two snap-fit arms 932, each having an outwardly facing protrusion 934, and exteriorly of which are located two outer positioning protrusions 936, each formed with an internally facing grooves 938. Additionally there are provided two outer snap-fit fingers 940, each having an inwardly-facing protrusion 942.

Extending internally and forwardly from rearward facing surface 915 and along walls 902 and 904 are four longitudinal ribs 943. Extending internally and forwardly from rearward facing surface 915 and along walls 906 and 908 are four longitudinal ribs 944.

Reference is now made to FIGS. 35A and 35B, which are simplified pictorial illustrations of trigger button element 174, which forms part of the reusable driving assembly 110 of the automatic injection device of FIG. 1, to FIGS. 36A, 36B and 36C, which are simplified respective side, top and front views thereof, and to FIG. 37, which is a simplified sectional illustration taken along section line A-A in FIG. 36B.

As seen in FIGS. 35A-37, the trigger button element 174 preferably is an integrally formed element, preferably injection molded of plastic and is arranged along a longitudinal axis 950. Trigger button element 174 includes a main outwardly-facing surface 952, arranged along axis 950. Forward of main outwardly-facing surface 952 there is provided a tapered engagement surface 954, which has an edge configuration which conforms to the inner configuration of rib 922 of rear cover element 170.

Rearward of main outwardly-facing surface 952 there is provided an inward outwardly-facing surface 956, which is joined to main outwardly-facing surface 952 by an inwardly extending wall portion 958, having a rearwardly-facing surface 960.

Underlying main outwardly-facing surface 952 and part of engagement surface 954 is a main inwardly-facing surface 962, forwardly of which is a slightly inclined forward inwardly-facing surface 964. Rearward of main inwardly-facing surface 962 there is provided an inward inwardly-facing surface 966, which is joined to main outwardly-facing surface 952 by inwardly extending wall portion 958, having a forwardly-facing surface 968.

Extending inwardly from main inwardly-facing surface 962 and inclined forward inwardly-facing surface 964 are a pair of mutually spaced parallel protrusions 970, each having a forward facing edge 972, an inward facing edge 974 and an inclined inward and rearward facing edge 976.

Extending inwardly from main inwardly-facing surface 962, rearwardly of protrusions 970 is a transverse upstanding wall 978, which terminates in a rearwardly extending finger 980 having an outer facing surface 982, which faces main inwardly-facing surface 962 and is spaced therefrom and is provided with a protrusion 984 which faces main inwardly-facing surface 962 and is spaced therefrom.

Reference is now made to FIGS. 38A and 38B, which are simplified pictorial illustrations of safety-catch element 176, which forms part of the reusable driving assembly 110 of the automatic injection device of FIG. 1, to FIGS. 39A, 39B and 39C, which are simplified respective side, front and back views thereof, and to FIG. 40, which is a simplified sectional illustration taken along section line A-A in FIG. 39A.

As seen in FIGS. 38A-40, the safety-catch element 176 preferably is an integrally formed element, preferably injection molded of plastic and is arranged along a longitudinal axis 1000. Safety-catch element 176 includes a generally tubular portion 1002 from which radially protrude a pair of engagement protrusions 1004. Generally tubular portion 1002 has a rearwardly and inwardly-facing flange 1006 having formed on a rearwardly-facing surface 1008 a raised ring protrusion 1010. A pair of mutually circumferentially-spaced curved cutouts 1012 extend through flange 1006.

Generally tubular portion 1002 has a forwardly facing edge 1020 which has a pair of mutually circumferentially-spaced curved cut-outs 1022, having forward facing cut-out edges 1024.

Extending forwardly from an forward-facing surface 1026 of flange 1006 are a pair of generally coaxially, radially-extending ribs 1030, which join an internal circumferential rib 1031 to an interior surface 1032 of generally tubular portion 1002. Internal circumferential rib 1031 includes a pair of mutually circumferentially spaced curved cam surface defining rib portions 1033, each extending counterclockwise in the sense of FIG. 39B from an interior edge of each of ribs 1030.

Internal circumferential rib 1031 also includes a pair of mutually circumferentially spaced generally circular rib portion 1034, each of which follows in a counterclockwise direction a corresponding curved cam surface defining rib portions 1033.

Cam surface defining rib portions 1033 each define a cam surface 1036 which extends in a non-circular manner, slightly outwardly of an imaginary circular pathway joining generally circular rib portions 1034, which is indicated in FIG. 39B by a circular line 1038.

Each of generally circular rib portions 1034 includes a pair of outwardly facing protrusions. The pairs of protrusions are here designated by reference numerals 1040 and 1042.

Figure 41A:
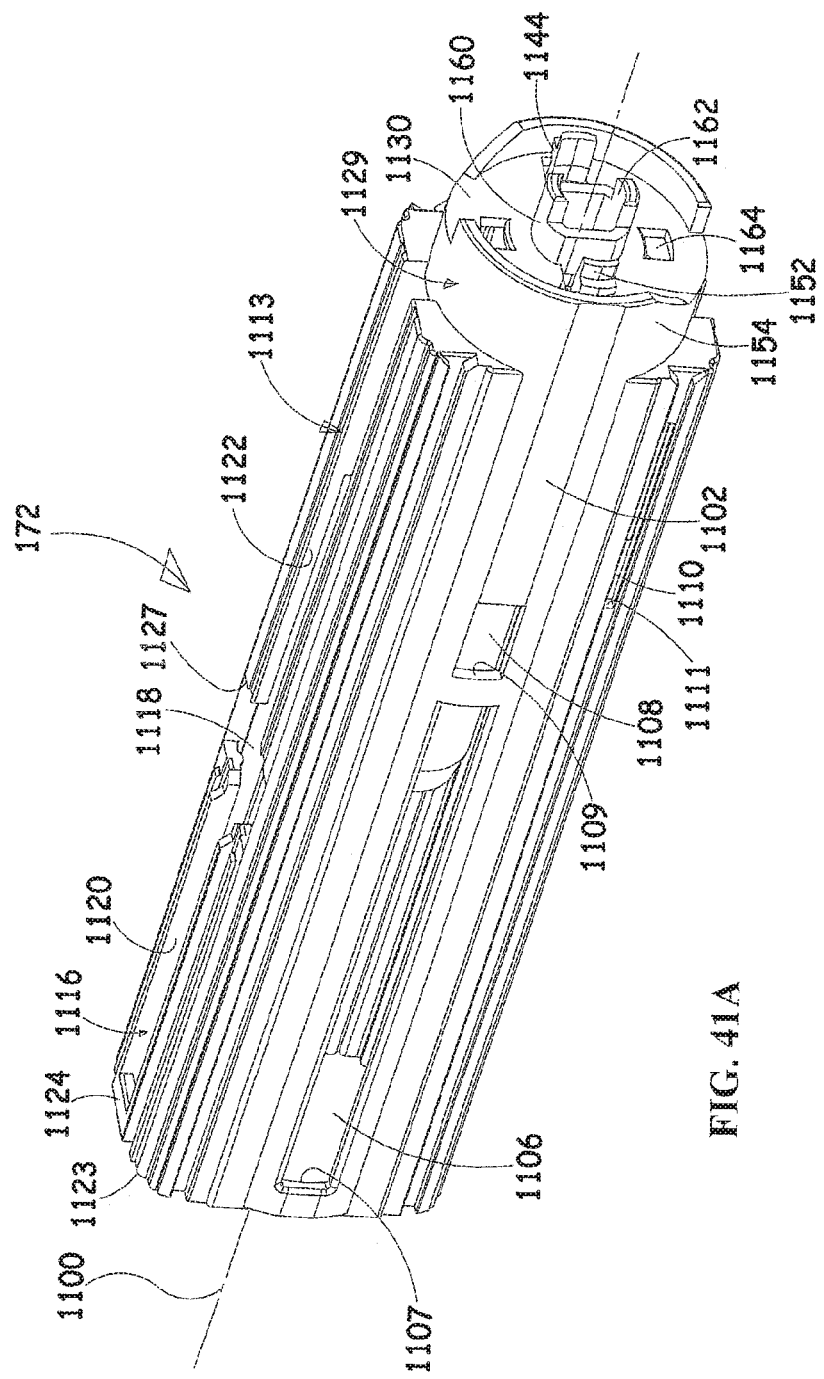
FIGS. 41A & 41B are simplified pictorial illustrations of a rear base element of the automatic injection device of FIG. 1.
Figure 41B:
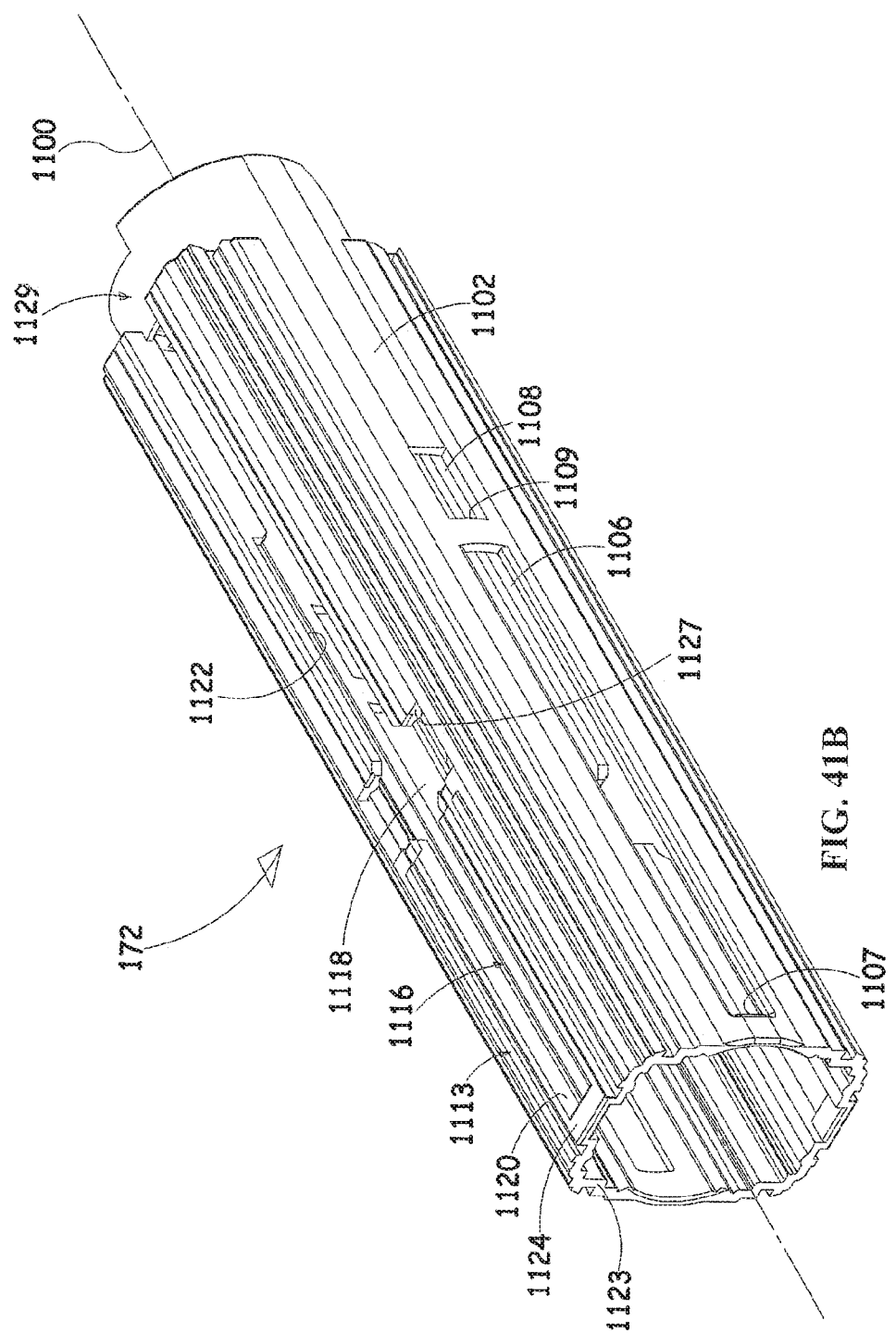
Figure 42C:
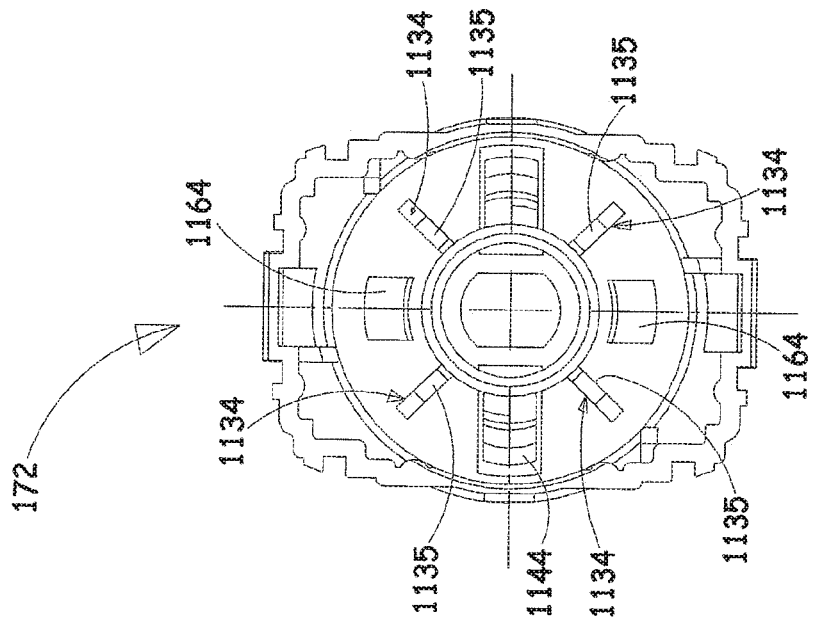
Figure 42D:
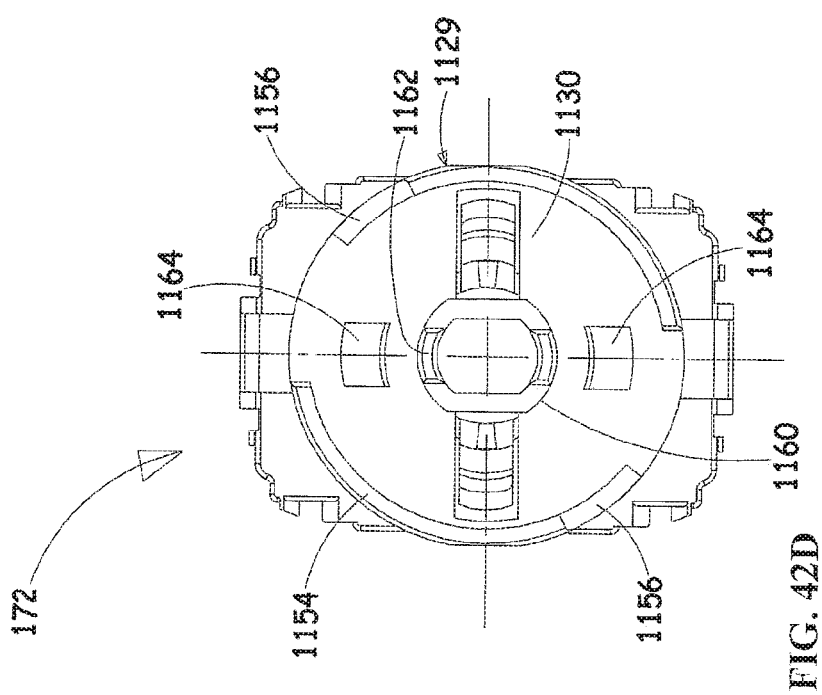

Reference is now made to FIGS. 41A and 41B, which are simplified pictorial illustrations of a rear base element 172, which forms part of the reusable driving assembly of the automatic injection device of FIG. 1, to FIGS. 42A, 42B, 42C and 42D, which are simplified respective side, top, front and back views thereof, and to FIGS. 43A and 43B, which are simplified sectional illustrations taken along respective section lines A-A and B-B in FIGS. 42A and 42B.

As seen in FIGS. 41A-43B, the rear base element 172 preferably is an integrally formed element, preferably injection molded of plastic and is arranged along a longitudinal axis 1100. The rear base element 172 preferably has a generally rectangular cross-section and includes slightly convex side walls 1102 and 1104 in the sense of FIG. 41A. Each of side walls 1102 and 1104 has a long rectangular slot 1106, having a forward edge 1107 and, rearwardly thereof, a short rectangular slot 1108 having a forward edge 1109. Each of side walls 1102 and 1104 also includes a narrow slot 1110, having a forward edge 1111. Interiorly of each of side walls 1102 and opposite narrow slot 1110 there is preferably provided an inwardly-directed axially extending rib 1112.

The rear base element 172 also includes top and bottom walls 1113 and 1114 respectively, each of which include an elongate slot 1116 having a relatively widened portion 1118, a relatively narrow forward portion 1120 and a relatively narrow rearward portion 1122. A forward end of relatively narrow forward portion 1120 is separated from a forward facing edge 1123 of rear base element 172 by a transverse portion 1124. An inwardly directed rib 1126 extends along part of one side of rearward portion 1122. Relatively widened portion 1118 defines a rearward edge 1127.

The rear base element 172 preferably defines along interior wall surfaces of respective side walls 1102 and 1104, elongate plunger travel guiding surfaces 1128.

The rear base element 172 terminates at a rearward end thereof in an end portion 1129 having a wall 1130, from a forwardly-facing surface 1131 of which extends forwardly a circular cylindrical tubular portion 1132 having four radially and longitudinally extending ribs 1134 extending outwardly therefrom and having forward facing edges 1135. Wall 1130 also defines a forward-facing shoulder 1136 interiorly of circular cylindrical tubular portion 1132. Tubular portion 1132 has a forward facing circumferential edge 1138.

A pair of side-to-side symmetric fingers 1140 extend backwardly from sides of cylindrical tubular portion 1132. Each of fingers 1140 includes a longitudinal portion 1142 which terminates a rearwardly- and outwardly-directed portion 1144. An undercut 1146 is defined by the junction between portions 1142 and 1144. Rearwardly- and outwardly-directed portion 1144 defines an outwardly-directed protrusion 1148 including a forwardly-facing tapered edge 1150 and a rearward outwardly-facing surface 1152.

A pair of circular partially circumferential ribs 1154 extend rearwardly from wall 1130. Each of ribs 1154 has a counterclockwise facing tapered edge 1156, in the sense of FIG. 42D.

A short tubular portion 1160, of generally rectangular cross section, also extends rearwardly from wall 1130 and terminates in a pair of rearward-facing protrusions 1162.

Wall 1130 is formed with a pair of mutually 180-degree spaced apertures 1164.

The foregoing describes the various elements of the automatic injection device of FIG. 1. The description which follows explains how the various elements of the automatic injection device of FIG. 1 cooperate in various operative orientations of the device.

Reference is now made to FIG. 44, which is a simplified assembled view illustration of the reusable driving assembly 110 of the automatic injection device of FIG. 1 in a storage operative orientation, to FIGS. 45A and 45B, which are simplified respective side and top views thereof, and to FIGS. 46A, 46B, 46C, 46D. 46E and 46F, which are simplified sectional illustrations taken along respective section lines A-A, B-B, C-C, D-D, E-E and F-F in FIGS. 45A and 45B.

As seen in FIGS. 44A-46C, in the storage operative orientation the forward cover element 158 is partially inserted in the rear cover element 170 along mutually coaxial axes 650 and 900. The extent of partial insertion is indicated by the fact that the forward end 912 of the rear cover element 170 lies generally along actuatable operative orientation indicating circumferentially extending line 712.

Details of the relative operative orientations of the various elements of the reusable driving assembly 110 of the automatic injection device of FIG. 1 in the storage operative orientation will now be described with reference to FIGS. 47-55.

Reference is now made to FIG. 47, which is a simplified side view illustration in the sense of FIGS. 44-46C of an assembly including the forward cover element 158 (FIGS. 22A-25B), the needle penetration depth selector 152 (FIGS. 17A-19) and the forward base element 150 (FIGS. 14A-16B). Reference is also made to FIGS. 48A, 48B and 48C, which are simplified cross-sectional illustrations taken along respective lines A-A, B-B and C-C in FIG. 47 and FIG. 48D is a pictorial cross-sectional illustration taken along lines C-C in FIG. 47.

As seen in FIGS. 47-48D, the needle penetration depth selector 152 (FIGS. 17A-19) is located within the forward cover element 158, such that its longitudinal axis 550 is coaxial with longitudinal axis 650 of forward cover element 158 and positioned therealong such that it protrudes through cutouts 680 formed in forward cover element 158. More specifically forward circumferential protrusion 554 lies adjacent forward edges of cutouts 680.

It is seen that snap engagement protrusions 704 of the forward cover element 158 are preferably located in two of four rearward-facing circumferentially distributed recesses 558 of needle penetration depth selector 152, depending on the rotational position of the needle penetration depth selector 152 about axes 550 and 650.

The forward base element 150 is arranged such that its longitudinal axis 400 is coaxial with axes 550 and 650 and is positioned transversely to axes 550 and 650 with respect to the forward cover element 158 and to needle penetration depth selector 152 by engagement of forward corner protrusions 456 and 458 of forward base element with internally facing ribs 710 of forward cover element 158.

The axial position of forward base element 150 relative to forward cover element 158 is selectably variable within predetermined limits, as a function of rotation of needle penetration depth selector 152 about axis 550 due to engagement of outwardly extending protrusions 404 and 406 of forward base element 150 with respective helical internal threadings 560 and 562 of needle penetration depth selector 152. Rotation of forward base element 150 about axes 400, 550 and 650 is prevented by the aforesaid engagement of forward corner protrusions 456 and 458 of forward base element with internally facing ribs 710 of forward cover element 158. The axial position of forward base element 150 relative to forward cover element 158 along axes 400, 550 and 650 is indicated by outer facing rib 446 of forward base element 150, which rib which can be viewed through windows 676 of forward cover element 158, relative to needle depth setting scale 678 appearing alongside windows 676.

A pair of tabs 702 of forward cover element 158 engage rectangular slots 492 of forward base element 150.

Figure 50B:
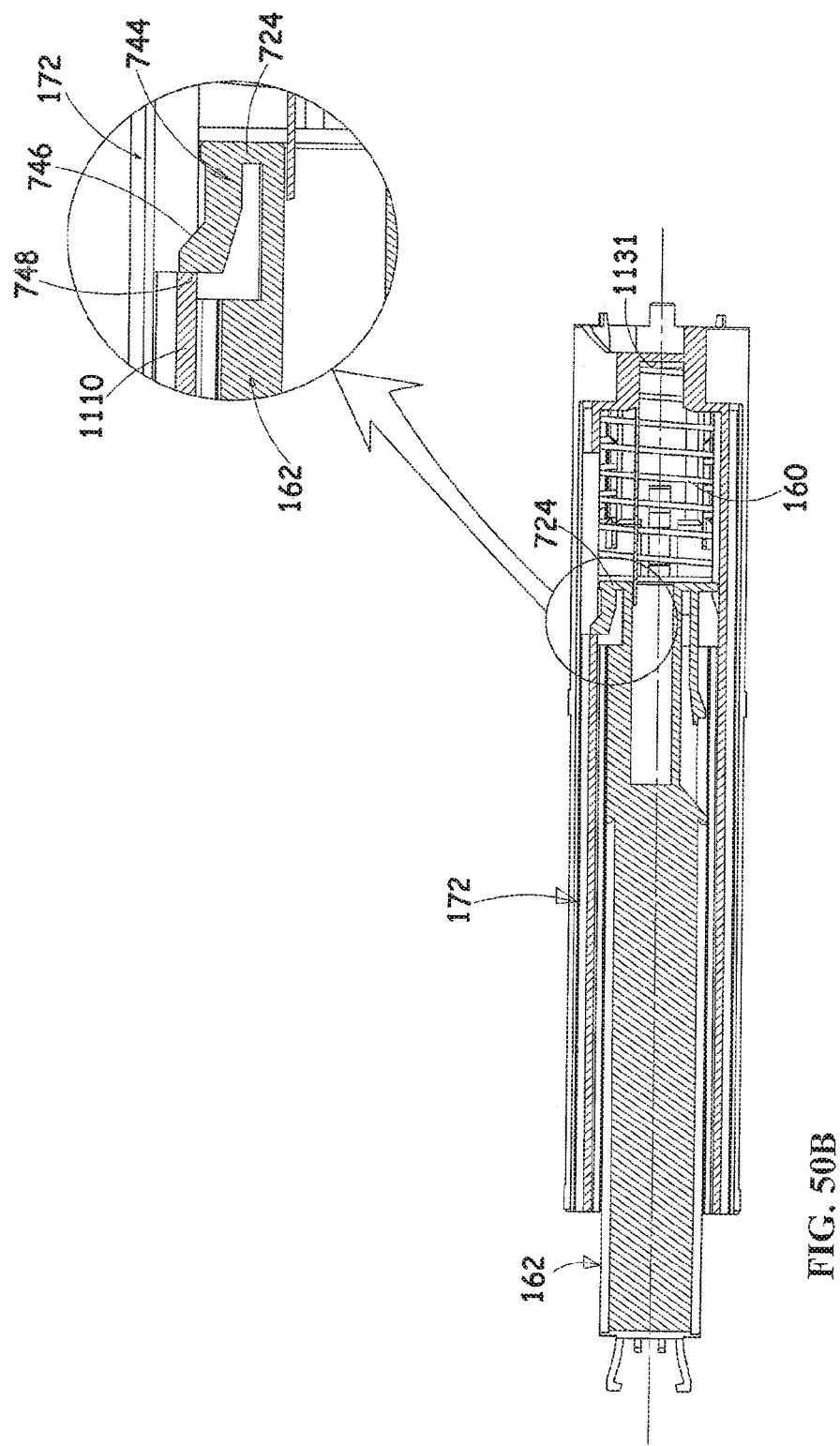

Reference is now made to FIGS. 49A and 49B, which are simplified respective side and top views, in the sense of FIGS. 44-46D, of an assembly of needle guard deploying spring 160, needle guard deploying element 162 (FIGS. 26A-28B) and rear base element 172 (FIGS. 41A-43B). Reference is also made to FIGS. 50A and 50B, which is simplified respective sectional illustrations taken along lines A-A and B-B in FIG. 49A.

As seen in FIGS. 49A-50B, needle guard deploying spring 160 and needle guard deploying element 162 are both disposed within rear base element 172 such that the longitudinal axis of spring 160 is coaxial with respective longitudinal axes 720 and 1100 of needle guard deploying element 162 and rear base element 172. Spring 160 is seated at a rearward end thereof on forwardly-facing surface 1131 of rear base element 172 and is seated at a forward end thereof on circumferential flange 724 of needle guard deploying element 162 and urges the needle guard deploying element 162 forwardly. Needle guard deploying element 162 is retained against forward displacement when in the storage operative orientation by engagement of fingers 744 thereof with corresponding narrow slots 1110 of rear base element 172.

Reference is now made to FIG. 51, which is a simplified side view, in the sense of FIGS. 44-46D, of an assembly of rear cover element 170 (FIGS. 32-34B), trigger button element 174 (FIGS. 35A-37) and safety catch element 176 (FIGS. 38A-40). Reference is also made to FIGS. 52A and 52B, which are simplified respective planar and pictorial cross-sectional view both taken along lines A-A in FIG. 51. Reference is also made to FIG. 53, which is a simplified cross-sectional view taken along lines B-B in FIG. 51.

As seen in FIGS. 51-53, the safety catch element 176 is located within the rear cover element 170, such that it's longitudinal axis 1000 is coaxial with longitudinal axis 900 of rear cover element 170. Longitudinal ribs 944 of the rear cover element 170 engage tubular portion 1002 of the safety catch element 176 for centering thereof about longitudinal axis 1000. Inwardly-facing protrusions 942 of rear cover element 170 engage forward facing cut-out edges 1024 of curved cut-outs 1022 of the safety catch element 176 and are operative to prevent forward displacement and limit rotation of the safety catch element 176 about axes 900 and 1000.

Outwardly facing protrusions 1040 of the safety catch element 176 engage a pair of internally facing grooves 938 formed in corresponding outer positioning protrusions 936 of rear cover element 170. This engagement ensures that in the storage operative orientation, the safety catch element 176 is in a disengaged operative orientation.

The positioning of trigger button element 174 relative to rear cover element 170 in the storage operative orientation is seen to be as follows:

Inward outwardly-facing surface 956 of trigger button element 174 underlies inner facing surface 927 of wall 902. Transverse support portion 926 of the rear cover element 170 is engaged by trigger button element 174 in a socket defined by main inwardly facing surface 962, transverse upstanding wall 978, rearwardly-extending finger 980 and protrusion 984 of trigger button element 174.

Figure 55:
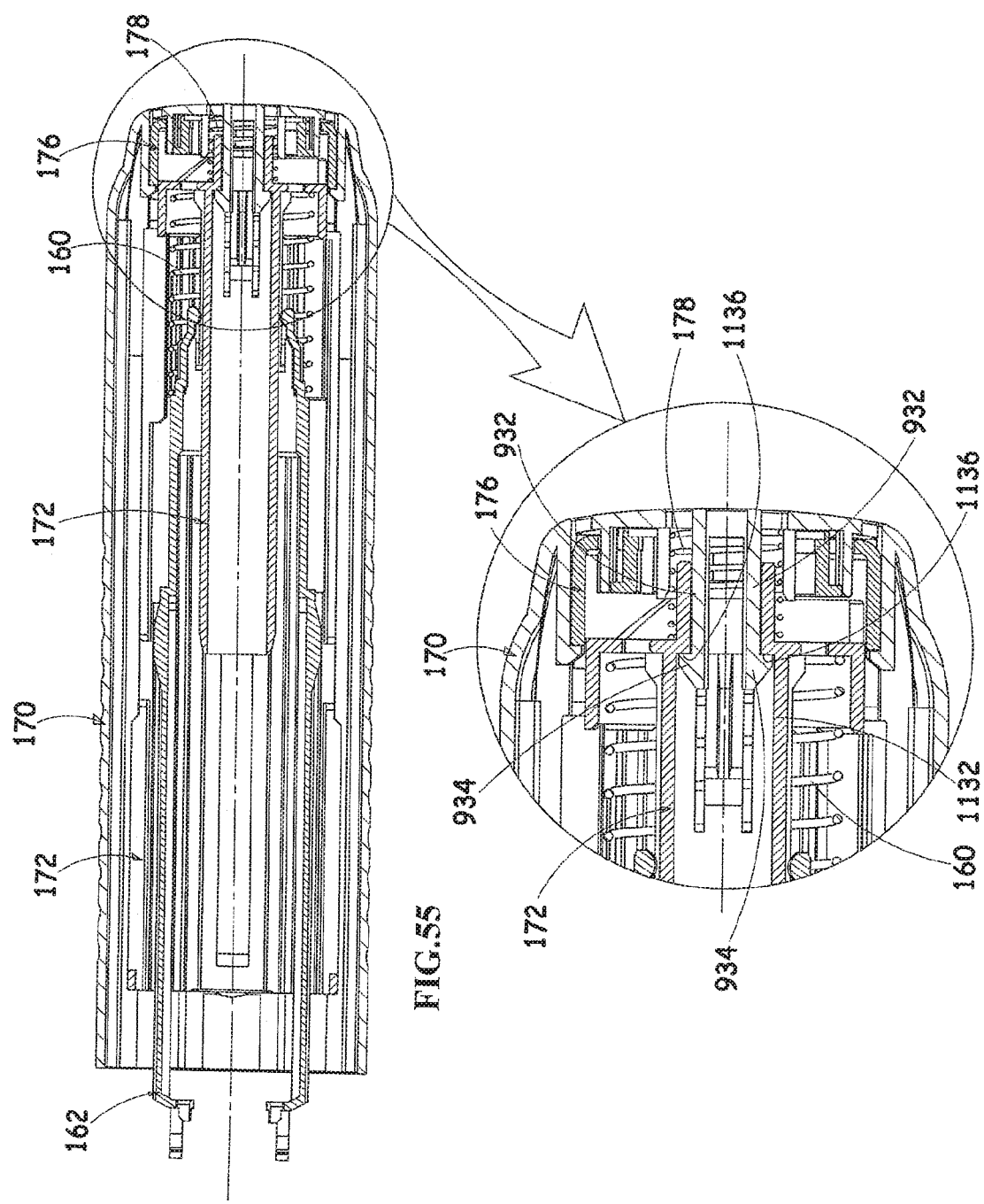
FIG. 55 is a simplified sectional illustration taken along lines A-A in FIG. 54B.

Reference is now made to FIGS. 54A and 54B which are simplified respective side and top view illustrations of an assembly which includes the assembly of FIGS. 49A-50B mounted within the assembly of FIGS. 51-53 such that axes 720, 900, 1000 and 1100 are all mutually coaxial. Reference is also made to FIG. 55, which is a simplified sectional illustration taken along lines A-A in FIG. 54B. The assembly of FIGS. 54A-55 also includes injection site engagement sensing spring 178 (FIG. 1), which urges the rear base element 172 forwardly along mutually coaxial axes 720, 900, 1000 and 1100.

As seen in FIGS. 54A-55, protrusions 934 of snap-fit arms 932 of rear cover element 170 engage forward-facing shoulder 1136, located interiorly of circular cylindrical tubular portion 1132 of rear base element 172. This engagement prevents spring 178 from displacing rear base element 172 forwardly.

Returning now to FIGS. 44-46F, it is seen that main spring 166 and plunger element 168 are assembled together with the assembly of FIGS. 54A-55 such that the longitudinal axis of the main spring 166 and the longitudinal axis 800 of plunger element 168 are coaxial with axes 720, 900, 1000 and 1100.

It is also seen that the cocked orientation retaining elements 154 and cocking springs 156 are assembled together with the assembly of FIGS. 47-48D.

The combined assembly of FIGS. 44-46F is arranged such that all of axes 400, 550, 650, 720, 800, 900, 1000 and 1100 are mutually coaxial.

Figure 46A:
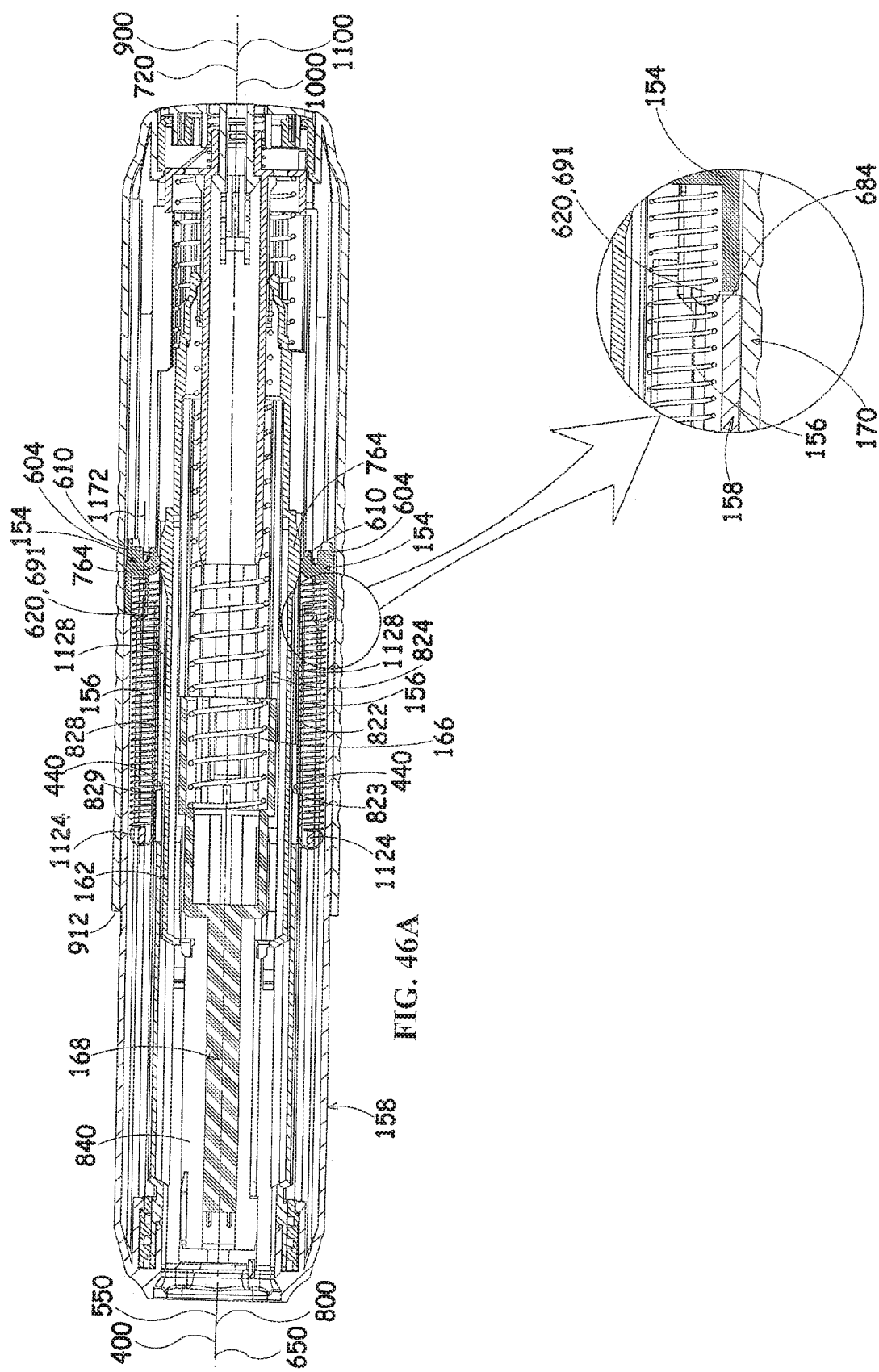
FIGS. 46A, 46B, 46C, 46D, 46E and 46F, which are simplified sectional illustrations taken along respective section lines A-A, B-B, C-C, D-D, E-E and F-F in FIGS. 45A and 45B.
Figure 46B:
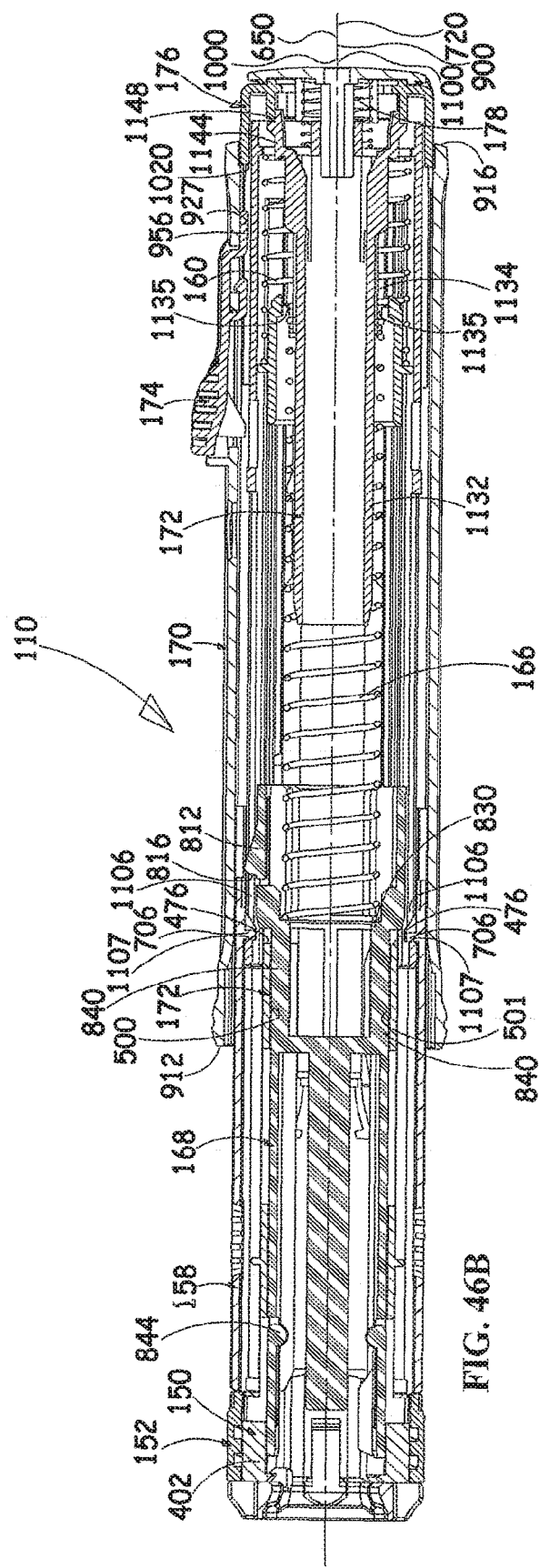

With particular reference to FIG. 46B, it can be seen that snap engagement finger 812 is located forwardly of trigger button element 174.

With particular reference to FIGS. 44 and 46A, it is noted that cocked orientation retaining elements 154 engage respective rearward facing edges 682 and 684 of the forward cover element 158 such that forward-facing protrusions 614 of cocked orientation retaining elements 154 lie in notches 690 formed in respective rearward facing edges 682 and 684 of the forward cover element 158, whereby the axis 620 of each of cocked orientation retaining elements 154 is coaxial with a corresponding axis 691 of one of respective rearward facing edges 682 and 684 of the forward cover element 158.

It is also noted that cocking springs 156 are each attached at a rearward end thereof to a corresponding hook 610 of a cocked orientation retaining element 154. Cocked springs 156 are each attached at a forward end thereof to a corresponding transverse portion 1124 of rear base element 172. Cocking springs 156 thus extend along respective tensioning axes 1170 and 1172, which extend transversely relative to coaxial axes 620 and 691 and thus apply a rotational moment to respective cocked orientation retaining elements 154 about coaxial axes 620 and 691, urging rotation of cocked orientation retaining elements 154 in a direction such that rearward facing end portions 604 are urged inwardly.

Inward displacement of rearward facing end portions 604 does not take place when the reusable driving assembly 110 is in the storage operative orientation due to engagement of hooks 610 of cocked orientation retaining elements 154 with corresponding elongate protrusions 764 of needle guard deploying element 162.

It is further appreciated that due to the engagement of hooks 610 with corresponding elongate protrusions 764 of needle guard deploying element 162, rearward ends 607 of cocked orientation retaining elements 154 lie outwardly of relatively widened portion 1118 of rear base element 172, thereby permitting relative longitudinal axial displacement of cocked orientation retaining elements 154, thus enabling relative longitudinal axial displacement of the forward cover element 158 and the rear cover element 170.

With particular reference to FIG. 46B, it is seen that rear base element 172 is slidably engaged with forward cover element 158 and the rearward displacement of rear base element 172 relative to forward cover element 158 is limited by engagement of internally facing protrusions 706 of the forward cover element 158 with slots 1106 of rear base element 172 and more specifically with forward edges 1107 of slots 1106.

With particular reference to FIGS. 46A-46C, 46E and 46F, it is noted that main spring 166 is seated at a rearward end thereof on forward edges 1135 of ribs 1134 of rear base element 172 and surrounds tubular portion 1132. A forward end of main spring 166 is seated on flange 830 of plunger element 168. Plunger element 168 is partially located within rear base element 172 wherein ribs 828 and fingers 822 of plunger element 168 slidably engage plunger travel guiding surfaces 1128 of rear base element 172.

Mounting arms 840 of plunger element 168 engage corresponding internal elongate recesses 500 and 501 of forward base element 150. Forward-facing edges 823 and 829 of respective fingers 822 and ribs 828 engage the rearward-most edge 440 of forward base element 150. As noted above with reference to FIGS. 47-48D, the forward displacement of forward base element 150 relative to forward cover element 158 is limited via engagement with the needle penetration depth selector 152. Accordingly, in the storage operative orientation, the forward displacement of plunger element 168 relative to forward cover element 158 along axis 1100 in response to urging of main spring 166, which is preferably partially compressed, is limited, to an extent selected by a user employing the needle penetration depth selector 152.

Figure 46C:
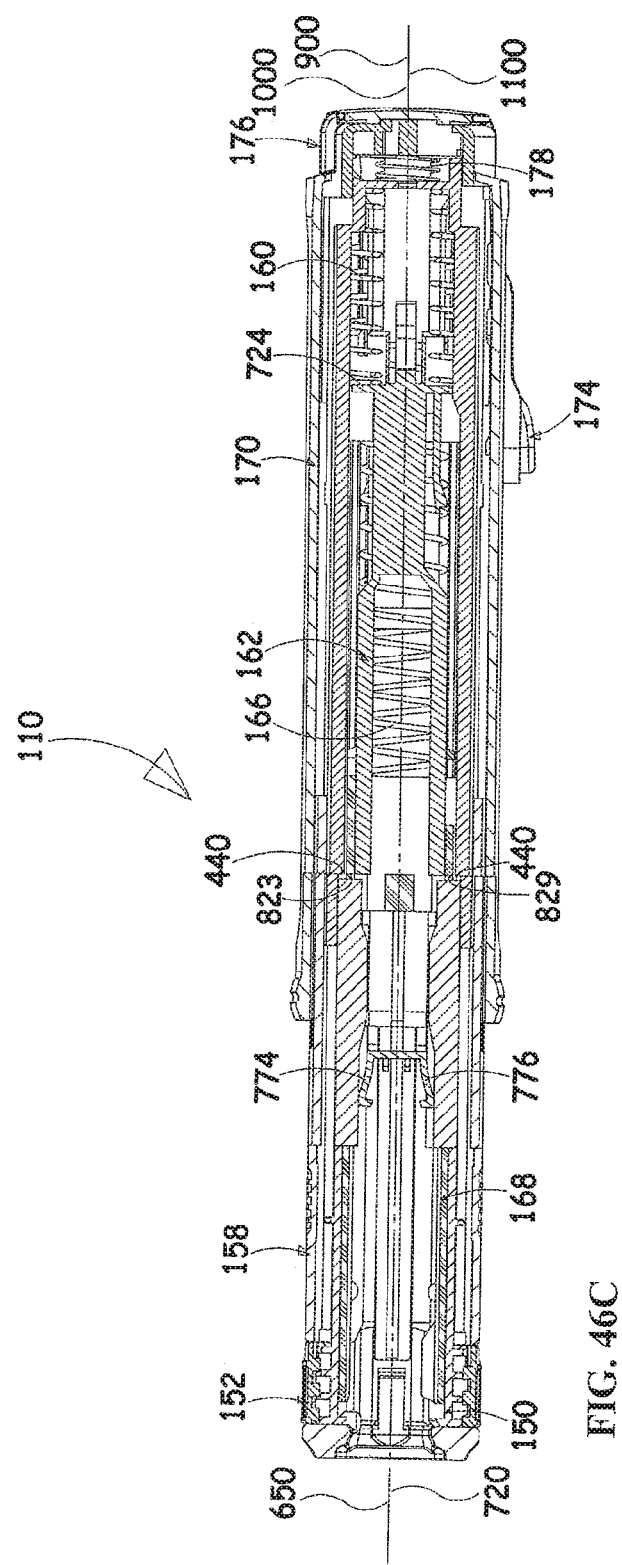
Figure 46E:
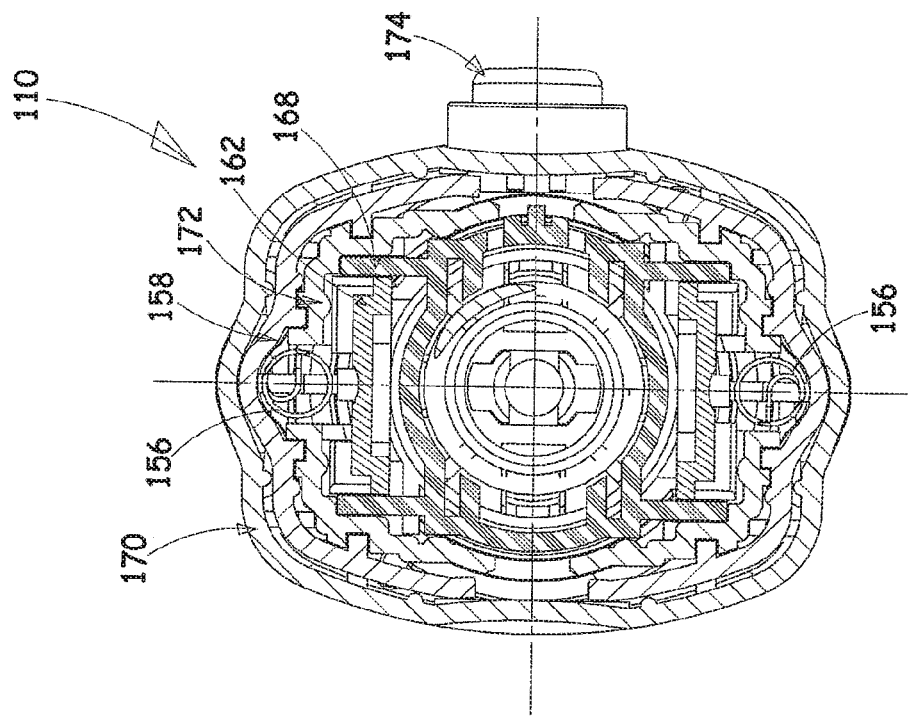
Figure 46D:
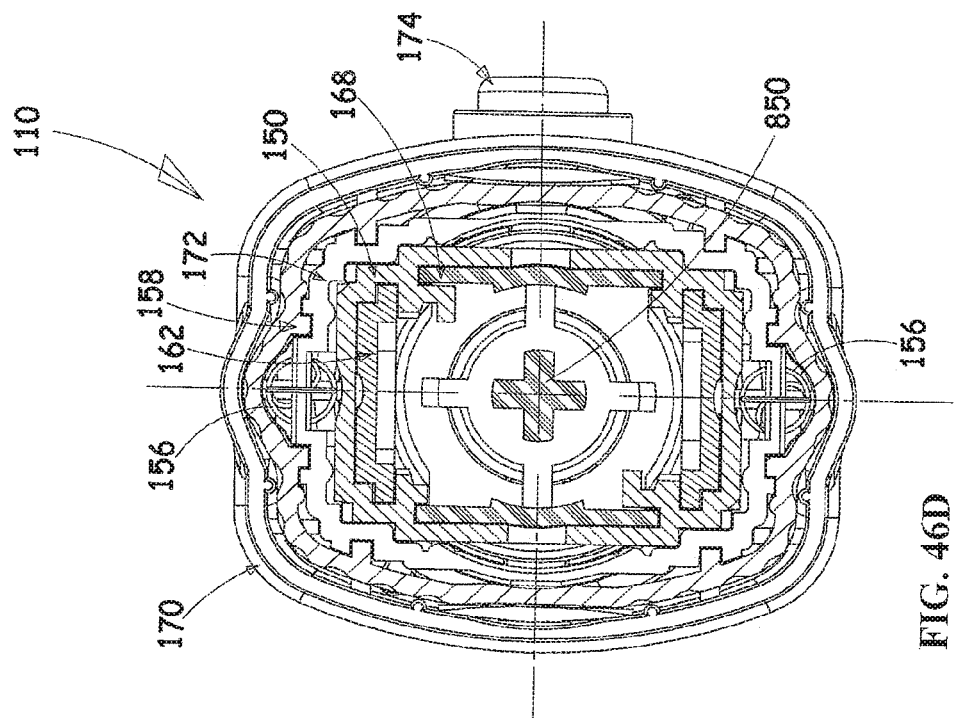
Figure 46F:
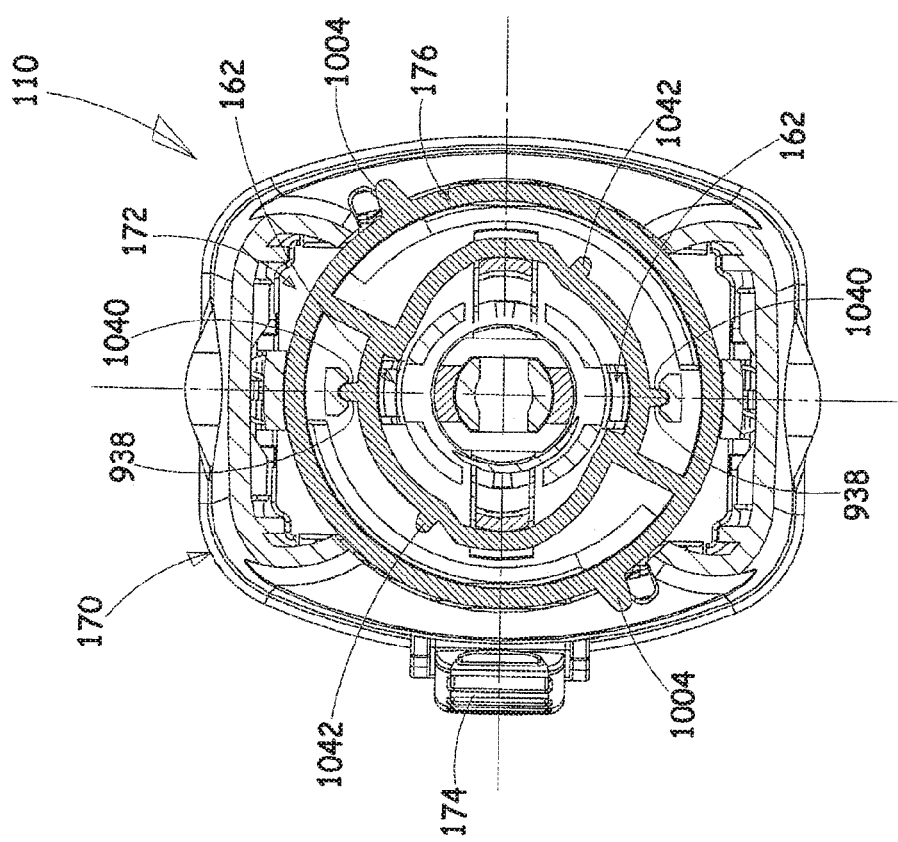

With particular reference to FIG. 46C, it is seen that axial fingers 774 and 776 of needle guard deploying element 162 are in a relative open orientation in the storage operative orientation of the reusable driving assembly 110.

With particular reference to FIG. 45A, it is seen that in the storage operative orientation, the main spring 166 is viewable via round window 928, indicating that the reusable driving assembly 110 is not cocked. It is also seen in FIG. 45A and in FIG. 46F that the safety catch element 176 is in a disengaged operative orientation, which does not prevent injection. As will be described hereinbelow, in other operative orientations, the safety catch element 176 is in an engaged operative orientation.

In the storage operative orientation, as required, the user sets the desired needle penetration depth by rotation of the needle penetration depth selector element 152. Four needle penetration depth settings are typically provided: 6 mm, 8 mm, 10 mm and 12 mm, where rotation of the needle penetration depth selector element 152 by 90° is required to move between one setting to the next. The user can observe the current setting through windows 676 at both sides of the injector, thus allowing both right-handed and left-handed users to easily observe the needle depth setting during rotation.

It is appreciated that needle penetration depth selection can be customized either for different depth settings, or obviated.

Figure 56:
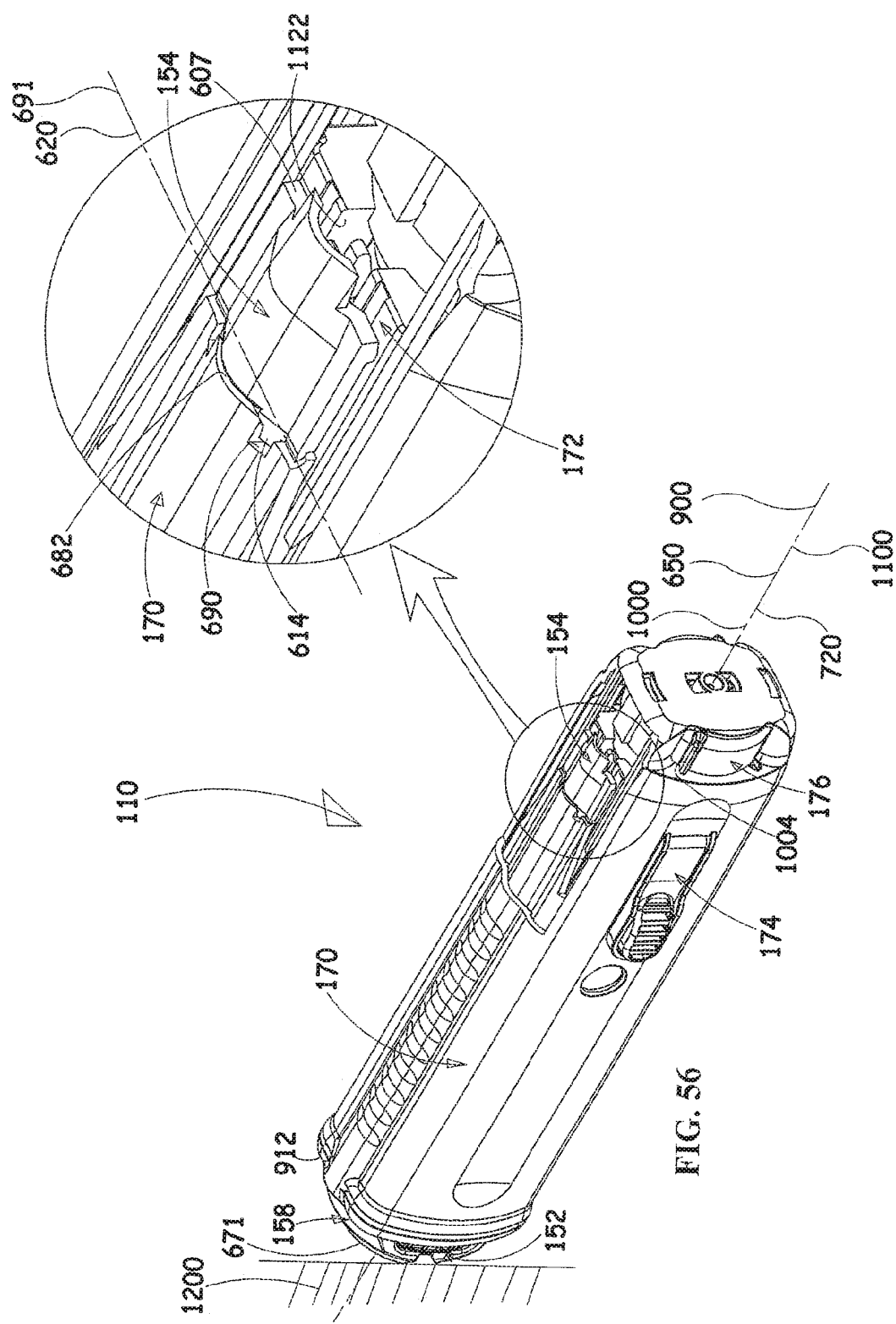
FIG. 56 is a simplified assembled view illustration of the reusable driving assembly of the automatic injection device of FIG. 1 in a cocking operative orientation.

Reference is now made to FIG. 56, which is a simplified assembled view illustration of the reusable driving assembly 110 of the automatic injection device of FIG. 1 in a cocking operative orientation, to FIGS. 57A and 57B, which are simplified respective side and top views thereof, and to FIGS. 58A, 58B, 58C and 58D, which are simplified sectional illustrations taken along respective section lines A-A, B-B, C-C and D-D in FIGS. 57A and 57B.

The cocking operative orientation seen in FIGS. 56-58D is preferably realized by a user taking the reusable driving assembly 110 in its storage operative orientation, as seen in FIGS. 44-55 and rotating safety catch element 176 by engaging engagement protrusions 1004, so that it is in a safety catch engaged operative orientation. The user, holds the reusable driving assembly 110 in one hand, by grasping the rear cover element 170. The user, while grasping the rear cover element 170, applies an axial force along axes 650 and 900 forcing forward edge 671 of the forward cover element 158 against a surface 1200, causing tensioning of cocking springs 156 and compression of main spring 166.

As seen in FIGS. 56-58D, in the cocking operative orientation, the forward cover element 158 is nearly fully inserted in the rear cover element 170 along mutually coaxial axes 650 and 900. The extent of insertion in the cocking operative orientation is generally seen in FIG. 58B, and is limited by engagement of forward facing circumferential edge 1138 of tubular portion 1132 of rear base element 172 with back surface 854 of base 852 of plunger element 168.

Figure 58A:
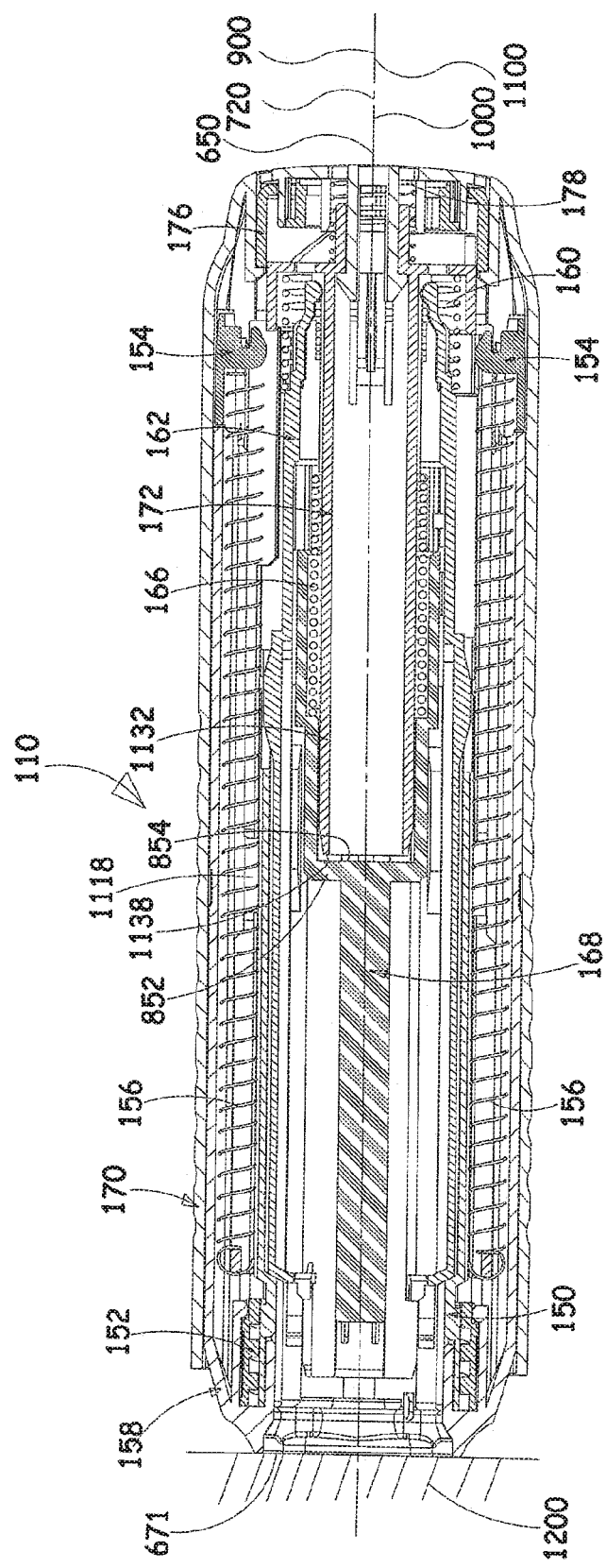
FIGS. 58A, 58B, 58C and 58D are simplified sectional illustrations taken along respective section lines A-A, B-B, C-C and D-D in FIGS. 57A and 57B.
Figure 58B:
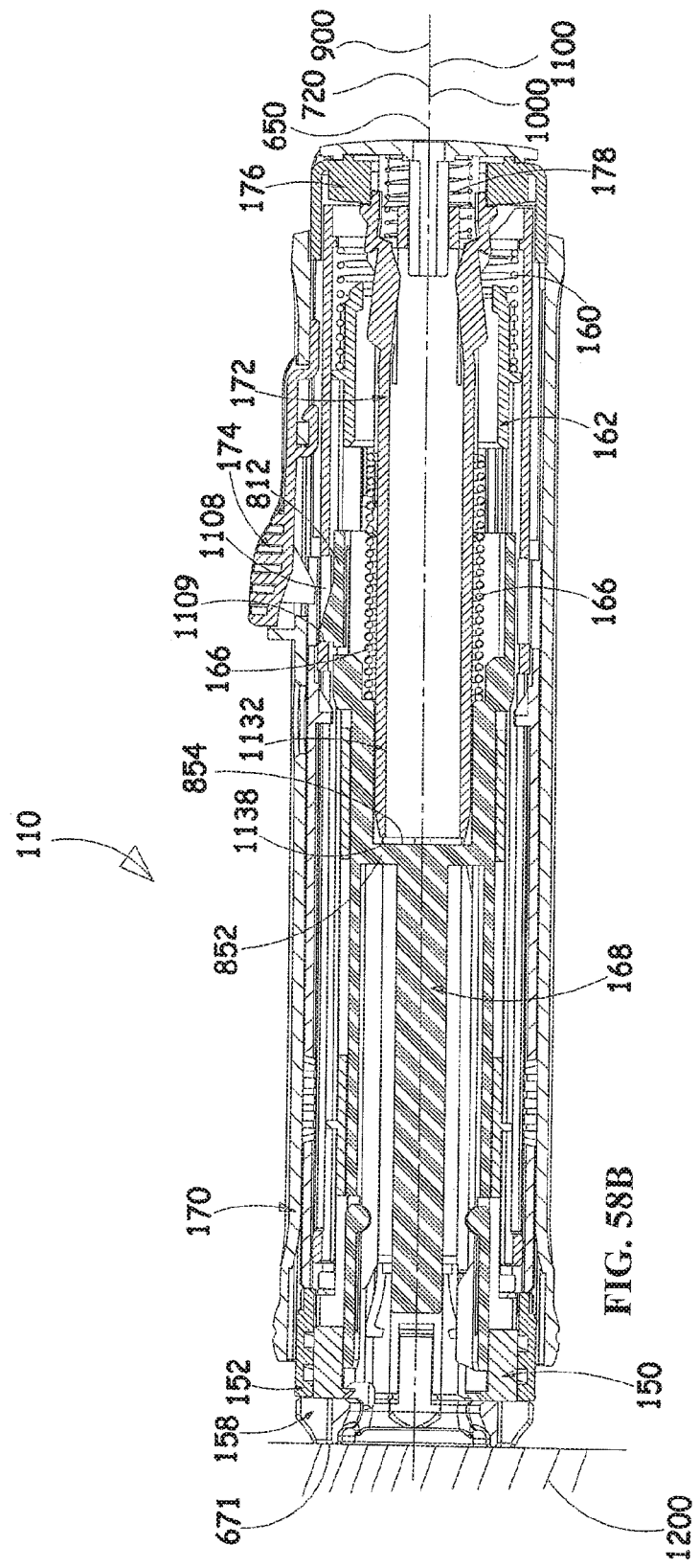

With particular reference to FIG. 58B, it can be seen that snap engagement finger 812 of plunger element 168 underlies trigger button element 174 and finger 812 is in engagement with forward edge 1109 of slot 1108 in rear base element 172, thereby retaining plunger element 168 in a cocked operative orientation.

Figure 58C:
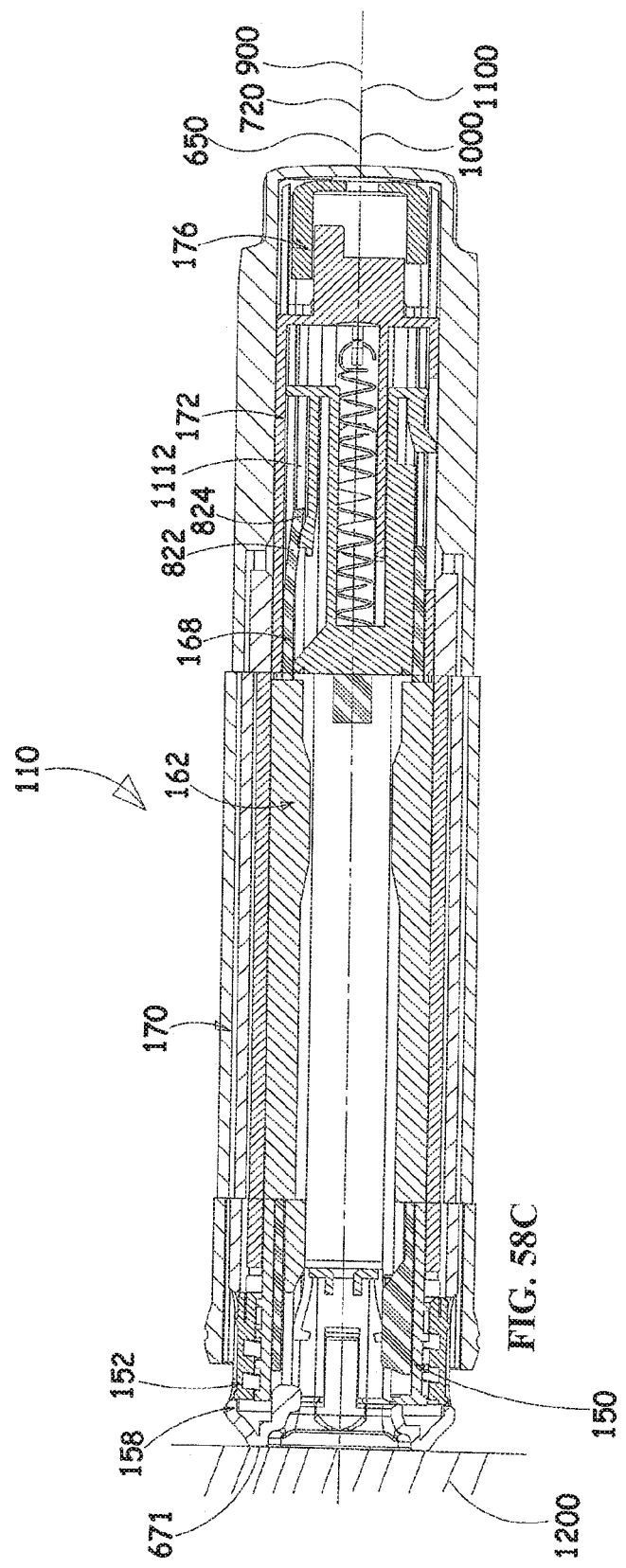
Figure 58D:
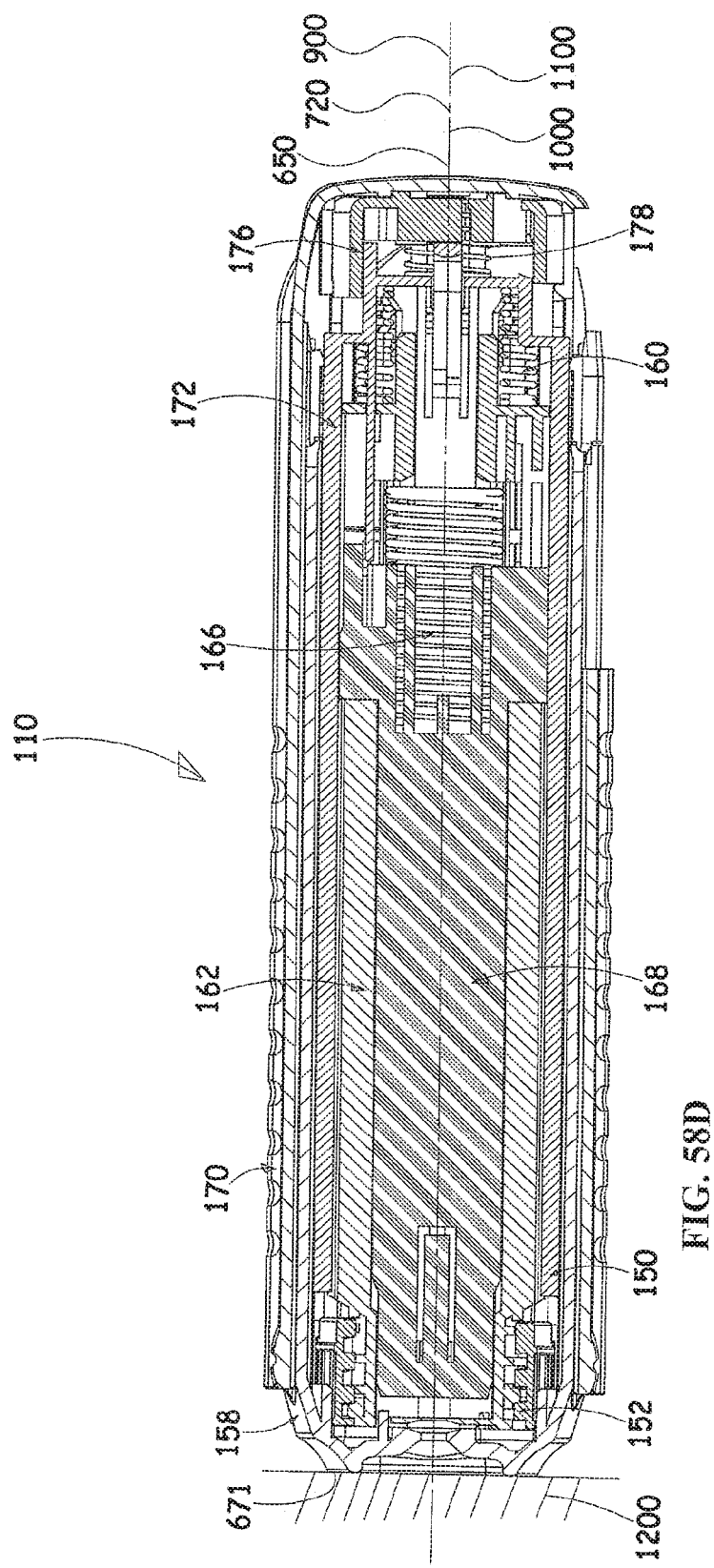

With particular reference to FIG. 58C, it can be seen that in the cocked operative orientation, that the inwardly facing protrusions 824 of flexible fingers 822 of plunger element 168 are urged towards each other by engagement thereof with inwardly-directed axially extending ribs 1112 of rear base element 172.

With particular reference to FIG. 56, it can be seen that in the cocked operative orientation, cocked orientation retaining elements 154 are rearwardly displaced relative to widened portion 1118 of elongate slot 1116 of rear base element 172, as compared with their operative orientation in the storage operative orientation and are located adjacent a rearward end of rearward portion 1122 of slot 1116.

Figure 59:
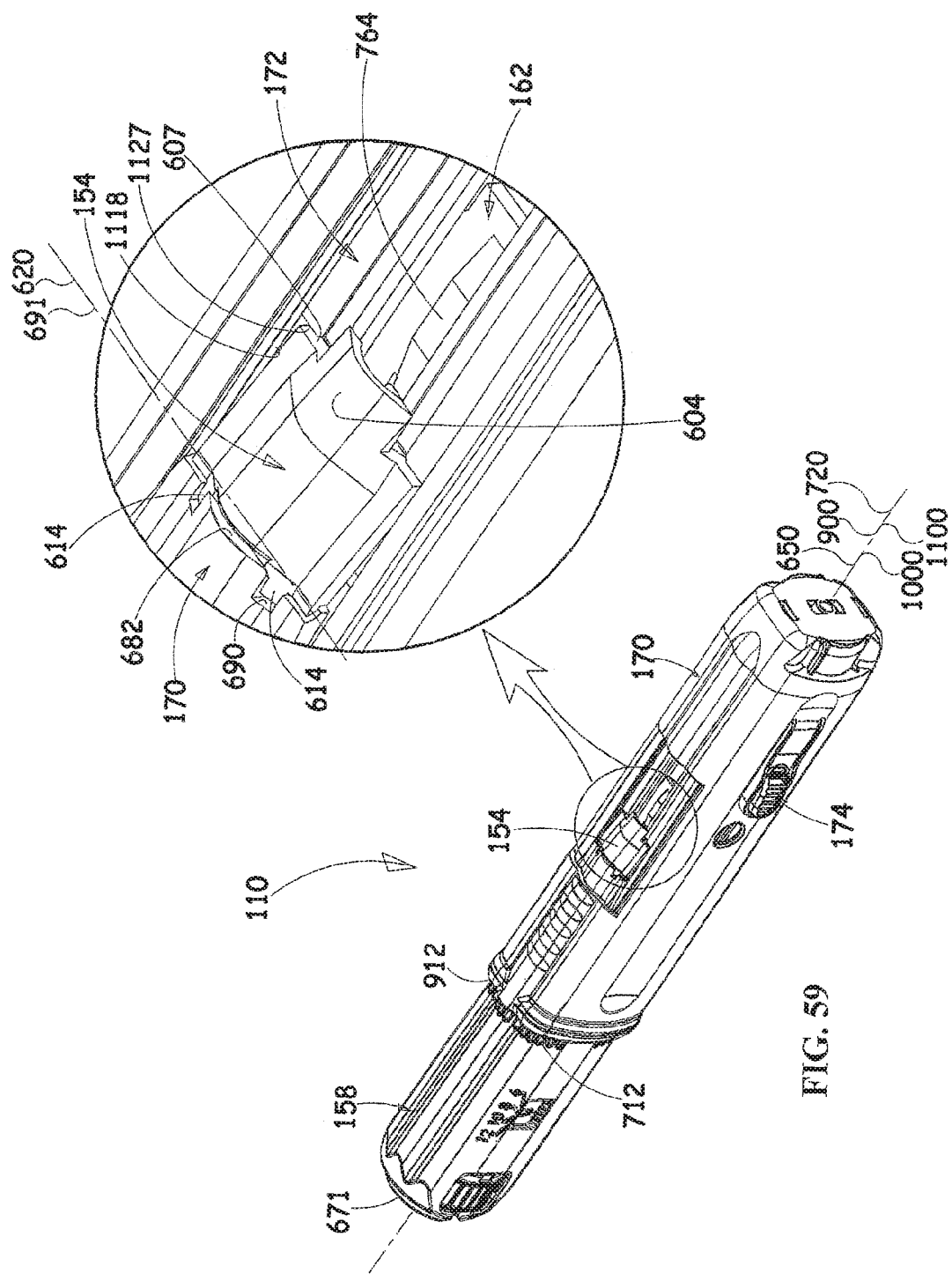
FIG. 59 is a simplified assembled view illustration of the reusable driving assembly of the automatic injection device of FIG. 1 in a cocked operative orientation.

Reference is now made to FIG. 59, which is a simplified assembled view illustration of the reusable driving assembly 110 of the automatic injection device of FIG. 1 in a cocked operative orientation, to FIGS. 60A and 60B, which are simplified respective side and top views of the reusable driving assembly 110 and of disposable cassette assembly 100 arranged coaxially therewith ready for insertion thereinto, and to FIGS. 61A, 61B, 61C and 61D, which are simplified sectional illustrations taken along respective section lines A-A, B-B, C-C and D-D in FIGS. 60A and 60B.

The cocked operative orientation seen in FIGS. 59-61D is preferably realized by a user taking the reusable driving assembly 110 in its cocking operative orientation, as seen in FIGS. 56-58D. The user, holding the reusable driving assembly 110 in one hand, by grasping the rear cover element 170 releases the axial force earlier applied along axes 650 and 900 by distancing forcing forward edge 671 of the forward cover element 158 from a surface 1200, thereby allowing tensioned cocking springs 156 to displace forward cover element 158 forwardly to its relative orientation vis a vis the rear cover element 170 in the storage operative orientation.

Figure 61A:
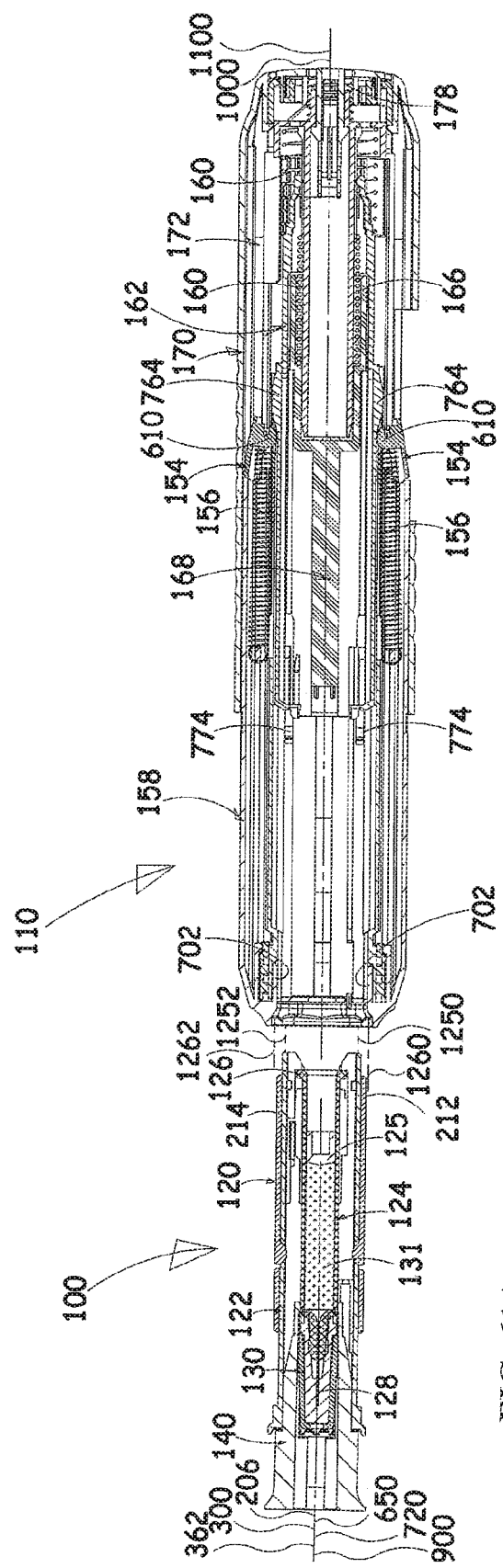
FIGS. 61A, 61B, 61C and 61D are simplified sectional illustrations taken along respective section lines A-A, B-B. C-C and D-D in FIGS. 60A and 60B.
Figure 61B:
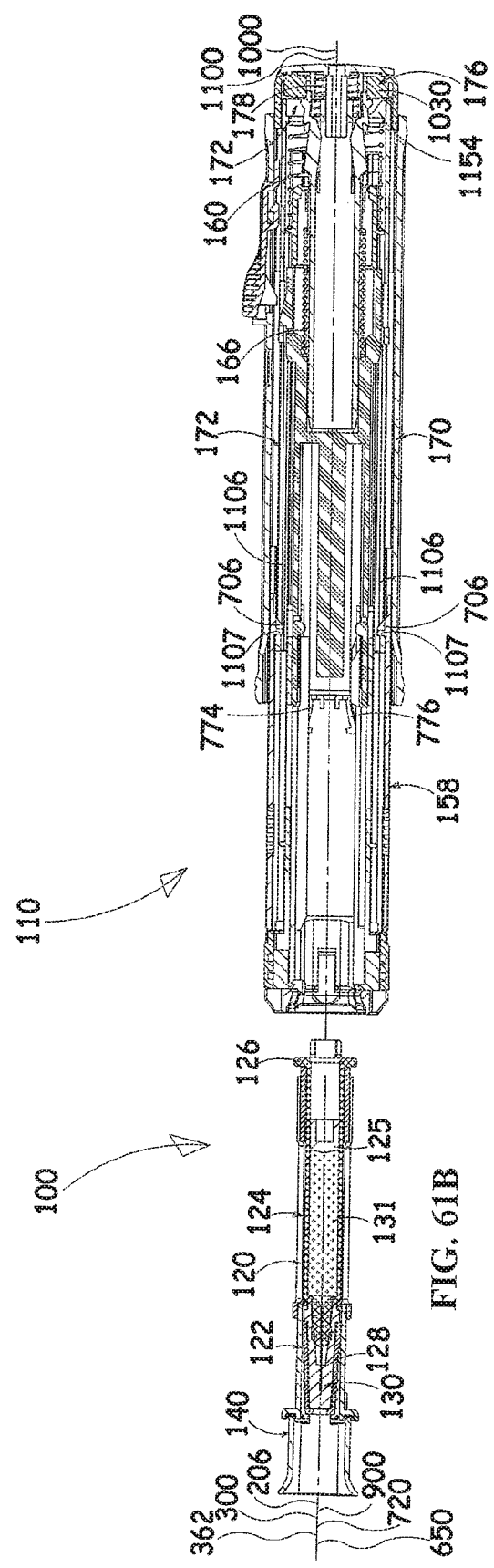
Figure 61C:
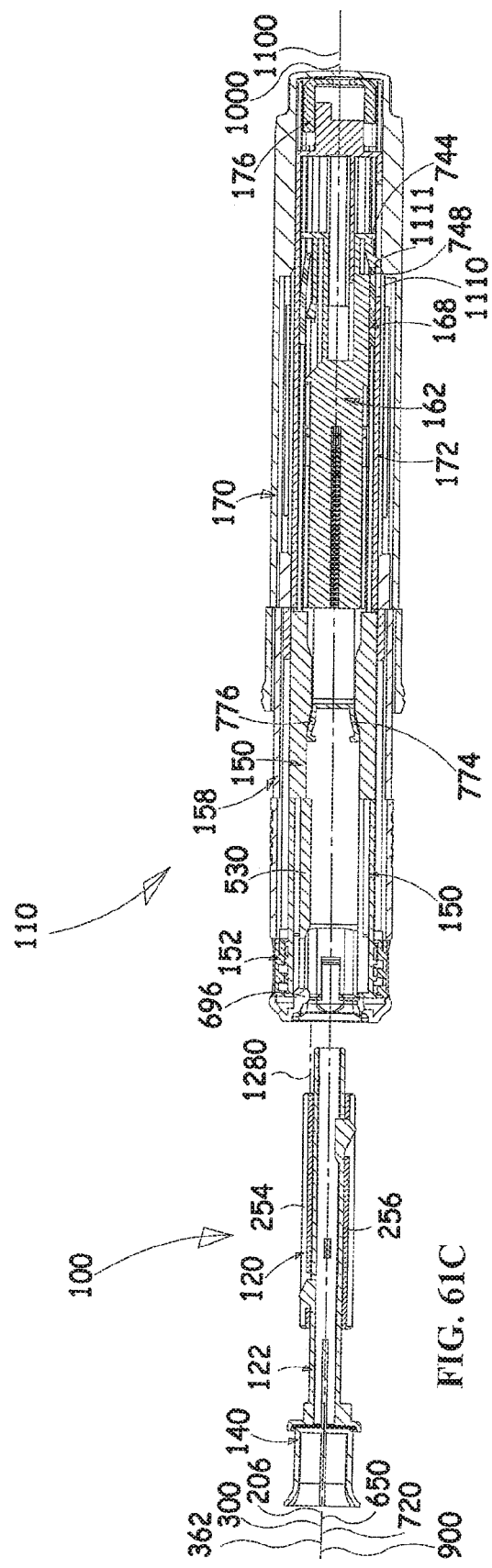
Figure 61D:
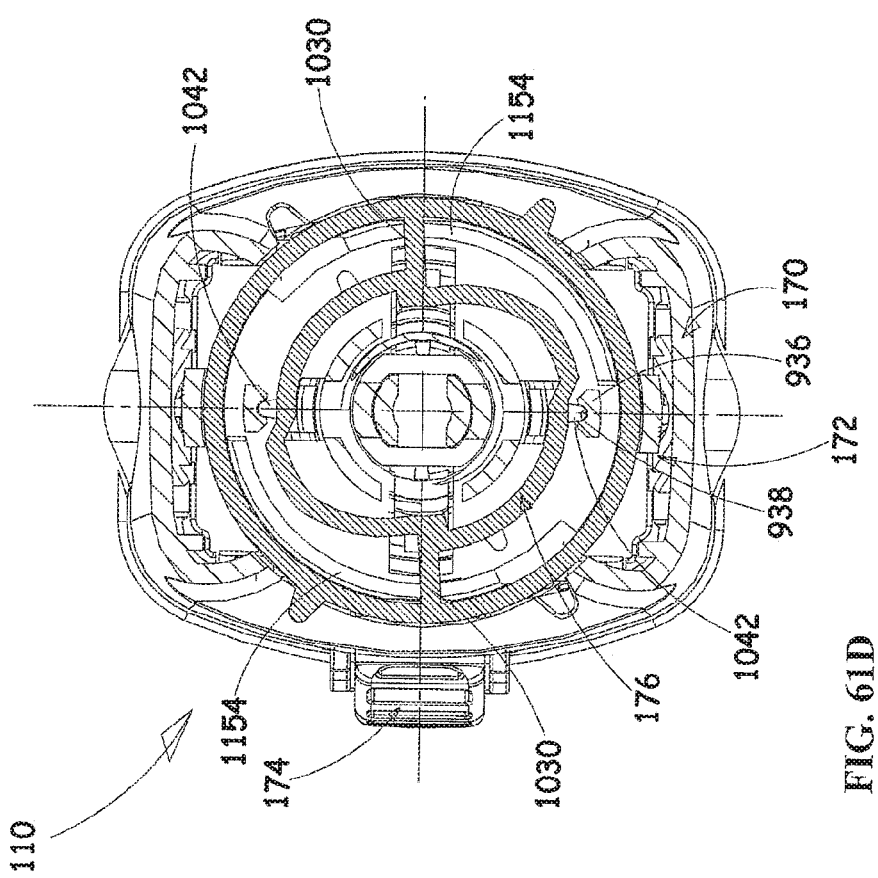

With particular reference to FIG. 61C, it is seen that engagement of forward-facing surfaces 748 of fingers 744 of needle guard deploying element 162 with forward edges 1111 of narrow slots 1110 formed in rear base element 172, retains needle guard deploying element 162 against forward displacement against the urging of needle guard deploying spring 160.

As a result elongate protrusions 764 of needle guard deploying element 162 are positioned rearwardly of hooks 610 of cocked orientation retaining elements 154. This orientation enables rearward displacement of forward cover element 158 relative to rear cover element 170 to be prevented by engagement of rearward ends 607 of cocked orientation retaining elements 154 with rearward edge 1127 of rear base element 172.

The engagement of rearward ends 607 of cocked orientation retaining elements 154 with rearward edge 1127 of rear base element 172 results from application by cocking springs 156 of a rotational moment to respective cocked orientation retaining elements 154 about coaxial axes 620 and 691, urging rotation of cocked orientation retaining elements 154 in a direction such that rearward facing end portions 604 are urged inwardly.

Forward displacement of forward cover element 158 relative to rear base element 172 is limited by engagement of internally facing protrusions 706 of the forward cover element 158 with slots 1106 of rear base element 172 and more specifically with forward edges 1107 of slots 1106.

With particular reference to FIG. 60A, it is appreciated that plunger element 168 can be seen through round window 928.

With particular reference to FIG. 60B, it is appreciated that if trigger button element 174 is inadvertently depressed when the reusable driving assembly 110 is in the cocked operative orientation, it will engage stop surface 924 and will thus not engage flexible finger 812 of plunger element 168 and thus will not release the plunger inadvertently.

With particular reference to FIGS. 61A & 61C, it is seen that axial fingers 774 and 776 of needle guard deploying element 162 are still in a relative open orientation in the cocked operative orientation of the reusable driving assembly 110.

Outwardly facing protrusions 1042 of the safety catch element 176 engage internally facing grooves 938 formed in corresponding outer positioning protrusions 936 of rear cover element 170. This engagement ensures that radially extending ribs 1030 of safety catch element 176 engage circumferential ribs 1154 of rear base element 172 and thus prevent rearward displacement of rear base element 172 relative to rear cover element 170.

It is appreciated that the mutual rotational orientation of the reusable driving assembly 110 and the disposable cassette assembly 100 when arranged coaxially therewith ready for insertion thereinto as seen in FIGS. 59-61D are preferably as follows:

As seen in FIG. 61A, rearward-facing flat protrusions 212 and 214 of cassette housing element 120 of disposable cassette assembly 100 are aligned along respective axes 1250 and 1252 which are tangential to respective axes 1260 and 1262 of tabs 702 of the forward cover element 158.

As seen in FIG. 61C, tracks 252 & 254 and 250 & 256 formed in cassette housing element 120 of disposable cassette assembly 100 are aligned with respect to respective protrusions 696 of forward cover element 158 and internally-facing ribs 530 of forward base element 150, of reusable driving assembly 110, such that one of protrusions 696 and one of internally-facing ribs 530 is aligned along an axis which is coaxial with an axis of one of tracks 250 and 252 and another of protrusions 696 and another of internally-facing ribs 530 is aligned along an axis 1280 which is coaxial with an axis of one of tracks 254 and 256.

Figure 62:
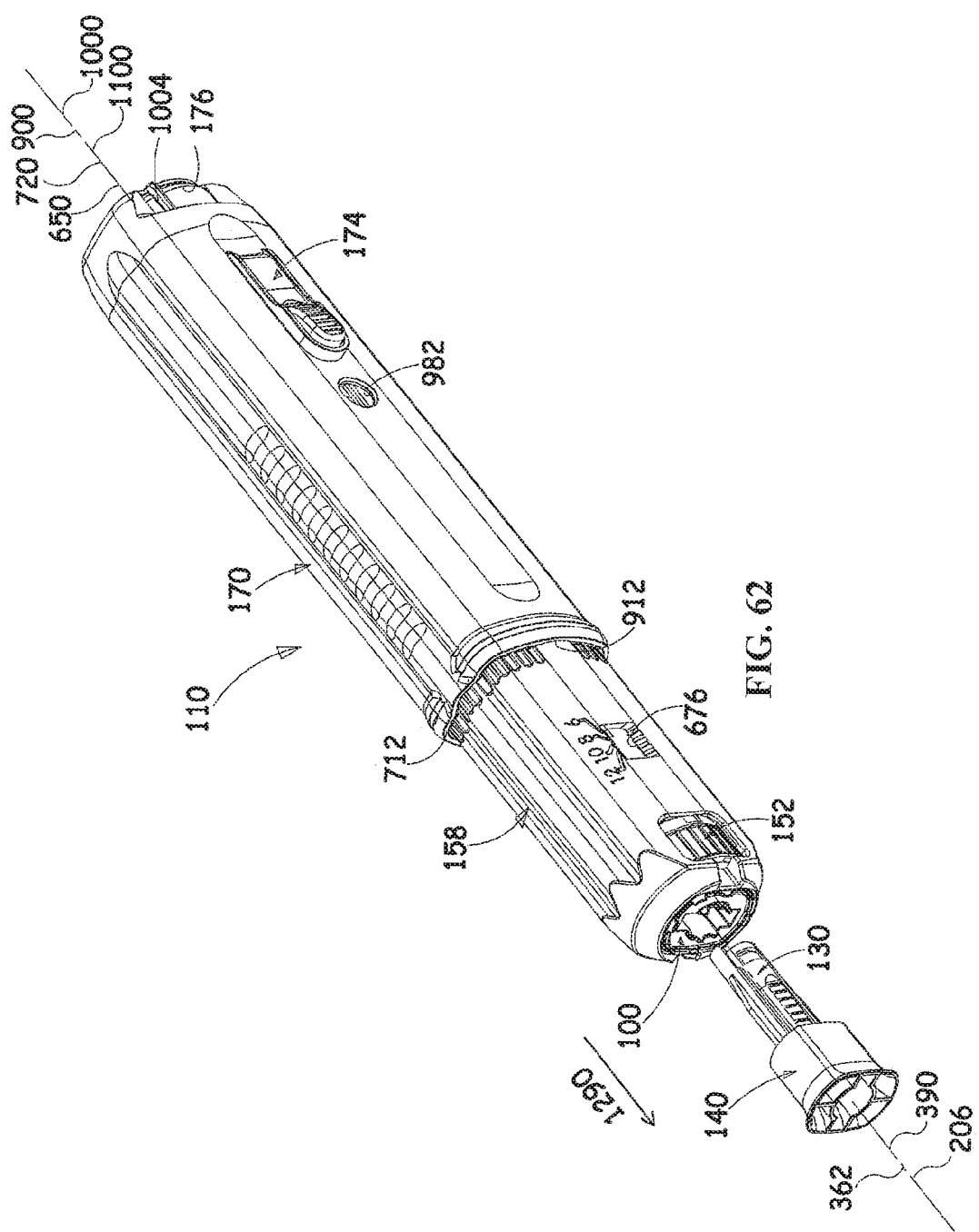
FIG. 62 is a simplified assembled view illustration of the reusable driving assembly of the automatic injection device of FIG. 1 in a pre-injection operative orientation, having the disposable cassette assembly fully inserted therein and the needle shield remover and the needle shield removed from the disposable cassette assembly.
Figure 63A:
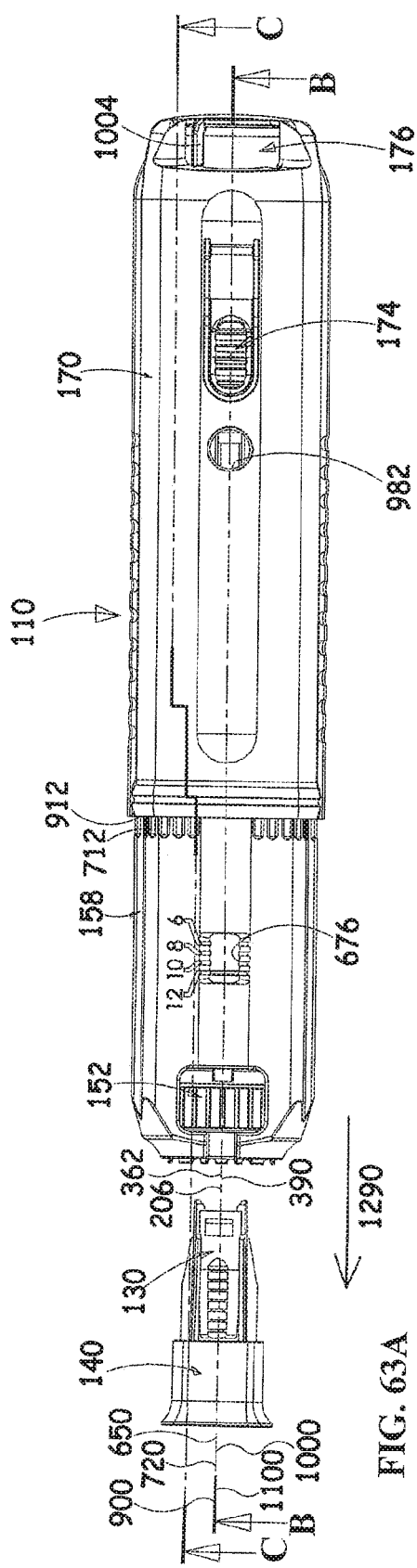
FIGS. 63A & 63B are simplified respective side and top views of the reusable driving assembly of FIG. 62.
Figure 63B:
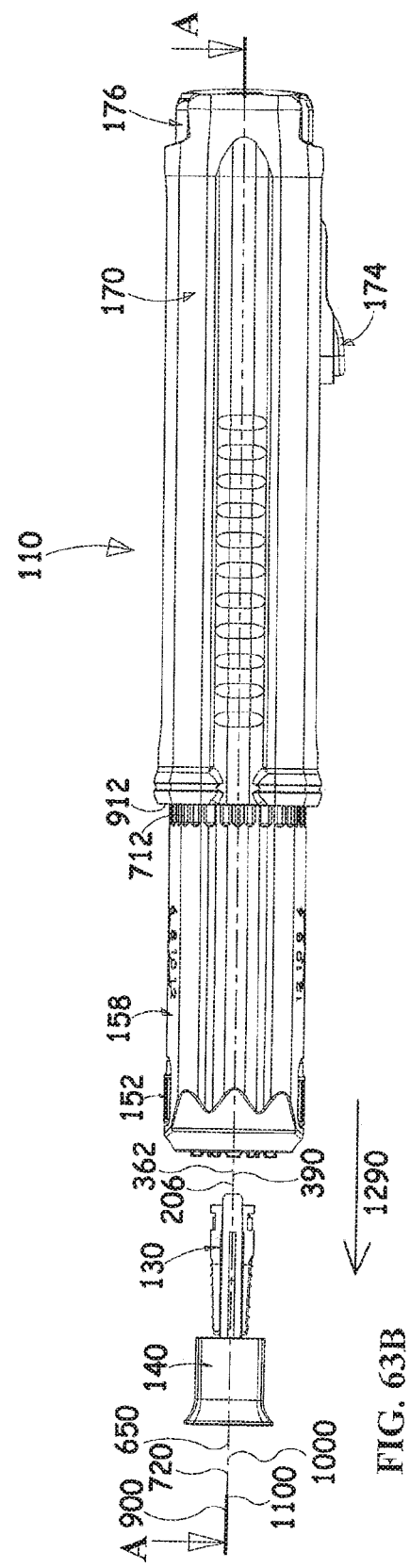
Figure 64A:
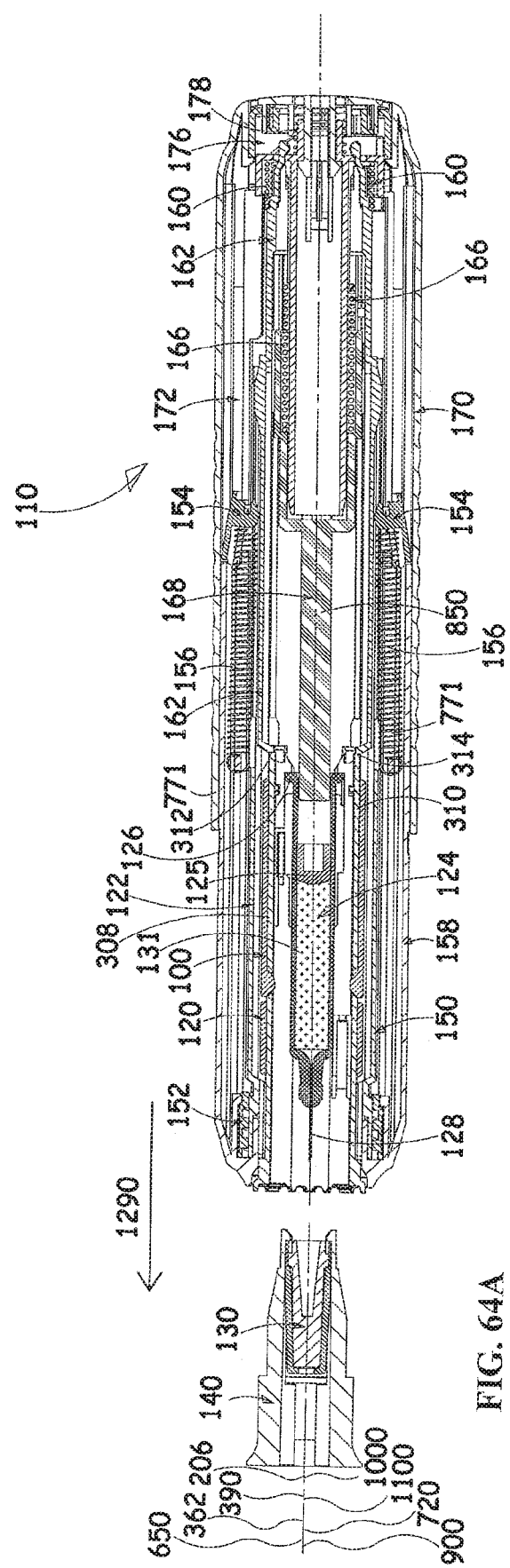
FIGS. 64A, 64B and 64C are simplified sectional illustrations taken along respective section lines A-A, B-B and C-C in FIGS. 63A and 63B.
Figure 64B:
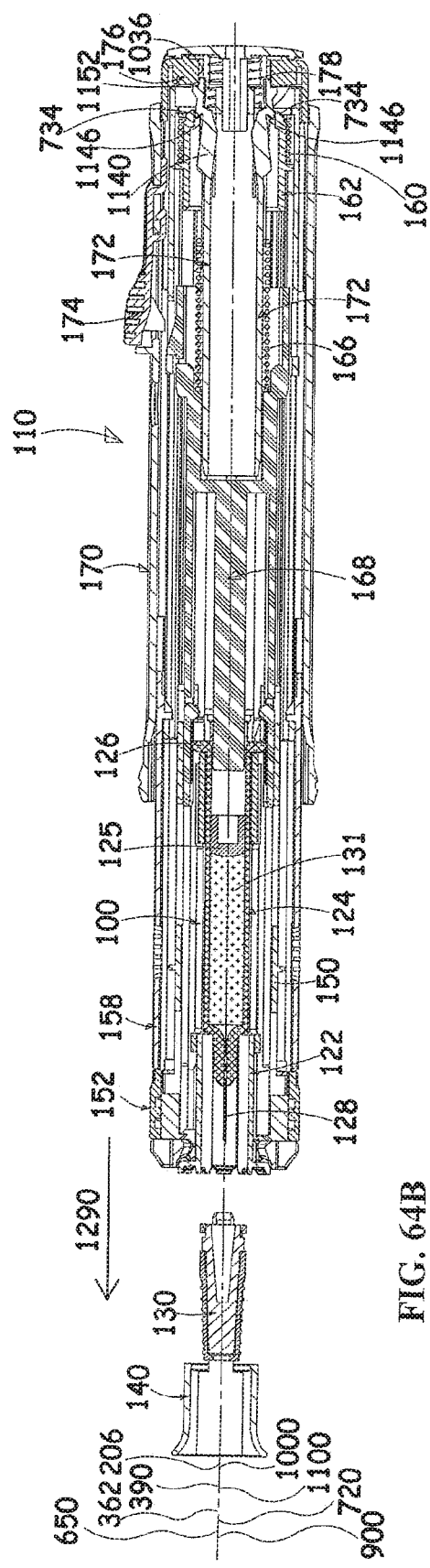
Figure 64C:
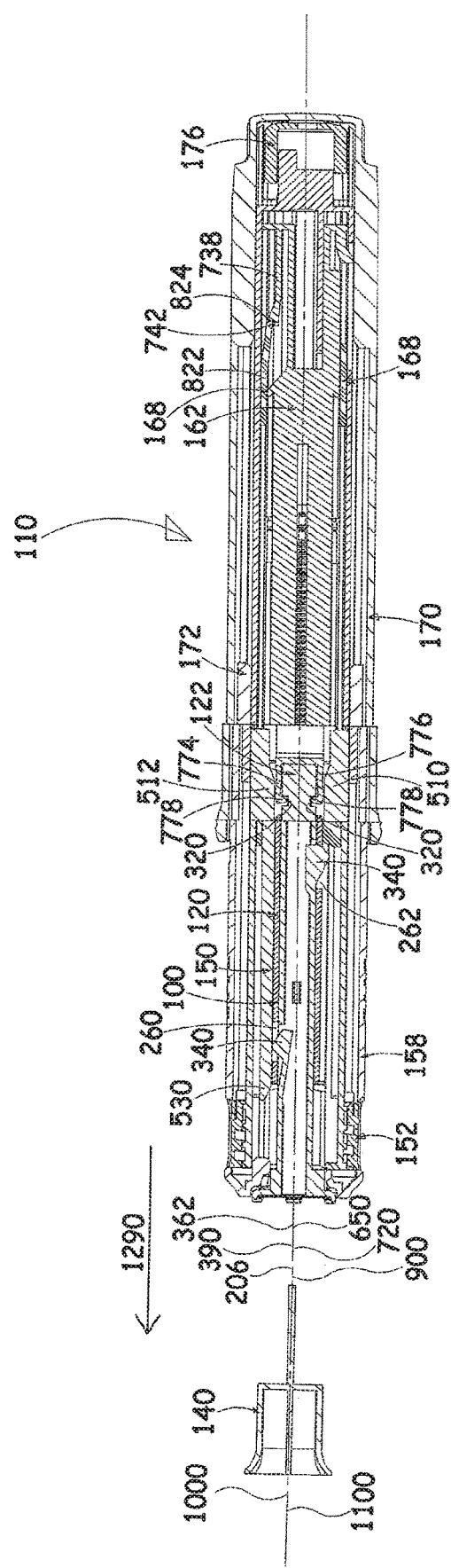

Reference is now made to FIG. 62, which is a simplified assembled view illustration of the reusable driving assembly 110 of the automatic injection device of FIG. 1 in a pre-injection operative orientation, having the disposable cassette assembly 100 fully inserted therein along mutually coaxial axes 362 and 390 and the needle shield remover 140 and the needle shield 130 removed from the disposable cassette assembly 100; to FIGS. 63A and 63B, which are simplified respective side and top views thereof, and to FIGS. 64A, 64B and 64C, which are simplified sectional illustrations taken along respective section lines A-A, B-B and C-C in FIGS. 63A and 63B.

Full engagement and retention of disposable cassette assembly 100 in reusable driving assembly 110 is provided by:

engagement of forwardly-facing shoulders 742 of fingers 738 of needle guard deploying element 162 with corresponding inwardly facing protrusions 824 of flexible fingers 822 of plunger element 168; and engagement of inwardly directed protrusions 778 of fingers 774 and 776 of needle guard deploying element 162 of reusable driving assembly 110 with corresponding notches 320 of needle guard element 122 of disposable cassette assembly 100.

Engagement of inwardly directed protrusions 778 of fingers 774 and 776 of needle guard deploying element 162 of reusable driving assembly 110 with corresponding notches 320 of needle guard element 122 of disposable cassette assembly 100 is enabled by rearward displacement of needle guard deploying element 162, which is urged rearwardly by axial insertion of the disposable cassette assembly, causing engagement of rearward facing edges 312 and 314 of mounting arms 308 and 310 of needle guard element 122 of the disposable cassette assembly with forward facing surface 771 of needle guard deploying element 162 of reusable driving assembly 110, against the urging of needle guard deploying spring 160.

It is noted that in order for the disposable cassette assembly 100 to be retained in the reusable driving assembly 110 the following conditions must be fulfilled:

The safety catch element 176 must be in the safety catch engaged operative orientation. As seen particularly in FIG. 64B, when the safety catch element 176 is in the safety catch engaged operative orientation, cam surfaces 1036 urge rearward outwardly facing surfaces 1152 of fingers 1140 of rear base element 172 inwardly and thus undercuts 1146 are not engaged by protrusions 734 of needle guard deploying element 162 and thus permit full rearward displacement of needle guard deploying element 162 to an extent that enables forwardly-facing shoulders 742 of fingers 738 of needle guard deploying element 162 to engage with corresponding inwardly facing protrusions 824 of flexible fingers 822 of plunger element 168; and Inwardly-facing protrusions 778 of fingers 774 and 776 are forced inwardly by engagement of fingers 774 and 776 with internally facing ribs 510 and 512 of forward base element 150.

Once the disposable cassette assembly 100 is retained in the reusable driving assembly 110, a user can readily remove the needle shield remover 140 together with the needle shield 130 by pulling it axially in a direction 1290 along axis 362.

With particular reference to FIG. 64C it is seen that insertion and retention of the disposable cassette assembly 100 in reusable driving assembly 110 cause disengagement of outwardly-facing protrusions 340 in needle guard element 122 from corresponding forward slots 260 and 262 in cassette housing element 120. This disengagement is the result of engagement of internally-facing ribs 530 of forward base element 150 of reusable driving assembly 110 with protrusions 340.

Figure 65:
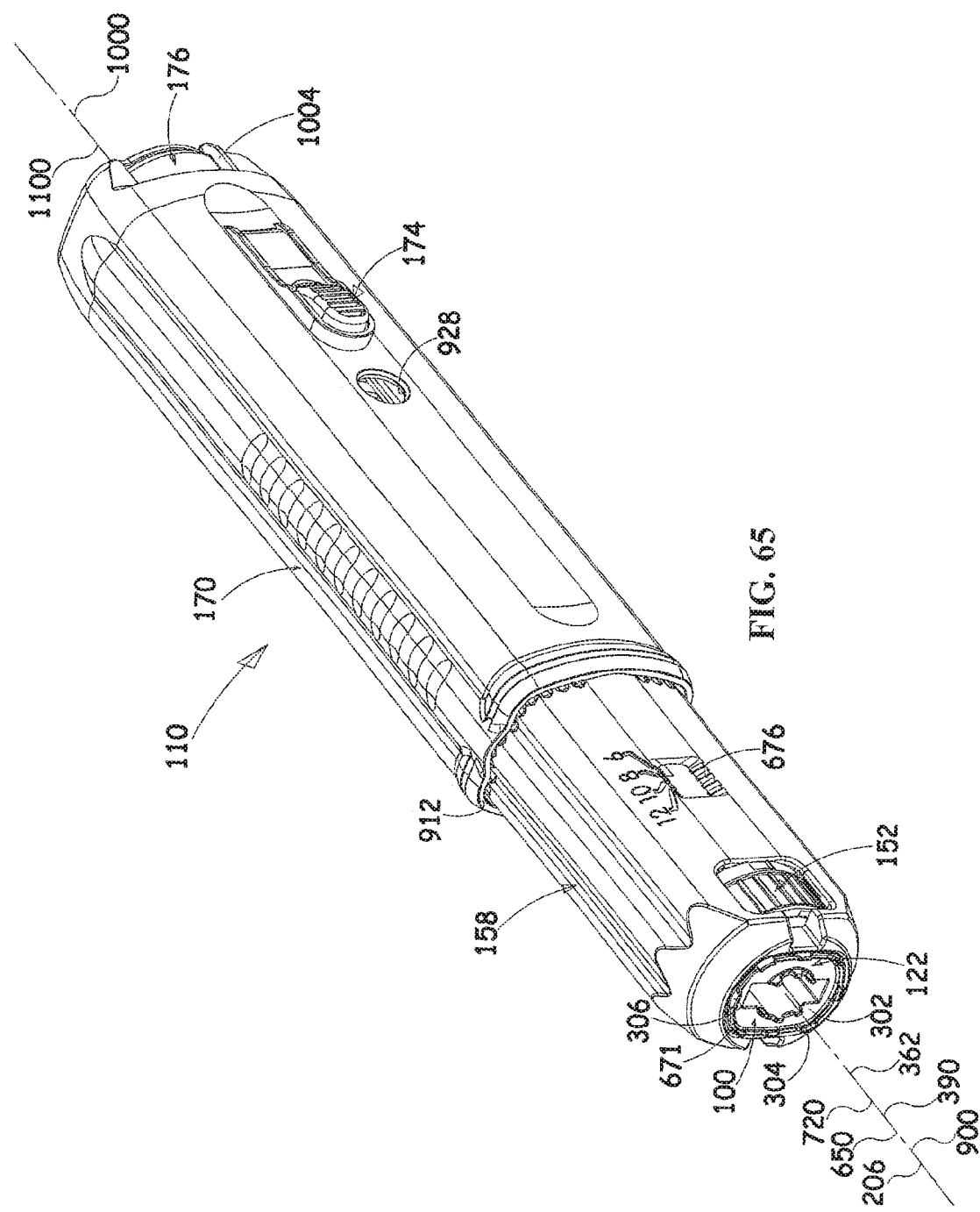
FIG. 65 is a simplified assembled view illustration of the reusable driving assembly of the automatic injection device of FIG. 1 in an injection site engagement operative orientation.
Figure 67A:
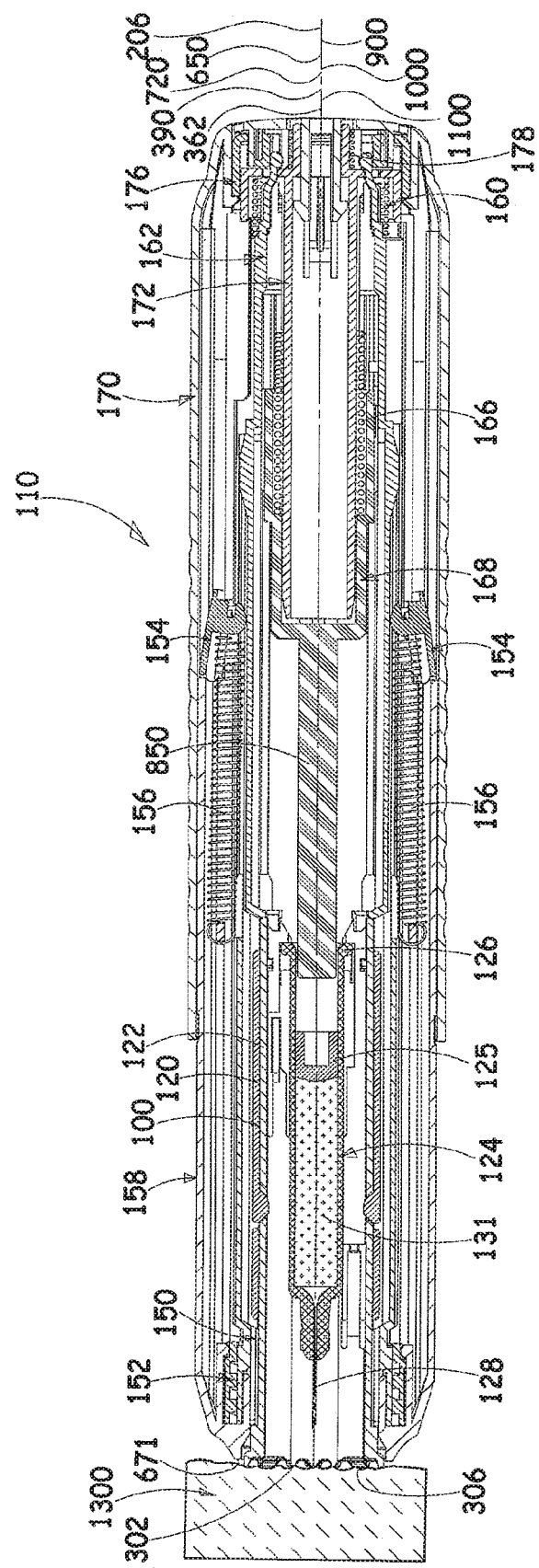
FIGS. 67A, 67B and 67C are simplified sectional illustrations taken along respective section lines A-A, B-B and C-C in FIGS. 66A and 66B.
Figure 67B:
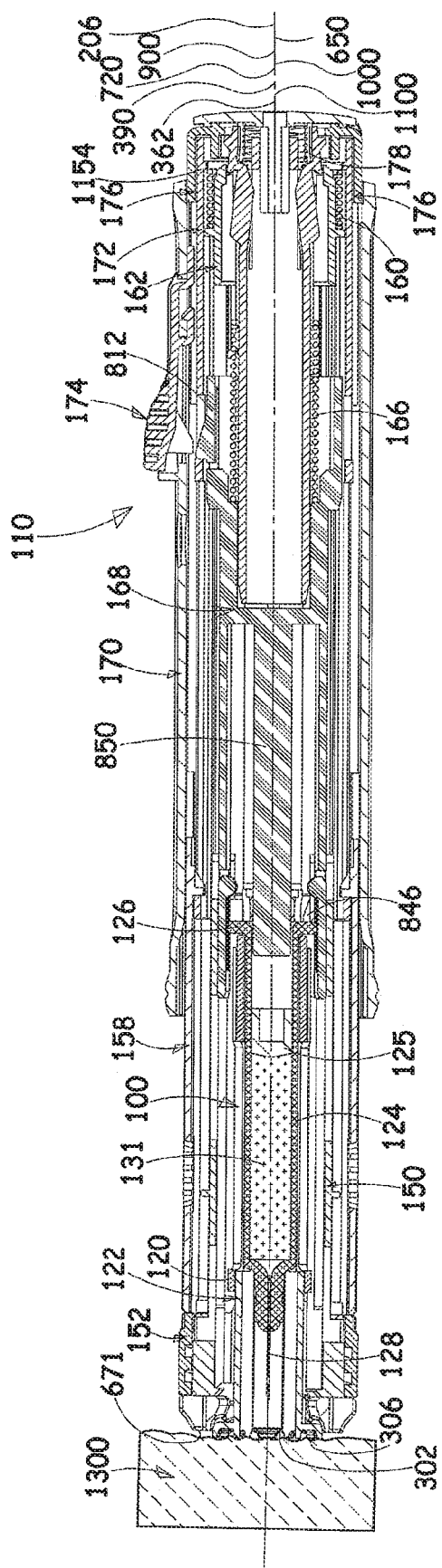
Figure 67C:
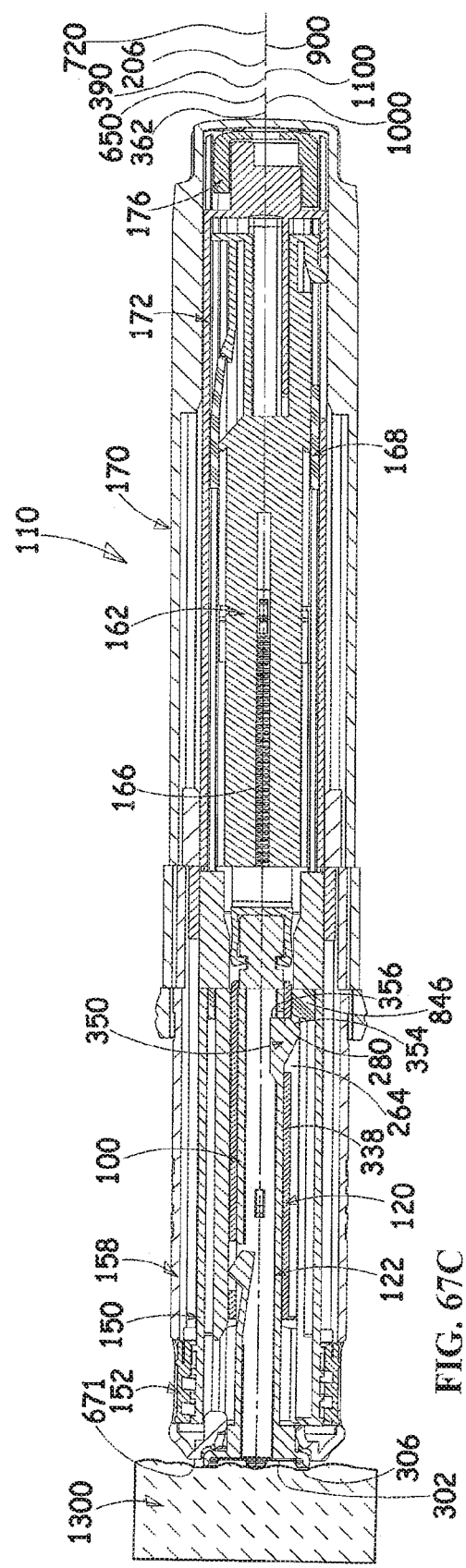

Reference is now made to FIG. 65, which is a simplified assembled view illustration of the reusable driving assembly 110 of the automatic injection device of FIG. 1 in an injection site engagement operative orientation; to FIGS. 66A and 66B, which are simplified respective side and top views thereof, and to FIGS. 67A, 67B and 67C, which are simplified sectional illustrations taken along respective section lines A-A, B-B and C-C in FIGS. 66A and 66B.

The injection site engagement operative orientation seen in FIGS. 65-67C is preferably realized by a user taking the reusable driving assembly 110 in pre-injection operative orientation, as seen in FIGS. 62-64C and rotating safety catch element 176 by engaging engagement protrusions 1004, so that it is in the disengaged operative orientation. The user holds the reusable driving assembly 110 in one hand, by grasping the rear cover element 170. The user, while grasping the rear cover element 170, applies an axial force along axes 390, 650 and 900 forcing the forward-facing injection site rings 304 and 306 of the needle guard element 122 of the disposable cassette assembly 100 and potentially also forward edge 671 of the forward cover element 158 against an injection site surface 1300, such as skin, causing compression of injection site engagement sensing spring 178.

In the injection site engagement operative orientation, as seen particularly in FIG. 67B, radially extending ribs 1030 of safety catch element 176, as particularly seen in FIG. 39B, do not engage circumferential ribs 1154 of rear base element 172 and thus do not prevent rearward displacement of rear base element 172 relative to rear cover element 170.

With particular reference to FIG. 66B, it is seen that in the injection site engagement operative orientation, with the safety catch element 176 in the disengaged operative orientation, if trigger button element 174 is depressed when the reusable driving assembly 110 is in the injection site engagement operative orientation, trigger button element 174 will engage flexible finger 812 of plunger element 168, thus causing forward edge 816 of flexible finger 812 to disengage from forward edge 1109 of rectangular slot 1108 of rear base element 172, thereby allowing forward displacement of plunger element 168 and corresponding forward displacement of syringe 124.

In the injection site engagement operative orientation, as seen particularly in FIGS. 65, 66A and 66B, the orientation indicating circumferentially extending line 712 is preferably not visible, thus indicating to the user that injection may be initiated by pressing on trigger button element 174.

It is appreciated that forward displacement of the syringe 124 is limited by engagement of forward facing edges 268 and 280 of cassette housing element 120 with rearward facing edges 356 of finger portions 328 and 338 of the needle guard element 122. Axial corner ribs 846 of plunger element 168 are positioned rearwardly with respect to rearward-facing tapered surfaces 354 of protrusions 350 of finger portions 328 and 338 of the needle guard element 122.

Figure 70A:
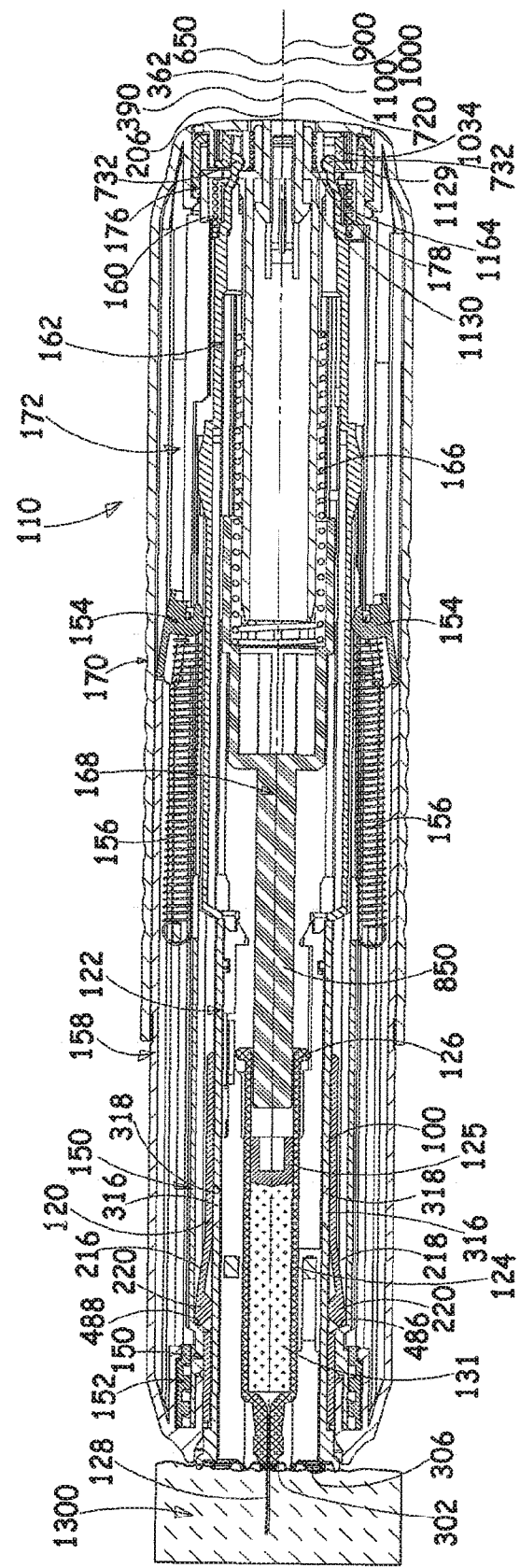
FIGS. 70A, 70B and 70C are simplified sectional illustrations taken along respective section lines A-A, B-B and C-C in FIGS. 69A & 69B.
Figure 70B:
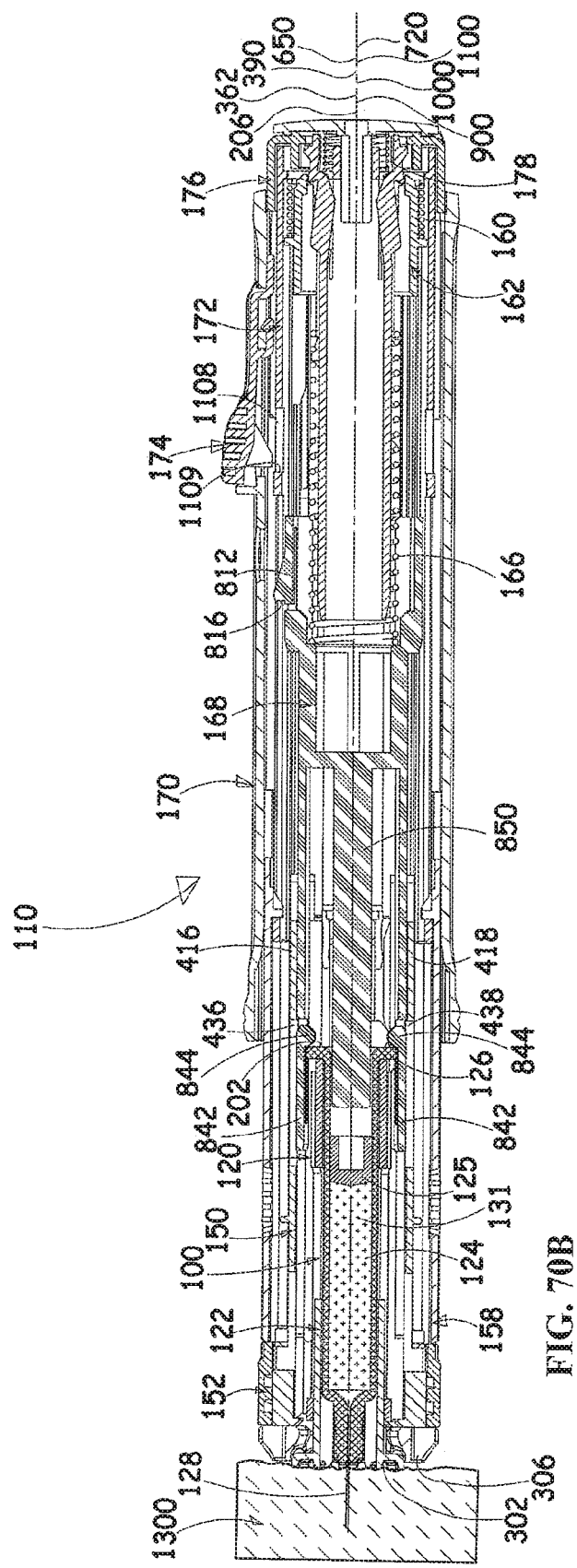
Figure 70C:
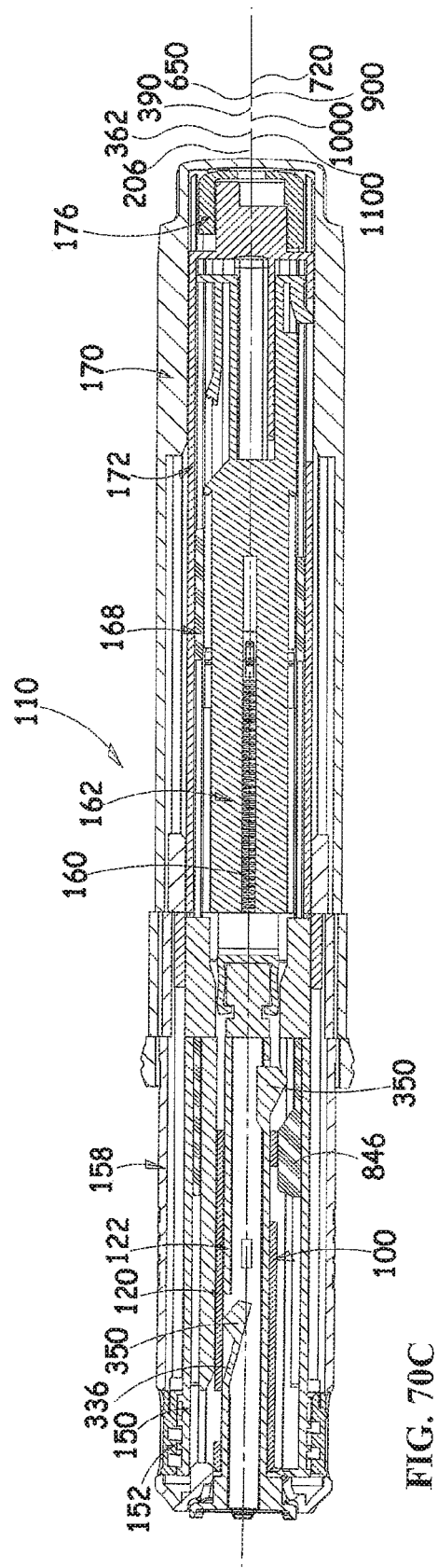

Reference is now made to FIG. 68, which is a simplified assembled view illustration of the reusable driving assembly 110 of the automatic injection device of FIG. 1 in a needle insertion operative orientation; to FIGS. 69A and 69B, which are simplified respective side and top views thereof, and to FIGS. 70A, 70B and 70C, which are simplified sectional illustrations taken along respective section lines A-A, B-B and C-C in FIGS. 69A and 69B.

The needle insertion operative orientation shown in FIGS. 68-70C is the operative orientation resulting from depression of the trigger button element 174 when the reusable driving assembly 110 is in the injection site engagement operative orientation. Trigger button element 174 engages flexible finger 812 of plunger element 168, thus causing forward edge 816 of flexible finger 812 to disengage from forward edge 1109 of rectangular slot 1108 of rear base element 172 which results in forward displacement of plunger element 168 and corresponding forward displacement of syringe 124 under the urging of main spring 166.

With particular reference to FIG. 70B, it is seen that main spring 166, which is under partial compression, urges plunger element 168 forwardly, causing inwardly-facing protrusions 844 of flexible fingers 842 of the plunger element 168. Forward axial displacement of the syringe 124 along axes 390 and 650 is limited by engagement of flange 126 with rearward edges 202 of cassette housing element 120 and by engagement of finger portions 216 and 218 of cassette housing element 120 with inwardly tapered surfaces 486 and 488 of forward base element 150 which were disengaged from respective slots 316 of needle guard element 122 by engagement of forward facing tapered surfaces 318 of needle guard element 122 with protrusions 220 of finger portions 216 and 218 of cassette housing element 120.

It is appreciated that the axial location of inwardly tapered surfaces 486 and 488 of forward base element 150 is determined by the setting of the needle penetration depth selector 152.

It is appreciated that in the needle insertion operative orientation of FIGS. 68-70C, injection of liquid via needle 128 has not yet occurred, inasmuch as plunger rod 850 is not yet engaged with the piston 125 of syringe 124. It is seen that flexible fingers 842 of plunger element 168, whose outwardly lateral displacement was previously prevented by engagement with side walls 416 and 418 of forward base element 150, now lie opposite respective rearward slots 436 and 438.

It is appreciated that forward displacement of the syringe 124 was enabled by inward displacement of protrusions 350 of finger portions 328 and 338 of the needle guard element 122 due to engagement thereof by corner ribs 846 of plunger element 168 during forward displacement thereof.

Figure 71:
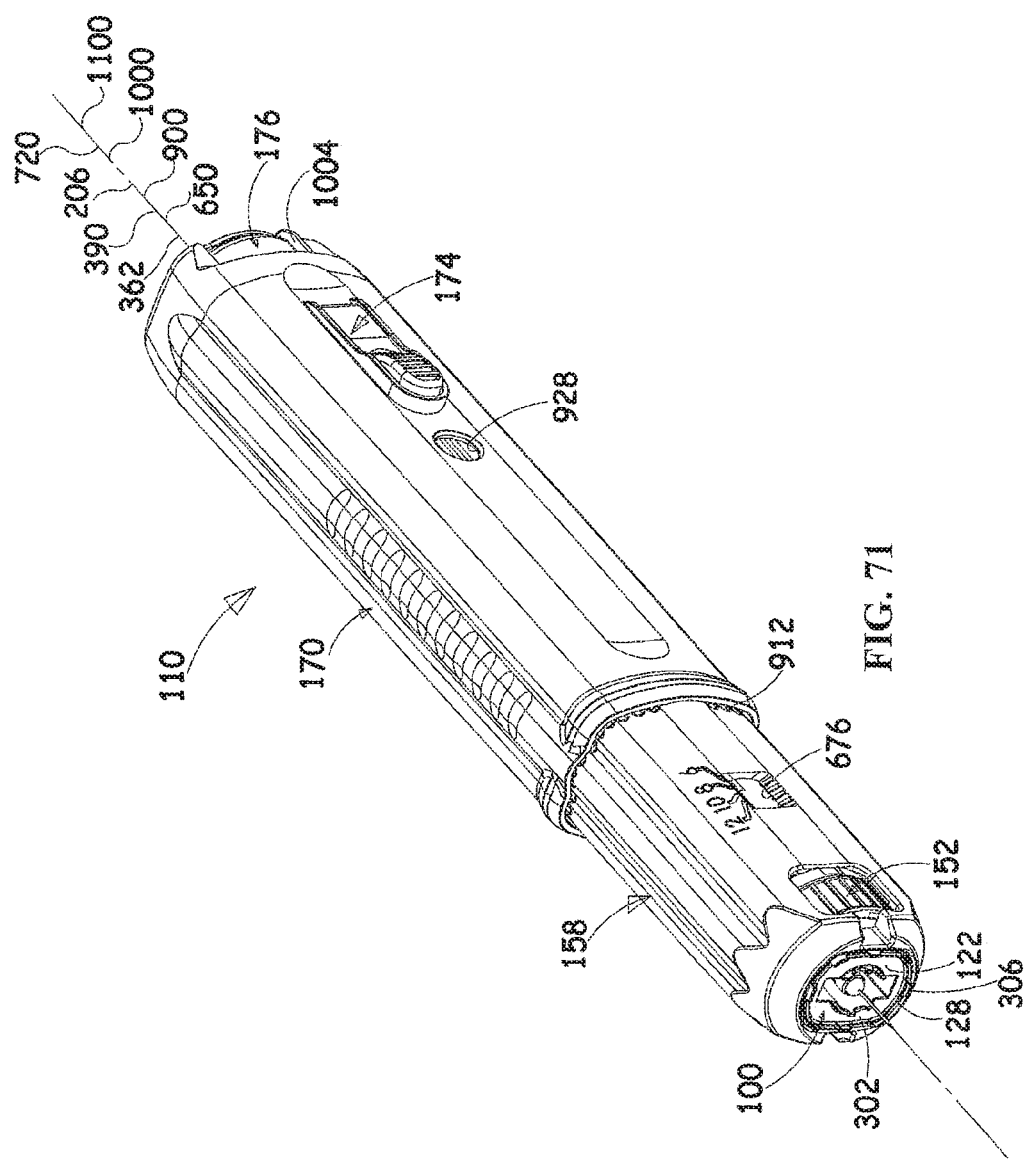
FIG. 71 is a simplified assembled view illustration of the reusable driving assembly of the automatic injection device of FIG. 1 in an end-of-injection operative orientation.
Figure 73A:
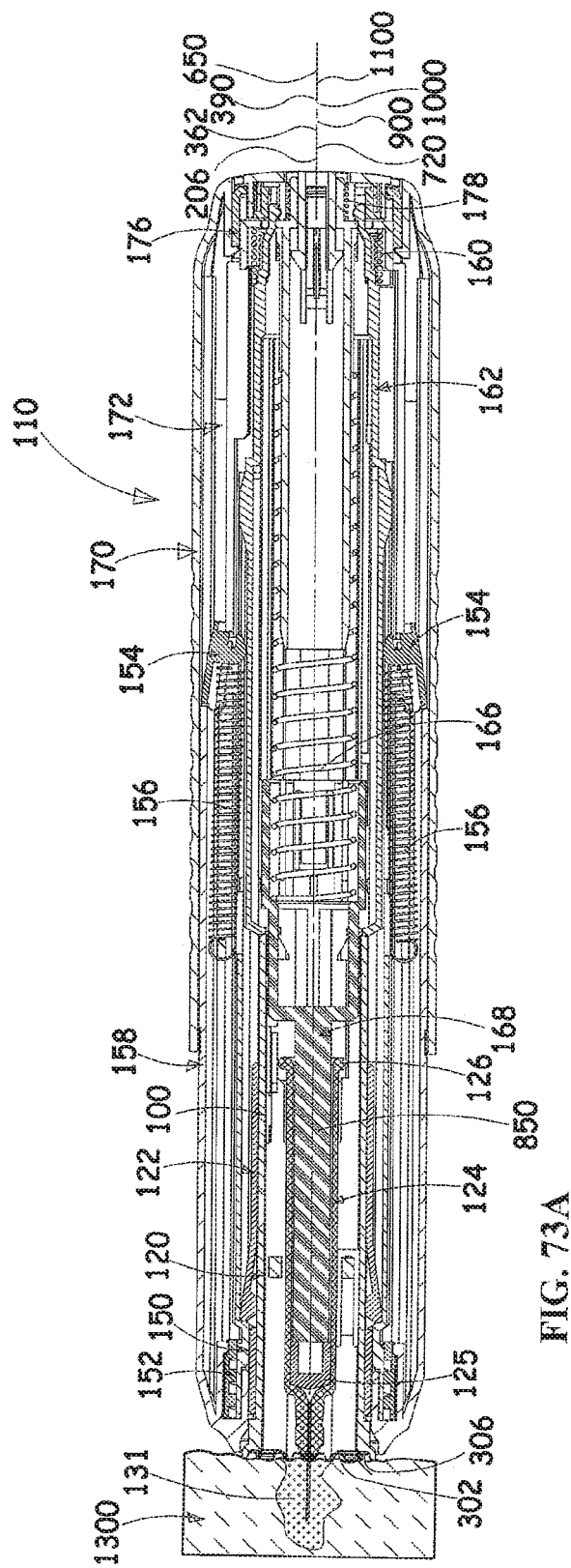
FIGS. 73A, 73B and 73C are simplified sectional illustrations taken along respective section lines A-A, B-B and C-C in FIGS. 72A & 72B.
Figure 73B:
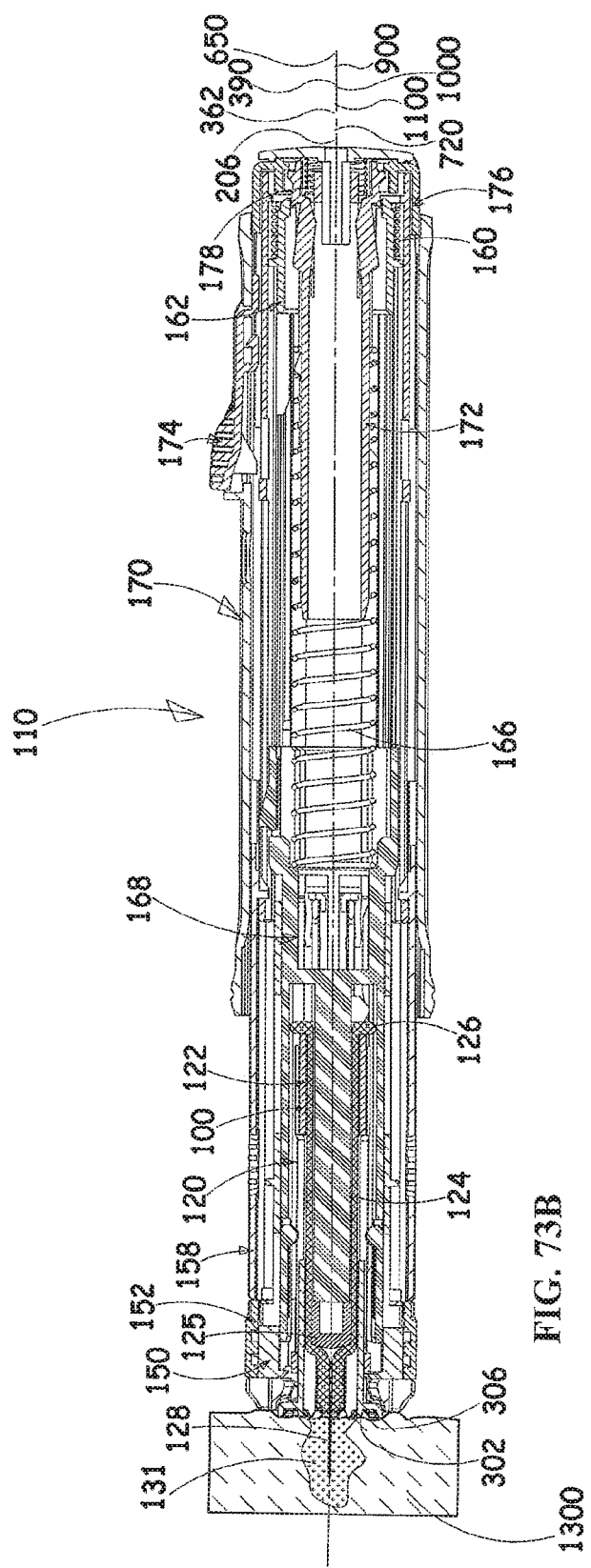
Figure 73C:
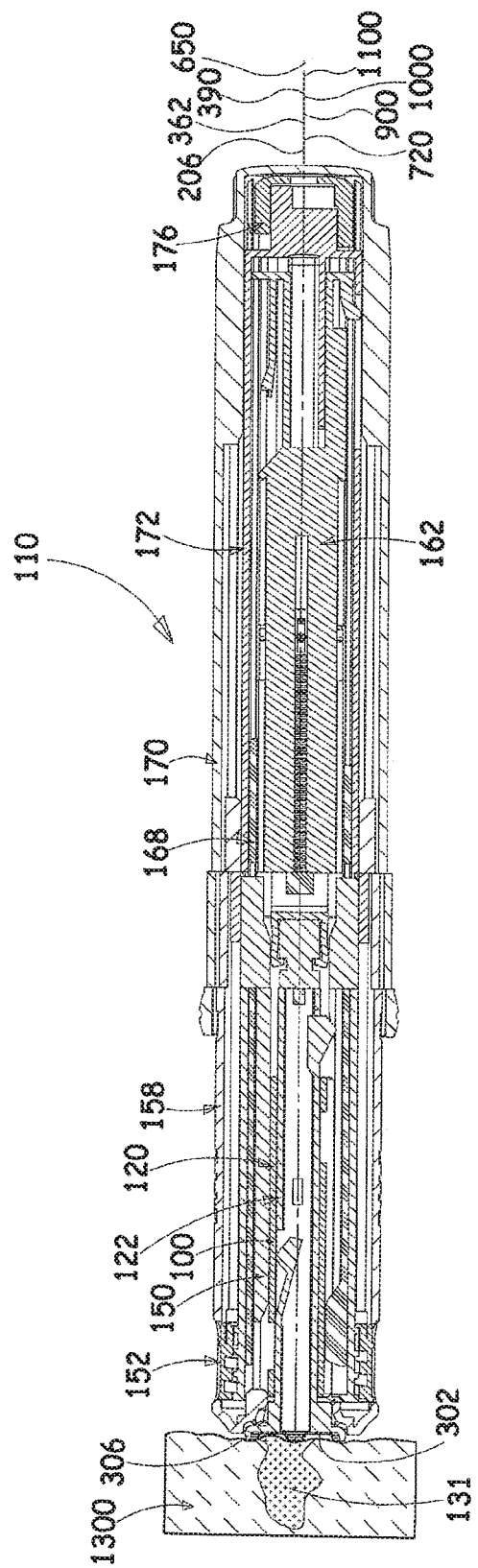

Reference is now made to FIG. 71, which is a simplified assembled view illustration of the reusable driving assembly 110 of the automatic injection device of FIG. 1 in an end-of-injection operative orientation; to FIGS. 72A and 72B, which are simplified respective side and top views thereof, and to FIGS. 73A, 73B and 73C, which are simplified sectional illustrations taken along respective section lines A-A. B-B and C-C in FIGS. 72A and 72B.

It is seen in FIGS. 73A-73C that plunger rod 850 of plunger element 168, which was urged forwardly by main spring 166, engaged piston 125 in order to inject liquid 131 contained in syringe 124 into the injection site 1300.

Figure 74:
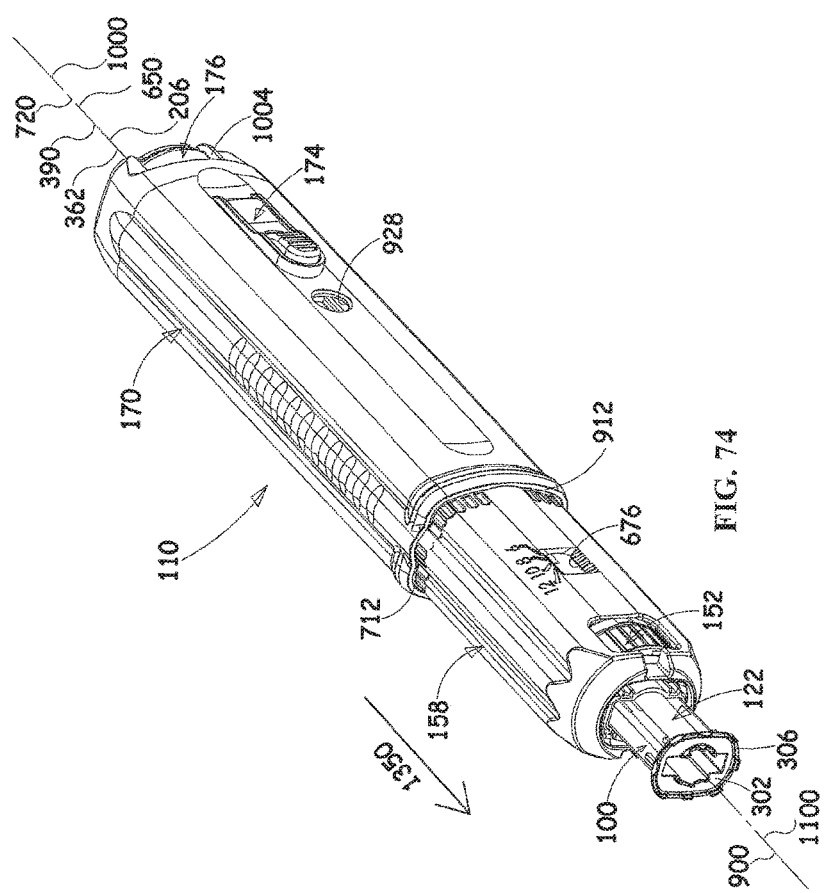
FIG. 74 is a simplified assembled view illustration of the reusable driving assembly of the automatic injection device of FIG. 1 in a post-injection operative orientation.
Figure 76A:
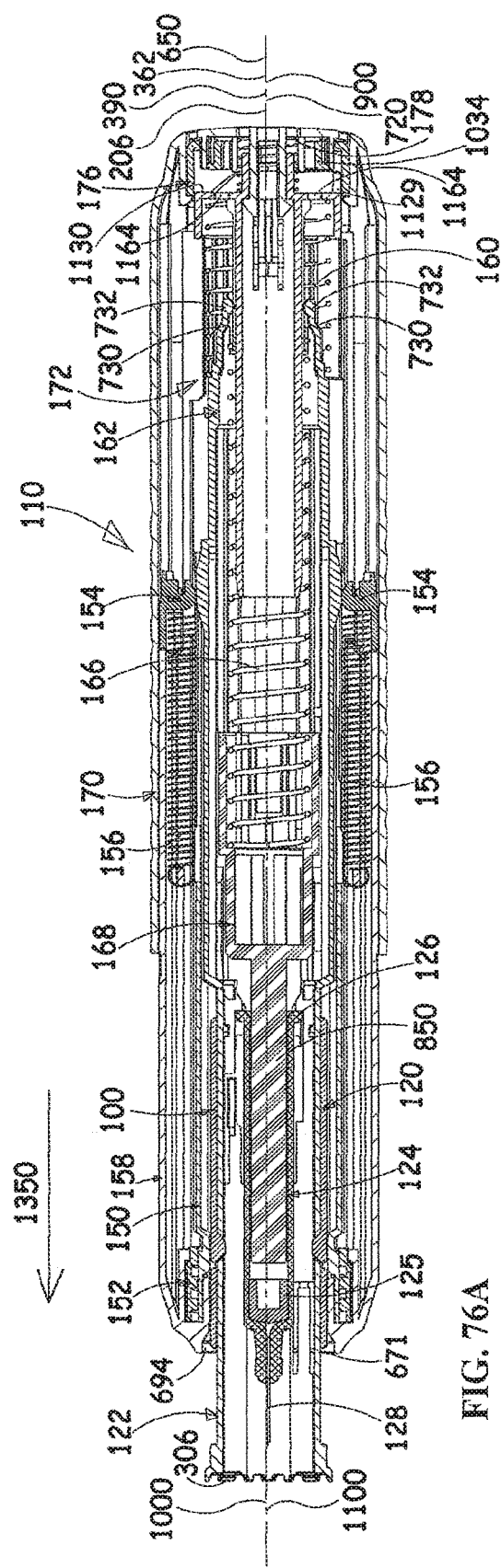
FIGS. 76A, 76B and 76C are simplified sectional illustrations taken along respective section lines A-A, B-B and C-C in FIGS. 75A & 75B.
Figure 76B:
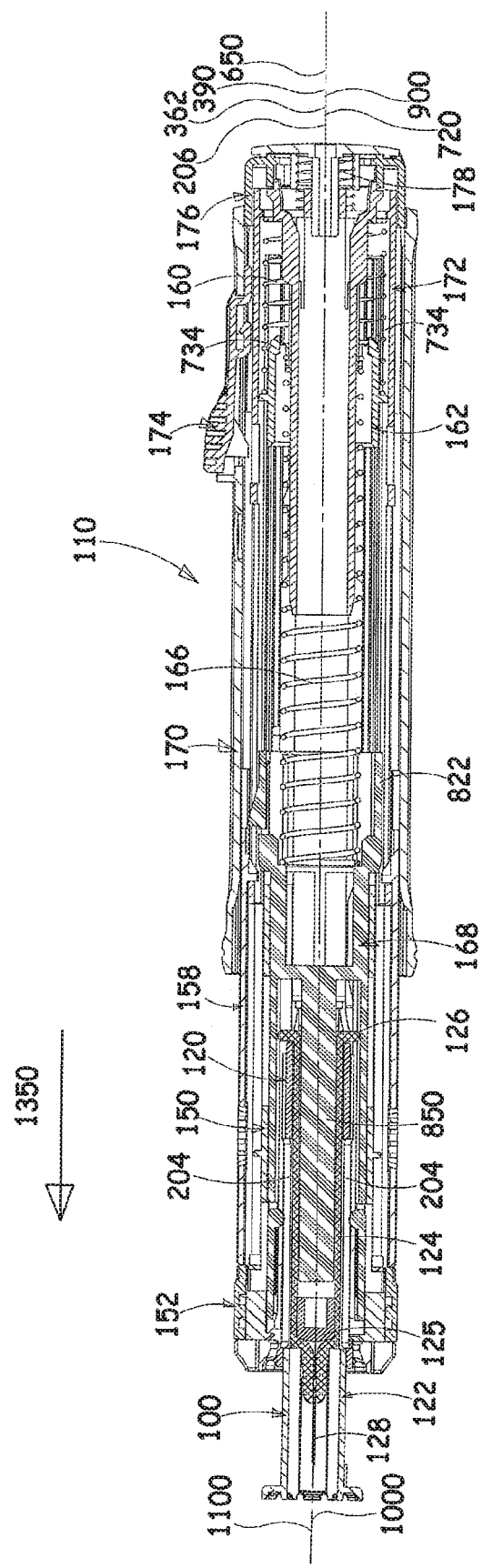
Figure 76C:
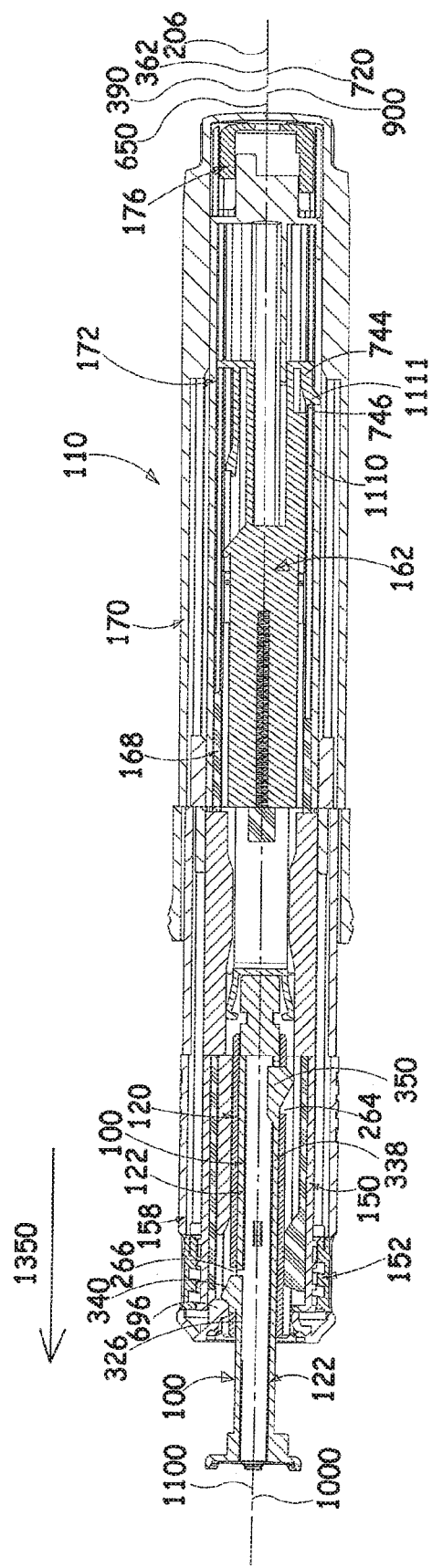

Reference is now made to FIG. 74, which is a simplified assembled view illustration of the reusable driving assembly 110 of the automatic injection device of FIG. 1 in a post-injection operative orientation; to FIGS. 75A and 75B, which are simplified respective side and top views thereof, and to FIGS. 76A, 76B and 76C, which are simplified sectional illustrations taken along respective section lines A-A, B-B and C-C in FIGS. 75A and 75B.

It is seen that the automatic injection device is disengaged from the injection site 1300 by the user. As the forward-facing injection site rings 304 and 306 are separate from the injection site, the needle guard element 122 emerges forwardly from axial opening 694 to surround the needle 128, such that the needle 128 is at all times substantially protected from finger engagement and the user is protected from inadvertent needle stick.

The forward displacement of the needle guard element 122 results from the following events:

Injection site engagement, as shown in FIGS. 65-67C, causes protrusions 732 of flexible fingers 730 of needle guard deploying element 162 to extend rearwardly through apertures 1164 in end portion 1129 of rear base element 172. Protrusions 732 engage wall 1130 of end portion 1129 and are locked thereto by engagement therewith of circular rib portions 1034 of safety catch element 176. This locking engagement prevents forward displacement of needle guard deploying element 162 as long as the automatic injection device is pressed against the injection site, as seen in FIGS. 65-73C.

Once the automatic injection device is no longer pressed against the injection site, circular rib portions 1034 of safety catch element 176 no longer engage end portion 1129, thus allowing protrusions 732 to be displaced forwardly through apertures 1164 and out of engagement with wall 1130 of rear base element 172. Under the urging of needle guard deploying spring 160, the needle guard deploying element 162 moves axially forwardly and pushes the needle guard element 122 forwardly of forward edge 671 of forward cover element 158, thus enabling the needle guard element 122 to surround the exposed needle 128.

Forward displacement of needle guard element 122 is limited by engagement of outward-facing protrusions 746 of fingers 744 of needle guard deploying element 162 with forward edges 1111 of narrow slots 1110.

The cassette housing element 120 is axially locked to needle guard element 122 by engagement of protrusions 350 of fingers 328 and 338 with slots 266 and 264 respectively.

The disposable cassette assembly 100 is meanwhile weakly retained against removal from the reusable driving assembly 110 by engagement of protrusions 340 of finger portions 326 and 336 with protrusions 696 of forward cover element 158.

Removal of the disposable cassette assembly 100 from the reusable driving assembly 110 is readily achieved by a user pulling axially on the disposable cassette assembly 100 in a direction 1350 along axes 390 and 650, thereby causing disengagement of protrusions 340 of finger portions 326 and 336 with protrusions 696 of forward cover element 158.

Once the disposable cassette assembly 100 has been removed from the reusable driving assembly 110, the amount of liquid 131 remaining in the syringe 124 can readily be visually ascertained, by viewing the interior of the syringe 124 via either of windows 204.

It will be appreciated by persons skilled in the art that the present invention is not limited by what has been specifically shown and described hereinabove. Rather the scope of the invention includes both combinations and sub-combinations of features described and shown hereinabove as well as modifications thereof which would occur to persons reading the foregoing description and which are not in the prior art.

The invention claimed is:

1. An automatic injection device comprising:
   a reusable driving assembly having a needle insertion operative orientation; and
   a disposable cassette assembly comprising a cassette housing element, a prefilled syringe including a needle, a needle shield mounted onto said needle and a needle guard element,
   said needle shield is configured to be removed from said disposable cassette assembly before said reusable driving assembly assumes said needle insertion operative orientation;
   said cassette housing element and said needle guard element being arranged such that prior to both said disposable cassette assembly having been inserted into said reusable driving assembly and said reusable driving assembly being in said needle insertion operative orientation, relative axial displacement between said cassette housing element and said needle guard element is prevented due to locking between said needle guard element and said cassette housing element, and wherein said needle protrudes from a forward end of said needle guard when said reusable driving assembly is in said needle insertion operative orientation,
   and wherein displacement of said cassette housing element relative to said needle guard element is permitted while said reusable driving assembly is in said needle insertion operative orientation when said needle guard element is pressed against the injection site, and
   wherein only following insertion and retention of said disposable cassette assembly in said reusable driving assembly, said reusable driving assembly may be caused to assume said needle insertion operative orientation by pressing a trigger button element, thereby causing forward axial displacement of said cassette housing element and resulting penetration of an injection site by said needle.

2. An automatic injection device according to claim 1 and wherein said arrangement of said cassette housing element and said needle guard element is such that said relative axial displacement between said cassette housing element and said needle guard element is prevented by a first engagement and a second engagement causing temporary locking between said cassette housing element and said needle guard element, said first engagement being released upon insertion of said disposable cassette assembly into said reusable driving assembly and said second engagement being released when said reusable driving assembly is in said needle insertion operative orientation, which is caused by pressing a trigger button element.

3. An automatic injection device according to claim 2 and wherein said first engagement is provided by mutual engagement of at least one first protrusion of said needle guard element with at least one first slot of said cassette housing element and said second engagement is provided by mutual engagement of at least one second protrusion of said needle guard element with at least one second slot of said cassette housing element.

4. An automatic injection device according to claim 1 and wherein:
said disposable cassette assembly has a pre-use operative orientation, which is suitable for storage;
in said pre-use operative orientation, said needle guard element is locked to said cassette housing element by snap fit engagement of at least one protrusion of said needle guard element in at least one slot formed in said cassette housing element.

5. An automatic injection device according to claim 1 and wherein:
said reusable driving assembly includes a forward injection end and multiple mutually axially displaceable elements;
said needle is suitable for injecting an injectable liquid at an injection site;
said disposable cassette assembly is removably insertable into said reusable driving assembly at said forward injection end; and
following insertion of said disposable cassette assembly into said reusable driving assembly, said automatic injection device may be caused to assume an injection site engagement operative orientation by pressing said forward injection end of said reusable driving assembly against said injection site, thereby producing mutual axial displacement of at least some of said multiple mutually axially displaceable elements but not producing relative axial displacement between said needle guard element and said cassette housing element of said disposable cassette assembly.

6. An automatic injection device according to claim 1 and wherein:
following insertion of said disposable cassette assembly into said reusable driving assembly, said reusable driving assembly may be caused to assume an injection site engagement operative orientation; and
following assumption of a pre-needle insertion operative orientation, said reusable driving assembly may be caused to assume said needle insertion operative orientation by pressing a trigger button element, thereby causing forward axial displacement of said cassette housing element and resulting penetration of said injection site by said needle to a penetration depth defined by engagement of said cassette housing element with a forward base element of said reusable driving assembly.

7. An automatic injection device according to claim 1 and wherein:
following injection, said disposable cassette assembly extends partially outside of said reusable driving assembly at a forward injection end thereof and is releasably retained in said reusable driving assembly; and
said disposable cassette assembly may thereafter be fully disengaged from said reusable driving assembly by axially pulling said disposable cassette assembly out of said reusable driving assembly.

8. An automatic injection device comprising:
a reusable driving assembly having a forward injection end and multiple mutually axially displaceable elements; and
a disposable cassette assembly including a cassette housing element, a prefilled syringe including a needle for injecting an injectable liquid at an injection site and a needle guard element,
wherein:
said disposable cassette assembly is removably insertable into said reusable driving assembly at said forward injection end;
following insertion of said disposable cassette assembly into said reusable driving assembly, said automatic injection device may be caused to assume an injection site engagement operative orientation by pressing said forward injection end of said reusable driving assembly against said injection site, thereby producing mutual axial displacement of at least some of said multiple mutually axially displaceable elements but not producing relative axial displacement between said needle guard element and said cassette housing element of said disposable cassette assembly.

9. An automatic injection device according to claim 8 and wherein:
said reusable driving assembly includes a forward base element and a trigger button element;
following assumption of said injection site engagement operative orientation, said automatic injection device may be caused to assume a needle insertion operative orientation by pressing said trigger button element, thereby causing forward axial displacement of said cassette housing element and resulting penetration of said injection site by said needle to a penetration depth defined by engagement of said cassette housing element with said forward base element of said reusable driving assembly.

10. An automatic injection device according to claim 9 and wherein:
following injection, said disposable cassette assembly extends partially outside of said reusable driving assembly at said forward injection end and is releasably retained in said reusable driving assembly; and
said disposable cassette assembly may thereafter be fully disengaged from said reusable driving assembly by axially pulling said disposable cassette assembly out of said reusable driving assembly.

11. An automatic injection device according to claim 9 and wherein only following insertion and retention of said disposable cassette assembly in said reusable driving assembly, said automatic injection device may be caused to assume said needle insertion operative orientation by pressing said trigger button element, thereby causing forward axial displacement of said cassette housing element and resulting penetration of said injection site by said needle.

12. An automatic injection device according to claim 8 and wherein said reusable driving assembly includes a plunger element, a forward cover element and a rearward cover element, a spring and at least one cocked orientation retaining element operative in a cocked operative orientation of said reusable driving assembly for cocking said plunger element against an urging of said spring and retaining said plunger element in said cocked operative orientation.

13. An automatic injection device comprising:
a reusable driving assembly having a rearward end and a forward injection end, said reusable driving assembly arranged along a longitudinal axis extending through both said rearward end and said forward injection end; and
a disposable cassette assembly;
wherein:
said disposable cassette assembly is removably insertable into said reusable driving assembly at said forward injection end, such that at least a portion of said disposable cassette assembly protrudes forwardly from said forward injection end to a first longitudinal extent;
following injection, said disposable cassette assembly extends forwardly from said forward injection end to a second longitudinal extent, which is greater than the first longitudinal extent and is releasably retained in said reusable driving assembly; and
said disposable cassette assembly may thereafter be fully disengaged from said reusable driving assembly by axially pulling said disposable cassette assembly out of said reusable driving assembly to along said longitudinal axis, and wherein:
said reusable driving assembly includes a trigger button element;
said disposable cassette assembly includes a cassette housing element, a needle and an injectable liquid to be injected at an injection site;
only following insertion and retention of said disposable cassette assembly in said reusable driving assembly, said automatic injection device may be caused to assume a needle insertion operative orientation by pressing said trigger button element, thereby causing forward axial displacement of said cassette housing element and resulting penetration of said injection site by said needle.

14. An automatic injection device according to claim 13 wherein said reusable driving assembly includes a plunger element, a forward cover element and a rearward cover element, a spring and at least one cocked orientation retaining element operative in a cocked operative orientation of said reusable driving assembly for cocking said plunger element against an urging of said spring and retaining said plunger element in said cocked operative orientation.

15. An automatic injection device according to claim 14 and wherein said forward cover element and said rearward cover element move towards each other before said reusable driving assembly assumes said cocked operative orientation and when said reusable driving assembly assumes said cocked operative orientation, said forward cover element and said rearward cover element are locked against mutual axial displacement.

16. An automatic injection device according to claim 14 and wherein:
said disposable cassette assembly includes a prefilled syringe including said needle for injecting said injectable liquid at said injection site and a needle guard element, and
following injection and removal of said needle from the injection site, assumption of said cocked operative orientation of said reusable driving assembly is possible thereafter only following forward displacement of said needle guard element relative to said needle.

17. An automatic injection device according to claim 13 and wherein:
said reusable driving assembly includes a safety catch element; and
said automatic injection device may be caused to assume a needle insertion operative orientation by pressing said trigger button element, thereby causing forward axial displacement of said cassette housing element and resulting penetration of said injection site by said needle, only when all of the following conditions are met:
said reusable driving assembly is in a cocked operative orientation;
said disposable cassette assembly is inserted and retained in said reusable driving assembly, and
said safety catch element is in a disengaged operative orientation.

18. An automatic injection device according to claim 17 and wherein said automatic injection device may be caused to assume said needle insertion operative orientation by pressing said trigger button element, thereby causing forward axial displacement of said cassette housing element and resulting penetration of said injection site by said needle, only when all of the following conditions are met:
said reusable driving assembly is in said cocked operative orientation; and thereafter
said disposable cassette assembly is fully inserted and retained in said reusable driving assembly, and thereafter
said safety catch element is in said disengaged operative orientation.

* * * * *